(12) United States Patent
Navratil et al.

(10) Patent No.: US 8,299,096 B2
(45) Date of Patent: Oct. 30, 2012

(54) METHOD FOR TREATING PULMONARY DISEASES USING RHO KINASE INHIBITOR COMPOUNDS

(75) Inventors: Tomas Navratil, Carrboro, NC (US);
Ward M. Peterson, Morrisville, NC (US); John W. Lampe, Cary, NC (US);
Emilee H. Fulcher, Cary, NC (US);
Scott D. Sorensen, Morrisville, NC (US)

(73) Assignee: Inspire Pharmaceuticals, Inc., Whitehouse Station, NJ (US)

( * ) Notice: Subject to any disclaimer, the term of this patent is extended or adjusted under 35 U.S.C. 154(b) by 552 days.

(21) Appl. No.: 12/492,494

(22) Filed: Jun. 26, 2009

(65) Prior Publication Data

US 2009/0325958 A1    Dec. 31, 2009

Related U.S. Application Data

(60) Provisional application No. 61/076,055, filed on Jun. 26, 2008, provisional application No. 61/169,239, filed on Apr. 14, 2009, provisional application No. 61/169,639, filed on Apr. 15, 2009, provisional application No. 61/169,635, filed on Apr. 15, 2009.

(51) Int. Cl.
*A01N 43/40* (2006.01)
*A61K 31/445* (2006.01)
*C07D 211/32* (2006.01)
*C07D 231/56* (2006.01)
*C07D 207/00* (2006.01)
*C07D 295/00* (2006.01)

(52) U.S. Cl. .................. 514/322; 546/199; 548/362.1; 548/518

(58) Field of Classification Search .............. 514/322; 546/199; 548/362.1, 518
See application file for complete search history.

(56) References Cited

U.S. PATENT DOCUMENTS

| | | | |
|---|---|---|---|
| 6,844,354 B1 | 1/2005 | Iizuka et al. | |
| 7,094,789 B2 | 8/2006 | Yamada et al. | |
| 7,160,894 B2 | 1/2007 | Yamada et al. | |
| 2004/0048776 A1 | 3/2004 | Satoh et al. | |
| 2004/0102437 A1* | 5/2004 | Takami et al. | 514/217.12 |
| 2004/0266755 A1 | 12/2004 | Islam et al. | |
| 2007/0088021 A1 | 4/2007 | Hidaka et al. | |
| 2007/0179127 A1 | 8/2007 | Yamada et al. | |
| 2008/0021026 A1 | 1/2008 | Kahraman et al. | |
| 2008/0021217 A1 | 1/2008 | Borchardt et al. | |
| 2008/0045566 A1 | 2/2008 | Ray et al. | |
| 2008/0214614 A1 | 9/2008 | Lampe et al. | |

FOREIGN PATENT DOCUMENTS

| | | |
|---|---|---|
| EP | 1163910 | 12/2001 |
| EP | 1550660 | 7/2005 |
| WO | WO 2006/135383 | 12/2006 |
| WO | WO 2008/077057 A2 | 6/2008 |
| WO | WO 2008077552 A1 * | 7/2008 |

OTHER PUBLICATIONS

International Search Report for PCT/US09/48807, mailed Sep. 10, 2009.
Dudek SM et al., *J Appl Physiol*, 91:1487-1500 (2001).
Fernandes et al., *Therapeutic Advances in Resp. Diseases*, 1(1):25-33 (2007).
Fukumoto Yet al., *Tohoku J Exp Med.*, 211(4):309-320 (2007).
Koksel O et al., *Eur J Pharmacol.*, 510(1-2):135-142 (Mar. 7, 2005).
Sawafuji et al., *Am J Physiol Lung Cell Mol Physiol*, 289:L946-L953 (2005).
Schaafsma et al., *Respiratory Research* 7:121-127 (2006).
Shimizu et al., *Am J Respir Crit Care Med* 163:210-217 (2001).
Taki F. et al., *Clin Exp Allergy*, 37:599-607 (2007).
Tasaka S et al., *Am J Resp Cell Mol Biol*, 32:504-510 (2004).
Yamaguchi et al., "Structural Basis for Induced-Fit Binding of Rho-Kinase to the Inhibitor Y-27632"; *Journal of Biochemistry*, vol. 140(3), pp. 305-311 (2006).

* cited by examiner

*Primary Examiner* — Sreeni Padmanabhan
*Assistant Examiner* — Sarah Pihonak
(74) *Attorney, Agent, or Firm* — Perkins Coie LLP.; Viola T. Kung

(57) ABSTRACT

This invention is directed to methods of preventing or treating diseases or conditions of the lungs associated with excessive cell proliferation, remodeling, inflammation, vasoconstriction, bronchoconstriction, airway hyperreactivity and edema. Particularly, this invention is directed to methods of treating pulmonary diseases such as asthma; chronic obstructive pulmonary disease; respiratory tract illness caused by respiratory syncytial virus; pulmonary arterial hypertension; acute respiratory distress syndrome and ventilator induced lung injury; cystic fibrosis; bronchiectasis; alpha-1-antitrypsin deficiency; rhinitis; rhinosinusitis; primary ciliary dyskinesia; pneumonia; bronchiolitis caused by agents other than respiratory syncytial virus; and interstitial lung disease including lymphangioleiomyomatosis; idiopathic pulmonary fibrosis; obliterative bronchiolitis or bronchiolitis obliterans organizing pneumonia due to lung transplantation or HSCT; nonspecific interstitial pneumonia; cryptogenic organizing pneumonia; acute interstitial pneumonia; respiratory bronchiolitis-associated interstitial lung disease; or pulmonary sarcoidosis. The method comprises administering to a subject an effective amount of a rho kinase inhibitor compound to treat the disease.

17 Claims, 15 Drawing Sheets

METHOD FOR TREATING PULMONARY DISEASES USING RHO KINASE INHIBITOR COMPOUNDS

This application claims the benefit of U.S. Provisional Application Nos. 61/076,055, filed Jun. 26, 2008; 61/169,239, filed Apr. 14, 2009; 61/169,639, filed Apr. 15, 2009; and 61/169,635, filed Apr. 15, 2009; which are incorporated herein by reference in their entirety.

TECHNICAL FIELD

This invention relates to methods of preventing or treating diseases or conditions of the lung associated with excessive cell proliferation, remodeling, inflammation, vasoconstriction, bronchoconstriction, airway hyperreactivity and edema. Particularly, this invention relates to methods of treating pulmonary diseases such as asthma, COPD, respiratory tract illness caused by respiratory syncytial virus infection, PAH, LAM, idiopathic pulmonary fibrosis, ARDS and VILI, CF, bronchiectasis, AATD, rhinitis, rhinosinusitis, PCD, pneumonia, bronchiolitis caused by agents other than RSV, OB/BOOP due to lung transplantation or HSCT, non-IPF IIP and ILD other than IPF, non-IPF IIPs and OB/BOOP, using novel rho kinase inhibitor compounds.

BACKGROUND OF THE INVENTION

Rho Kinase as a Target

The Rho family of small GTP binding proteins can be activated by several extracellular stimuli such as growth factors, hormones and mechanic stress and function as a molecular signaling switch by cycling between an inactive GDP-bound form and an active GTP-bound form to elicit cellular responses. Rho kinase (ROCK) functions as a key downstream mediator of Rho and exists as two isoforms (ROCK 1 and ROCK 2) that are ubiquitously expressed. ROCKs are serine/threonine kinases that regulate the function of a number of substrates including cytoskeletal proteins such as adducin, moesin, $Na^+$—$H^+$ exchanger 1 (NHE1), LIM-kinase and vimentin, contractile proteins such as the myosin light chain phosphatase binding subunit (MYPT-1), CPI-17, myosin light chain and calponin, microtubule associated proteins such as Tau and MAP-2, neuronal growth cone associate proteins such as CRMP-2, signaling proteins such as PTEN and transcription factors such as serum response factor (Loirand et al, Circ Res 98:322-334 (2006)). ROCK is also required for cellular transformation induced by RhoA. As a key intermediary of multiple signaling pathways, ROCK regulates a diverse array of cellular phenomena including cytoskeletal rearrangement, actin stress fiber formation, proliferation, chemotaxis, cytokinesis, cytokine and chemokine secretion, endothelial or epithelial cell junction integrity, apoptosis, transcriptional activation and smooth muscle contraction. As a result of these cellular actions, ROCK regulates physiologic processes such as vasoconstriction, bronchoconstriction, tissue remodeling, inflammation, edema, platelet aggregation and proliferative disorders.

One well documented example of ROCK activity is in smooth muscle contraction. In smooth muscle cells ROCK mediates calcium sensitization and smooth muscle contraction. Agonists (noradrenaline, acetylcholine, endothelin, etc.) that bind to G protein coupled receptors produce contraction by increasing both the cytosolic $Ca^+$ concentration and the $Ca^{2+}$ sensitivity of the contractile apparatus. The $Ca^{2+}$-sensitizing effect of smooth muscle constricting agents is ascribed to ROCK-mediated phosphorylation of MYPT-1, the regulatory subunit of myosin light chain phosphatase (MLCP), which inhibits the activity of MLCP resulting in enhanced phosphorylation of the myosin light chain and smooth muscle contraction (WO 2005/003101 A2, WO 2005/034866A2).

The use of prototype non-potent Rho-kinase inhibitors, Y27632 or fasudil, in animal models has suggested a number of potential benefits of Rho-kinase inhibitors. Y27632 has shown favorable activity in animal models of respiratory disorders such as airway hyperreactivity and asthma (Schaafsma et al. Respiratory Research 7:121-127, 2006), airway remodeling and idiopathic pulmonary fibrosis (Shimizu et al. Am J Respir Crit. Care Med 163:210-217, 2001) and RSV infection (Hashimoto et al. Thorax 57:524-527, 2002). Fasudil has been shown to have favorable activity in models of asthma (Taki F et al. Clin Exp Allergy, 37:599-607, 2007); pulmonary hypertension (Shimokawa et al, Arterioscler Thromb Vasc Biol 25:1767-1775, 2005).

Asthma

Asthma is a common chronic disorder of the airways characterized by variable and recurring symptoms, reversible airway obstruction, bronchial hyperresponsiveness, and an underlying inflammation. Acute symptoms of asthma include cough, wheezing, shortness of breath and nocturnal awakening. These symptoms usually arise from bronchospasm and require and respond to bronchodilator therapy (see Expert Panel Report 3: Guidelines for the Diagnosis and Management of Asthma, NIH Publication No. 07-4051, Bethesda, Md.: U.S. Department of Health and Human Services; National Institutes of Health; National Heart, Lung, and Blood Institute; National Asthma Education and Prevention Program, (2007) and references therein).

Central to the pathophysiology of asthma is the presence of underlying airway inflammation mediated by the recruitment and activation of multiple cell types including mast cells, eosinophils, T lymphocytes, macrophages, dendritic cells and neutrophils. Type 2 T-helper (Th2) cells appear to play a central role in the activation of the immune cascade that results in inflammation. Th2-derived cytokines include IL-5, which is needed for eosinophil differentiation and survival, and IL-4 which is important for Th2 cell differentiation and with IL-13 is important for IgE formation and leads to overproduction of IgE and eosinophilia. IgE-driven activation of mucosal mast cells releases bronchoconstrictor mediators such as histamine and cysteinyl-leukotrienes as well as inflammatory cytokines. Eosinophils contain inflammatory enzymes, generate leukotrienes, and express a wide variety of pro-inflammatory cytokines. Airway epithelial cells also play a role in the inflammatory process via release of cytokines such as eotaxin that direct and modify the inflammatory response. Acute and chronic inflammation can affect not only the airway caliber and airflow but also can increase the existing bronchial hyperresponsiveness to a variety of stimuli, which enhances susceptibility to bronchospasm.

As a consequence of airway inflammation and the generation of growth factors, the airway smooth muscle cell can undergo proliferation, activation, contraction, and hypertrophy—events that can influence airway airflow limitation. In asthma, the dominant physiological event leading to clinical symptoms is airway narrowing and a subsequent interference with airflow. In acute exacerbations of asthma, bronchial smooth muscle contraction (bronchoconstriction) occurs quickly to narrow the airways in response to exposure to a variety of stimuli including allergens or irritants. Allergen-induced acute bronchoconstriction results from an IgE-dependent release of mediators from mast cells that includes histamine, tryptase, leukotrienes, and prostaglandins that directly contract airway smooth muscle. The mechanisms influencing airway hyperresponsiveness are multiple and include inflammation, dysfunctional neuroregulation, and airway remodeling. Airway remodeling involves structural changes including thickening of the sub-basement membrane, subepithelial fibrosis, airway smooth muscle hypertrophy and hyperplasia, blood vessel proliferation and dilation with consequent permanent changes in the airway that increase airflow obstruction and that is not prevented by or fully reversible by current therapies.

Airway epithelium and endothelial cell function are also critically involved in asthma. Upon disease progression, epithelial subbasement membranes thicken with mucus hypersecretion and the formation of inspissated mucus plugs. Changes in endothelial cell integrity lead to edema, another key pathophysiology defining asthmatic change of the airway. These factors serve to further limit airflow and are not directly addressed by current therapies.

Current standard therapies for asthma are a combination of corticosteroids and $\beta_2$-agonists (anti-inflammatory and bronchodilator drugs). These drugs provide acceptable control of the disease for many asthmatics. However, it is estimated that 5 to 10% of the asthma patients have symptomatic disease despite treatment with this combination of corticosteroids and $\beta_2$-agonists (Chanez et al., J Allergy Clin Immunol 119: 1337-1348 (2007)).

Chronic Obstructive Pulmonary Disease

Chronic obstructive pulmonary disease (COPD) is the most common chronic lung disease associated with significant morbidity and mortality. In the United States, COPD is the fourth leading cause of death and accounts for more than $30 billion in annual health care costs. An estimated 16 million adults are affected by COPD, and each year ~120,000 Americans die of the disease. COPD is defined as a chronic disease characterized by airway/alveolar/systemic inflammation, with measured airflow obstruction ($FEV_1/FVC<70\%$ and $FEV_1<80\%$ predicted) that is partially improved with bronchodilator therapy. The local and systemic release of inflammatory mediators by the lung cells leads to airway disease (chronic obstructive bronchitis) and, in a minority of patients, to destruction of parenchymal tissue (emphysema), both of which can result in the airflow limitation that characterizes COPD (see Doherty D E et al, Clin Cornerstone 6:S5-16 (2004) and MacNee, Clin Ches Med 28:479-513 (2007)). The release of these inflammatory mediators by the lung cells may also exacerbate inflammation in other organ systems, such as that observed in coronary, cerebrovascular, and peripheral vascular conditions.

The chronic inflammation, airway obstruction, and tissue damage that occur in COPD all result from chronic exposure to inhaled toxic substances, primarily cigarette smoke. In response to the chemical insult of inhaled tobacco smoke, inflammatory cells (including macrophages, neutrophils, and T-lymphocytes, primarily CD8 lymphocytes) are activated in the small and large airways as well as in the lung parenchyma. These activated inflammatory cells release a host of cytokines and other mediators (including tumor necrosis factor-$\alpha$, interleukin [IL]-8, and leukotriene $B_4$), which can cause damage to lung tissue. The end result of the release of these cytokines and mediators may be the development of chronic inflammation of the airways, mucus gland hypertrophy and goblet-cell hyperplasia with increased mucus secretion, fibrosis and narrowing of smaller airways, destruction of the parenchyma (the connective tissue/cells in the lungs), and changes in the blood vessels that may result in the development of pulmonary hypertension. These pathologic changes manifest themselves as mucus hypersecretion, limited airflow, hyperinflation, and gas exchange abnormalities which are the major physiologic abnormalities that characterize COPD. A loss in the integrity of the lung's connective tissue leads to a decrease of elastic recoil and hyperinflation.

Current therapies to treat COPD include bronchodilators, especially anticholinergic agents, that help to some degree decrease hyperinflation, therefore increasing inspiratory capacity and relieving dyspnea. Although corticosteroids are an effective treatment for most cases of asthma, the inflammatory cells and mediators in COPD are not sensitive to treatment with systemic or inhaled corticosteroids making treatment with these agents of limited usefulness in COPD.

RSV Infection

Respiratory syncytial virus (RSV) causes acute respiratory tract illness in persons of all ages. RSV is a leading cause of lower respiratory tract infection (LRTI) in children younger than 2 years. It is associated with up to 120,000 pediatric hospitalizations each year, and is increasing in frequency. RSV also is a significant cause of morbidity and mortality from LRTI in elderly patients (Collins et al., J Virol 82:2040-2055 (2008); Peebles et al., Proc Am Thorac Soc 2:110-115 (2005)).

After replicating in the nasopharynx, RSV infects the small bronchiolar epithelium and extends to the type 1 and 2 alveolar pneumocytes in lung. Pathologic findings of RSV include necrosis of epithelial cells, occasional proliferation of the bronchiolar epithelium, infiltrates of monocytes and T cells centered on bronchial and pulmonary arterioles, and neutrophils between the vascular structures and small airways. This leads to airway obstruction, air trapping and increased airway resistance, and also is associated with a finding of neutrophilia in bronchoalveolar lavage. The immune response to RSV, especially cytokine and chemokine release, appears to play a role in the pathogenesis and severity of bronchiolitis. There is a distinct pattern of cytokines and chemokines induced by RSV infection and some have been associated with disease severity. The cytokines IL-8, IL-6, TNF-alpha, and IL-1 beta can be detected in airway secretions of infected children (Smyth et al. Arch Dis Child 76:210 (1997)), and IL-6 levels correlate with severe disease. Chemokines identified in respiratory tract secretions of children include CCL3, CCL2, CCL11 and CCL5, but only the beta-chemokines, particularly MIP-1 alpha, are associated with severe disease (Welliver et al. Pediatr Infect Dis J 21:457 (2002)).

RSV can involve both lower and upper respiratory tract. Severe lower respiratory tract disease can involve bronchiolitis, bronchospasm, pneumonia, and acute respiratory failure in children. Lower respiratory tract involvement usually occurs with primary infection, and may occur in second infections and can cause wheezing, tachypnea and apnea. Repeat RSV infections occur frequently in children and young adults and result in significant upper respiratory tract symptoms. Signs include cough, coryza, rhinorrhea, and conjunctivitis. RSV infection in adults also may cause short-term airway reactivity.

There is no direct treatment for RSV infection and the respiratory complications it causes. The current therapy for RSV is primarily supportive. Bronchodilator therapy in infants with bronchiolitis, largely caused by RSV infection, did not demonstrate benefit in large randomized trials and systematic reviews. Prophylaxis with palivizumab, a humanized monoclonal antibody, has been indicated for a limited fraction of the pediatric patient population.

Pulmonary Arterial Hypertension

Pulmonary arterial hypertension (PAH) is a disease of the small pulmonary arteries, characterized by vascular narrowing leading to a progressive increase in pulmonary vascular resistance. The consequence of this increased right ventricle after-load is the failure of the afterload-intolerant right ventricle. The pulmonary vascular injury underlying PAH occurs in an idiopathic form or in association with other disease states such as congenital heart disease or COPD. Vasoconstriction, remodeling of the pulmonary vessel wall, and thrombosis contribute to the increased pulmonary vascular resistance in PAH. However, it is now recognized that pulmonary arterial obstruction by vascular proliferation and remodeling is the hallmark of PAH pathogenesis (Humbert et al. J Am Coll Cardiol 43:13 S-24S (2004) and Rubin Proc Am Thorac Soc 3:111-115 (2006)). The process of pulmonary vascular remodeling involves all layers of the vessel wall. Indeed, each cell type (endothelial, smooth muscle, and fibroblast), as well as inflammatory cells and platelets, may play a significant role in PAH. A feature common to all forms of PAH remodeling is the distal extension of smooth muscle into small peripheral, normally nonmuscular, pulmonary arteries within the respiratory acinus. In addition, a hallmark of severe pulmonary hypertension is the formation of a layer of myofibroblasts and extracellular matrix between the endothelium and the internal elastic lamina, termed the neointima.

Pulmonary vasoconstriction is believed to be an early component of the pulmonary hypertensive process. Excessive vasoconstriction has been related to abnormal function or expression of potassium channels and to endothelial dysfunction. Endothelial dysfunction leads to chronically impaired production of vasodilators such as nitric oxide and prostacyclin along with overexpression of vasoconstrictors such as endothelin 1.

Inflammatory mechanisms appear to play a significant role in some types of pulmonary hypertension. Indeed, a subset of PAH patients have circulating autoantibodies including antinuclear antibodies, as well as elevated circulating levels of proinflammatory cytokines IL-1 and IL-6. Lung histology also revealed inflammatory infiltrates (macrophages and lymphocytes) in the range of plexiform lesions in severe PAH as well as an increased expression of chemokines RANTES and fractalkine.

Current therapies for PAH include prostanoids, endothelin receptor antagonists, and phosphodiesterase type V inhibitors. Despite these treatments, the average life expectancy of a PAH patient is generally under five years from the diagnosis of the disease.

Lymphangioleiomyomatosis

Lymphangioleiomyomatosis (LAM) and tuberous sclerosis complex (TSC) are caused by mutations in either of the tuberous sclerosis genes, TSC1 or TSC2, which control cell growth, survival, and motility through the Akt/mammalian target of rapamycin (mTOR) signaling pathway (McCormack Chest 133:507-516 (2008)). Deficiency or dysfunction of the encoded proteins, hamartin or tuberin, respectively, result in a loss of regulation of signals from upstream sources including cell surface tyrosine kinase and G protein coupled receptors. The constitutive activation of mTOR kinase and the downstream S6 kinase (S6K) leads to increased protein translation, and ultimately to inappropriate cellular proliferation, migration, and invasion. These changes lead to smooth muscle cell infiltration and cystic destruction of the lung resulting in progressive dyspnea on exertion, recurrent pneumothoraces, abdominal and thoracic lymphadenopathy, and abdominal tumors, including angiomyolipomas and lymphangiomyomas.

LAM occurs in about 30% of women with tuberous sclerosis complex (TSC) and also in women who do not have TSC (ie, sporadic LAM [S-LAM]). Both S-LAM and TSC-LAM are associated with mutations in tuberous sclerosis genes. In patients with TSC or TSC-LAM, germline mutations in TSC genes are present in all cells of the body and neoplasms and dysplasias occur when somatic TSC mutations result in a loss of heterozygosity for the normal allele. In patients with S-LAM, somatic TSC mutations are confined to lesions in the lung, kidney, and lymph nodes although respiratory involvement predominates.

There are no proven therapies for LAM although bronchodilator therapy is useful for some patients.

Idiopathic Pulmonary Fibrosis

Idiopathic pulmonary fibrosis (IPF) is a chronic, progressives fibrotic disorder of the lower respiratory tract that typically affects adults beyond the age of 40. IPF is thought to occur as a result of initial injury to the lung by environmental factors such as cigarette smoke leading to recruitment of neutrophils, lymphocytes and macrophages to the lung alveoli. Release of fibrogenic cytokines, such as TGF-β by alveolar epithelial cells results in fibroblast proliferation, migration, and fibrosis. These fibroblasts not only fill the respiratory space but also secrete collagen and matrix proteins in response to many cytokines leading to parenchymal remodeling (Shimizu et al., Am J Respir Crit. Care Med 163:210-217 (2001)). This differentiation of fibroblasts is likely key to the chronic nature of IPF. These events lead to cough and progressive shortness of breath. IPF patients have compromised lung function and have shown restrictive lung volumes and capacities. Although corticosteroids, immunosupressive agents, neutrophil elastase inhibitor, hepatocyte growth factor, and interferon gamma-1b have been proposed as treatment agents for IPF, no treatment other than lung transplantation is known to prolong survival and IPF remains a fatal disorder with a 3 to 6 yr median range of survival (Khalil et al. CMAJ 171:153-160 (2004)). Thus, the first line of treatment of IPF has not yet been established.

Acute Respiratory Distress Syndrome (ARDS) and Ventilator Induced Lung Injury (VILI)

Acute respiratory distress syndrome is a critical illness characterized by acute lung injury leading to permeability pulmonary edema and respiratory failure. ARDS respiratory failure can be caused by various acute pulmonary injuries and is characterized by noncardiogenic pulmonary edema, respiratory distress, and hypoxemia. Despite significant advances in critical care management, overall mortality from ARDS ranges from 25 to 58% (Berstan A D et al. *Am J Respir Crit. Care Med,* 165:443, 2002).

More than 60 causes of ARDS have been identified. A few common causes include sepsis, aspiration of gastric contents, primary bacterial or viral pneumonias, direct chest trauma, ventilator-induced lung injury, prolonged or profound shock, burns, fat embolism, near drowning, massive blood transfusion, transfusion-related lung injury (TRALI), cardiopulmonary bypass, pneumonectomy, acute pancreatitis, inhalation of smoke or other toxic gas, and ingestion of certain drugs (Pepe P et al. Am J Surg, 144:124, 1982; Hudson L D, *J Respir Crit. Care Med,* 151:293, 1995; Zaccardelli D S and Pattishall E N, *Crit. Care Med,* 24:247, 1996; Fowler A et al. *Ann Intern Med,* 98:593, 1983).

ARDS is described as a "syndrome of acute and persistent inflammation with increased vascular permeability associated with a constellation of clinical, radiological and physiological abnormalities" (Bernard G et al. *Am J Respir Crit. Care Med,* 149:818, 1994; Artigas A et al. *Am J Respir Crit. Care Med,* 157:1332, 1998). The hallmark of ARDS is deterioration in blood oxygenation and respiratory system compliance as a consequence of permeability edema. Whereas a variety of different insults may lead to ARDS, a common pathway probably results in the lung damage and/or failure, leukocyte activation within the lung, along with the release of oxygen free radicals, arachidonic acid metabolites, and inflammatory mediators, resulting in an increase in alveolocapillary membrane permeability. With the loss of this macromolecular barrier, alveoli are flooded with serum proteins, which impair the function of pulmonary surfactant (Said et al. J. Clin, Invest. 44: 458-464; Holm et al. J. Appl. Physio. 63: 1434-1442, 1987). This creates hydrostatic forces that further exacerbate the condition (Jefferies et al., J. Appl. Physio. 64: 5620-5628, 1988), leading to alveolar edema and a concomitant deterioration in gas exchange and lung compliance.

Mechanical ventilation is a common and generally effective means of treating a failing lung. Unfortunately, positive-pressure mechanical support can create or contribute to lung injury (ventilator-induced lung injury, VILI). Mechanical ventilators applying high volumes and pressures can lead to an influx of fluid into the lung. In addition to edema, the injured or ruptured cells trigger a cascade of cellular and biochemical events leading to the inflammation in the lung. Pulmonary sheer stress can develop due to the increased volume as well as due to atelectasis. VILI is also believed to provoke distal airway and alveolar cell inflammation by increasing the production of proinflammatory cytokines. In light of the fact that more than 280,000 Americans are at risk for VILI each year, and mechanical ventilation support and associated intensive care expenditures are estimated in the billions of dollars, VILI is a major public health concern (WO/2007/109582).

Rho kinase signaling pathways are implicated in an array of cellular phenomena many of which play roles in the pathophysiology of ARDS and VILI. These include cytoskeletal rearrangement, actin stress fiber formation, proliferation, chemotaxis, cytokinesis, cytokine and chemokine secretion, endothelial or epithelial cell junction integrity, apoptosis, transcriptional activation and smooth muscle contraction, Several mechanisms such as increased endothelial permeability, inflammatory cell recruitment, and inflammation have been implicated in the pathogenesis of ARDS. Endothelial cells form a major part of the capillary permeability barrier in the lungs and changes are associated with increased capillary permeability (due to endothelial cell contraction and barrier dysfunction; Tinsley J H et al. *Am J Physiol Cell Physiol*, 279:C1285-1289, 2000). Inflammatory reactions may lead to endothelial paracellular gaps and extravasation of fluid and macromolecules. Airway epithelium can also contribute to inflammation by releasing inflammatory mediators, an event governed in part by Rho signaling (Cummings R J et al. J Biol Chem, 277:30227-30235, 2002).

Cystic Fibrosis (CF)

CF is the most common, life threatening, recessively inherited disease of Caucasian populations, with a carrier rate of 1 in 25 and an incidence of 1 in 2,500 live births. CF is a multisystem disease affecting the digestive system, sweat glands, and the reproductive tract, but progressive lung disease continues to be the major cause of morbidity and mortality (Ratjen, F. and Doring, G. Lancet 361:681, 2003). CF patients have abnormal transport of chloride and sodium across the respiratory epithelium, resulting in thickened, viscous airway secretions (Rowe S M et al. *N Engl J Med;* 352:1992, 2005). Patients develop chronic infection of the respiratory tract with a characteristic array of bacterial flora (Gibson, R L et al. *Am J Respir Crit. Care Med* 168:918, 2003), leading to progressive respiratory insufficiency and eventual respiratory failure. CF is caused by mutations in a single large gene on chromosome 7 that encodes the cystic fibrosis transmembrane conductance regulator (CFTR) protein (Rommens J M et al. Science; 245:1059, 1989; Collins F S. *Science;* 256:774, 1992; Drumm, M L et al. *Mol Genet Med;* 3:33, 1993). CFTR has been shown to function as a regulated chloride channel, which in turn may regulate the activity of other chloride and sodium channels at the cell surface (Boucher R C. *Am J Respir Crit. Care Med.* 150:271-281, 1994). Defective CFTR results in abnormal ion transport and airway surface liquid volume with alterations in the rheology of airway secretions, which become thick and difficult to clear (Wine J J. *J Clin Invest;* 103:309, 1999). These changes result in reduced mucociliary clearance and a propensity for chronic infection of the respiratory tract with resulting inflammation, progressive airway damage, bronchiectasis, progressive respiratory failure, and death (Mickle J E and Cutting G R. *Clinics in Chest Med,* 19(3):443-458, 1998).

Respiratory symptoms of CF usually begin early in life (Ratjen, F. and Doring, G. Lancet 361:681, 2003). Respiratory manifestations include recurrent, progressively more persistent cough becoming productive, chronic infection (particularly *Pseudomonas aeruginosa*), and inflammation leading to progressive tissue damage in the airways. Once infection is established, neutrophils are unable to control the bacteria, even though there is massive infiltration of these inflammatory cells into the lung tissue. Recruited neutrophils subsequently release inflammatory cytokines, reactive oxygen species, and elastase, the latter of which overwhelms the antiproteases of the lung and contributes to progressive destruction of the airway walls. In addition, large amounts of DNA and cytosol matrix proteins are released by degranulating neutrophils, contributing to the increased viscosity of the airway mucus (Davis, P B. Pathophysiology of the lung disease in cystic fibrosis. In: Cystic Fibrosis, Davis, P B (Ed), Marcel Dekker, New York 1993. p. 193). Toxic metabolites released by *P. aeruginosa* increase the rate of neutrophil apoptosis and decreased removal of apoptotic cells by pulmonary macrophages (Bianchi S M et al. *Am J Respir Crit. Care Med* 177:35-43, 2008), contributing to the accumulation of DNA, protein, and cellular debris in the airway and exacerbating inflammation. Lung damage ultimately advances to the stage of irreversible bronchiectasis (dilated, collapsible airways), leading to progressive air and mucus trapping and ultimate respiratory failure. Other late complications include spontaneous pneumothorax (collapsed lung) and hemoptysis (coughing up blood), which may be massive (Flume P A et al. *Chest;* 128:720, 2005; Flume P A et al. *Chest* 128:729, 2005). Terminal findings often include severely congested parenchyma, with grossly purulent secretions in dilated airways. The airway epithelium is hyperplastic, often with areas of erosion and squamous metaplasia. Plugs of mucoid material and inflammatory cells are often present in the airway lumen. Submucosal gland hypertrophy and hyperplasia of airway smooth muscle may also be present (Hays S R et al. *Thorax* 60:226, 2005.)

Airway hyperreactivity is a common finding in CF patients (Hiatt P et al. *Am Rev Respir Dis* 137:119, 1988). Many CF patients continue to demonstrate bronchial hyperresponsiveness into adolescence and adulthood, with positive correlations between the degree of airway reactivity and the overall severity of lung disease. The response to bronchodilators does not always persist with increasing age, and some patients demonstrate worsening of expiratory airflow in response to treatment with beta-adrenergic reagents (Gibson, R L et al. *Am J Respir Crit. Care Med* 168:918, 2003). This phenomenon may occur when progressive airway damage leads to a loss of cartilaginous support, resulting in an increased reliance on muscle tone for maintenance of airway patency.

Muscle relaxation in this setting can cause collapse of such "floppy" airways, leading to increased airflow obstruction.

The chest radiography may appear normal for an extended period in patients with mild lung disease. As the disease progresses, hyperinflation becomes persistent, and interstitial markings become more prominent. Increasing hyperinflation leads to progressive flattening of the diaphragms, a prominent retrosternal space, and kyphosis (curvature of upper spine) in late stages of disease. Thin-walled cysts may appear to extend to the lung surface, and pneumothorax is observed with increasing frequency in older patients. Computed tomography (CT) of the chest may be helpful in defining the extent of bronchiectasis in some patients (de Jong, P A et al. *Radiology* 231:434, 2004.]. This is of particular interest in patients who have focal areas of advanced disease, which may sometimes be amenable to surgical resection.

Changes in pulmonary function may be identifiable from a very early age, even before clinical signs of disease are apparent (Long F R et al. *J Pediatr* 144:154, 2004; Castile R G et al. *Pediatr Pulmonol* 37:461, 2004). Over time, the majority of CF patients develop an obstructive pattern on pulmonary function testing (PFT). Increases in the ratio of residual volume to total lung capacity (RV/TLC) and decreases in the forced expiratory flow at 25 to 75 percent of lung volume ($FEF_{25-75}$) provide the most sensitive measures of early airway obstruction. As disease progresses, the forced expiratory volume in one second ($FEV_1$) and the ratio of $FEV_1$ to forced vital capacity ($FEV_1/FVC$) decline (Davis, P B. Pathophysiology of the lung disease in cystic fibrosis. In: Cystic Fibrosis, Davis, P B (Ed), Marcel Dekker, New York 1993. p. 193). The $FEV_1$ is correlated with subsequent survival in CF patients. An $FEV_1$ persistently lower than 30 percent of predicted may be a useful indicator of the need for transplant evaluation in patients who are considered appropriate candidates for that procedure (Kerem E et al. *N Engl J Med;* 326:1187, 1992). Lung volumes demonstrate increases in total lung capacity (TLC) and residual volume (RV) as hyperinflation progresses. Despite aggressive therapy, baseline pulmonary function gradually decreases as patients get older.

As bronchiectasis and airway obstruction become pronounced, ventilation-perfusion mismatch leads to hypoxemia. This may initially occur only during sleep or exercise, but patients with advanced disease often require continuous oxygen supplementation. Hypercapnia occurs relatively late in the course of CF lung disease. Chronic hypoxemia and hypercapnia may lead to muscular hypertrophy of the pulmonary vasculature, pulmonary hypertension, right ventricular hypertrophy, and eventually cor pulmonale with right heart failure (Eckles M and Anderson P. *Semin Respir Crit. Care Med* 24:323-30, 2003).

Therapeutic intervention for cystic fibrosis includes inhaled and oral antibiotics (tobramycin, azithromycin), bronchodilators (β-adrenergic agonists), DNase I (dornase alpha), hypertonic saline, chest physiotherapy, anti-inflammatory agents (azithromycin, ibuprofen, glucocorticoids), and lung transplantation. Although improved treatment of lung disease has increased survival, the median age for survival is still only 35 years (Cystic Fibrosis Foundation Patient Registry Annual Data Report, 2004), and patients continue to have significant morbidity, including hospitalizations (Ramsey B W. *N Engl J Med,* 335(3):179-188, 1996).

Bronchiectasis

Bronchiectasis is currently defined as the irreversible and sometimes progressive dilatation and destruction of the bronchial wall caused by a vicious pathogenic cycle of impaired local defense mechanisms, infection, and airway inflammation (Garcia, Arch Bronconeumol, 41(8):407-9, 2005). Bronchiectasis is a syndrome of chronic cough and daily viscid sputum production associated with airway dilatation and bronchial wall thickening. Hemoptysis can also occur. Multiple conditions are associated with the development of bronchiectasis, but all require an infectious insult plus impairment of drainage, airway obstruction, and/or a defect in host defense (Barker, A. F. Clinical manifestations and diagnosis of bronchiectasis. In: UpToDate, King T E (Ed), UpToDate, Wellesley, Mass., 2008).

All types of bronchiectasis are characterized by predominately neutrophilic and mononuclear inflammation with scores of cellular mediators that modulate both acute and chronic inflammatory response and perpetuate the bronchial lesion (Garcia, Arch Bronconeumol, 41(8):407-9, 2005) The ensuing host response, immune effector cells, neutrophilic proteases, reactive oxygen intermediates (eg, hydrogen peroxide [$H_2O_2$]), and inflammatory cytokines, causes transmural inflammation, mucosal edema, cratering, ulceration, and neovascularization in the airways. The result is permanent abnormal dilatation and destruction of the major bronchi and bronchiole walls. Recurrent infection is common, which can lead to further scarring, obstruction, and distortion of the airways, as well as temporary or permanent damage to the lung parenchyma (Barker, A. F. Clinical manifestations and diagnosis of bronchiectasis. In: UpToDate, King T E (Ed), UpToDate, Wellesley, Mass., 2008). The characteristic clinical picture is chronic purulent sputum, functional impairment in the form of air flow obstruction, multiple exacerbations of an infectious type that occasionally involve atypical microorganisms, and dyspnea in advanced stages of the disease— all of which cause progressive deterioration of the patient's quality of life (Garcia, Arch Bronconeumol, 41(8):407-9, 2005). Mortality is difficult to estimate given the difficulty in identifying prevalence and the lack of definitive studies. One study from Finland identified 842 patients aged 35-74 years with bronchiectasis and followed them for 8-13 years. These patients were also compared with asthma and COPD controls. The mortality was not found to be significantly different among the 3 groups (bronchiectasis, asthma, COPD) with mortality rates of 28%, 20%, and 38% respectively. Currently, mortality is more often related to progressive respiratory failure and cor pulmonale than to uncontrolled infection. Life-threatening hemoptysis may also occur but is uncommon (Emmons Bronchiectasis. In:WebMD Hollingsworth, H M (Ed) 2008). Bronchiectasis is the prototypical disease for which secretion loosening or thinning combined with enhanced removal techniques should be salutary, although large population and long-term studies of efficacy are lacking. This is particularly important as tenacious secretions and mucous plugs are frequently present. Potential approaches include hydration, nebulization with saline solutions and mucolytic agents, mechanical techniques, bronchodilators, and anti-inflammatory therapy. (Barker, A. F. Treatment of bronchiectasis. In: UpToDate, King T E (Ed), UpToDate, Wellesley, Mass., 2008.) Treatment of bronchiectasis is aimed at controlling infection and improving bronchial hygiene. Since infection plays a major role in causing and perpetuating bronchiectasis, reducing the microbial load and attendant mediators is a cornerstone of therapy (Barker, A. F. Treatment of bronchiectasis. In: UpToDate, King T E (Ed), UpToDate, Wellesley, Mass., 2008).

Treatment strategies including daily oral antibiotic treatment, daily or three times weekly use of a macrolide antibiotic treatment, aerosolization of an antibiotic, and intermittent intravenous antibiotics have not been established in long-term studies (Barker, A. F.). Several antibiotic treatment strategies are expensive and require extra equipment and personnel and only target part of the pathophysiology of the disease. Other treatments include physiotherapy, hydration with oral liquids and nebulization with hyperosmolar or mucolytic agents, bronchodilators, anti-inflammatory medications such as corticosteroids, and surgery. (Barker, A. F.) Thus, the treatments for bronchiectasis are limited in their ability to affect key pathophysiologies of the disease.

Alpha-1-Antitrypsin Deficiency (AATD)

AATD is a common inherited genetic disorder which severely affects up to 100,000 people in the US alone. (Campos, M A et al. Chest, 128:1179, 2005). An important physiological role for alpha-1-antitrypsin (AAT) is to protect lung elastin from degradation by serine proteases such as neutrophil elastase, which is repeatedly produced by lung tissues as a normal immune response to inhaled airborne pathogens. Low levels of AAT and/or secretion of defective AAT can lead to an imbalance between antiproteases and their target serine proteases, leading to tissue damage by these potent degrading enzymes (Koehlein, T et al. Am J. Med., 121:3-9, 2008).

A further aspect of the secretion of defective protein is the loss of the anti-inflammatory properties exerted by the normal protein. AAT is mainly produced in the hepatocytes, with the most common inherited AAT defect giving rise to an accumulation of abnormal protein in these cells, often resulting in cell damage (Lomas, D A, et al. Nature, 357:605, 1992). In the lung, the alveoli show low levels of functional AAT, often leading to an imbalance between antiprotease and protease, and consequential tissue destruction. While the correlation between the severity of the protein deficiency and resultant disease is somewhat variable (Silverman, E K et al. Ann Intern Med, 111:982, 1989), AATD is associated with increased risk for COPD, emphysema, asthma, chronic bronchitis, and brochiectasis in the lung, as well as cirrhosis, hepatitis, hepatocarcinoma or liver failure.

A major risk factor for COPD and emphysema in AATD patients is smoking, thus a smoking cessation program is a critical first-line defense against the progression of disease. Current available therapies for COPD and emphysema include use of long acting beta-agonists and anticholinergics to promote bronchorelaxation, treatment with steroids to reduce inflammation, or supplementation of AAT levels with AAT isolated from the pooled blood of human donors. (Koehlein, T et al. Am J. Med., 121:3-9, 2008). A recombinant form of AAT is not yet available for clinical use (Trexler, M M, et al. Biotechnol Prog, 18:501, 2002). However, as none of these therapies are particularly effective, there is an unmet medical need for improved drugs for the treatment of AATD induced lung disease.

Rhinitis

Rhinitis is irritation and inflammation of the mucosal lining of the nose, which may be caused by allergies or other factors such as cigarette smoke, changes in temperatures, and exercise and stress. The resulting irritation and inflammation generate excessive amounts of mucus producing a runny nose, nasal congestion, and post-nasal drip. Rhinitis is a global health concern and is often combined with asthma in determining morbidity due to respiratory diseases. It is a complex disease affecting approximately 20% of the population. Rhinitis occurs in different types: allergic or atopic rhinitis including seasonal and perennial forms. The mechanism of perennial rhinitis with non-allergic triggers is not well understood. It is an allergy-like condition but not triggered by allergens. (Braunstahl et al. Current Opinion in Pulmonary Medicine 2003, 9:46-51). Idiopathic non-allergic rhinitis or vasomotor rhinitis is characterize by nasal congestion and post nasal drip in responses to temperature and humidity changes, smoke, odors, and emotional upsets. In general rhinitis is characterized by a symptoms complex that consists of any combination of the following: sneezing, nasal congestion, nasal itching and irritation, sneezing and watery rhinorrhea, frequently accompanied by nasal congestion. Perennial allergic rhinitis clinical symptoms are similar, except that nasal blockage may be more pronounced. Each type of allergic rhinitis may cause additional symptoms such as itching of the throat and/or eyes, excessive tearing, and edema around the eyes. These symptoms may vary in intensity from the nuisance level to debilitating. Other types of rhinitis present the same symptoms (Kim et al. Current Opinions in Otolaryngology & Head and Neck Surgery 2007, 15: 268-273).

Rho-kinase (ROCK) regulates endothelial permeability by reorganization of the actin-based cytoskeleton and contraction of endothelial cells, resulting in the formation of an intercellular gap, (Walsh et. al. Gastroenterology 2001. 121 (3): 566-579) Rho-kinase (ROCK) regulates also regulates epithelial permeability by reorganization of the actin-based cytoskeleton and contraction of epithelial cells (Sawafuji et al, Am J Physiol Lung Cell Mol Physiol 289: L946-L953).

Rhinosinusitis

Rhinosinusitis, an inflammation of the sinus cavity, is the most commonly diagnosed chronic illness in the United States. The name of the disease "rhinosinusitis" is preferred over sinusitis as the inflammation of the sinuses rarely occurs without inflammation of the nasal mucosal at the same time. The disease affects over thirty million people in the United States alone. The treatments for rhinosinusitis are costly, exceeding $200 million per year. This illness is detrimental to both the overall quality of life and economic welfare of sufferers. Currently there is no universally accepted treatment for rhinosinusitis; therefore a need to identify new molecular pathways targeting the disease exists.

Sinusitis is the inflammation of the mucus membranes involving the paranasal sinuses, nasal cavity, and underlying bone. A leading theory suggests that exposure to allergens induces inflammation in the small channels of the ostiomeatal complex (OMC), which results in mucosal edema and ultimately impaired mucociliary clearance of the sinus ostia leading to blockage. As a result the trapped mucus becomes a breeding ground for bacteria and other microorganisms which can lead to infection. Common symptoms include pain varying from forehead to teeth, cheeks, ears, and neck, nasal drainage or postnasal drip and decreased sense of smell (Metson, R. et al. Chronic rhinosinusitis, In: UpToDate, Calderwood, S B (Ed), UpToDate, Wellesley, Mass., 2008).

Depending upon the durations of symptoms, rhinosinusitis may be classified as acute, sub acute, or chronic. Chronic sinusitis has long-term effects that could last over twelve weeks and accounts for >90% of all cases of rhinosinusitis The effects of chronic rhinosinusitis are debilitating even when compared to other chronic illnesses such as heart failure or pulmonary disease because it has potential to cause physical and physiological impairment (Metson, R. et al. Chronic rhinosinusitis, In: UpToDate, Calderwood, S B (Ed), UpToDate, Wellesley, Mass., 2008).

Other Respiratory Diseases Characterized by Airway Inflammation, Lung Tissue Edema, Bronchoconstriction and/or Airway Hyperreactivity Primary ciliary diskinesia (PCD), pneumonia, and bronchiolitis caused by agents other than RSV are respiratory disorders with medical need unmet by existing treatments and at least one of the following pathophysiologies accompanying these diseases: increased airway inflammation, lung tissue edema and/or bronchoconstriction or airway hyperreactivity. Pneumonia is a cause of significant morbidity and/or mortality in developed and developing world with World Health Organization estimates of 150.7 million cases worldwide every year. There is a variety of etiologic agents with large portion being viral and bacterial (i.e. *M. pneumoniae* or Influenza A and B). Pneumonia is accompanied by lung inflammation and lung tissue edema. PCD is a rare genetic mutation leading to defect in cilia. The main consequence is decreased ciliary clearance and increased airway inflammation due to recurrent respiratory infections and mucus accumulation in the airway. Bronchiolitis is a common cause of illness and hospitalization in infants and children younger than two years. Bronchiolitis is broadly defined as an illness characterized by wheezing and airways obstruction that is caused by infection with a viral or, less commonly, a bacterial pathogen resulting in inflammation of the small airways/bronchioles. Although respiratory syncytial virus (RSV) is the most common cause, parainfluenza virus, human metapneumovirus, influenza virus, adenovirus, rhinovirus, coronavirus, and human bocavirus are other infectious agents know to cause bronchiolitis.

OB/BOOP due to lung transplantation and HSCT

Obliterative bronchiolitis (OB) is characterised by the onset of new air flow obstruction due to functional obstruction of the bronchioles. OB is a common late noninfectious pulmonary complication following both lung transplantation and allogeneic haematopoietic stem cell transplantation (HSCT) with an incidence of 50-60% in patients who survive for 5 years after lung transplantation and 0-48% following HSCT. OB accounts for more than 30% of all deaths occurring after the third postoperative year for lung transplant patients. The mortality rate in patients with OB following HSCT varies from 14-100%, with a median of 65%. Graft versus host disease is an established risk factor for OB after lung transplantation and HSCT. The histopathologic features of OB suggest that injury and inflammation of epithelial cells and subepithelial structures of small airways lead to excessive fibroproliferation, seemingly due to ineffective epithelial regeneration and aberrant tissue repair. The respiratory symptoms of OB include dry cough, dyspnea, and wheezing. Lung biopsies show small airway involvement with fibrinous obliteration of the lumen. BAL shows neutrophilic and/or lymphocytic inflammation. Despite treatment with corticosteroids and immunosuppression, improvement in lung function is noted in only 8% to 20% of patients with OB. Most patients with OB progress to respiratory failure, and some patients develop bronchiectasis with frequent bacterial exacerbations (Afessa B, *Bone Marrow Transplantation* 28: 524-434, 2001; Nicod L P, *Proc Am Thorac Soc* 3: 444-449, 2006; Estenne M, Am J Respir Crit. Care Med 166: 440-444, 2002).

Bronchiolitis obliterans organizing pneumonia (BOOP) is a complication of both lung transplantation and HSCT and is defined by the patchy distribution of plugs of granulation tissue that fill the lumens of the distal airways, extending into the alveolar ducts and alveolar sacs in association with chronic interstitial inflammation. Organizing pneumonia results from alveolar epithelial injury with subsequent intra-alveolar fibrosis, angiogenesis and inflammation. Clinically, patients present with fever, cough, dyspnea, and crackles on physical examination with onset between 1 and 13 months following HSCT. The clinical spectrum of BOOP ranges from a mild illness to respiratory failure and death. BOOP usually responds well to corticosteroid treatment, however, frequent relapse occurs and new therapeutic options are needed to treat BOOP. (Cordier et al, *Eur Resp J*, 28:422-446, 2006; Freudenberger T D et al. *Blood,* 102:3822-3828, 2003; Travis W D et al. *Am J Respir Crit. Care Med* 165: 277-304, 2002).

The therapeutic options for OB/BOOP include corticosteroids and immunosuppressive agents. However, these treatments are often of limited efficacy and new treatment options are needed to address OB/BOOP following lung transplantation and HSCT.

Non-IPF Idiopathic Interstitial Pneumonia

The idiopathic interstitial pneumonias (IIPs) are a group of interstial lung diseases (ILD, also know as diffuse parenchymal lung disease or DPLD) that result from damage to the lung parenchyma by varying patterns of inflammation and fibrosis. The interstitium includes the space between the epithelial and endothelial basement membranes and it is the primary site of injury in the IIPs. However, these disorders frequently affect not only the interstitium, but also the airspaces, peripheral airways, and vessels along with their respective epithelial and endothelial linings. The IIPs described comprise a number of clinicopathologic entities, which are sufficiently different from one another to be designated as separate disease entities. The idiopathic interstitial pneumonias include the entities of idiopathic pulmonary fibrosis (IPF), nonspecific interstitial pneumonia (NSIP), cryptogenic organizing pneumonia (COP), acute interstitial pneumonia (AIP), respiratory bronchiolitis-associated interstitial lung disease (RB-ILD), desquamative interstitial pneumonia (DIP), and lymphocytic interstitial pneumonia (LIP). Several clinical findings common to the IIPs are exertional dyspnea or cough, bilateral diffuse interstitial infiltrates on chest radiographs, physiological and gas exchange abnormalities including a decreased carbon monoxide diffusion capacity (DLCO) and an abnormal alveolar-arteriolar $PO_2$ difference, and histopathologic abnormalities of the pulmonary parenchyma that are characterized by varying marked inflammation, fibrosis and remodeling (Raghu G et al. *Clin Chest Med* 25:409-419, 2004; Travis W D et al. *Am J Respir Crit. Care Med* 165: 277-304, 2002). The clinical prognosis of these diseases ranges from mild illness to respiratory failure and death. Therapies for the IIPs include corticosteroids and immunosuppressive agents but current treatments are variably effective and new treatment options are needed to treat these diseases.

ILD Other Than IPF, non-IPF IIP, and OB/BOOP

Interstitial Lung Disease (ILD), also known as diffuse parenchymal lung disease (DPLD), represent a variety of disorders that lead to diffuse remodeling, architectural damage to normal lung tissue and inflammation that lead to progressive loss of lung function. In addition to the inflammation and fibrosis that is often seen in the lung parenchyma in ILD, the airways and the vasculature may also be prominently affected. The ILDs can be classified into 7 main groups: iatrogenic or drug-induced; occupational or environmental; granulomatous diseases including pulmonary sarcoidosis collagen-vascular disease; unique entities such as alveolar proteinosis, Langerhans cell granulomatosis, and lymphangioleiomyomatosis; idiopathic interstitial pneumonias including interstitial pulmonary fibrosis (IPF); and inherited disorders such as tuberous sclerosis, neurofibromatosis, metabolic storage disorders and Hermansky-Pudlak syndrome. The most prominent forms of ILD are IPF and pulmonary sarcoidosis. Several clinical findings are common to the ILDs: exertional dyspnea or cough; bilateral diffuse interstitial infiltrates on chest radiographs; physiological and gas exchange abnormalities including a decreased carbon monoxide diffusion capacity (DLCO) and an abnormal alveolar-arteriolar $PO_2$ difference; and histopathologic abnormalities of the pulmonary parenchyma that are characterized by varying degrees of inflammation, fibrosis and remodeling. The incidence of ILD is estimated to be 31.5 per 100,000/yr in males and 26.1 per 100,000/yr in females and the clinical prognosis of these diseases range from mild illness to respiratory failure and death (Raghu G et al, *Clin Chest Med* 25:409-419, 2004). The standard therapies for ILD include corticosteroids and immunosuppressive agents but current treatments are variably effective depending on the specific disease entity being treated and new treatment options that suppress inflammation and prevent fibroblast and myofibroblast proliferation are needed to treat these diseases (Kim et al. *Ther Adv Respir Dis* 2:319-338, 2008).

There is a need for an effective or improved method for treating asthma, COPD, respiratory tract illness caused by respiratory syncytial virus infection, PAH, LAM, idiopathic pulmonary fibrosis, ARDS and VILI, CF, bronchiectasis, AATD, rhinitis, rhinosinusitis, PCD, pneumonia, bronchiolitis caused by agents other than RSV, OB/BOOP due to lung transplantation or HSCT, non-IPF IIP and ILD other than IPF, non-IPF IIPs and OB/BOOP.

SUMMARY OF THE INVENTION

The present invention is directed to methods of preventing or treating diseases or conditions of the lung associated with excessive cell proliferation, remodeling, inflammation, vasoconstriction, bronchoconstriction, airway hyperreactivity and edema. Particularly, this invention is directed to methods of treating pulmonary diseases such as asthma; chronic obstructive pulmonary disease; respiratory tract illness caused by respiratory syncytial virus; pulmonary arterial hypertension; acute respiratory distress syndrome and ventilator induced lung injury; cystic fibrosis; bronchiectasis; alpha-1-antitrypsin deficiency; rhinitis; rhinosinusitis; primary ciliary dyskinesia; pneumonia; bronchiolitis caused by agents other than respiratory syncytial virus; and interstitial lung disease including lymphangioleiomyomatosis; idiopathic pulmonary fibrosis; obliterative bronchiolitis or bronchiolitis obliterans organizing pneumonia due to lung transplantation or HSCT; nonspecific interstitial pneumonia; cryptogenic organizing pneumonia; acute interstitial pneumonia; respiratory bronchiolitis-associated interstitial lung disease; or pulmonary sarcoidosis. The method comprises administering to a subject an effective amount of a rho kinase inhibitor compound to treat the disease.

The method comprises identifying a subject in need of the treatment, and administering to the subject an effective amount of a novel rho kinase inhibitor compound of Formula I or Formula II to treat the disease.

The active compound is delivered to a subject either by systemic administration or local administration.

DETAILED DESCRIPTION OF THE INVENTION

Definitions

Figure 1A:
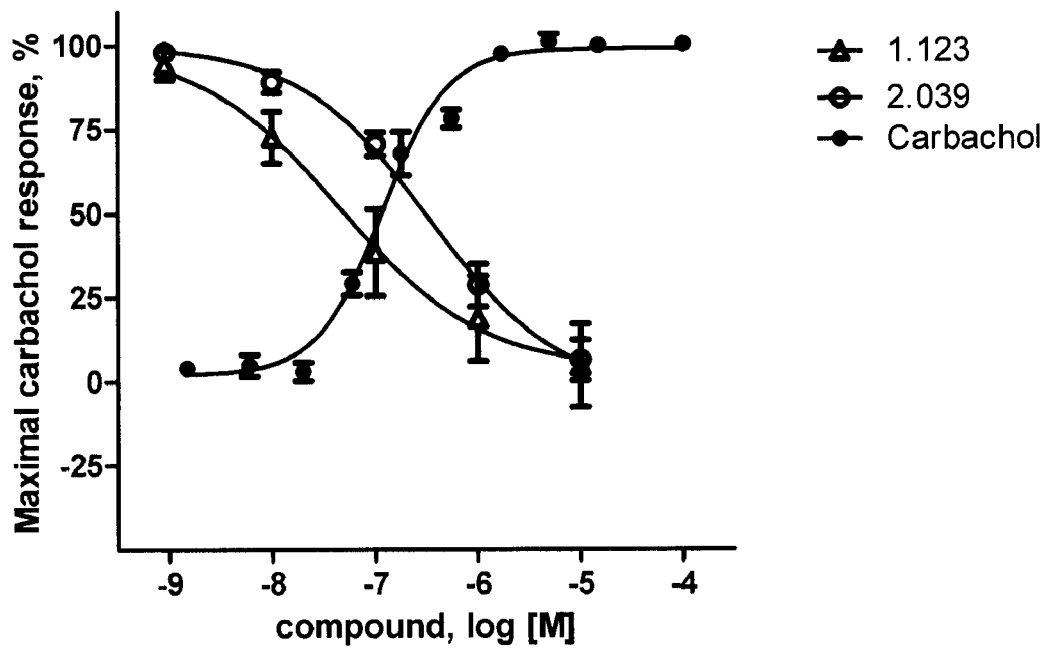
FIG. 1A shows the dose response curves for representative compounds, 1.123 and 2.039, to induce relaxation in 1 μM carbachol precontracted rings. Data are reported as a percent of the maximal carbachol response and are mean±SEM of at least 4 replicates.
Figure 1B:
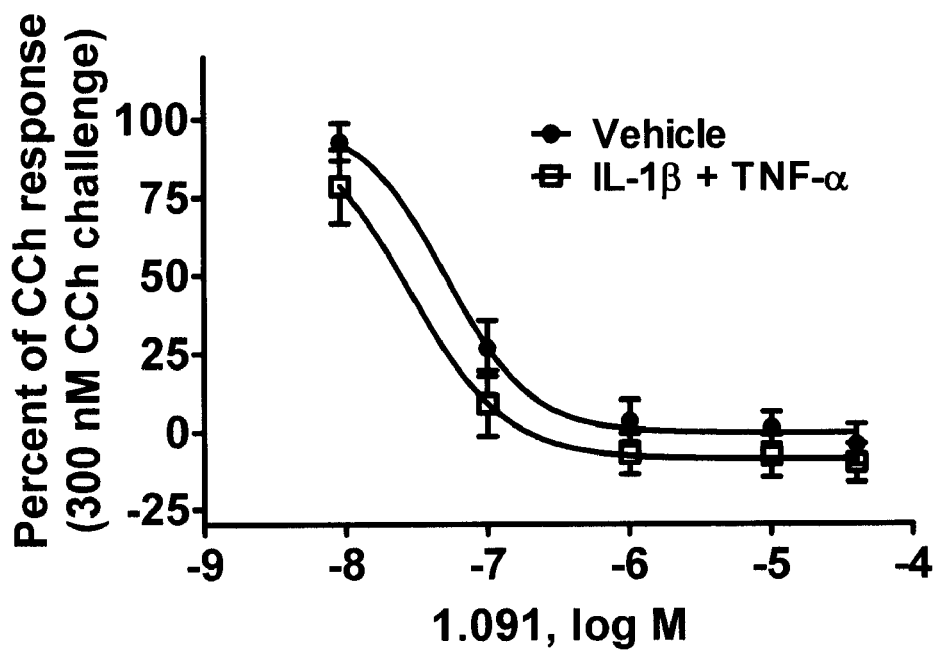
FIG. 1B shows the dose response curve for the representative compound, 1.091, to induce relaxation in rat tracheal rings pretreated with either vehicle alone or the inflammatory cytokines, IL-1β and TNF-α. Data are reported as a percent of the maximal carbachol (300 nM carbachol) response.

When present, unless otherwise specified, the following terms are generally defined as, but are not limited to, the following:

Halo substituents are taken from fluorine, chlorine, bromine, and iodine.

"Alkyl" refers to groups of from 1 to 12 carbon atoms inclusively, either straight chained or branched, more preferably from 1 to 8 carbon atoms inclusively, and most preferably 1 to 6 carbon atoms inclusively.

"Alkenyl" refers to groups of from 2 to 12 carbon atoms inclusively, either straight or branched containing at least one double bond but optionally containing more than one double bond.

"Alkynyl" refers to groups of from 2 to 12 carbon atoms inclusively, either straight or branched containing at least one triple bond but optionally containing more than one triple bond, and additionally optionally containing one or more double bonded moieties.

"Alkoxy" refers to the group alkyl-O— wherein the alkyl group is as defined above including optionally substituted alkyl groups as also defined above.

"Alkenoxy" refers to the group alkenyl-O— wherein the alkenyl group is as defined above including optionally substituted alkenyl groups as also defined above.

"Alkynoxy" refers to the group alkynyl-O— wherein the alkynyl group is as defined above including optionally substituted alkynyl groups as also defined above.

"Aryl" refers to an unsaturated aromatic carbocyclic group of from 6 to 14 carbon atoms inclusively having a single ring (e.g., phenyl) or multiple condensed rings (e.g., naphthyl or anthryl). Preferred aryls include phenyl, naphthyl and the like.

"Arylalkyl" refers to aryl-alkyl-groups preferably having from 1 to 6 carbon atoms inclusively in the alkyl moiety and from 6 to 10 carbon atoms inclusively in the aryl moiety. Such arylalkyl groups are exemplified by benzyl, phenethyl and the like.

"Arylalkenyl" refers to aryl-alkenyl-groups preferably having from 2 to 6 carbon atoms in the alkenyl moiety and from 6 to 10 carbon atoms inclusively in the aryl moiety.

"Arylalkynyl" refers to aryl-alkynyl-groups preferably having from 2 to 6 carbon atoms inclusively in the alkynyl moiety and from 6 to 10 carbon atoms inclusively in the aryl moiety.

"Cycloalkyl" refers to cyclic alkyl groups of from 3 to 12 carbon atoms inclusively having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Cycloalkenyl" refers to cyclic alkenyl groups of from 4 to 12 carbon atoms inclusively having a single cyclic ring or multiple condensed rings and at least one point of internal unsaturation, which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Cycloalkylalkyl" refers to cycloalkyl-alkyl-groups preferably having from 1 to 6 carbon atoms inclusively in the alkyl moiety and from 6 to 10 carbon atoms inclusively in the cycloalkyl moiety. Such cycloalkylalkyl groups are exemplified by cyclopropylmethyl, cyclohexylethyl and the like.

"Cycloalkylalkenyl" refers to cycloalkyl-alkenyl-groups preferably having from 2 to 6 carbon atoms inclusively in the alkenyl moiety and from 6 to 10 carbon atoms inclusively in the cycloalkyl moiety. Such cycloalkylalkenyl groups are exemplified by cyclohexylethenyl and the like.

"Cycloalkylalkynyl" refers to cycloalkyl-alkynyl-groups preferably having from 2 to 6 carbon atoms inclusively in the alkynyl moiety and from 6 to 10 carbon atoms inclusively in the cycloalkyl moiety. Such cycloalkylalkynyl groups are exemplified by cyclopropylethynyl and the like.

"Heteroaryl" refers to a monovalent aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to heteroaryl-alkyl-groups preferably having from 1 to 6 carbon atoms inclusively in the alkyl moiety and from 6 to 10 atoms inclusively in the heteroaryl moiety. Such heteroarylalkyl groups are exemplified by pyridylmethyl and the like.

"Heteroarylalkenyl" refers to heteroaryl-alkenyl-groups preferably having from 2 to 6 carbon atoms inclusively in the alkenyl moiety and from 6 to 10 atoms inclusively in the heteroaryl moiety.

"Heteroarylalkynyl" refers to heteroaryl-alkynyl-groups preferably having from 2 to 6 carbon atoms inclusively in the alkynyl moiety and from 6 to 10 atoms inclusively in the heteroaryl moiety.

"Heterocycle" refers to a saturated or unsaturated group having a single ring or multiple condensed rings, from 1 to 8 carbon atoms inclusively and from 1 to 4 hetero atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Preferred heterocycles include piperidinyl, pyrrolidinyl and tetrahydrofuryl.

"Heterocycle-alkyl" refers to heterocycle-alkyl-groups preferably having from 1 to 6 carbon atoms inclusively in the alkyl moiety and from 6 to 10 atoms inclusively in the heterocycle moiety. Such heterocycle-alkyl groups are exemplified by morpholino-ethyl, pyrrolidinylmethyl, and the like.

"Heterocycle-alkenyl" refers to heterocycle-alkenyl-groups preferably having from 2 to 6 carbon atoms inclusively in the alkenyl moiety and from 6 to 10 atoms inclusively in the heterocycle moiety.

"Heterocycle-alkynyl" refers to heterocycle-alkynyl-groups preferably having from 2 to 6 carbon atoms inclusively in the alkynyl moiety and from 6 to 10 atoms inclusively in the heterocycle moiety.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above subtitutions can be made provided that replacing the hydrogen with the substituent does not introduce unacceptable instability to the molecules of the present invention, and is otherwise chemically reasonable.

The term "heteroatom-containing substituent" refers to substituents containing at least one non-halogen heteroatom. Examples of such substituents include, but are not limited to, hydroxy, oxo, nitro, methoxy, ethoxy, alkoxy, substituted alkoxy, trifluoromethoxy, haloalkoxy, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, aryloxy, pyridyl, imidazolyl, heteroaryl, substituted heteroaryl, heteroaryloxy, heteroarylalkyl, heteroarylalkenyl, heteroarylalkynyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above subtitutions can be made provided that replacing the hydrogen with the substituent does not introduce unacceptable instability to the molecules of the present invention, and is otherwise chemically reasonable.

"Pharmaceutically acceptable salts" are salts that retain the desired biological activity of the parent compound and do not impart undesired toxicological effects. Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, naphthoic, oxalic, succinic, maleic, fumaric, malic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$).

"Tautomers" are compounds that can exist in one or more forms, called tautomeric forms, which can interconvert by way of a migration of one or more hydrogen atoms in the compound accompanied by a rearrangement in the position of adjacent double bonds. These tautomeric forms are in equilibrium with each other, and the position of this equilibrium will depend on the exact nature of the physical state of the compound. It is understood that where tautomeric forms are possible, the current invention relates to all possible tautomeric forms.

"Solvates" are addition complexes in which a compound of Formula I or Formula II is combined with a pharmaceutically acceptable cosolvent in some fixed proportion. Cosolvents include, but are not limited to, water, methanol, ethanol, 1-propanol, isopropanol, 1-butanol, isobutanol, tert-butanol, acetone, methyl ethyl ketone, acetonitrile, ethyl acetate, benzene, toluene, xylene(s), ethylene glycol, dichloromethane, 1,2-dichloroethane, N-methylformamide, N,N-dimethylformamide, N-methylacetamide, pyridine, dioxane, and diethyl ether. Hydrates are solvates in which the cosolvent is water. It is to be understood that the definitions of compounds in Formula I and Formula II encompass all possible hydrates and solvates, in any proportion, which possess the stated activity.

The term "edema" refers to an abnormal accumulation of extra-vascular fluid. Of particular relevance here is "pulmonary edema" which refers specifically to fluid accumulation within the lung interstitium or the lumen of the lung. Pulmonary edema is associated with a variety of systemic or lung diseases including respiratory syncytial virus infection (RSV), human metapneumovirus, pneumonia, influenza, ventilator induced lung injury (VILI), acute respiratory distress syndrome (ARDS), acute lung injury (ALI), and chronic obstructive pulmonary disease (COPD) such as chronic bronchitis and emphysema.

"Inflammation" generally refers to a localized reaction of tissue, characterized by the influx of immune cells, which occurs in reaction to injury or infection. Specifically, "pulmonary inflammation" is characterized by migration of inflammatory cells into the interstitium and the lumen of the lung, release of pro-inflammatory cytokines and chemokines, lung tissue remodeling and lung tissue apoptosis or necrosis. Pulmonary inflammation accompanies a variety of systemic or lung diseases including those noted in the aforementioned pulmonary edema definition.

"An effective amount" is the amount effective to treat a disease by ameliorating the pathological condition or reducing the symptoms of the disease. "An effective amount" is the amount effective to improve at least one of the parameters relevant to measurement of the disease.

The inventors of the present invention have discovered that compounds of Formula I or II, which are Rho kinase inhibitors, are effective in treating lung diseases in that they are effective in reducing cell proliferation, decreasing remodeling that is defined by cell migration and/or proliferation, reducing inflammation via the inhibition of leukocytes chemotaxis and the inhibition of cytokine and chemokine secretion, lowering or preventing tissue or organ edema via the increase of endothelial cell junction integrity, reducing vasoconstriction, bronchoconstriction and airway hyperreactivity via the disruption of acto-myosin-based cytoskeleton within smooth muscle cells, thereby reducing smooth muscle tone and contractibility, and preventing airway hyperreactivity by reducing the inflammatory response. Furthermore, the inventors of the present invention have discovered that compounds of Formula I or II, which are Rho kinase inhibitors, are effective in reducing bronchoconstriction, reducing inflammation and preventing airway hyperreactivity upon either systemic administration or upon local administration to the lung with limited systemic exposure. By having the above properties, compounds of Formula I or II are useful in a method of preventing or treating diseases or conditions of the lung associated with excessive cell proliferation, remodeling, inflammation, vasoconstriction, bronchoconstriction, airway hyperreactivity and edema.

The invention provides a method of reducing excessive cell proliferation, a method of decreasing remodeling that is defined by cell migration and/or proliferation, a method of reducing inflammation via inhibition of leukocytes chemotaxis and via decreasing cytokine and chemokine secretion, a method of lowering or preventing tissue or organ edema via increasing endothelial and epithelial cell junction integrity, a method of reducing vasoconstriction, bronchoconstriction and airway hyperreactivity via disruption of acto-myosin-based cytoskeleton within smooth muscle cells and thus reducing smooth muscle tone and contractibility, and a method of preventing airway hyperreactivity by reducing the inflammatory response. By resolving one or more of the above-described pathophysiologies, the present invention provides a method of treating pulmonary diseases, particularly asthma, COPD, respiratory tract illness caused by respiratory syncytial virus infection such as RSV-induced wheezing and hyperreactivity or bronchiolitis, PAH, LAM, idiopathic pulmonary fibrosis, ARDS and VILI, CF, bronchiectasis, AATD, rhinitis, rhinosinusitis, PCD, pneumonia, bronchiolitis caused by agents other than RSV, OB/BOOP due to lung transplantation or HSCT, non-IPF IIP and ILD other than IPF, non-IPF IIPs and OB/BOOP.

The present method comprises the steps of identifying a subject in need of treatment for the above conditions, and administering to the subject an effective amount of rho kinase inhibitor compound of Formula I or II.

Rho Kinase Inhibitor Compounds

The rho kinase inhibitor compounds useful for this invention include compounds of general Formula I and Formula II, and/or tautomers thereof, and/or pharmaceutically-acceptable salts, and/or solvates, and/or hydrates thereof. Compounds of general Formula I and Formula II can be prepared according to the methods disclosed in co-pending application US2008/0214614, which is incorporated herein by reference.

A compound according to Formula I or Formula II can exist in several diastereomeric forms. The general structures of Formula I and Formula II include all diastereomeric forms of such materials, when not specified otherwise. Formula I and Formula II also include mixtures of compounds of these Formulae, including mixtures of enantiomers, diastereomers and/or other isomers in any proportion.

A. Formula I

Compounds of Formula I are as Follows:

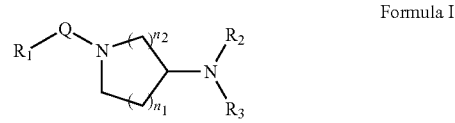

Formula I wherein: $R_1$ is aryl or heteroaryl, optionally substituted;
Q is C=O, $SO_2$, or $(CR_4R_5)_{n3}$;
$n_1$ is 1, 2, or 3;
$n_2$ is 1 or 2;
$n_3$ is 0, 1, 2, or 3;
wherein the ring represented by is optionally substituted by alkyl, halo, oxo, $OR_6$, $NR_6R_7$, or $SR_6$;
$R_2$ is selected from the following heteroaryl systems, optionally substituted:

$R_2$-1

$R_2$-2

$R_2$-3

$R_2$-4

$R_2$-5

$R_3$-$R_7$ are independently H, alkyl, alkenyl, alkynyl, cycloalkyl, cycloalkenyl, cycloalkylalkyl, cycloalkylalkenyl, or cycloalkylalkynyl optionally substituted.

In Formula I, a preferred $R_1$ is substituted aryl, a more preferred $R_1$ is substituted phenyl, the preferred Q is $(CR_4R_5)_{n3}$, the more preferred Q is $CH_2$, the preferred $n_1$ is 1 or 2, the preferred $n_2$ is 1, the preferred $n_3$ is 1 or 2, and the preferred $R_3$-$R_7$ are H.

In Formula I, a preferred $R_2$ substituent is halo, alkyl, cycloalkyl, hydroxyl, alkoxy, cycloalkyloxy, amino, alkylamino, or $R_2$ is unsubstituted. A more preferred $R_2$ substituent is halo, methyl, ethyl, isopropyl, cyclopropyl, hydroxyl, methoxy, ethoxy, amino, methylamino, dimethylamino, or $R_2$ is unsubstituted.

[1] One embodiment of the invention is represented by Formula I, in which $R_2$ is 5-indazolyl or 6-indazolyl ($R_2$-1), optionally substituted.

[1a] In embodiment 1, $R_2$-1 is substituted by one or more alkyl or halo substituents.

[1b] In embodiment 1, $R_2$-1 is substituted by one or more amino, alkylamino, hydroxyl, or alkoxy substituents.

[1c] In embodiment 1, $R_2$-1 is unsubstituted.

[2] In another embodiment, the invention is represented by Formula I in which $R_2$ is 5-isoquinolinyl or 6-isoquinolinyl ($R_2$-2), optionally substituted.

[2a] In embodiment 2, $R_2$-2 is substituted by one or more alkyl or halo substituents.

[2b] In embodiment 2, $R_2$-2 is substituted by one or more amino, alkylamino, hydroxyl, or alkoxy substituents.

[2c] In embodiment 2, $R_2$-2 is unsubstituted.

[3] In another embodiment, the invention is represented by Formula I in which $R_2$ is 4-pyridyl or 3-pyridyl ($R_2$-3), optionally substituted.

[3a] In embodiment 3, $R_2$-3 is substituted by one or more alkyl or halo substituents.

[3b] In embodiment 3, $R_2$-3 is substituted by one or more amino, alkylamino, hydroxyl, or alkoxy substituents.

[3c] In embodiment 3, $R_2$-3 is unsubstituted.

[4] In another embodiment, the invention is represented by Formula I in which $R_2$ is 7-azaindol-4-yl or 7-azaindol-5-yl ($R_2$-4), optionally substituted.

[4a] In embodiment 4, $R_2$-4 is substituted by one or more alkyl or halo substituents.

[4b] In embodiment 4, $R_2$-4 is substituted by one or more amino, alkylamino, hydroxyl, or alkoxy substituents.

[4c] In embodiment 4, $R_2$-4 is unsubstituted.

[5] In another embodiment, the invention is represented by Formula I in which $R_2$ is 4-(3-amino-1,2,5-oxadiazol-4-yl)phenyl or 3-(3-amino-1,2,5-oxadiazol-4-yl)phenyl ($R_2$-5), optionally substituted.

[5a] In embodiment 5, $R_2$-5 is unsubstituted.

[6] In another embodiment, the invention is represented by Formula I in which $R_2$ is one of the groups $R_2$-1-$R_2$-5, substituted by one or more alkyl, halo, amino, alkylamino, hydroxyl, or alkoxy substituents.

[6a] In embodiment 6, $R_2$ is substituted by one or more alkyl or halo substituents.

[6b] In embodiment 6, $R_2$ is substituted by one or more amino, alkylamino, hydroxyl, or alkoxy substituents.

[7] In another embodiment, the invention is represented by Formula I in which $R_2$ is one of the groups $R_2$-1-$R_2$-5, and is unsubstituted.

[8] In another embodiment, the invention is represented by Formula I in which $R_3$ is H.

[9] In another embodiment, the invention is represented by Formula I in which Q is $(CR_4R_5)_{n3}$, and $n_3$ is 1 or 2.

[10] In another embodiment, the invention is represented by Formula I in which Q is $(CH_2)_{n3}$, and $n_3$ is 1.

[11] In another embodiment, the invention is represented by Formula I in which $R_1$ is aryl or heteroaryl substituted with one or more alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, optionally further substituted.

Compounds exemplifying embodiment 11 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table A.

[12] In another embodiment, the invention is represented by Formula I in which $R_1$ is aryl or heteroaryl substituted with one or more heteroatom-containing substituents, with the proviso that if the $R_1$ substituent is acyclic and is connected to $R_1$ by a carbon atom, then this substituent contains at least one nitrogen or sulfur atom, with the second proviso that if the substituent is acyclic and is connected to $R_1$ by an oxygen or nitrogen atom, then this substituent contains at least one additional oxygen, nitrogen or sulfur atom, and with the third proviso that if the substituent is connected to $R_1$ by a sulfone linkage "—$SO_2$—", then $R_2$ is not nitrogen- or oxygen-substituted $R_2$-2.

[12a] In embodiment 12, the heteroatom-containing substituent is connected to $R_1$ by an oxygen or nitrogen atom.

[12b] In embodiment 12, the heteroatom-containing substituent is connected to $R_1$ by a sulfide linkage, "—S—".

Compounds exemplifying embodiment 12 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table A.

[13] In another embodiment, the invention is represented by Formula I in which $R_1$ is aryl or heteroaryl substituted with one or more alkyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, which are further substituted with one or more heteroatom-containing substituents, with the proviso that if the $R_1$ substituent is acyclic and its heteroatom-containing substituent falls on the carbon by which it is attached to $R_1$, then the heteroatom-containing substituent contains at least one nitrogen or sulfur atom.

Compounds exemplifying embodiment 13 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, 1.122, and 1.123, shown below in Table A.

[14] In another embodiment, the invention is represented by Formula I in which $R_1$ is aryl or heteroaryl substituted with one or more alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, optionally further substituted, and $R_2$ is 5-indazolyl ($R_2$-1) or 5-isoquinolinyl ($R_2$-2), optionally substituted.

[14a] In embodiment 14, $R_2$ is 5-indazolyl ($R_2$-1), optionally substituted by one or more alkyl, halo, amino, alkylamino, hydroxyl, or alkoxy substituents.

[14b] In embodiment 14, $R_2$ is 5-isoquinolinyl ($R_2$-2), optionally substituted by one or more alkyl, halo, amino, alkylamino, hydroxyl, or alkoxy substituents.

[14c] In embodiment 14, $R_2$ is unsubstituted.

Compounds exemplifying embodiment 14 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table A.

[15] In another embodiment, the invention is represented by Formula I in which $R_1$ is aryl or heteroaryl substituted with one or more heteroatom-containing substituents, and $R_2$ is 5-indazolyl ($R_2$-1) or 5-isoquinolinyl ($R_2$-2), optionally substituted, with the proviso that if the $R_1$ substituent is acyclic and is connected to $R_1$ by a carbon atom, then this substituent contains at least one nitrogen or sulfur atom, with the second proviso that if the substituent is acyclic and is connected to $R_1$ by an oxygen or nitrogen atom, then this substituent contains at least one additional oxygen, nitrogen or sulfur atom, and with the third proviso that if the substituent is connected to $R_1$ by a sulfone linkage "—$SO_2$—", then $R_2$ is not nitrogen- or oxygen-substituted $R_2$-2.

[15a] In embodiment 15, $R_2$ is 5-indazolyl ($R_2$-1), optionally substituted by one or more alkyl, halo, amino, alkylamino, hydroxyl, or alkoxy substituents.

[15b] In embodiment 15, $R_2$ is 5-isoquinolinyl ($R_2$-2), optionally substituted by one or more alkyl, halo, amino, alkylamino, hydroxyl, or alkoxy substituents.

[15c] In embodiment 15, $R_2$ is unsubstituted.

[15d] In embodiment 15, the heteroatom-containing substituent is connected to $R_1$ by an oxygen or nitrogen atom.

[15e] In embodiment 15, the heteroatom-containing substituent is connected to $R_1$ by a sulfide linkage, "—S—".

Compounds exemplifying embodiment 15 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table A.

[16] In another embodiment, the invention is represented by Formula I in which $R_1$ is aryl or heteroaryl substituted with one or more alkyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, at least one of which is further substituted with one or more heteroatom-containing substituents, and $R_2$ is 5-indazolyl ($R_2$-1) or 5-isoquinolinyl ($R_2$-2), optionally substituted, with the proviso that if the $R_1$ substituent is acyclic and its heteroatom-containing substituent falls on the carbon by which it is attached to $R_1$, then the heteroatom-containing substituent contains at least one nitrogen or sulfur atom.

[16a] In embodiment 16, $R_2$ is 5-indazolyl ($R_2$-1), optionally substituted by one or more alkyl, halo, amino, alkylamino, hydroxyl, or alkoxy substituents.

[16b] In embodiment 16, $R_2$ is 5-isoquinolinyl ($R_2$-2), optionally substituted by one or more alkyl, halo, amino, alkylamino, hydroxyl, or alkoxy substituents.

[16c] In embodiment 16, $R_2$ is unsubstituted.

Compounds exemplifying embodiment 16 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, 1.122, and 1.123, shown below in Table A.

The inventors have discovered certain compounds of Formula I that have properties that render them particularly useful for treating the conditions addressed by the invention. In particular, these preferred compounds can be described as compounds of Formula I in which $R_2$, $R_3$, $n_1$, and $n_2$ are limited to the combinations shown in Formulae Ia, Ib, and Ic:

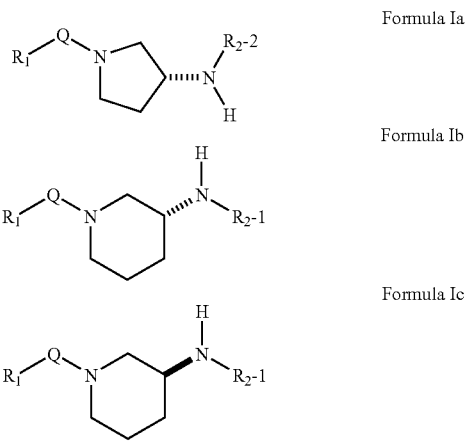

Formula Ia

Formula Ib

Formula Ic

In Formulae Ia, Ib, and Ic, the stereochemistry of the central pyrrolidine or piperidine ring is limited to the R, R, and S configurations respectively, as drawn. Further, the group $R_1$ in these Formulae is limited to phenyl, thiophene, and 6,5- or 6,6-fused bicyclic heteroaryl rings. The group $R_1$ is either unsubstituted or is optionally substituted with 1, 2 or 3 substituents independently selected from halogen, methyl, ethyl, hydroxyl, methoxy, or ethoxy.

In Formula Ia, Ib, and Ic, Q is C=O, $SO_2$, or $(CR_4R_5)_{n3}$; where $R_4$ and $R_5$ are independently H, alkyl, cycloalkyl, optionally substituted. The preferred $R_4$ and $R_5$ are H or unsubstituted alkyl. The preferred Q is $CH_2$.

In Formula Ia, Ib, and Ic, a preferred $R_2$ substituent is halo, alkyl, cycloalkyl, hydroxyl, alkoxy, cycloalkyloxy, amino, alkylamino, or $R_2$ is unsubstituted. A more preferred $R_2$ substituent is halo, methyl, ethyl, isopropyl, cyclopropyl, hydroxyl, methoxy, ethoxy, amino, methylamino, dimethylamino, or $R_2$ is unsubstituted.

In a more preferred form of Formulae Ia, Ib, and Ic, $R_1$ is phenyl or a 6,5-fused bicyclic heteroaryl ring, optionally substituted by 1 or 2 substituents, Q is $CH_2$, and the group $R_2$ is unsubstituted. The most preferred 6,5-fused bicyclic heteroaryl rings are benzofuran, benzothiophene, indole, and benzimidazole.

In another more preferred form, $R_1$ of Formulae Ia, Ib, and Ic is mono- or disubstituted when $R_1$ is phenyl, with 3-substituted, 4-substituted, 2,3-disubstituted, and 3,4-disubstituted being most preferred. When $R_1$ is bicyclic heteroaryl, an unsubstituted or monosubstituted $R_1$ is most preferred.

The inventors have found that certain members of Formulae Ia, Ib, and Ic, as defined above, are particularly useful in treating the conditions addressed in this invention. The compounds of the invention are multikinase inhibitors, with inhibitory activity against ROCK1 and ROCK2, in addition to several other kinases in individual compound cases. These kinase inhibitory properties endow the compounds of the invention not only with smooth muscle relaxant properties, but additionally with antiproliferative, antichemotactic, and cytokine secretion inhibitory properties that render them particularly useful in treating conditions with proliferative or inflammatory components as described in the invention.

[17] In particular, we have found that compounds in which $R_2$ is $R_2$-2 are particularly potent inhibitors of both ROCK1 and ROCK2, and that these agents inhibit the migration of neutrophils toward multiple chemotactic stimuli and inhibit the secretion of the cytokines IL-1β, TNF-α and IL-9 from LPS-stimulated human monocytes. Compounds in which $R_1$ is heteroaryl, particularly 6,5-fused bicyclic heteroaryl, are especially preferred. These compounds are of particular value in addressing conditions with an inflammatory component.

Compounds exemplifying embodiment 17 include compounds 2.025, 2.027, 2.046, 2.047, 2.048, 2.055, 2.056, 2.057, 2.061, 2.062, 2.065, 2.074, 2.075, 2.088, and 2.090.

[18] In another embodiment, we have found that compounds of Formula Ic are potent and selective inhibitors of ROCK2, with comparatively lower inhibitory potency against ROCK1. We have demonstrated that compounds of this class typically show good smooth muscle relaxation properties and that smooth muscle relaxation effects in this class are generally correlated with ROCK2 potency. Compounds in which $R_1$ is phenyl are particularly preferred. Compounds of this embodiment are of particular value in addressing conditions where relaxation of smooth muscle, in particular vascular and bronchial smooth muscle, is of highest importance.

Compounds exemplifying embodiment 18 include compounds 1.072, 1.078, 1.079, 1.080, 1.141, 1.142, 1.148, 1.149, 1.150, 1.151, 1.154, 1.155, 1.156, 1.163, 1.164, 1.166, 1.170, 1.171, 1.175, 1.179, 1.183, 1.227, 1.277, and 1.278.

[19] In another embodiment, the inventors have found that compounds of Formula Ib are potent mixed inhibitors of ROCK1 and ROCK2, display additional inhibitory activity against the kinases Akt3 and p70S6K, and that these compounds generally display potent antiproliferative activity in models of smooth muscle cell proliferation. Compounds of this class are of particular value in addressing conditions in which an antiproliferative component is desired in combination with a smooth muscle relaxing effect.

Compounds exemplifying embodiment 19 include compounds 1.073, 1.110, 1.131, 1.132, 1.133, 1.134, 1.135, 1.136, 1.137, 1.138, 1.143, 1.144, 1.145, 1.146, 1.172, 1.173, 1.177, 1.191, 1.192, 1.203, 1.210, 1.226, 1.241, 1.242, 1.245, 1.246, 1.252, and 1.254.

[20] In another embodiment, the inventors have found that certain compounds of Formulae Ia, Ib, and Ic distribute preferentially to the lung on oral dosing. In particular, compounds in which $R_1$ is a lipophilic bicyclic heteroaryl group are preferred for this dosing behavior. Compounds of this type are especially useful for treating diseases of the lung by oral dosing while minimizing impact on other tissues.

Compounds exemplifying embodiment 20 include compounds 1.131, 1.137, 1.138, 1.143, 1.148, 1.149, 1.150, 1.166, 1.175, 1.177, 1.246, 1.252, 2.055, 2.056, 2.057, 2.065, 2.074, and 2.075.

[21] In another embodiment, the inventors have found that certain compounds of Formulae Ia, Ib, and Ic produce low plasma concentrations of the compound when dosed by the oral route. Compounds in which one substituent on $R_1$ is selected from the group methyl, ethyl, or hydroxyl are preferred for typically exhibiting this pharmacokinetic behavior. Compounds displaying this property are particularly useful for inhalation dosing, since a large portion of the material dosed in this way is typically swallowed, and it is advantageous for this swallowed portion to remain unabsorbed or to be cleared rapidly so as to minimize the impact of the compound on other tissues.

Compounds exemplifying embodiment 21 include compounds 1.078, 1.133, 1.135, 1.136, 1.145, 1.151, 1.154, 1.155, 1.156, 1.163, 1.171, 1.172, 1.173, 1.192, 1.242, 2.025, and 2.061.

Preparation of compounds of Formulae Ia, Ib, and Ic can be problematic using methods commonly known in the art. In particular, syntheses of compounds of Formulae Ib and Ic using transition metal mediated coupling reactions to form the critical bond between $R_2$-1 and the nitrogen atom are hampered by low yields when the indazole ring is not protected properly to allow a successful reaction. Specifically, the methods disclosed in UA2006/0167043 fail to provide the desired amino indazole products when the indazole is unprotected or is protected with a standard acyl protecting group such as pivalate or alkoxycarbonyl protecting groups. The inventors prepare compounds of Formulae Ia, Ib, and Ic according to the methods disclosed in the co-pending application US2008/0214614, which allows the successful protection, coupling, and deprotection of the indazole ring, thereby allowing the successful preparation of the compounds of Formulae Ib and Ic and the demonstration of their useful biological properties.

B. Formula II

A preferred compound of Formula I is where $R_1$=Ar—X, shown below as Formula II:

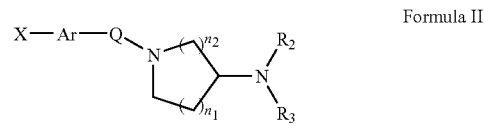

Formula II wherein:

Ar is a monocyclic or bicyclic aryl or heteroaryl ring, such as phenyl;

X is from 1 to 3 substituents on Ar, each independently in the form Y-Z, in which Z is attached to Ar;

Y is one or more substituents on Z, and each is chosen independently from H, halogen, or the heteroatom-containing substituents, including but not limited to $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$;

Each instance of Z is chosen independently from alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, heterocycle, (heterocycle)alkyl, (heterocycle)alkenyl, (heterocycle)alkynyl, or is absent; $R_8$ is H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; optionally substituted by one or more halogen or heteroatom-containing substituents, including but not limited to $OR_{11}$, $NR_{11}R_{12}$, $NO_2$, $SR_{11}$, $SOR_{11}$, $SO_2R_{11}$, $SO_2NR_{11}R_{12}$, $NR_{11}SO_2R_{12}$, $OCF_3$, $CONR_{11}R_{12}$, $NR_{11}C(=O)R_{12}$, $NR_{11}C(=O)OR_{12}$, $OC(=O)NR_{11}R_{12}$, or $NR_{11}C(=O)NR_{12}R_{13}$;

$R_9$ and $R_{10}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; optionally substituted by one or more halogen or heteroatom-containing substituents, including but not limited to $OR_{14}$, $NR_{14}R_{15}$, $NO_2$, $SR_{14}$, $SOR_{14}$, $SO_2R_{14}$, $SO_2NR_{14}R_{15}$, $NR_{14}SO_2R_{15}$, $OCF_3$, $CONR_{14}R_{15}$, $NR_{14}C(=O)R_{15}$, $NR_{14}C(=O)OR_{15}$, $OC(=O)NR_{14}R_{15}$, or $NR_{14}C(=O)NR_{15}R_{16}$; any two of the groups $R_8$, $R_9$ and $R_{10}$ are optionally joined with a link selected from the group consisting of bond, —O—, —S—, —SO—, —$SO_2$—, and —$NR_{17}$— to form a ring; $R_{11}$-$R_{17}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle.

In Formula II, the preferred Y is H, halogen, $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$, the more preferred Y is H, halogen, $OR_8$, $SR_8$, $SOR_8$, $SO_2R_8$, $SO_2NR_8R_9$, $NR_8SO_2R_9$, $CONR_8R_9$, or $NR_8C(=O)NR_9R_{10}$, the preferred Z is alkyl, alkenyl, alkynyl, cycloalkyl, cycloalkenyl, cycloalkylalkyl, or is absent; the more preferred Z is alkyl, alkenyl, alkynyl, cycloalkyl, or is absent, the preferred Q is $(CR_4R_5)_{n3}$, the more preferred Q is $CH_2$, the preferred $n_1$ is 1 or 2, the preferred $n_2$ is 1, the preferred $n_3$ is 1 or 2, the preferred $R_3$-$R_7$ are H, the preferred $R_8$ is H, alkyl, arylalkyl, cycloalkyl, cycloalkylalkyl, or heterocycle, the preferred $R_8$ substituents are H, halogen, $OR_{11}$, $NR_{11}R_{12}$, $SR_{11}$, $SOR_{11}$, $SO_2R_{11}$, $SO_2NR_{11}R_{12}$, $NR_{11}SO_2R_{12}$, $CONR_{11}R_{12}$, $NR_{11}C(=O)R_{12}$, and the preferred $R_9$-$R_{17}$ are H or alkyl.

In Formula II, a preferred $R_2$ substituent is halo, alkyl, cycloalkyl, hydroxyl, alkoxy, cycloalkyloxy, amino, alkylamino, or $R_2$ is unsubstituted. A more preferred $R_2$ substituent is halo, methyl, ethyl, isopropyl, cyclopropyl, hydroxyl, methoxy, ethoxy, amino, methylamino, dimethylamino, or $R_2$ is unsubstituted.

[1] One embodiment of the invention is represented by Formula II in which $R_2$ is 5-indazolyl or 6-indazolyl ($R_2$-1), optionally substituted.

[1a] In embodiment 1, $R_2$-1 is substituted by one or more alkyl or halo substituents.

[1b] In embodiment 1, $R_2$-1 is substituted by one or more amino, alkylamino, hydroxyl, or alkoxy substituents.

[1c] In embodiment 1, $R_2$-1 is unsubstituted.

[2] In another embodiment, the invention is represented by Formula II in which $R_2$ is 5-isoquinolinyl or 6-isoquinolinyl ($R_2$-2), optionally substituted.

[2a] In embodiment 2, $R_2$-2 is substituted by one or more alkyl or halo substituents.

[2b] In embodiment 2, $R_2$-2 is substituted by one or more amino, alkylamino, hydroxyl, or alkoxy substituents.

[2c] In embodiment 2, $R_2$-2 is unsubstituted.

[3] In another embodiment, the invention is represented by Formula II in which $R_2$ is 4-pyridyl or 3-pyridyl ($R_2$-3), optionally substituted.

[3a] In embodiment 3, $R_2$-3 is substituted by one or more alkyl or halo substituents.

[3b] In embodiment 3, $R_2$-3 is substituted by one or more amino, alkylamino, hydroxyl, or alkoxy substituents.

[3c] In embodiment 3, $R_2$-3 is unsubstituted.

[4] In another embodiment, the invention is represented by Formula II in which $R_2$ is 7-azaindol-4-yl or 7-azaindol-5-yl ($R_2$-4), optionally substituted.

[4a] In embodiment 4, $R_2$-4 is substituted by one or more alkyl or halo substituents.

[4b] In embodiment 4, $R_2$-4 is substituted by one or more amino, alkylamino, hydroxyl, or alkoxy substituents.

[4c] In embodiment 4, $R_2$-4 is unsubstituted.

[5] In another embodiment, the invention is represented by Formula II in which $R_2$ is 4-(3-amino-1,2,5-oxadiazol-4-yl)phenyl or 3-(3-amino-1,2,5-oxadiazol-4-yl)phenyl ($R_2$-5), optionally substituted.

[5a] In embodiment 5, $R_2$-5 is unsubstituted.

[6] In another embodiment, the invention is represented by Formula II in which $R_2$ is one of the groups $R_2$-1-$R_2$-5, substituted by one or more alkyl, halo, amino, alkylamino, hydroxyl, or alkoxy substituents.

[6a] In embodiment 6, $R_2$ is substituted by one or more alkyl or halo substituents.

[6b] In embodiment 6, $R_2$ is substituted by one or more amino, alkylamino, hydroxyl, or alkoxy substituents.

[7] In another embodiment, the invention is represented by Formula II in which $R_2$ is one of the groups $R_2$-1-$R_2$-5, and is unsubstituted.

[8] In another embodiment, the invention is represented by Formula II in which $R_3$ is H.

[9] In another embodiment, the invention is represented by Formula II in which Q is $(CR_4R_5)_{n3}$, and $n_3$ is 1 or 2.

[10] In another embodiment, the invention is represented by Formula II in which Q is $(CH_2)_{n3}$, and $n_3$ is 1.

[11] In another embodiment, the invention is represented by Formula II in which for at least one substituent X, Z is alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkylalkenyl, cycloalkylalkynyl, cycloalkenyl, cycloalkylalkyl, heterocycle, (heterocycle)alkyl, (heterocycle)alkenyl, or (heterocycle)alkynyl.

Compounds exemplifying embodiment 11 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table A.

[12] In another embodiment, the invention is represented by Formula II in which for at least one substituent X, Z is absent, and Y is a heteroatom-containing substituent, including but not limited to $OR_8$, $NR_8R_9$, $SR_8$, $SOR_8$, $SO_2R_8$, $SO_2NR_8R_9$, $NR_8SO_2R_9$, $CONR_8R_9$, $NR_8C(=O)R_9$, $NR_8C(=O)OR_9$, $OC(=O)NR_9R_9$, or $NR_8C(=O)NR_9R_{10}$, with the proviso that if the substituent Y is acyclic and is connected to Ar by a carbon atom, then this substituent contains at least one nitrogen or sulfur atom, with the second proviso that if the substituent Y is acyclic and is connected to Ar by an oxygen or nitrogen atom, then this substituent contains at least one additional oxygen, nitrogen or sulfur atom, and with the third proviso that if the substituent Y is connected to Ar by a sulfone linkage "—$SO_2$-", then $R_2$ is not nitrogen- or oxygen-substituted $R_2$-2.

[12a] In embodiment 12, the heteroatom-containing substituent is connected to $R_1$ by an oxygen or nitrogen atom.

[12b] In embodiment 12, the heteroatom-containing substituent is connected to $R_1$ by a sulfide linkage, "—S-".

Compounds exemplifying embodiment 12 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table A.

[13] In another embodiment, the invention is represented by Formula II in which for at least one substituent X, Z is alkyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl, and Y is a hetero atom-containing substituent, including but not limited to $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$, with the proviso that if Z is acyclic and Y falls on the carbon by which Z is attached to Ar, then Y contains at least one nitrogen or sulfur atom.

Compounds exemplifying embodiment 13 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, 1.122, and 1.123, shown below in Table A.

[14] In another embodiment, the invention is represented by Formula II in which for at least one substituent X, Z is alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl, and $R_2$ is 5-indazolyl ($R_2$-1) or 5-isoquinolinyl ($R_2$-2), optionally substituted.

[14a] In embodiment 14, $R_2$ is 5-indazolyl ($R_2$-1), optionally substituted by one or more alkyl, halo, amino, alkylamino, hydroxyl, or alkoxy substituents.

[14b] In embodiment 14, $R_2$ is 5-isoquinolinyl ($R_2$-2), optionally substituted by one or more alkyl, halo, amino, alkylamino, hydroxyl, or alkoxy substituents.

[14c] In embodiment 14, $R_2$ is unsubstituted.

Compounds exemplifying embodiment 14 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table A.

[15] In another embodiment, the invention is represented by Formula II in which for at least one substituent X, Z is absent, and Y is a heteroatom-containing substituent, including but not limited to $OR_8$, $NR_8R_9$, $SR_8$, $SOR_8$, $SO_2R_8$, $SO_2NR_8R_9$, $NR_8SO_2R_9$, $CONR_8R_9$, $NR_8C(=O)R_9$, $NR_8C(=O)OR_9$, $OC(=O)NR_8R_9$, or $NR_9C(=O)NR_9R_{10}$, and $R_2$ is 5-indazolyl ($R_2$-1) or 5-isoquinolinyl ($R_2$-2), optionally substituted, with the proviso that if the substituent Y is acyclic and is connected to Ar by a carbon atom, then this substituent contains at least one nitrogen or sulfur atom, with the second proviso that if the substituent Y is acyclic and is connected to Ar by an oxygen or nitrogen atom, then this substituent contains at least one additional oxygen, nitrogen or sulfur atom, and with the third proviso that if the substituent Y is connected to Ar by a sulfone linkage "—$SO_2$-", then $R_2$ is not nitrogen- or oxygen-substituted $R_2$-2.

[15a] In embodiment 15, $R_2$ is 5-indazolyl ($R_2$-1), optionally substituted by one or more alkyl, halo, amino, alkylamino, hydroxyl, or alkoxy substituents.

[15b] In embodiment 15, $R_2$ is 5-isoquinolinyl ($R_2$-2), optionally substituted by one or more alkyl, halo, amino, alkylamino, hydroxyl, or alkoxy substituents.

[15c] In embodiment 15, $R_2$ is unsubstituted.

[15d] In embodiment 15, the heteroatom-containing substituent is connected to $R_1$ by an oxygen or nitrogen atom.

[15e] In embodiment 15, the heteroatom-containing substituent is connected to $R_1$ by a sulfide linkage, "—S—".

Compounds exemplifying embodiment 15 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table A.

[16] In another embodiment, the invention is represented by Formula II in which for at least one substituent X, Z is alkyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl, and Y is a heteroatom-containing substituent, including but not limited to $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$, and $R_2$ is 5-indazolyl ($R_2$-1) or 5-isoquinolinyl ($R_2$-2), optionally substituted, with the proviso that if Z is acyclic and Y falls on the carbon by which Z is attached to Ar, then Y contains at least one nitrogen or sulfur atom.

[16a] In embodiment 16, $R_2$ is 5-indazolyl ($R_2$-1), optionally substituted by one or more alkyl, halo, amino, alkylamino, hydroxyl, or alkoxy substituents.

[16b] In embodiment 16, $R_2$ is 5-isoquinolinyl ($R_2$-2), optionally substituted by one or more allyl, halo, amino, alkylamino, hydroxyl, or alkoxy substituents.

[16c] In embodiment 16, $R_2$ is unsubstituted.

[16d] In embodiment 16, Ar is heteroaryl.

Compounds exemplifying embodiment 16 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, 1.122, and 1.123, shown below in Table A.

In Embodiments 11-16 of Formula II, the preferred Q is $(CR_4R_5)_{n3}$, the more preferred Q is $CH_2$, the preferred $n_1$ is 1 or 2, the preferred $n_2$ is 1, the preferred $n_3$ is 1 or 2, and the preferred $R_3$ is H.

The inventors have discovered certain compounds of Formula II that have properties that render them particularly useful for treating the conditions addressed by the invention. In particular, these preferred compounds of Embodiments 14, 15 and 16 can be described as compounds of Formula II in which $R_2$, $R_3$, $n_1$, and $n_2$ are limited to the combinations shown in Formulae IIa, IIb, and IIc:

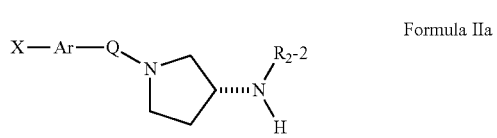

Formula IIa

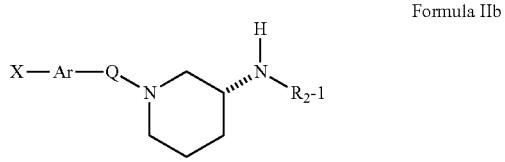

Formula IIb

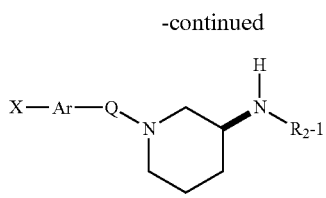

Formula IIc

In Formulae IIa, IIb, and IIc, the stereochemistry of the central pyrrolidine or piperidine ring is limited to the R, R, and S configurations respectively, as drawn.

In Formula IIa, IIb, and IIc, Q is C=O, SO$_2$, or (CR$_4$R$_5$)$_{n3}$; where R$_4$ and R$_5$ are independently H, alkyl, cycloalkyl, optionally substituted. The preferred R$_4$ and R$_5$ are H or unsubstituted alkyl. The preferred Q is CH$_2$.

In Formula Ia, IIb, and IIc, a preferred R$_2$ substituent is halo, alkyl, cycloalkyl, hydroxyl, alkoxy, cycloalkyloxy, amino, alkylamino, or R$_2$ is unsubstituted. A more preferred R$_2$ substituent is halo, methyl, ethyl, isopropyl, cyclopropyl, hydroxyl, methoxy, ethoxy, amino, methylamino, dimethylamino, or R$_2$ is unsubstituted.

In a more preferred form of Formulae IIa, IIb, and IIc, Ar is phenyl or a 6,5- or 6,6-fused bicyclic heteroaryl ring, substituted by 1 or 2 substituents X, and Q is CH$_2$. The most preferred 6,5-fused bicyclic heteroaryl rings are benzofuran, benzothiophene, indole, and benzimidazole.

In its more preferred form, Ar of Formulae Ia, IIb, and IIc is mono- or disubstituted when Ar is phenyl, with 3-substituted, 4-substituted, 2,3-disubstituted, and 3,4-disubstituted being most preferred. When Ar is bicyclic heteroaryl, a monosubstituted Ar is most preferred.

The inventors have found that certain members of Formulae IIa, IIb, and IIc, as defined above, are particularly useful in treating the conditions addressed in this invention. The compounds of the invention are multikinase inhibitors, with inhibitory activity against ROCK1 and ROCK2, in addition to several other kinases in individual compound cases. These kinase inhibitory properties endow the compounds of the invention not only with smooth muscle relaxant properties, but additionally with antiproliferative, antichemotactic, and cytokine secretion inhibitory properties that render them particularly useful in treating conditions with proliferative or inflammatory components as described in the invention.

[17] In particular, we have found that compounds in which R$_2$ is R$_2$-2 are particularly potent inhibitors of both ROCK1 and ROCK2, and that these agents inhibit the migration of neutrophils toward multiple chemotactic stimuli and inhibit the secretion of the cytokines IL-1β, TNF-α and IL-9 from LPS-stimulated human monocytes. Compounds in which Ar is heteroaryl, particularly 6,5-fused bicyclic heteroaryl, are especially preferred. These compounds are of particular value in addressing conditions with an inflammatory component.

Compounds exemplifying embodiment 17 include compounds 2.020, 2.021, 2.022, 2.026, 2.031, 2.033, 2.034, 2.038, 2.039, 2.040, 2.041, 2.043, 2.044, 2.054, 2.058, 2.059, 2.060, 2.063, 2.064, 2.066, 2.067, 2.068, 2.069, 2.070, 2.071, 2.072, 2.073, 2.076, 2.077, 2.078, 2.079, 2.080, 2.081, 2.082, 2.087, 2.092, 2.093, 2.094, 2.095, 2.096, 2.097, 2.098, 2.099, and 2.100.

[18] In another embodiment, we have found that compounds of Formula IIc are potent and selective inhibitors of ROCK2, with comparatively lower inhibitory potency against ROCK1. We have demonstrated that compounds of this class typically show good smooth muscle relaxation properties and that smooth muscle relaxation effects in this class are generally correlated with ROCK2 potency. Compounds in which Ar is phenyl are particularly preferred, and compounds bearing one polar group X1 in the 3-position and a second group X2 in the 4-position are most preferred. Compounds of this embodiment are of particular value in addressing conditions where relaxation of smooth muscle, in particular vascular and bronchial smooth muscle, is of highest importance.

Compounds exemplifying embodiment 18 include compounds 1.075, 1.077, 1.090, 1.091, 1.094, 1.095, 1.107, 1.109, 1.117, 1.118, 1.124, 1.152, 1.153, 1.157, 1.158, 1.165, 1.168, 1.176, 1.181, 1.182, 1.184, 1.185, 1.186, 1.187, 1.195, 1.196, 1.197, 1.198, 1.199, 1.200, 1.201, 1.213, 1.214, 1.215, 1.217, 1.218, 1.219, 1.223, 1.224, 1.228, 1.229, 1.230, 1.233, 1.234, 1.236, 1.237, 1.238, 1.239, 1.240, 1.253, 1.255, 1.261, 1.269, 1.270, 1.272, 1.274, 1.275, 1.280, and 1.282.

[19] In another embodiment, the inventors have found that compounds of Formula IIb are potent mixed inhibitors of ROCK1 and ROCK2, display additional inhibitory activity against the kinases Akt3 and p70S6K, and that these compounds generally display potent antiproliferative activity in models of smooth muscle cell proliferation. Compounds of this class are of particular value in addressing conditions in which an antiproliferative component is desired in combination with a smooth muscle relaxing effect.

Compounds exemplifying embodiment 19 include compounds 1.074, 1.076, 1.092, 1.093, 1.096, 1.097, 1.106, 1.108, 1.113, 1.115, 1.116, 1.123, 1.125, 1.126, 1.127, 1.128, 1.129, 1.139, 1.140, 1.147, 1.159, 1.160, 1.161, 1.162, 1.174, 1.188, 1.189, 1.193, 1.194, 1.202, 1.205, 1.206, 1.207, 1.208, 1.211, 1.212, 1.221, 1.222, 1.225, 1.231, 1.232, 1.235, 1.244, 1.248, 1.249, 1.258, 1.259, 1.260, 1.262, 1.263, 1.264, 1.265, 1.266, 1.267, 1.268, 1.271, 1.273, 1.276, and 1.281.

[20] In another embodiment, the inventors have found that certain compounds of Formulae IIa, IIb, and IIc distribute preferentially to the lung on oral dosing. In particular, compounds in which Ar is a lipophilic bicyclic heteroaryl group are preferred for this dosing behavior. Compounds of this type are especially useful for treating diseases of the lung by oral dosing while minimizing impact on other tissues.

Compounds exemplifying embodiment 20 include compounds 1.107, 1.109, 1.165, 1.106, 1.108, 2.058, 1.162, 1.264, 1.268, 1.271, 1.273, 1.217, 1.269, 2.059, 2.060, 2.066, and 2.072.

As discussed above for the compounds of Formulae Ia, Ib, and Ic, preparation of compounds of Formulae IIa, IIb, and IIc can be problematic using methods commonly known in the art. The inventors have disclosed and exemplified in US2008/0214614A1 methods to allow successful protection, coupling, and deprotection sequence that allows the successful preparation of the compounds of Formulae IIb and 11c and the demonstration of their useful biological properties.

The present compounds are useful for both oral and topical use, including use by the inhalation route. To be therapeutically effective in in this way, the compounds must have both adequate potency and proper pharmacokinetic properties such as good permeability across the biological surface relevant to the delivery route. In general, compounds of Formulae I and II bearing polar functionality, particularly on Ar, have preferred absorption properties and are particularly suitable for topical use. In general, compounds bearing small lipophilic functional groups have good ROCK inhibitory potency.

R$_1$ substitution in Formula I and X in Formula II are important factors for pharmacokinetic properties and ROCK inhibitory potency. Specifically, compounds bearing polar functionality, especially those specified in the embodiments 11, 12, 13, 14, 15, and 16 in Formulae I and II, above, are particularly suitable for topical use with adequate ROCK inhibiting activity. Compounds bearing small lipophilic functional groups, as specified in the embodiments 11, 12, 13, 14, 15, and 16 in Formulae I and II, above, display ROCK inhibition with adequate permeability across biological surfaces. Compounds bearing substituents of both types are particularly preferred, and when $R_1$ (Formula I) or Ar (Formula II) is a phenyl ring, compounds with small lipophilic groups in the 4-position and polar functionality in the 3-position are most preferred.

Specific compounds illustrative of Formula I and Formula II are shown in the following Table A. The example compounds have been numbered in such a way that numbers of the form 1.nnn indicate compounds in which $R_2$ is $R_2$-1, numbers of the form 2.nnn indicate compounds in which $R_2$ is $R_2$-2, and so on in a similar fashion for the remaining compound numbers and groups $R_2$. In the following structures, hydrogens are omitted from the drawings for the sake of simplicity. Tautomers drawn represent all tautomers possible. Structures are drawn to indicate the preferred stereochemistry; where stereoisomers may be generated in these compounds, structures are taken to mean any of the possible stereoisomers alone or a mixture of stereoisomers in any ratio.

TABLE A

Exemplified Compounds.

| Compound | Structure | Select Embodiments 1-16 |
|---|---|---|
| 1.001 | N-(1-(4-(methylsulfonyl)benzyl)piperidin-3-yl)-1H-indazol-5-amine | 1c, 7, 8, 9, 10, 12, 15c |
| 1.002 | 3-((3-(1H-indazol-5-ylamino)piperidin-1-yl)methyl)benzonitrile | 1c, 7, 8, 9, 10, 12, 15c |
| 1.003 | N-(4-((3-(1H-indazol-5-ylamino)piperidin-1-yl)methyl)phenyl)acetamide | 1c, 7, 8, 9, 10, 12a, 15c, 15d |
| 1.004 | N-(1-(4-(methylsulfonyl)benzyl)pyrrolidin-3-yl)-1H-indazol-5-amine | 1c, 7, 8, 9, 10, 12, 15c |
| 1.005 | 3-((3-(1H-indazol-5-ylamino)pyrrolidin-1-yl)methyl)benzonitrile | 1c, 7, 8, 9, 10, 12, 15c |

TABLE A-continued

Exemplified Compounds.

| Compound | Structure | Select Embodiments 1-16 |
|---|---|---|
| 1.006 | N-(4-((3-(1H-indazol-5-ylamino)pyrrolidin-1-yl)methyl)phenyl)acetamide | 1c, 7, 8, 9, 10, 12a, 15c, 15d |
| 1.007 | N-(1-(4-(3-(dimethylamino)propoxy)benzyl)pyrrolidin-3-yl)-1H-indazol-5-amine | 1c, 7, 8, 9, 10, 12a, 15c, 15d |
| 1.008 | N-(1-(4-(methylthio)benzyl)piperidin-3-yl)-1H-indazol-5-amine | 1c, 7, 8, 9, 10, 12b, 15c, 15e |
| 1.009 | N-(1-(biphenyl-4-ylmethyl)piperidin-3-yl)-1H-indazol-5-amine | 1c, 7, 8, 9, 10, 11, 14c |
| 1.010 | N-(1-(1H-imidazol-1-yl)benzyl)piperidin-3-yl)-1H-indazol-5-amine | 1c, 7, 8, 9, 10, 11, 14c |
| 1.011 | N-(1-(4-(pyrrolidin-1-yl)benzyl)piperidin-3-yl)-1H-indazol-5-amine | 1c, 7, 8, 9, 10, 11, 14c |

TABLE A-continued

Exemplified Compounds.

| Compound | Structure | Select Embodiments 1-16 |
|---|---|---|
| 1.012 | 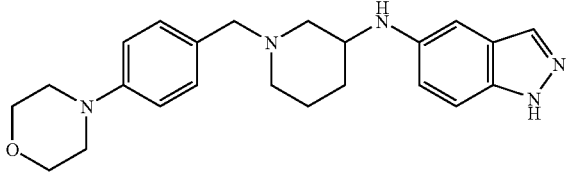<br>N-(1-(4-morpholinobenzyl)piperidin-3-yl)-1H-indazol-5-amine | 1c, 7, 8, 9, 10, 11, 14c |
| 1.013 | 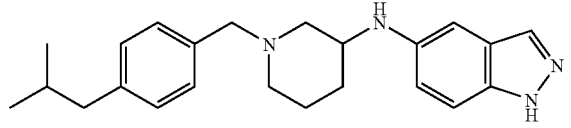<br>N-(1-(4-isobutylbenzyl)piperidin-3-yl)-1H-indazol-5-amine | 1c, 7, 8, 9, 10 |
| 1.014 | 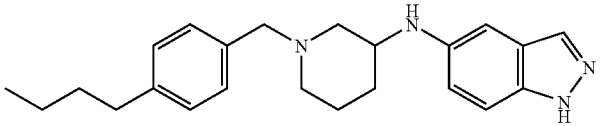<br>N-(1-(4-butylbenzyl)piperidin-3-yl)-1H-indazol-5-amine | 1c, 7, 8, 9, 10 |
| 1.015 | 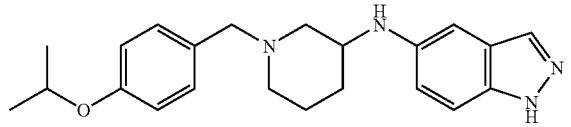<br>N-(1-(4-isopropoxybenzyl)piperidin-3-yl)-1H-indazol-5-amine | 1c, 7, 8, 9, 10 |
| 1.016 | 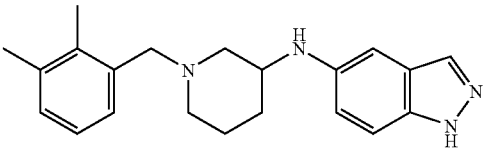<br>N-(1-(2,3-dimethylbenzyl)piperidin-3-yl)-1H-indazol-5-amine | 1c, 7, 8, 9, 10 |
| 1.017 | 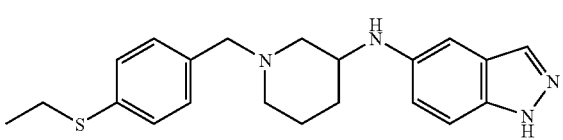<br>N-(1-(4-(ethylthio)benzyl)piperidin-3-yl)-1H-indazol-5-amine | 1c, 7, 8, 9, 10, 12b, 15c, 15e |
| 1.018 | 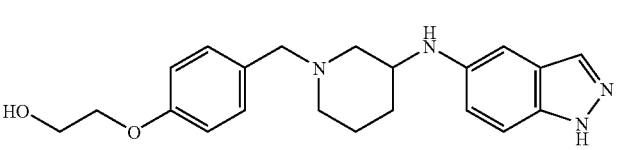<br>2-(4-((3-(1H-indazol-5-ylamino)piperidin-1-yl)methyl)phenoxy)ethanol | 1c, 7, 8, 9, 10, 12a, 15c, 15d |

TABLE A-continued

Exemplified Compounds.

| Compound | Structure | Select Embodiments 1-16 |
| --- | --- | --- |
| 1.019 | N-(1-(4-((dimethylamino)methyl)benzyl)piperidin-3-yl)-1H-indazol-5-amine | 1c, 7, 8, 9, 10, 13, 16c |
| 1.020 | N-(1-(4-cyclopropylbenzyl)piperidin-3-yl)-1H-indazol-5-amine | 1c, 7, 8, 9, 10, 11, 14c |
| 1.021 | N-(1-(3-cyclopropylbenzyl)piperidin-3-yl)-1H-indazol-5-amine | 1c, 7, 8, 9, 10, 11, 14c |
| 1.022 | N-(1-(4-(trifluoromethoxy)benzyl)piperidin-3-yl)-1H-indazol-5-amine | 1c, 7, 8, 9, 10 |
| 1.023 | N-(1-(4-isopropylbenzyl)piperidin-3-yl)-1H-indazol-5-amine | 1c, 7, 8, 9, 10 |
| 1.024 | N-(1-(2,4-dimethylbenzyl)piperidin-3-yl)-1H-indazol-5-amine | 1c, 7, 8, 9, 10 |
| 1.025 | (4-((3-(1H-indazol-5-ylamino)piperidin-1-yl)methyl)phenyl)methanol | 1c, 7, 8, 9, 10 |

TABLE A-continued

Exemplified Compounds.

| Compound | Structure | Select Embodiments 1-16 |
|---|---|---|
| 1.026 | 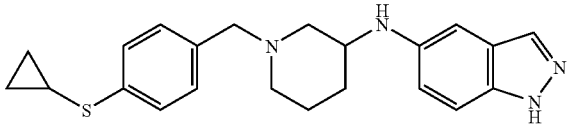<br>N-(1-(4-(cyclopropylthio)benzyl)piperidin-3-yl)-1H-indazol-5-amine | 1c, 7, 8, 9, 10, 12b, 15c, 15e |
| 1.027 | 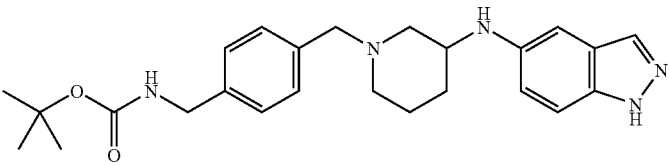<br>tert-butyl 4-((3-(1H-indazol-5-ylamino)piperidin-1-yl)methyl)benzylcarbamate | 1c, 7, 8, 9, 10, 13, 16c |
| 1.028 | 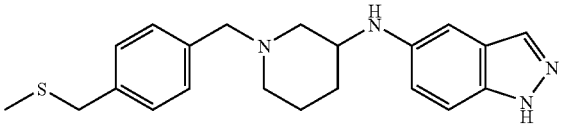<br>N-(1-(4-(methylthiomethyl)benzyl)piperidin-3-yl)-1H-indazol-5-amine | 1c, 7, 8, 9, 10, 13, 16c |
| 1.029 | 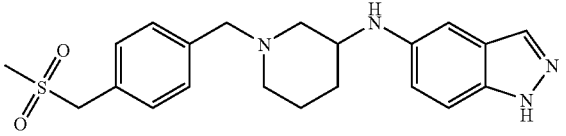<br>N-(1-(4-(methylsulfonylmethyl)benzyl)piperidin-3-yl)-1H-indazol-5-amine | 1c, 7, 8, 9, 10, 13, 16c |
| 1.030 | 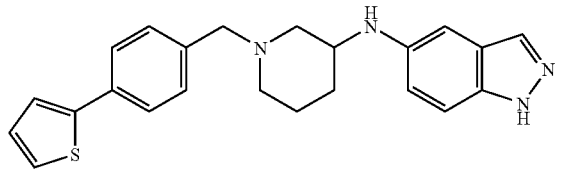<br>N-(1-(4-(thiophen-2-yl)benzyl)piperidin-3-yl)-1H-indazol-5-amine | 1c, 7, 8, 9, 10, 11, 14c |
| 1.031 | 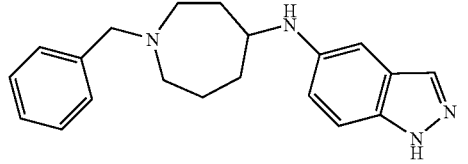<br>N-(1-benzylazepan-4-yl)-1H-indazol-5-amine | 1c, 7, 8, 9, 10 |
| 1.032 | 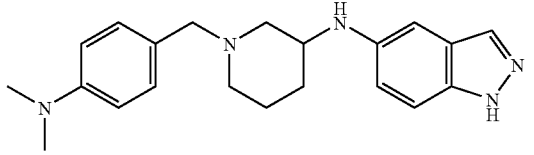<br>N-(1-(4-(dimethylamino)benzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.033 | 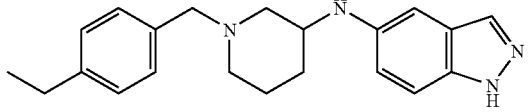<br>N-(1-(4-ethylbenzyl)piperidin-3-yl)-1H-indazol-5-amine | 1c, 7, 8, 9, 10 |
| 1.034 | 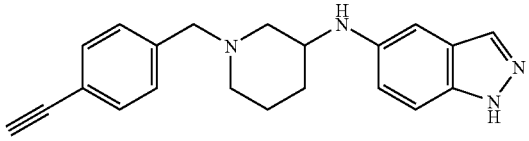<br>N-(1-(4-ethynylbenzyl)piperidin-3-yl)-1H-indazol-5-amine | 1c, 7, 8, 9, 10, 11, 14c |
| 1.035 | 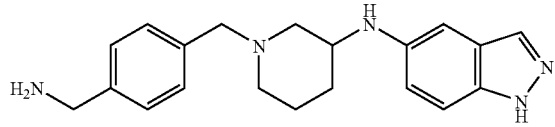<br>N-(1-(4-(aminomethyl)benzyl)piperidin-3-yl)-1H-indazol-5-amine | 1c, 7, 8, 9, 10, 13, 16c |
| 1.036 | 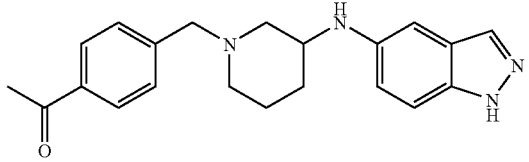<br>1-(4-((3-(1H-indazol-5-ylamino)piperidin-1-yl)methyl)phenyl)ethanone | 1c, 7, 8, 9, 10 |
| 1.037 | 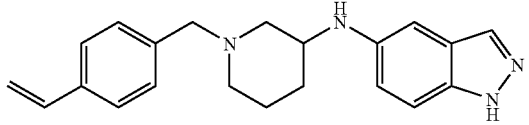<br>N-(1-(4-vinylbenzyl)piperidin-3-yl)-1H-indazol-5-amine | 1c, 7, 8, 9, 10, 11, 14c |
| 1.038 | 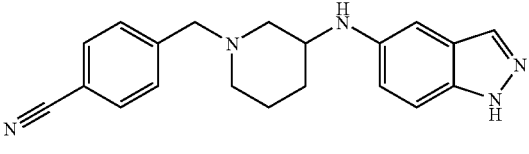<br>4-((3-(1H-indazol-5-ylamino)piperidin-1-yl)methyl)benzonitrile | 1c, 7, 8, 9, 10, 12, 15c |
| 1.039 | 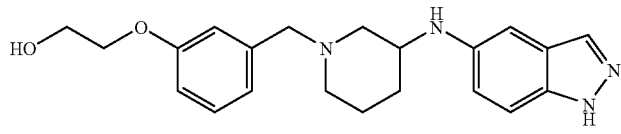<br>2-(3-((3-(1H-indazol-5-ylamino)piperidin-1-yl)methyl)phenoxy)ethanol | 1c, 7, 8, 9, 10, 12a, 15c, 15d |

TABLE A-continued

Exemplified Compounds.

| Compound | Structure | Select Embodiments 1-16 |
|---|---|---|
| 1.040 | 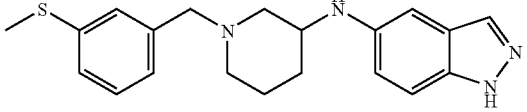<br>N-(1-(3-(methylthio)benzyl)piperidin-3-yl)-1H-indazol-5-amine | 1c, 7, 8, 9, 10, 12b, 15c, 15e |
| 1.041 | 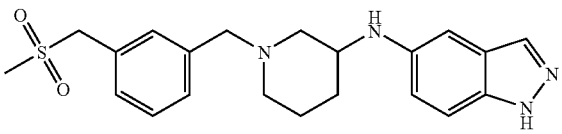<br>N-(1-(3-(methylsulfonylmethyl)benzyl)piperidin-3-yl)-1H-indazol-5-amine | 1c, 7, 8, 9, 10, 13, 16c |
| 1.042 | 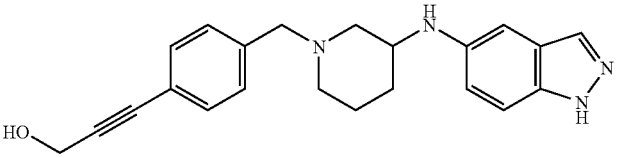<br>3-(4-((3-(1H-indazol-5-ylamino)piperidin-1-yl)methyl)phenyl)prop-2-yn-1-ol | 1c, 7, 8, 9, 10, 13, 16c |
| 1.043 | 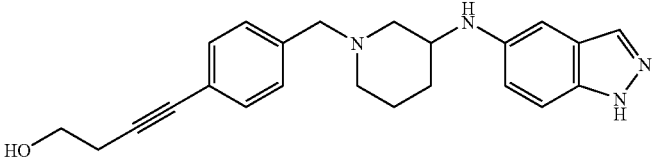<br>4-(4-((3-(1H-indazol-5-ylamino)piperidin-1-yl)methyl)phenyl)but-3-yn-1-ol | 1c, 7, 8, 9, 10, 13, 16c |
| 1.044 | 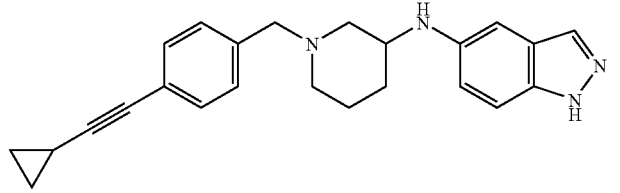<br>N-(1-(4-(cyclopropylethynyl)benzyl)piperidin-3-yl)-1H-indazol-5-amine | 1c, 7, 8, 9, 10, 11, 14c |
| 1.045 | 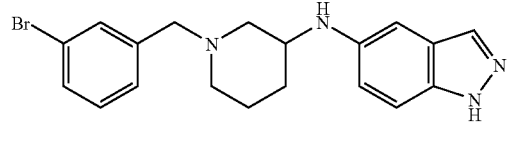<br>N-(1-(3-bromobenzyl)piperidin-3-yl)-1H-indazol-5-amine | 1c, 7, 8, 9, 10 |
| 1.046 | 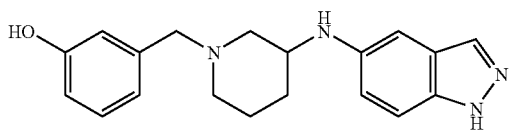<br>3-((3-(1H-indazol-5-ylamino)piperidin-1-yl)methyl)phenol | 1c, 7, 8, 9, 10 |

TABLE A-continued

Exemplified Compounds.

| Compound | Structure | Select Embodiments 1-16 |
|---|---|---|
| 1.047 | N-(1-(3-ethynylbenzyl)piperidin-3-yl)-1H-indazol-5-amine | 1c, 7, 8, 9, 10, 11, 14c |
| 1.048 | N-(1-(3-(methylsulfonyl)benzyl)piperidin-3-yl)-1H-indazol-5-amine | 1c, 7, 8, 9, 10, 12, 15c |
| 1.049 | N-(1-benzylpiperidin-3-yl)-3-methyl-1H-indazol-5-amine | 1a, 6a, 8, 9, 10 |
| 1.050 | N5-(1-benzylpiperidin-3-yl)-1H-indazole-3,5-diamine | 1b, 6b, 8, 9, 10 |
| 1.051 | N-(3-((3-(1H-indazol-5-ylamino)piperidin-1-yl)methyl)phenyl)methanesulfonamide | 1c, 7, 8, 9, 10, 12a, 15c, 15d |
| 1.052 | N-(1-(benzofuran-5-ylmethyl)piperidin-3-yl)-1H-indazol-5-amine | 1c, 7, 8, 9, 10 |
| 1.053 | N-(1-((2,3-dihydrobenzo[b][1,4]dioxin-6-yl)methyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.054 | N-(1-(benzo[b]thiophen-5-ylmethyl)piperidin-3-yl)-1H-indazol-5-amine | 1c, 7, 8, 9, 10 |
| 1.055 | 3-((3-(1H-indazol-5-ylamino)piperidin-1-yl)methyl)benzamide | 1c, 7, 8, 9, 10, 12, 15c |
| 1.056 | 3-((3-(1H-indazol-5-ylamino)piperidin-1-yl)methyl)benzenesulfonamide | 1c, 7, 8, 9, 10, 12, 15c |
| 1.057 | tert-butyl 3-((3-(1H-indazol-5-ylamino)piperidin-1-yl)methyl)benzylcarbamate | 1c, 7, 8, 9, 10, 13, 16c |
| 1.058 | 2-(5-((3-(1H-indazol-5-ylamino)piperidin-1-yl)methyl)-2-methylphenoxy)ethanol | 1c, 7, 8, 9, 10, 12a, 15c, 15d |
| 1.059 | 5-((3-(1H-indazol-5-ylamino)piperidin-1-yl)methyl)-2-methylphenol | 1c, 7, 8, 9, 10 |
| 1.060 | ethyl 2-(3-((3-(1H-indazol-5-ylamino)piperidin-1-yl)methyl)phenoxy)acetate | 1c, 7, 8, 9, 10, 12a, 15c, 15d |

TABLE A-continued

Exemplified Compounds.

| Compound | Structure | Select Embodiments 1-16 |
|---|---|---|
| 1.061 | 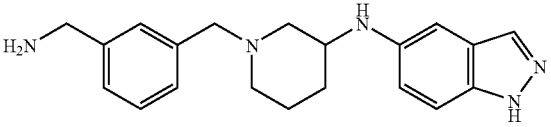<br>N-(1-(3-(aminomethyl)benzyl)piperidin-3-yl)-1H-indazol-5-amine | 1c, 7, 8, 9, 10, 13, 16c |
| 1.062 | 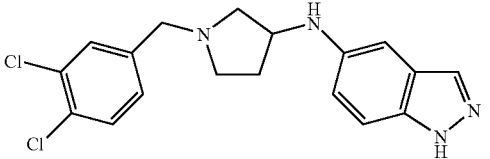<br>N-(1-(3,4-dichlorobenzyl)pyrrolidin-3-yl)-1H-indazol-5-amine | 1c, 7, 8, 9, 10 |
| 1.063 | 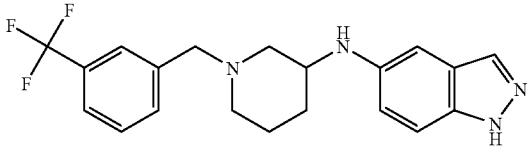<br>N-(1-(3-(trifluoromethyl)benzyl)piperidin-3-yl)-1H-indazol-5-amine | 1c, 7, 8, 9, 10 |
| 1.064 | 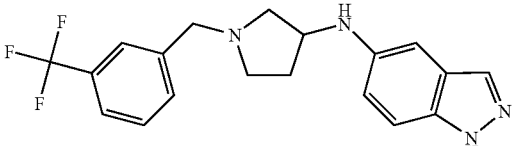<br>N-(1-(3-(trifluoromethyl)benzyl)pyrrolidin-3-yl)-1H-indazol-5-amine | 1c, 7, 8, 9, 10 |
| 1.065 | 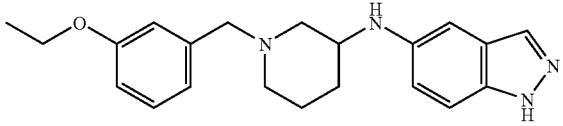<br>N-(1-(3-ethoxybenzyl)piperidin-3-yl)-1H-indazol-5-amine | 1c, 7, 8, 9, 10 |
| 1.066 | 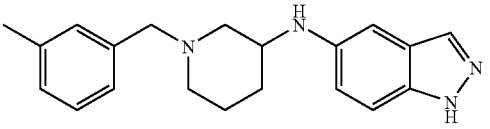<br>N-(1-(3-methylbenzyl)piperidin-3-yl)-1H-indazol-5-amine | 1c, 7, 8, 9, 10 |
| 1.067 | 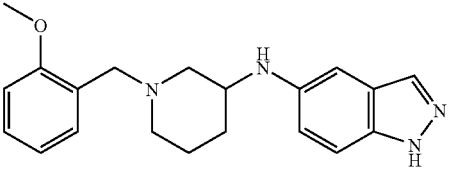<br>N-(1-(2-methoxybenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.068 | 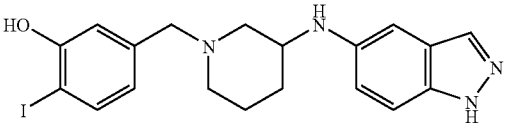<br>5-((3-(1H-indazol-5-ylamino)piperidin-1-yl)methyl-2-iodophenol | 1c, 7, 8, 9, 10 |
| 1.069 | 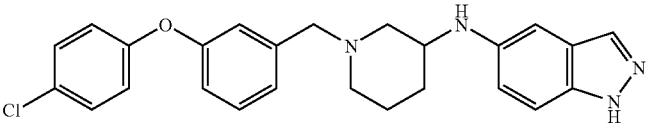<br>N-(1-(3-(4-chlorophenoxy)benzyl)piperidin-3-yl)-1H-indazol-5-amine | 1c, 7, 8, 9, 10 |
| 1.070 | 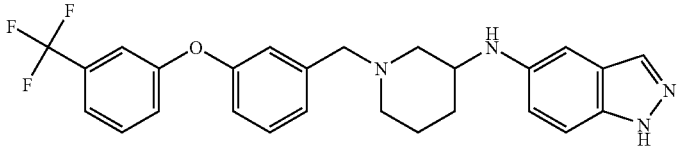<br>N-(1-(3-(3-(trifluoromethyl)phenoxy)benzyl)piperidin-3-yl)-1H-indazol-5-amine | 1c, 7, 8, 9, 10 |
| 1.071 | 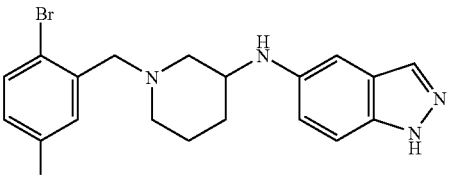<br>N-(1-(2,5-dibromobenzyl)piperidin-3-yl)-1H-indazol-5-amine | 1c, 7, 8, 9, 10 |
| 1.072 | 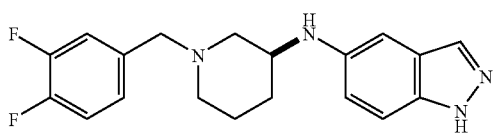<br>(S)-N-(1-(3,4-difluorobenzyl)piperidin-3-yl)-1H-indazol-5-amine | 1c, 7, 8, 9, 10 |
| 1.073 | 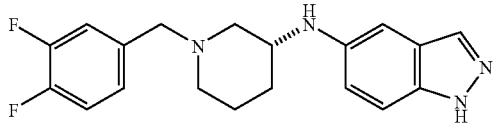<br>(R)-N-(1-(3,4-difluorobenzyl)piperidin-3-yl)-1H-indazol-5-amine | 1c, 7, 8, 9, 10 |
| 1.074 | 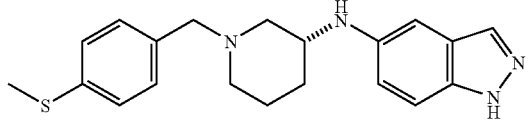<br>(R)-N-(1-(4-(methylthio)benzyl)piperidin-3-yl)-1H-indazol-5-amine | 1c, 7, 8, 9, 10, 12b, 15c, 15e |

TABLE A-continued

Exemplified Compounds.

| Compound | Structure | Select Embodiments 1-16 |
|---|---|---|
| 1.075 | (S)-N-(1-(4-(methylthio)benzyl)piperidin-3-yl)-1H-indazol-5-amine | 1c, 7, 8, 9, 10, 12b, 15c, 15e |
| 1.076 | (R)-N-(1-(4-ethynylbenzyl)piperidin-3-yl)-1H-indazol-5-amine | 1c, 7, 8, 9, 10, 11, 14c |
| 1.077 | (S)-N-(1-(4-ethynylbenzyl)piperidin-3-yl)-1H-indazol-5-amine | 1c, 7, 8, 9, 10, 11, 14c |
| 1.078 | (S)-N-(1-(4-methylbenzyl)piperidin-3-yl)-1H-indazol-5-amine | 1c, 7, 8, 9, 10 |
| 1.079 | (S)-N-(1-(4-methylbenzyl)piperidin-3-yl)-1H-indazol-5-amine | 1c, 7, 8, 9, 10 |
| 1.080 | (S)-N-(1-(3,4-dichlorobenzyl)piperidin-3-yl)-1H-indazol-5-amine | 1c, 7, 8, 9, 10 |
| 1.082 | N-(1-((1H-indol-6-yl)methyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.083 | 5-((3-(1H-indazol-5-ylamino)piperidin-1-yl)methyl)-2-ethynylphenol | 1c, 7, 8, 9, 10, 11, 14c |
| 1.084 | 3-(3-((3-(1H-indazol-5-ylamino)piperidin-1-yl)methyl)phenoxy)propan-1-ol | 1c, 7, 8, 9, 10, 12a, 15c, 15d |
| 1.085 | N-(1-(3-(2-aminoethoxy)benzyl)piperidin-3-yl)-1H-indazol-5-amine | 1c, 7, 8, 9, 10, 12a, 15c, 15d |
| 1.086 | 2-(3-((3-(1H-indazol-5-ylamino)piperidin-1-yl)methyl)phenoxy)acetic acid | 1c, 7, 8, 9, 10, 12a, 15c, 15d |
| 1.087 | N-(3-((3-(1H-indazol-5-ylamino)pyrrolidin-1-yl)methyl)phenyl)methanesulfonamide | 1c, 7, 8, 9, 10, 12a, 15c, 15d |
| 1.088 | 2-(3-((3-(1H-indazol-5-ylamino)pyrrolidin-1-yl)methyl)phenoxy)ethanol | 1c, 7, 8, 9, 10, 12a, 15c, 15d |
| 1.089 | N-(1-(3-amino-4-chlorobenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.090 | (S)-2-(3-((3-(1H-indazol-5-ylamino)piperidin-1-yl)methyl)phenoxy)ethanol | 1c, 7, 8, 9, 10, 12a, 15c, 15d |
| 1.091 | (S)-N-(3-((3-(1H-indazol-5-ylamino)piperidin-1-yl)methyl)phenyl)methanesulfonamide | 1c, 7, 8, 9, 10, 12a, 15c, 15d |
| 1.092 | (R)-2-(3-((3-(1H-indazol-5-ylamino)piperidin-1-yl)methyl)phenoxy)ethanol | 1c, 7, 8, 9, 10, 12a, 15c, 15d |
| 1.093 | (R)-N-(3-((3-(1H-indazol-5-ylamino)piperidin-1-yl)methyl)phenyl)methanesulfonamide | 1c, 7, 8, 9, 10, 12a, 15c, 15d |
| 1.094 | (S)-2-(3-((3-(1H-indazol-5-ylamino)pyrrolidin-1-yl)methyl)phenoxy)ethanol | 1c, 7, 8, 9, 10, 12a, 15c, 15d |
| 1.095 | (S)-N-(3-((3-(1H-indazol-5-ylamino)pyrrolidin-1-yl)methyl)phenyl)methanesulfonamide | 1c, 7, 8, 9, 10, 12a, 15c, 15d |
| 1.096 | (R)-2-(3-((3-(1H-indazol-5-ylamino)pyrrolidin-1-yl)methyl)phenoxy)ethanol | 1c, 7, 8, 9, 10, 12a, 15c, 15d |

TABLE A-continued

Exemplified Compounds.

| Compound | Structure | Select Embodiments 1-16 |
| --- | --- | --- |
| 1.097 | (R)-N-(3-((3-(1H-indazol-5-ylamino)pyrrolidin-1-yl)methyl)phenyl)methanesulfonamide | 1c, 7, 8, 9, 10, 12a, 15c, 15d |
| 1.098 | 2-(3-((3-(1H-indazol-5-ylamino)piperidin-1-yl)methyl)phenoxy)acetamide | 1c, 7, 8, 9, 10, 12a, 15c, 15d |
| 1.099 | 2-(6-((3-(1H-indazol-5-ylamino)piperidin-1-yl)methyl)-1H-indol-1-yl)acetamide | 1c, 7, 8, 9, 10, 13, 16c |
| 1.100 | N-(1-((1H-indol-5-yl)methyl)piperidin-3-yl)-1H-indazol-5-amine | 1c, 7, 8, 9, 10, 13, 16c |
| 1.101 | 2-(6-((3-(1H-indazol-5-ylamino)piperidin-1-yl)methyl)-1H-indol-1-yl)ethanol | 1c, 7, 8, 9, 10, 13, 16c |
| 1.102 | N-(5-((3-(1H-indazol-5-ylamino)piperidin-1-yl)methyl)-2-chlorophenyl)methanesulfonamide | 1c, 7, 8, 9, 10, 12a, 15c, 15d |

TABLE A-continued

Exemplified Compounds.

| Compound | Structure | Select Embodiments 1-16 |
|---|---|---|
| 1.103 | 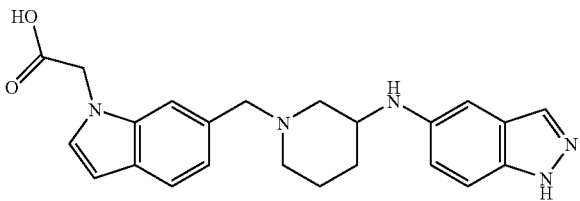<br>2-(6-((3-(1H-indazol-5-ylamino)piperidin-1-yl)methyl)-1H-indol-1-yl)acetic acid | 1c, 7, 8, 9, 10, 13, 16c |
| 1.104 | 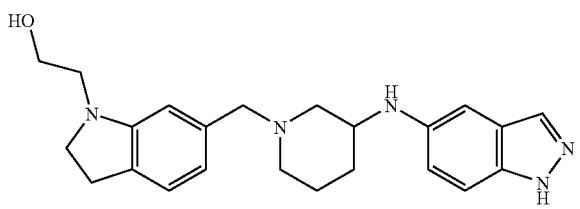<br>2-(6-((3-(1H-indazol-5-ylamino)piperidin-1-yl)methyl)indolin-1-yl)ethanol | 1c, 7, 8, 9, 10, 13, 16c |
| 1.105 | 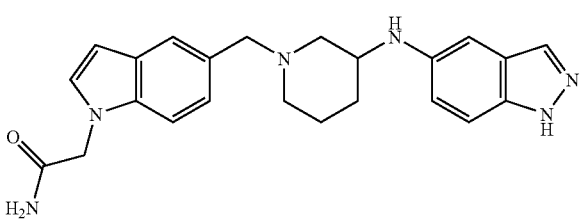<br>2-(5-((3-(1H-indazol-5-ylamino)piperidin-1-yl)methyl)-1H-indol-1-yl)acetamide | 1c, 7, 8, 9, 10, 13, 16c |
| 1.106 | 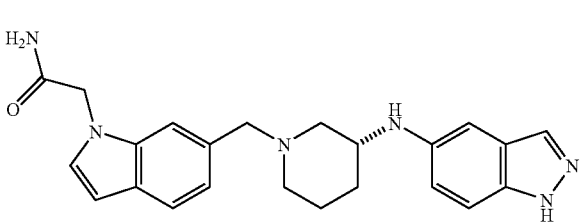<br>(R)-2-(6-((3-(1H-indazol-5-ylamino)piperidin-1-yl)methyl)-1H-indol-1-yl)acetamide | 1c, 7, 8, 9, 10, 13, 16c |
| 1.107 | 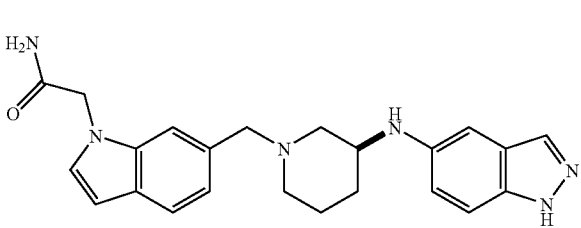<br>(S)-2-(6-((3-(1H-indazol-5-ylamino)piperidin-1-yl)methyl)-1H-indol-1-yl)acetamide | 1c, 7, 8, 9, 10, 13, 16c |

TABLE A-continued

Exemplified Compounds.

| Compound | Structure | Select Embodiments 1-16 |
|---|---|---|
| 1.108 | 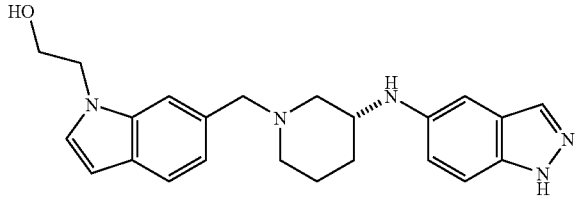<br>(R)-2-(6-((3-(1H-indazol-5-ylamino)piperidin-1-yl)methyl)-1H-indol-1-yl)ethanol | 1c, 7, 8, 9, 10, 13, 16c |
| 1.109 | 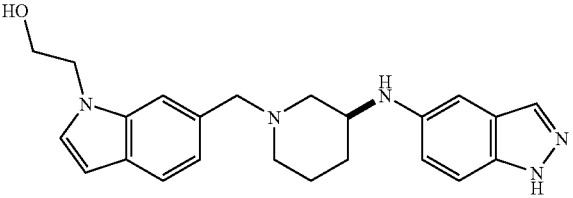<br>(S)-2-(6-((3-(1H-indazol-5-ylamino)piperidin-1-yl)methyl)-1H-indol-1-yl)ethanol | 1c, 7, 8, 9, 10, 13, 16c |
| 1.110 | 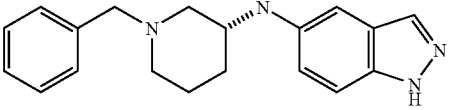<br>(R)-N-(1-benzylpiperidin-3-yl)-1H-indazol-5-amine | 1c, 7, 8, 9, 10 |
| 1.111 | 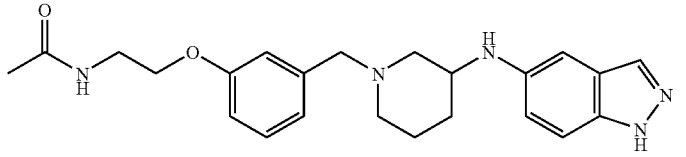<br>N-(2-(3-((3-(1H-indazol-5-ylamino)piperidin-1-yl)methyl)phenoxy)ethyl)acetamide | 1c, 7, 8, 9, 10, 12a, 15c, 15d |
| 1.112 | 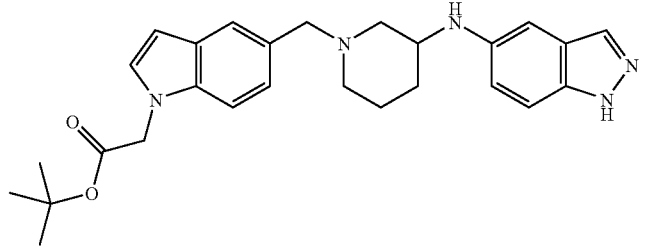<br>tert-butyl 2-(5-((3-(1H-indazol-5-ylamino)piperidin-1-yl)methyl)-1H-indol-1-yl)acetate | 1c, 7, 8, 9, 10, 13, 16c |
| 1.113 | 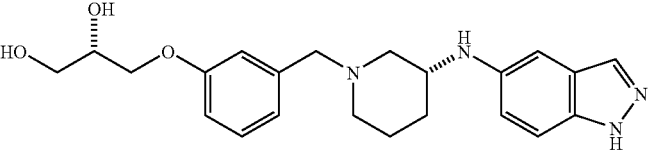<br>(S)-3-(3-(((R)-3-(1H-indazol-5-ylamino)piperidin-1-yl)methyl)phenoxy)propane-1,2-diol | 1c, 7, 8, 9, 10, 12a, 15c, 15d |

TABLE A-continued

Exemplified Compounds.

| Compound | Structure | Select Embodiments 1-16 |
|---|---|---|
| 1.114 | 2-(5-((3-(1H-indazol-5-ylamino)piperidin-1-yl)methyl-1H-indol-1-yl)ethanol | 1c, 7, 8, 9, 10, 13, 16c |
| 1.115 | (R)-3-(3-(((R)-3-(1H-indazol-5-ylamino)piperidin-1-yl)methyl)phenoxy)propane-1,2-diol | 1c, 7, 8, 9, 10, 12a, 15c, 15d |
| 1.116 | (R)-1-(3-(((R)-3-(1H-indazol-5-ylamino)piperidin-1-yl)methyl)phenoxy)propan-2-ol | 1c, 7, 8, 9, 10, 12a, 15c, 15d |
| 1.117 | (R)-3-(3-(((S)-3-(1H-indazol-5-ylamino)piperidin-1-yl)methyl)phenoxy)propane-1,2-diol | 1c, 7, 8, 9, 10, 12a, 15c, 15d |
| 1.118 | (R)-1-(3-(((S)-3-(1H-indazol-5-ylamino)piperidin-1-yl)methyl)phenoxy)propan-2-ol | 1c, 7, 8, 9, 10, 12a, 15c, 15d |
| 1.119 | 2-(5-((3-(1H-indazol-5-ylamino)piperidin-1-yl)methyl-1H-indol-1-yl)acetic acid | 1c, 7, 8, 9, 10, 13, 16c |

TABLE A-continued

Exemplified Compounds.

| Compound | Structure | Select Embodiments 1-16 |
|---|---|---|
| 1.120 | 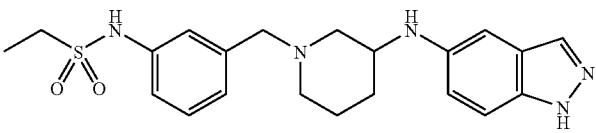<br>N-(3-((3-(1H-indazol-5-ylamino)piperidin-1-yl)methyl)phenyl)ethanesulfonamide | 1c, 7, 8, 9, 10, 12a, 15c, 15d |
| 1.121 | 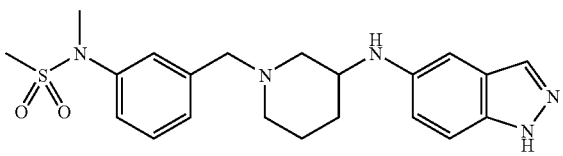<br>N-(3-((3-(1H-indazol-5-ylamino)piperidin-1-yl)methyl)phenyl)-N-methylmethanesulfonamide | 1c, 7, 8, 9, 10, 12a, 15c, 15d |
| 1.122 | 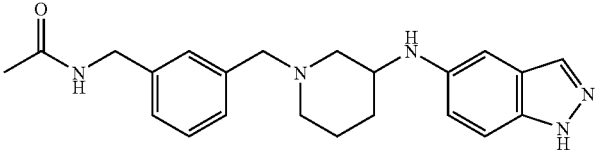<br>N-(3-((3-(1H-indazol-5-ylamino)piperidin-1-yl)methyl)benzyl)acetamide | 1c, 7, 8, 9, 10, 13, 16c |
| 1.123 | 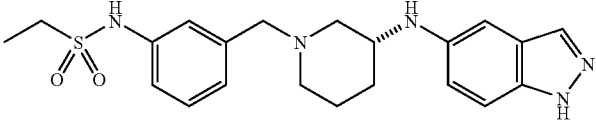<br>(R)-N-(3-((3-(1H-indazol-5-ylamino)piperidin-1-yl)methyl)phenyl)ethanesulfonamide | 1c, 7, 8, 9, 10, 12a, 15c, 15d |
| 1.124 | 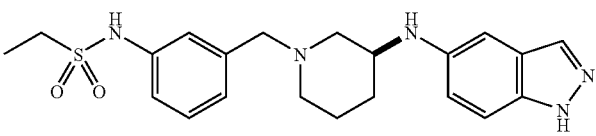<br>(S)-N-(3-((3-(1H-indazol-5-ylamino)piperidin-1-yl)methyl)phenyl)ethanesulfonamide | 1c, 7, 8, 9, 10, 12a, 15c, 15d |
| 1.125 | 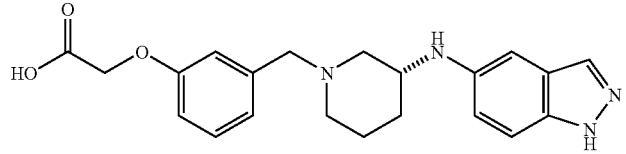<br>(R)-2-(3-((3-(1H-indazol-5-ylamino)piperidin-1-yl)methyl)phenoxy)acetic acid | 1c, 7, 8, 9, 10, 12a, 15c, 15d |
| 1.126 | 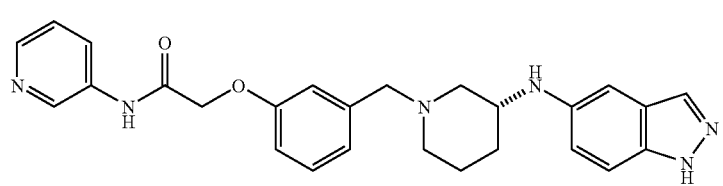<br>(R)-2-(3-((3-(1H-indazol-5-ylamino)piperidin-1-yl)methyl)phenoxy)-N-(pyridin-3-yl)acetamide | 1c, 7, 8, 9, 10, 12a, 15c, 15d |

TABLE A-continued

Exemplified Compounds.

| Compound | Structure | Select Embodiments 1-16 |
|---|---|---|
| 1.127 | (R)-2-(3-((3-(1H-indazol-5-ylamino)piperidin-1-yl)methyl)phenoxy)-1-morpholinoethanone | 1c, 7, 8, 9, 10, 12a, 15c, 15d |
| 1.128 | (R)-2-(3-((3-(1H-indazol-5-ylamino)piperidin-1-yl)methyl)phenoxy)-1-(4-methylpiperazin-1-yl)ethanone | 1c, 7, 8, 9, 10, 12a, 15c, 15d |
| 1.129 | (R)-diethyl (3-((3-(1H-indazol-5-ylamino)piperidin-1-yl)methyl)phenoxy)methylphosphonate | 1c, 7, 8, 9, 10, 12a, 15c, 15d |
| 1.130 | 2-(3-((4-(1H-indazol-5-ylamino)piperidin-1-yl)methyl)phenoxy)ethanol | 1c, 7, 8, 9, 10, 12a, 15c, 15d |
| 1.131 | (R)-N-(1-(benzofuran-5-ylmethyl)piperidin-3-yl)-1H-indazol-5-amine | 1c, 7, 8, 9, 10 |
| 1.132 | (R)-N-(1-(4-chlorobenzyl)piperidin-3-yl)-1H-indazol-5-amine | 1c, 7, 8, 9, 10 |
| 1.133 | (R)-N-(1-(4-methylbenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.134 | (R)-N-(1-(4-bromobenzyl)piperidin-3-yl)-1H-indazol-5-amine | 1c, 7, 8, 9, 10 |
| 1.136 | (R)-N-(1-(4-ethylbenzyl)piperidin-3-yl)-1H-indazol-5-amine | 1c, 7, 8, 9, 10 |
| 1.137 | (R)-N-(1-(2,4-dimethylbenzyl)piperidin-3-yl)-1H-indazol-5-amine | 1c, 7, 8, 9, 10 |
| 1.138 | (R)-N-(1-(benzo[b]thiophen-5-ylmethyl)piperidin-3-yl)-1H-indazol-5-amine | 1c, 7, 8, 9, 10 |
| 1.139 | (R)-N-(1-(3-(methylsulfonylmethyl)benzyl)piperidin-3-yl)-1H-indazol-5-amine | 1c, 7, 8, 9, 10, 12, 15c |
| 1.140 | (R)-tert-butyl 3-((3-(1H-indazol-5-ylamino)piperidin-1-yl)methyl)benzylcarbamate | 1c, 7, 8, 9, 10, 13, 16c |
| 1.141 | (S)-N-(1-(4-chlorobenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.142 | (S)-N-(1-(4-bromobenzyl)piperidin-3-yl)-1H-indazol-5-amine | 1c, 7, 8, 9, 10 |
| 1.143 | (R)-N-(1-((1H-indol-5-yl)methyl)piperidin-3-yl)-1H-indazol-5-amine | 1c, 7, 8, 9, 10, 13, 16c |
| 1.144 | (R)-N-(1-(3,4-dichlorobenzyl)piperidin-3-yl)-1H-indazol-5-amine | 1c, 7, 8, 9, 10 |
| 1.145 | (R)-3-((3-(1H-indazol-5-ylamino)piperidin-1-yl)-1H-indazol-5-amine | 1c, 7, 8, 9, 10 |
| 1.146 | (R)-N-(1-(4-fluorobenzyl)piperidin-3-yl)-1H-indazol-5-amine | 1c, 7, 8, 9, 10 |
| 1.147 | (R)-ethyl 2-(3-((3-(1H-indazol-5-ylamino)piperidin-1-yl)methyl)phenoxy)acetate | 1c, 7, 8, 9, 10, 12a, 15c, 15d |
| 1.148 | (S)-N-(1-((1H-indol-6-yl)methyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.149 | (S)-N-(1-((1H-indol-5-yl)methyl)piperidin-3-yl)-1H-indazol-5-amine | 1c, 7, 8, 9, 10 |
| 1.150 | (S)-N-(1-(benzofuran-5-ylmethyl)piperidin-3-yl)-1H-indazol-5-amine | 1c, 7, 8, 9, 10 |
| 1.151 | (S)-5-((3-(1H-indazol-5-ylamino)piperidin-1-yl)methyl-2-methylphenol | 1c, 7, 8, 9, 10 |
| 1.152 | (S)-2-(5-((3-(1H-indazol-5-ylamino)piperidin-1-yl)methyl)-2-methylphenoxy)ethanol | 1c, 7, 8, 9, 10, 12a, 15c, 15d |
| 1.153 | (S)-N-(1-(3-ethynylbenzyl)piperidin-3-yl)-1H-indazol-5-amine | 1c, 7, 8, 9, 10, 11, 14c |
| 1.154 | (S)-N-(1-(4-ethylbenzyl)piperidin-3-yl)-1H-indazol-5-amine | 1c, 7, 8, 9, 10 |
| 1.155 | (S)-N-(1-(2,4-dimethylbenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.156 | (S)-N-(1-(2,3-dimethylbenzyl)piperidin-3-yl)-1H-indazol-5-amine | 1c, 7, 8, 9, 10 |
| 1.157 | (S)-N-(1-(3-(methylsulfonylmethyl)benzyl)piperidin-3-yl)-1H-indazol-5-amine | 1c, 7, 8, 9, 10, 12, 15c |
| 1.158 | (S)-N-(1-(3-(methylthio)benzyl)piperidin-3-yl)-1H-indazol-5-amine | 1c, 7, 8, 9, 10, 12b, 15c, 15e |
| 1.159 | (R)-N-(1-(3-(methylthio)benzyl)piperidin-3-yl)-1H-indazol-5-amine | 1c, 7, 8, 9, 10, 12b, 15c, 15e |
| 1.160 | (R)-N-(1-(3-(methylsulfonyl)benzyl)piperidin-3-yl)-1H-indazol-5-amine | 1c, 7, 8, 9, 10, 12, 15c |
| 1.161 | (R)-2-(5-((3-(1H-indazol-5-ylamino)piperidin-1-yl)methyl)-2-methylphenoxy)ethanol | 1c, 7, 8, 9, 10, 12a, 15c, 15d |
| 1.162 | (R)-2-(5-((3-(1H-indazol-5-ylamino)piperidin-1-yl)methyl)-1H-indol-1-yl)acetamide | 1c, 7, 8, 9, 10, 13, 16c |

TABLE A-continued

Exemplified Compounds.

| Compound | Structure | Select Embodiments 1-16 |
| --- | --- | --- |
| 1.163 | (S)-3-((3-(1H-indazol-5-ylamino)piperidin-1-yl)methyl)phenol | 1c, 7, 8, 9, 10 |
| 1.164 | (S)-N-(1-(4-fluorobenzyl)piperidin-3-yl)-1H-indazol-5-amine | 1c, 7, 8, 9, 10 |
| 1.165 | (S)-2-(5-((3-(1H-indazol-5-ylamino)piperidin-1-yl)methyl)-1H-indol-1-yl)acetamide | 1c, 7, 8, 9, 10, 13, 16c |
| 1.166 | (S)-N-(1-((2,3-dihydrobenzo[b][1,4]dioxin-6-yl)methyl)piperidin-3-yl)-1H-indazol-5-amine | 1c, 7, 8, 9, 10 |
| 1.167 | (S)-N-(1-(4-trifluoromethyl)benzyl)piperidin-3-yl)-1H-indazol-5-amine | 1c, 7, 8, 9, 10 |
| 1.168 | (S)-N-(1-(4-(ethylthio)benzyl)piperidin-3-yl)-1H-indazol-5-amine | 1c, 7, 8, 9, 10, 12b, 15c, 15e |
| 1.169 | (S)-N-(1-(3-(trifluoromethyl)benzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.170 | 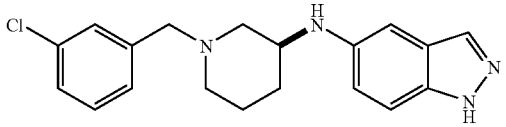<br>(S)-N-(1-(3-chlorobenzyl)piperidin-3-yl)-1H-indazol-5-amine | 1c, 7, 8, 9, 10 |
| 1.171 | 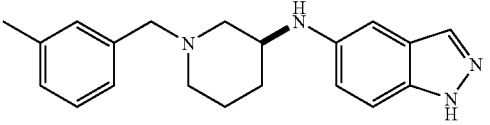<br>(S)-N-(1-(3-methylbenzyl)piperidin-3-yl)-1H-indazol-5-amine | 1.171 |
| 1.172 | 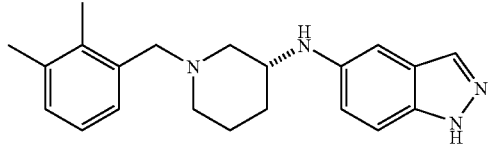<br>(R)-N-(1-(2,3-dimethylbenzyl)piperidin-3-yl)-1H-indazol-5-amine | 1.172 |
| 1.173 | 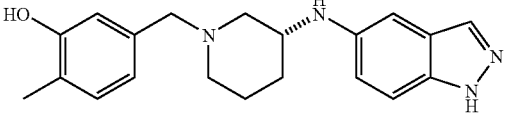<br>(R)-5-((3-(1H-indazol-5-ylamino)piperidin-1-yl)methyl)-2-methylphenol | 1.173 |
| 1.174 | 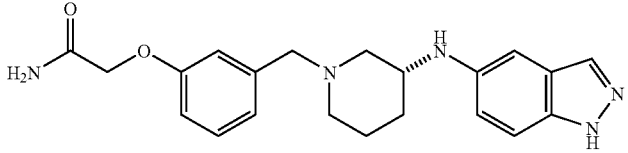<br>(R)-2-(3-((3-(1H-indazol-5-ylamino)piperidin-1-yl)methyl)phenoxy)acetamide | 1.174 |
| 1.175 | 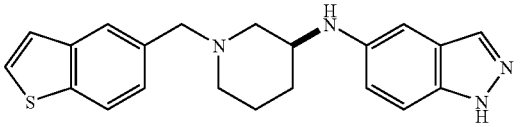<br>(S)-N-(1-(benzo[b]thiophen-5-ylmethyl)piperidin-3-yl)-1H-indazol-5-amine | 1.175 |
| 1.176 | 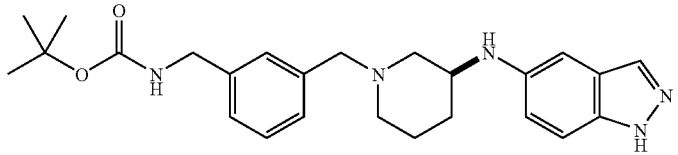<br>(S)-tert-butyl 3-((3-(1H-indazol-5-ylamino)piperidin-1-yl)methyl)benzylcarbamate | 1.176 |

TABLE A-continued

Exemplified Compounds.

| Compound | Structure | Select Embodiments 1-16 |
|---|---|---|
| 1.177 | (R)-N-(1-((2,3-dihydrobenzo[b][1,4]dioxin-6-yl)methyl)piperidin-3-yl)-1H-indazol-5-amine | 1.177 |
| 1.178 | (R)-N-(1-(4-(trifluoromethyl)benzyl)piperidin-3-yl)-1H-indazol-5-amine | 1.178 |
| 1.179 | (S)-N-(1-(3-ethoxybenzyl)piperidin-3-yl)-1H-indazol-5-amine | 1.179 |
| 1.180 | (S)-N-(1-(4-isopropylbenzyl)piperidin-3-yl)-1H-indazol-5-amine | 1.180 |
| 1.181 | (S)-N-(1-(4-(methylsulfonyl)benzyl)piperidin-3-yl)-1H-indazol-5-amine | 1.181 |
| 1.182 | (S)-N-(1-(3-(methylsulfonyl)benzyl)piperidin-3-yl)-1H-indazol-5-amine | 1.182 |
| 1.183 | (S)-N-(1-(3-bromobenzyl)piperidin-3-yl)-1H-indazol-5-amine | 1.183 |

TABLE A-continued

Exemplified Compounds.

| Compound | Structure | Select Embodiments 1-16 |
|---|---|---|
| 1.184 | (S)-N-(1-(3-(aminomethyl)benzyl)piperidin-3-yl)-1H-indazol-5-amine | 1.184 |
| 1.185 | (S)-N-(1-(4-cyclopropylbenzyl)piperidin-3-yl)-1H-indazol-5-amine | 1.185 |
| 1.186 | (S)-N-(1-(3-cyclopropylbenzyl)piperidin-3-yl)-1H-indazol-5-amine | 1.186 |
| 1.187 | (S)-tert-butyl 2-(3-((3-((1H-indazol-5-ylamino)piperidin-1-yl)methyl)phenoxy)acetate | 1.187 |
| 1.188 | (R)-N-(1-(4-(aminomethyl)benzyl)piperidin-3-yl)-1H-indazol-5-amine | 1.188 |
| 1.189 | (R)-N-(1-(4-(ethylthio)benzyl)piperidin-3-yl)-1H-indazol-5-amine | 1.189 |
| 1.190 | (R)-N-(1-(3-(trifluoromethyl)benzyl)piperidin-3-yl)-1H-indazol-5-amine | 1.190 |

TABLE A-continued

Exemplified Compounds.

| Compound | Structure | Select Embodiments 1-16 |
|---|---|---|
| 1.191 | 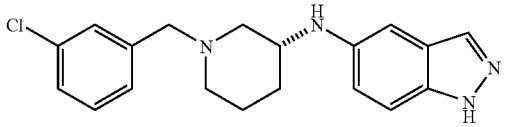<br>(R)-N-(1-(3-chlorobenzyl)piperidin-3-yl)-1H-indazol-5-amine | 1c, 7, 8, 9, 10 |
| 1.192 | 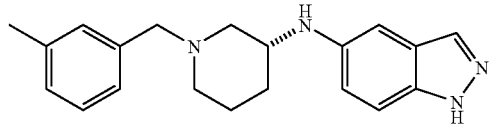<br>(R)-N-(1-(3-methylbenzyl)piperidin-3-yl)-1H-indazol-5-amine | 1c, 7, 8, 9, 10 |
| 1.193 | 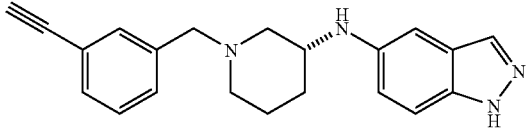<br>(R)-N-(1-(3-ethynylbenzyl)piperidin-3-yl)-1H-indazol-5-amine | 1c, 7, 8, 9, 10, 11, 14c |
| 1.194 | 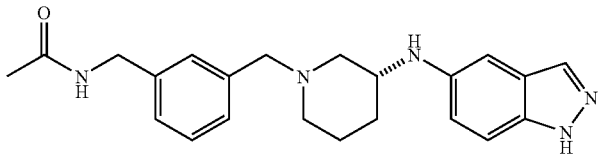<br>(R)-N-(1H-indazol-5-ylamino)piperidin-1-yl)methyl)benzyl)acetamide | 1c, 7, 8, 9, 10, 13, 16c |
| 1.195 | 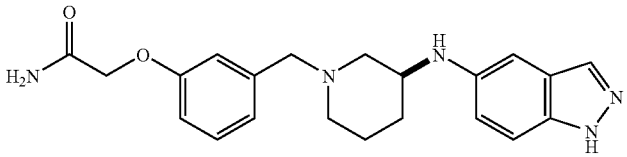<br>(S)-2-(3-((3-(1H-indazol-5-ylamino)piperidin-1-yl)methyl)phenyl-1H-indazol-5-ylamino)piperidin-1-yl)methyl)phenoxy)acetamide | 1c, 7, 8, 9, 10, 12a, 15c, 15d |
| 1.196 | 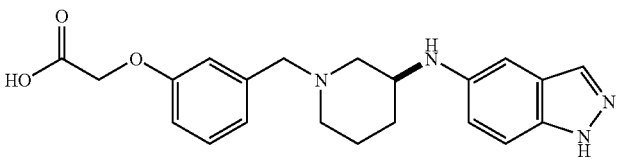<br>(S)-2-(3-((3-(1H-indazol-5-ylamino)piperidin-1-yl)methyl)phenoxy)acetic acid | 1c, 7, 8, 9, 10, 12a, 15c, 15d |
| 1.197 | 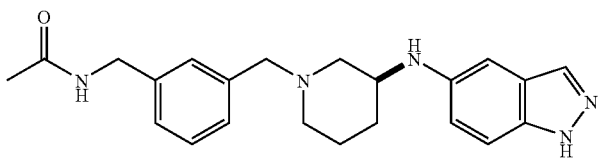<br>(S)-N-(1H-indazol-5-ylamino)piperidin-1-yl)methyl)benzyl)acetamide | 1c, 7, 8, 9, 10, 13, 16c |

TABLE A-continued

Exemplified Compounds.

| Compound | Structure | Select Embodiments 1-16 |
|---|---|---|
| 1.198 | (S)-N-(3-((3-(1H-indazol-5-ylamino)piperidin-1-yl)methyl)phenyl)-N-methylmethanesulfonamide | 1c, 7, 8, 9, 10, 12a, 15c, 15d |
| 1.199 | (S)-tert-butyl 4-((3-(1H-indazol-5-ylamino)piperidin-1-yl)methyl)benzylcarbamate | 1c, 7, 8, 9, 10, 13, 16c |
| 1.200 | (S)-ethyl 2-(3-((3-(1H-indazol-5-ylamino)piperidin-1-yl)methyl)phenoxy)acetate | 1c, 7, 8, 9, 10, 12a, 15c, 15d |
| 1.201 | (S)-N-(1-(4-(aminomethyl)benzyl)piperidin-3-yl)-1H-indazol-5-amine | 1c, 7, 8, 9, 10, 13, 16c |
| 1.202 | (R)-N-(1-(3-cyclopropylbenzyl)piperidin-3-yl)-1H-indazol-5-amine | 1c, 7, 8, 9, 10, 11, 14c |
| 1.203 | (R)-N-(1-(3-ethoxybenzyl)piperidin-3-yl)-1H-indazol-5-amine | 1c, 7, 8, 9, 10 |
| 1.204 | (R)-N-(1-(4-isopropylbenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.205 | (R)-N-(1-(4-(methylsulfonyl)benzyl)piperidin-3-yl)-1H-indazol-5-amine | 1c, 7, 8, 9, 10, 12, 15c |
| 1.206 | (R)-N-(1-(4-cyclopropylbenzyl)piperidin-3-yl)-1H-indazol-5-amine | 1c, 7, 8, 9, 10, 11, 14c |
| 1.207 | (R)-N-(3-((3-(1H-indazol-5-ylamino)piperidin-1-yl)methyl)phenyl)-N-methylmethanesulfonamide | 1c, 7, 8, 9, 10, 12a, 15c, 15d |
| 1.208 | (R)-N-(1-(4-vinylbenzyl)piperidin-3-yl)-1H-indazol-5-amine | 1c, 7, 8, 9, 10, 11, 14c |
| 1.209 | (R)-ethyl 4-((3-(1H-indazol-5-ylamino)piperidin-1-yl)methyl)benzoate | 1c, 7, 8, 9, 10 |
| 1.210 | (R)-N-(1-(3-bromobenzyl)piperidin-3-yl)-1H-indazol-5-amine | 1c, 7, 8, 9, 10 |
| 1.211 | (R)-N-(2-(3-((3-(1H-indazol-5-ylamino)piperidin-1-yl)methyl)phenoxy)ethyl)acetamide | 1c, 7, 8, 9, 10, 12a, 15c, 15d |

TABLE A-continued

Exemplified Compounds.

| Compound | Structure | Select Embodiments 1-16 |
|---|---|---|
| 1.212 | (R)-N-(5-((3-(1H-indazol-5-ylamino)piperidin-1-yl)methyl)-2-chlorophenyl)methanesulfonamide | 1c, 7, 8, 9, 10, 12a, 15c, 15d |
| 1.213 | (S)-N-(5-((3-(1H-indazol-5-ylamino)piperidin-1-yl)methyl)-2-chlorophenyl)methanesulfonamide | 1c, 7, 8, 9, 10, 12a, 15c, 15d |
| 1.214 | N-((S)-1-(3-(((S)-2,2-dimethyl-1,3-dioxolan-4-yl)methoxy)benzyl)piperidin-3-yl)-1H-indazol-5-amine | 1c, 7, 8, 9, 10, 12a, 15c, 15d |
| 1.215 | (S)-3-((3-(1H-indazol-5-ylamino)piperidin-1-yl)methyl)benzenesulfonamide | 1c, 7, 8, 9, 10, 12, 15c |
| 1.216 | (S)-ethyl 4-((3-(1H-indazol-5-ylamino)piperidin-1-yl)methyl)benzoate | 1c, 7, 8, 9, 10 |
| 1.217 | (S)-2-(6-((3-(1H-indazol-5-ylamino)piperidin-1-yl)methyl)indolin-1-yl)ethanol | 1c, 7, 8, 9, 10, 13, 16c |

TABLE A-continued

Exemplified Compounds.

| Compound | Structure | Select Embodiments 1-16 |
| --- | --- | --- |
| 1.218 | (S)-N-(2-(3-((3-(1H-indazol-5-ylamino)piperidin-1-yl)methyl)phenoxy)ethyl)acetamide | 1c, 7, 8, 9, 10, 12a, 15c, 15d |
| 1.219 | (S)-3-((3-(1H-indazol-5-ylamino)piperidin-1-yl)methyl)benzamide | 1c, 7, 8, 9, 10, 12, 15c |
| 1.221 | (R)-3-((3-(1H-indazol-5-ylamino)piperidin-1-yl)methyl)benzamide | 1c, 7, 8, 9, 10, 12, 15c |
| 1.222 | N-((R)-1-(3-(((S)-2,2-dimethyl-1,3-dioxolan-4-yl)methoxy)benzyl)piperidin-3-yl)-1H-indazol-5-amine | 1c, 7, 8, 9, 10, 12a, 15c, 15d |
| 1.223 | (S)-(4-((3-(1H-indazol-5-ylamino)piperidin-1-yl)methyl)phenyl)methanol | 1c, 7, 8, 9, 10, 13, 16c |
| 1.224 | (S)-2-(3-((3-(1H-indazol-5-ylamino)piperidin-1-yl)methyl)phenoxy)ethyl benzoate | 1c, 7, 8, 9, 10, 12a, 15c, 15d |

TABLE A-continued

Exemplified Compounds.

| Compound | Structure | Select Embodiments 1-16 |
|---|---|---|
| 1.225 | (R)-2-(3-((3-(1H-indazol-5-ylamino)piperidin-1-yl)methyl)phenoxy)ethyl benzoate | 1c, 7, 8, 9, 10, 12a, 15c, 15d |
| 1.226 | (R)-N-(1-(4-methoxybenzyl)piperidin-3-yl)-1H-indazol 5-amine | 1c, 7, 8, 9, 10 |
| 1.227 | (S)-N-(1-benzylpiperidin-3-yl)-1H-indazol-5-amine | 1c, 7, 8, 9, 10 |
| 1.228 | (S)-2-(4-((3-(1H-indazol-5-ylamino)piperidin-1-yl)methyl)phenoxy)ethanol | 1c, 7, 8, 9, 10, 12a, 15c, 15d |
| 1.229 | (S)-N-(1-(4-vinylbenzyl)piperidin-3-yl)-1H-indazol-5-amine | 1c, 7, 8, 9, 10, 11, 14c |
| 1.230 | (S)-3-(3-((3-(1H-indazol-5-ylamino)piperidin-1-yl)methyl)phenoxy)propan-1-ol | 1c, 7, 8, 9, 10, 12a, 15c, 15d |
| 1.231 | (R)-3-(3-((3-(1H-indazol-5-ylamino)piperidin-1-yl)methyl)phenoxy)propan-1-ol | 1c, 7, 8, 9, 10, 12a, 15c, 15d |

| Compound | Structure | Select Embodiments 1-16 |
|---|---|---|
| 1.232 | (R)-(4-((3-(1H-indazol-5-ylamino)piperidin-1-yl)methyl)phenyl)methanol | 1c, 7, 8, 9, 10 |
| 1.233 | (S)-N-(5-((3-(1H-indazol-5-ylamino)piperidin-1-yl)methyl)-2-methylphenyl)methanesulfonamide | 1c, 7, 8, 9, 10, 12a, 15c, 15d |
| 1.234 | (S)-N-(5-((3-(1H-indazol-5-ylamino)piperidin-1-yl)methyl)-2-methoxyphenyl)methanesulfonamide | 1c, 7, 8, 9, 10, 12a, 15c, 15d |
| 1.235 | (R)-N-(1-(3-(aminomethyl)benzyl)piperidin-3-yl)-1H-indazol-5-amine | 1c, 7, 8, 9, 10, 13, 16c |
| 1.236 | (S)-N-(5-((3-(1H-indazol-5-ylamino)piperidin-1-yl)methyl)-2-methylphenyl)butane-1-sulfonamide | 1c, 7, 8, 9, 10, 12a, 15c, 15d |
| 1.237 | (S)-N-(2-((3-(1H-indazol-5-ylamino)piperidin-1-yl)methyl)-5-methylphenyl)-N',N'-dimethylaminosulfamide | 1c, 7, 8, 9, 10, 12a, 15c, 15d |
| 1.238 | (S)-N-(5-((3-(1H-indazol-5-ylamino)piperidin-1-yl)methyl)-2-methylphenyl)propane-1-sulfonamide | 1c, 7, 8, 9, 10, 12a, 15c, 15d |

TABLE A-continued

Exemplified Compounds.

| Compound | Structure | Select Embodiments 1-16 |
|---|---|---|
| 1.239 | 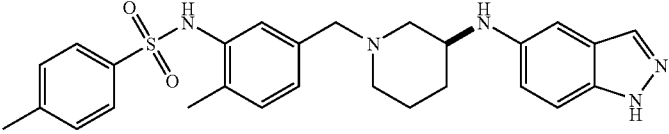<br>(S)-N-(5-((3-(1H-indazol-5-ylamino)piperidin-1-yl)methyl)-2-methylphenyl)-4-methylbenzenesulfonamide | 1c, 7, 8, 9, 10, 12a, 15c, 15d |
| 1.240 | 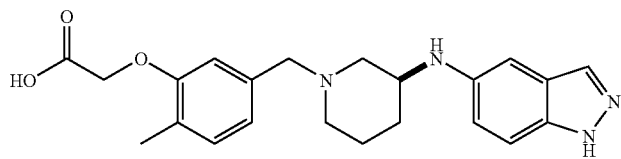<br>(S)-2-(5-((3-(1H-indazol-5-ylamino)piperidin-1-yl)methyl)-2-methylphenyl)-1H-indazol-5-ylamino)piperidin-1-yl)methyl)-2-methylphenoxy)acetic acid | 1c, 7, 8, 9, 10, 12a, 15c, 15d |
| 1.241 | 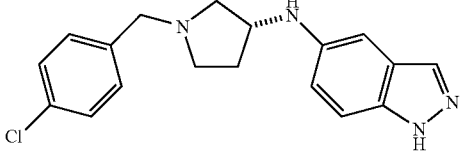<br>(R)-N-(1-(4-chlorobenzyl)pyrrolidin-3-yl)-1H-indazol-5-amine | 1c, 7, 8, 9, 10 |
| 1.242 | 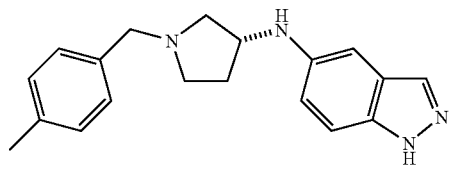<br>(R)-N-(1-(4-methylbenzyl)pyrrolidin-3-yl)-1H-indazol-5-amine | 1c, 7, 8, 9, 10 |
| 1.243 | 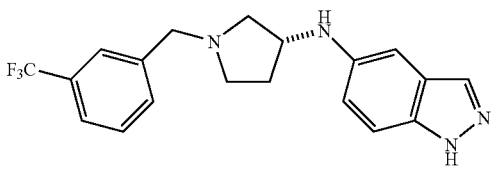<br>(R)-N-(1-(3-(trifluoromethyl)benzyl)pyrrolidin-3-yl)-1H-indazol-5-amine | 1c, 7, 8, 9, 10 |
| 1.244 | 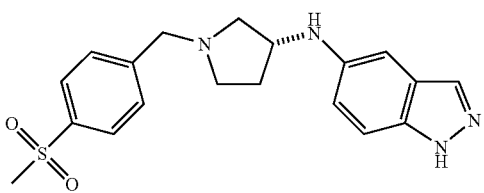<br>(R)-N-(1-(4-(methylsulfonyl)benzyl)pyrrolidin-3-yl)-1H-indazol-5-amine | 1c, 7, 8, 9, 10, 12b, 15c, 15e |

TABLE A-continued

Exemplified Compounds.

| Compound | Structure | Select Embodiments 1-16 |
|---|---|---|
| 1.245 | (R)-N-(1-(4-methoxybenzyl)pyrrolidin-3-yl)-1H-indazol-5-amine | 1c, 7, 8, 9, 10 |
| 1.246 | (R)-N-(1-((2,3-dihydrobenzofuran-5-yl)methyl)piperidin-3-yl)-1H-indazol-5-amine | 1c, 7, 8, 9, 10 |
| 1.247 | (R)-N-(1-(pyridin-4-ylmethyl)piperidin-3-yl)-1H-indazol-5-amine | 1c, 7, 8, 9, 10 |
| 1.248 | (R)-N-(1-(4-(pyrrolidin-1-yl)benzyl)piperidin-3-yl)-1H-indazol-5-amine | 1c, 7, 8, 9, 10, 11, 14c |
| 1.249 | (R)-3-((3-(1H-indazol-5-ylamino)piperidin-1-yl)methyl)benzenesulfonamide | 1c, 7, 8, 9, 10, 12b, 15c, 15e |
| 1.250 | (R)-N-(1-(3-(furan-2-yl)benzyl)piperidin-3-yl)-1H-indazol-5-amine | 1c, 7, 8, 9, 10, 11, 14c |

TABLE A-continued

Exemplified Compounds.

| Compound | Structure | Select Embodiments 1-16 |
|---|---|---|
| 1.251 | N-((3R)-1-(2-phenylpropyl)piperidin-3-yl)-1H-indazol-5-amine | 1c, 7, 8, 9 |
| 1.252 | (R)-N-(1-((1H-indol-3-yl)methyl)piperidin-3-yl)-1H-indazol-5-amine | 1c, 7, 8, 9, 10 |
| 1.253 | (S)-N-(5-((3-(1H-indazol-5-ylamino)piperidin-1-yl)methyl)-2-methylphenyl)ethanesulfonamide | 1c, 7, 8, 9, 10, 12a, 15c, 15d |
| 1.254 | (R)-N-(1-(3,4-dichlorobenzyl)pyrrolidin-3-yl)-1H-indazol-5-amine | 1c, 7, 8, 9, 10 |
| 1.255 | (S)-N-(1-(1H-imidazol-1-yl)benzyl)piperidin-3-yl)-1H-indazol-5-amine | 1c, 7, 8, 9, 10, 11, 14c |
| 1.256 | (S)-N-(1-((1H-imidazol-2-yl)methyl)piperidin-3-yl)-1H-indazol-5-amine | 1c, 7, 8, 9, 10 |
| 1.257 | (S)-N-(1-((1-methyl-1H-imidazol-2-yl)methyl)piperidin-3-yl)-1H-indazol-5-amine | 1c, 7, 8, 9, 10 |

TABLE A-continued

Exemplified Compounds.

| Compound | Structure | Select Embodiments 1-16 |
| --- | --- | --- |
| 1.258 | (R)-N-(5-((3-(1H-indazol-5-ylamino)piperidin-1-yl)methyl)-2-methylphenyl)methanesulfonamide | 1c, 7, 8, 9, 10, 12a, 15c, 15d |
| 1.259 | (R)-N-(5-((3-(1H-indazol-5-ylamino)piperidin-1-yl)methyl)-2-methylphenyl)ethanesulfonamide | 1c, 7, 8, 9, 10, 12a, 15c, 15d |
| 1.260 | (R)-N-(5-((3-(1H-indazol-5-ylamino)piperidin-1-yl)methyl)-2-methylphenyl)-4-methylbenzenesulfonamide | 1c, 7, 8, 9, 10, 12a, 15c, 15d |
| 1.261 | (S)-N-(3-((3-(1H-indazol-5-ylamino)piperidin-1-yl)methyl)phenyl)-N',N' dimethylaminosulfonamide | 1c, 7, 8, 9, 10, 12a, 15c, 15d |
| 1.262 | (R)-N-(2-((3-(1H-indazol-5-ylamino)piperidin-1-yl)methyl)-5-methylphenyl)-N',N' dimethylaminosulfamide | 1c, 7, 8, 9, 10, 12a, 15c, 15d |
| 1.263 | (R)-N-(1-((1-benzyl-1H-imidazol-2-yl)methyl)piperidin-3-yl)-1H-indazol-5-amine | 1c, 7, 8, 9, 10, 11, 14c |

TABLE A-continued

Exemplified Compounds.

| Compound | Structure | Select Embodiments 1-16 |
|---|---|---|
| 1.264 | (7-(((R)-3-(1H-indazol-5-ylamino)piperidin-1-yl)methyl)-2,3-dihydrobenzo[b][1,4]dioxin-2-yl)methanol | 1c, 7, 8, 9, 10, 13, 16c |
| 1.265 | (R)-1-(3-((3-(1H-indazol-5-ylamino)piperidin-1-yl)methyl)phenyl)-3-methylurea | 1c, 7, 8, 9, 10, 12a, 15c, 15d |
| 1.266 | (R)-N-(3-((3-(1H-indazol-5-ylamino)piperidin-1-yl)methyl)phenyl)pyrrolidine-1-carboxamide | 1c, 7, 8, 9, 10, 12a, 15c, 15d |
| 1.267 | (R)-3-(3-((3-(1H-indazol-5-ylamino)piperidin-1-yl)methyl)phenyl)-1,1-diethylurea | 1c, 7, 8, 9, 10, 12a, 15c, 15d |
| 1.268 | (R)-2-(5-((3-(1H-indazol-5-ylamino)piperidin-1-yl)methyl)-1H-indol-1-yl)ethanol | 1c, 7, 8, 9, 10, 13, 16c |
| 1.269 | (S)-2-(5-((3-(1H-indazol-5-ylamino)piperidin-1-yl)methyl)-1H-indol-1-yl)ethanol | 1c, 7, 8, 9, 10, 13, 16c |

TABLE A-continued

Exemplified Compounds.

| Compound | Structure | Select Embodiments 1-16 |
|---|---|---|
| 1.270 | (S)-N-(3-((3-(1H-indazol-5-ylamino)piperidin-1-yl)methyl)phenyl)piperidine-1-sulfonamide | 1c, 7, 8, 9, 10, 12a, 15c, 15d |
| 1.271 | (R)-N-(1-((1-benzyl-1H-indol-3-yl)methyl)piperidin-3-yl)-1H-indazol-5-amine | 1c, 7, 8, 9, 10, 11, 14c |
| 1.272 | (S)-N-(1-((1-(methylsulfonyl)-1,2,3,4-tetrahydroquinolin-6-yl)methyl)piperidin-3-yl)-1H-indazol-5-amine | 1c, 7, 8, 9, 10, 12b, 15c, 15e |
| 1.273 | (R)-2-(3-((3-(1H-indazol-5-ylamino)pipeeridin-1-yl)methyl)-1H-indol-1-yl)ethanol | 1c, 7, 8, 9, 10, 13, 16c |
| 1.274 | (S)-N-(3-((3-(1H-indazol-5-ylamino)piperidin-1-yl)methyl)-2-methylphenyl)methanesulfonamide | 1c, 7, 8, 9, 10, 12a, 15c, 15d |
| 1.275 | (S)-N-(3-((3-(1H-indazol-5-ylamino)piperidin-1-yl)methyl)-2-methylphenyl)-N',N' dimethylaminosulfonamide | 1c, 7, 8, 9, 10, 12a, 15c, 15d |

TABLE A-continued

Exemplified Compounds.

| Compound | Structure | Select Embodiments 1-16 |
|---|---|---|
| 1.276 | (R)-2-(5-((3-(1H-indazol-5-ylamino)pyrrolidin-1-yl)methyl)-2-methylphenyl-1H-indazol-5-ylamino)pyrrolidin-1-yl)methyl)-2-methylphenoxy)ethanol | 1c, 7, 8, 9, 10, 12a, 15c, 15d |
| 1.277 | (S)-N-(1-thiophen-3-ylmethyl)piperidin-3-yl)-1H-indazol-5-amine | 1c, 7, 8, 9, 10 |
| 1.278 | (S)-N-(1-(thiophen-2-ylmethyl)piperidin-3-yl)-1H-indazol-5-amine | 1c, 7, 8, 9, 10 |
| 1.279 | (S)-N-(1-((2,5-dimethyloxazol-4-yl)methyl)piperidin-3-yl)-1H-indazol-5-amine | 1c, 7, 8, 9, 10 |
| 1.280 | (S)-N-(3-((3-(1H-indazol-5-ylamino)piperidin-1-yl)methyl)-2-methoxyphenyl)methanesulfonamide | 1c, 7, 8, 9, 10, 12a, 15c, 15d |
| 1.281 | (R)-2-(5-((3-(1H-indazol-5-ylamino)piperidin-1-yl)methyl)-2-methylphenyl-1H-indazol-5-ylamino)piperidin-1-yl)methyl)-2-methylphenoxy)acetamide | 1c, 7, 8, 9, 10, 12a, 15c, 15d |

TABLE A-continued

Exemplified Compounds.

| Compound | Structure | Select Embodiments 1-16 |
|---|---|---|
| 1.282 | 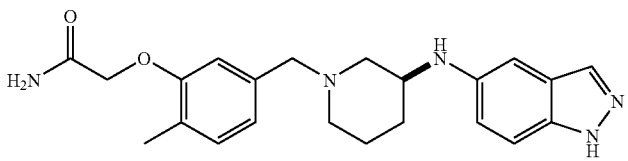<br>(S)-2-(5-((3-(1H-indazol-5-ylamino)piperidin-1-yl)methyl)-2-methylphenyl-1H-indazol-5-ylamino)piperidin-1-yl)methyl)-2-methylphenoxy)acetamide | 1c, 7, 8, 9, 10, 12a, 15c, 15d |
| 2.001 | 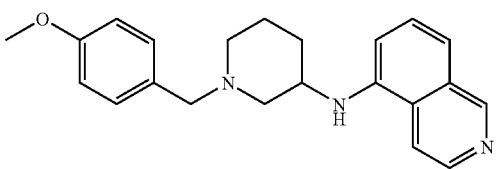<br>N-(1-(4-methoxybenzyl)piperidin-3-yl)isoquinolin-5-amine | 2c, 7, 8, 9, 10 |
| 2.002 | 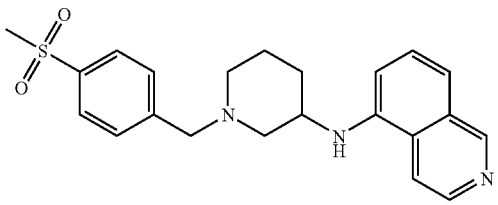<br>N-(1-(4-(methylsulfonyl)benzyl)piperidin-3-yl)isoquinolin-5-amine | 2c, 7, 8, 9, 10, 12, 15c |
| 2.003 | 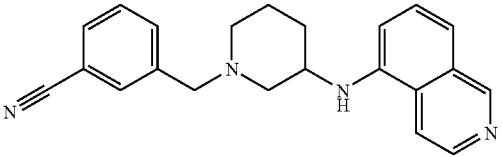<br>3-((3-(isoquinolin-5-ylamino)piperidin-1-yl)methyl)benzonitrile | 2c, 7, 8, 9, 10, 12, 15c |
| 2.004 | 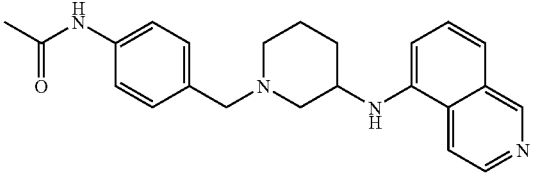<br>N-(4-((3-(isoquinolin-5-ylamino)piperidin-1-yl)methyl)phenyl)acetamide | 2c, 7, 8, 9, 10, 12a, 15c, 15d |
| 2.005 | 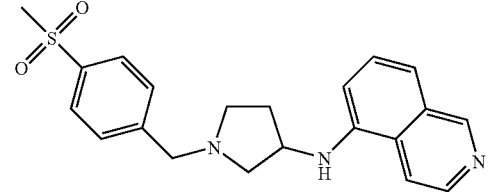<br>N-(1-(4-(methylsulfonyl)benzyl)pyrrolidin-3-yl)isoquinolin-5-amine | 2c, 7, 8, 9, 10, 12, 15c |

TABLE A-continued

Exemplified Compounds.

| Compound | Structure | Select Embodiments 1-16 |
|---|---|---|
| 2.006 | N-(1-benzylpyrrolidin-3-yl)isoquinolin-5-amine | 2c, 7, 8, 9, 10 |
| 2.007 | 3-((3-(isoquinolin-5-ylamino)pyrrolidin-1-yl)methyl)benzonitrile | 2c, 7, 8, 9, 10, 12, 15c |
| 2.008 | N-(4-((3-(isoquinolin-5-ylamino)pyrrolidin-1-yl)methyl)phenyl)acetamide | 2c, 7, 8, 9, 10, 12a, 15c, 15d |
| 2.009 | N-(1-(4-(methylthio)benzyl)piperidin-3-yl)isoquinolin-5-amine | 2c, 7, 8, 9, 10, 12b, 15c, 15e |
| 2.010 | N-(1-(4-cyclopropylbenzyl)piperidin-3-yl)isoquinolin-5-amine | 2c, 7, 8, 9, 10, 11, 14c |
| 2.011 | N-(1-(3-cyclopropylbenzyl)piperidin-3-yl)isoquinolin-5-amine | 2c, 7, 8, 9, 10, 11, 14c |

… TABLE A-continued

Exemplified Compounds.

| Compound | Structure | Select Embodiments 1-16 |
|---|---|---|
| 2.012 | N-(1-(4-cyclopropylthio)benzyl)piperidin-3-yl)isoquinolin-5-amine | 2c, 7, 8, 9, 10, 12b, 15c, 15e |
| 2.013 | N-(1-benzylazepan-4-yl)isoquinolin-5-amine | 2c, 7, 8, 9, 10 |
| 2.014 | N-(1-(3,4-dichlorobenzyl)piperidin-3-yl)isoquinolin-5-amine | 2c, 7, 8, 9, 10 |
| 2.015 | N-(1-(3-(trifluoromethyl)benzyl)piperidin-3-yl)isoquinolin-5-amine | 2c, 7, 8, 9, 10 |
| 2.016 | N-(1-(3,4-dichlorobenzyl)pyrrolidin-3-yl)isoquinolin-5-amine | 2c, 7, 8, 9, 10 |
| 2.017 | N-(1-(4-methoxybenzyl)pyrrolidin-3-yl)isoquinolin-5-amine | 2c, 7, 8, 9, 10 |

TABLE A-continued

| Compound | Structure | Select Embodiments 1-16 |
|---|---|---|
| 2.018 | 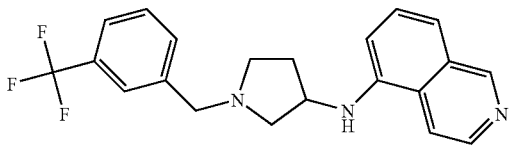<br>N-(1-(3-(trifluoromethyl)benzyl)pyrrolidin-3-yl)isoquinolin-5-amine | 2c, 7, 8, 9, 10 |
| 2.019 | 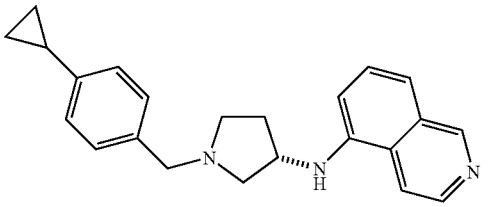<br>(S)-N-(1-(4-cyclopropylbenzyl)pyrrolidin-3-yl)isoquinolin-5-amine | 2c, 7, 8, 9, 10, 11, 14c |
| 2.020 | 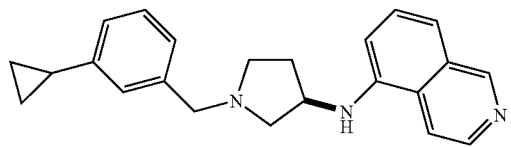<br>(R)-N-(1-(3-cyclopropylbenzyl)pyrrolidin-3-yl)isoquinolin-5-amine | 2c, 7, 8, 9, 10, 11, 14c |
| 2.021 | 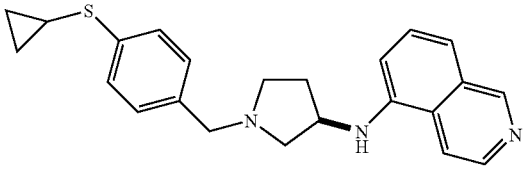<br>(R)-N-(1-(4-(cyclopropylthio)benzyl)pyrrolidin-3-yl)isoquinolin-5-amine | 2c, 7, 8, 9, 10, 12b, 15c, 15e |
| 2.022 | 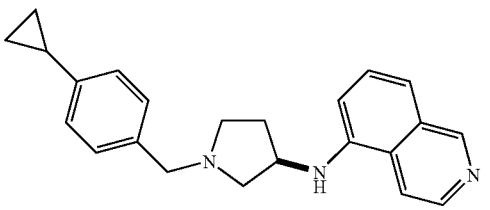<br>(R)-N-(1-(4-(cyclopropylbenzyl)pyrrolidin-3-yl)isoquinolin-5-amine | 2c, 7, 8, 9, 10, 11, 14c |
| 2.023 | 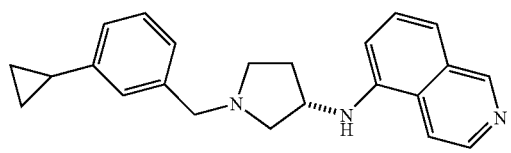<br>(S)-N-(1-(3-cyclopropylbenzyl)pyrrolidin-3-yl)isoquinolin-5-amine | 2c, 7, 8, 9, 10, 11, 14c |

TABLE A-continued

Exemplified Compounds.

| Compound | Structure | Select Embodiments 1-16 |
|---|---|---|
| 2.024 | (S)-N-(1-(4-(cyclopropylthio)benzyl)pyrrolidin-3-yl)isoquinolin-5-amine | 2c, 7, 8, 9, 10, 12b, 15c, 15e |
| 2.025 | (R)-N-(1-(4-methylbenzyl)pyrrolidin-3-yl)isoquinolin-5-amine | 2c, 7, 8, 9, 10 |
| 2.026 | (R)-N-(1-(4-(methylthio)benzyl)pyrrolidin-3-yl)isoquinolin-5-amine | 2c, 7, 8, 9, 10, 12b, 15c, 15e |
| 2.027 | (R)-N-(1-(4-chlorobenzyl)pyrrolidin-3-yl)isoquinolin-5-amine | 2c, 7, 8, 9, 10 |
| 2.028 | (S)-N-(1-(4-methylbenzyl)pyrrolidin-3-yl)isoquinolin-5-amine | 2c, 7, 8, 9, 10 |
| 2.029 | (S)-N-(1-(4-(methylthio)benzyl)pyrrolidin-3-yl)isoquinolin-5-amine | 2c, 7, 8, 9, 10, 12b, 15c, 15e |

TABLE A-continued

Exemplified Compounds.

| Compound | Structure | Select Embodiments 1-16 |
|---|---|---|
| 2.030 | 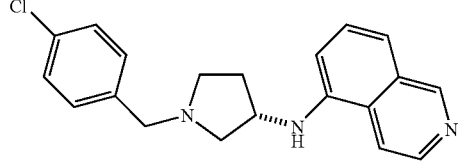<br>(S)-N-(1-(4-chlorobenzyl)pyrrolidin-3-yl)isoquinolin-5-amine | 2c, 7, 8, 9, 10 |
| 2.031 | 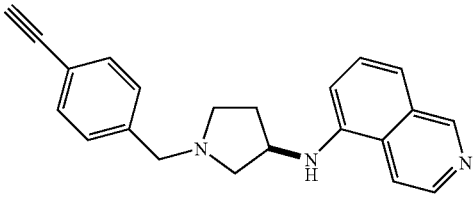<br>(R)-N-(1-(4-ethynylbenzyl)pyrrolidin-3-yl)isoquinolin-5-amine | 2c, 7, 8, 9, 10, 11, 14c |
| 2.032 | 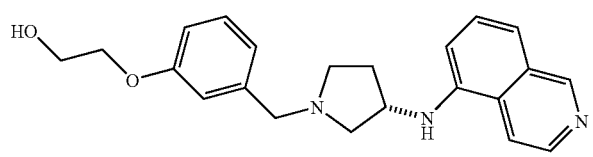<br>(S)-2-(3-((3-(isoquinolin-5-ylamino)pyrrolidin-1-yl)methyl)phenoxy)ethanol | 2c, 7, 8, 9, 10, 12a, 15c, 15d |
| 2.033 | 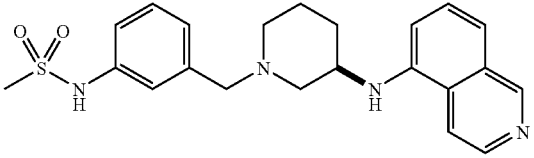<br>(R)-N-(3-((3-(isoquinolin-5-ylamino)piperidin-1-yl)methyl)phenyl)methanesulfonamide | 2c, 7, 8, 9, 10, 12a, 15c, 15d |
| 2.034 | 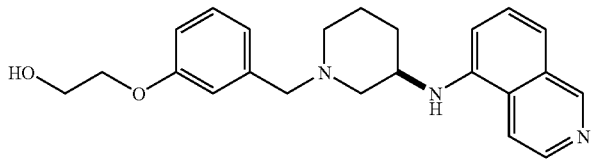<br>(R)-2-(3-((3-(isoquinolin-5-ylamino)piperidin-1-yl)methyl)phenoxy)ethanol | 2c, 7, 8, 9, 10, 12a, 15c, 15d |
| 2.035 | 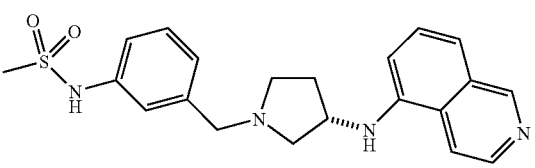<br>(S)-N-(3-((3-(isoquinolin-5-ylamino)pyrrolidin-1-yl)methyl)phenyl)methanesulfonamide | 2c, 7, 8, 9, 10, 12a, 15c, 15d |

TABLE A-continued

Exemplified Compounds.

| Compound | Structure | Select Embodiments 1-16 |
|---|---|---|
| 2.036 | 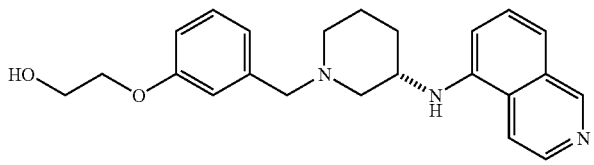<br>(S)-2-(3-((3-(isoquinolin-5-ylamino)piperidin-1-yl)methyl)phenoxy)ethanol | 2c, 7, 8, 9, 10, 12a, 15c, 15d |
| 2.037 | 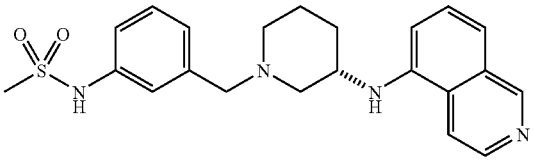<br>(S)-N-(3-((3-(isoquinolin-5-ylamino)piperidin-1-yl)methyl)phenyl)methanesulfonamide | 2c, 7, 8, 9, 10, 12a, 15c, 15d |
| 2.038 | 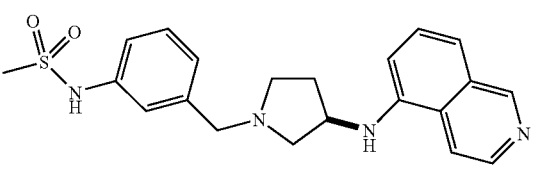<br>(R)-N-(3-((3-(isoquinolin-5-ylamino)pyrrolidin-1-yl)methyl)phenyl)methanesulfonamide | 2c, 7, 8, 9, 10, 12a, 15c, 15d |
| 2.039 | 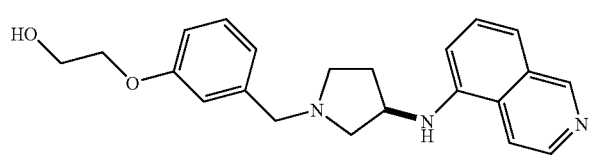<br>(R)-2-(3-((3-(isoquinolin-5-ylamino)pyrrolidin-1-yl)methyl)phenoxy)ethanol | 2c, 7, 8, 9, 10, 12a, 15c, 15d |
| 2.040 | 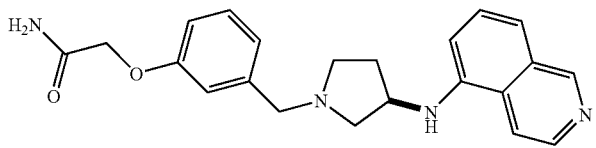<br>(R)-2-(3-((3-(isoquinolin-5-ylamino)pyrrolidin-1-yl)methyl)phenoxy)acetamide | 2c, 7, 8, 9, 10, 12a, 15c, 15d |
| 2.041 | 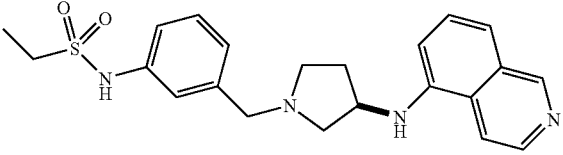<br>(R)-N-(3-((3-(isoquinolin-5-ylamino)pyrrolidin-1-yl)methyl)phenyl)ethanesulfonamide | 2c, 7, 8, 9, 10, 12a, 15c, 15d |
| 2.042 | 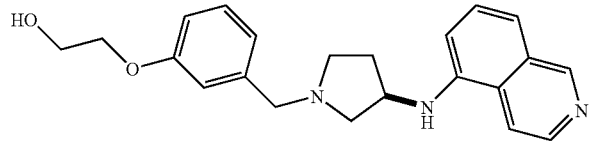<br>2-(3-((3-(isoquinolin-5-ylamino)pyrrolidin-1-yl)methyl)phenoxy)ethanol | 2c, 7, 8, 9, 10, 12a, 15c, 15d |

TABLE A-continued

Exemplified Compounds.

| Compound | Structure | Select Embodiments 1-16 |
|---|---|---|
| 2.043 | (R)-2-(3-((3-(isoquinolin-5-ylamino)pyrrolidin-1-yl)methyl)phenoxy)-1-morpholinoethanone | 2c, 7, 8, 9, 10, 12a, 15c, 15d |
| 2.044 | (R)-2-(3-((3-(isoqinolin-5-ylamino)pyrrolidin-1-yl)methyl)phenoxy)acetic acid | 2c, 7, 8, 9, 10, 12a, 15c, 15d |
| 2.045 | (S)-N-(1-(4-methylbenzyl)piperidin-3-yl)isoquinolin-5-amine | 2c, 7, 8, 9, 10 |
| 2.046 | (R)-N-(1-benzylpyrrolidin-3-yl)isoquinolin-5-amine | 2c, 7, 8, 9, 10 |
| 2.047 | (R)-N-(1-(4-methoxybenzyl)pyrrolidin-3-yl)isoquinolin-5-amine | 2c, 7, 8, 9, 10 |
| 2.048 | (R)-N-(1-(3,4-dichlorobenzyl)pyrrolidin-3-yl)isoquinolin-5-amine | 2c, 7, 8, 9, 10 |

TABLE A-continued

Exemplified Compounds.

| Compound | Structure | Select Embodiments 1-16 |
|---|---|---|
| 2.049 | (R)-N-(1-(3-(trifluoromethyl)benzyl)pyrrolidin-3-yl)isoquinolin-5-amine | 2c, 7, 8, 9, 10 |
| 2.050 | (S)-N-(1-benzylpiperidin-3-yl)isoquinolin-5-amine | 2c, 7, 8, 9, 10 |
| 2.051 | (S)-N-(1-(4-(methylthio)benzyl)piperidin-3-yl)isoquinolin-5-amine | 2c, 7, 8, 9, 10, 12b, 15c, 15e |
| 2.052 | (S)-N-(1-(4-chlorobenzyl)piperidin-3-yl)isoquinolin-5-amine | 2c, 7, 8, 9, 10 |
| 2.053 | (S)-N-(1-(4-methoxybenzyl)piperidin-3-yl)isoquinolin-5-amine | 2c, 7, 8, 9, 10 |
| 2.054 | (R)-N-(5-((3-(isoquinolin-5-ylamino)pyrrolidin-1-yl)methyl)-2-methylphenyl)ethanesulfonamide | 2c, 7, 8, 9, 10, 12a, 15c, 15d |

TABLE A-continued

Exemplified Compounds.

| Compound | Structure | Select Embodiments 1-16 |
|---|---|---|
| 2.055 | (R)-N-(1-(benzofuran-5-ylmethyl)pyrrolidin-3-yl)isoquinolin-5-amine | 2c, 7, 8, 9, 10 |
| 2.056 | (R)-N-(1-((2,3-dihydrobenzo[b][1,4]dioxin-6-yl)methyl)pyrrolidin-3-yl)isoquinolin-5-amine | 2c, 7, 8, 9, 10 |
| 2.057 | (R)-N-(1-((1H-indol-6-yl)methyl)pyrrolidin-3-yl)isoquinolin-5-amine | 2c, 7, 8, 9, 10 |
| 2.058 | (R)-2-(6-((3-(isoquinolin-5-ylamino)pyrrolidin-1-yl)methyl)-1H-indol-1-yl)acetamide | 2c, 7, 8, 9, 10, 13, 16c |
| 2.059 | (R)-2-(5-((3-(isoquinolin-5-ylamino)pyrrolidin-1-yl)methyl)-1H-indol-1-yl)acetamide | 2c, 7, 8, 9, 10, 13, 16c |
| 2.060 | (R)-2-(6-((3-(isoquinolin-5-ylamino)pyrrolidin-1-yl)methyl)-1H-indol-1-yl)ethanol | 2c, 7, 8, 9, 10, 13, 16c |

TABLE A-continued

Exemplified Compounds.

| Compound | Structure | Select Embodiments 1-16 |
| --- | --- | --- |
| 2.061 | (R)-3-((3-(isoquinolin-5-ylamino)pyrrolidin-1-yl)methyl)phenol | 2c, 7, 8, 9, 10 |
| 2.062 | (R)-N-(1-(3,4-difluorobenzyl)pyrrolidin-3-yl)isoquinolin-5-amine | 2c, 7, 8, 9, 10 |
| 2.063 | (R)-N-(3-((3-(isoquinolin-5-ylamino)pyrrolidin-1-yl)methyl)benzyl)acetamide | 2c, 7, 8, 9, 10, 13, 16c |
| 2.064 | (R)-2-(5-((3-(isoquinolin-5-ylamino)pyrrolidin-1-yl)methyl)-2-methylphenoxy)ethanol | 2c, 7, 8, 9, 10, 12a, 15c, 15d |
| 2.065 | (R)-N-(1-((1H-indol-5-yl)methyl)pyrrolidin-3-yl)isoquinolin-5-amine | 2c, 7, 8, 9, 10 |
| 2.066 | (R)-2-(5-((3-(isoquinolin-5-ylamino)pyrrolidin-1-yl)methyl)-1H-indol-1-yl)ethanol | 2c, 7, 8, 9, 10, 13, 16c |

TABLE A-continued

Exemplified Compounds.

| Compound | Structure | Select Embodiments 1-16 |
|---|---|---|
| 2.067 | 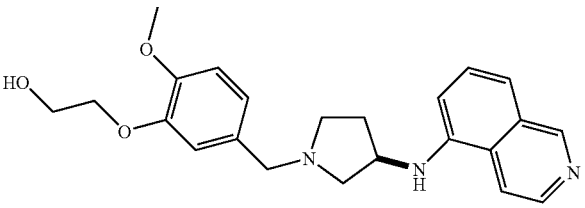(R)-2-(5-((3-(isoquinolin-5-ylamino)pyrrolidin-1-yl)methyl)-2-methoxyphenoxy)ethanol | 2c, 7, 8, 9, 10, 12a, 15c, 15d |
| 2.068 | 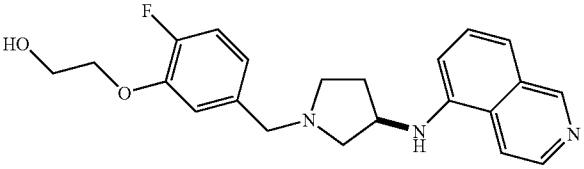(R)-2-(2-fluoro-5-((3-(isoquinolin-5-ylamino)pyrrolidin-1-yl)methyl)phenoxy)ethanol | 2c, 7, 8, 9, 10, 12a, 15c, 15d |
| 2.069 | 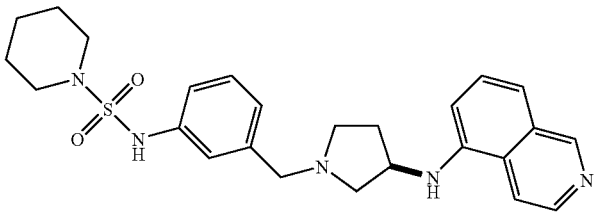(R)-N-(3-((3-(isoquinolin-5-ylamino)pyrrolidin-1-yl)methyl)phenyl)piperidine-1-sulfonamide | 2c, 7, 8, 9, 10, 12a, 15c, 15d |
| 2.070 | 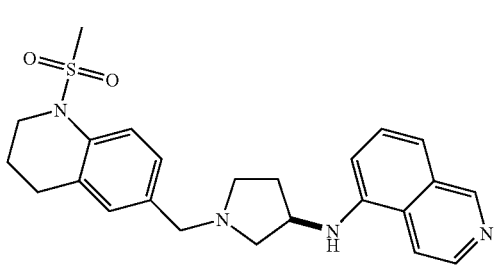(R)-N-(1-((1-(methylsulfonyl)-1,2,3,4-tertahydroquinolin-6-yl)methyl)pyrrolidin-3-yl)isoquinolin-5-amine | 2c, 7, 8, 9, 10, 12b, 15c, 15e |
| 2.071 | 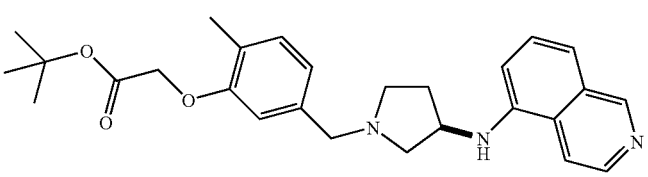(R)-tert-butyl 2-(5-((3-(isoquinolin-5-ylamino)pyrrolidin-1-yl)methyl)-2-methylphenoxy)acetate | 2c, 7, 8, 9, 10, 12a, 15c, 15d |

TABLE A-continued

Exemplified Compounds.

| Compound | Structure | Select Embodiments 1-16 |
|---|---|---|
| 2.072 | 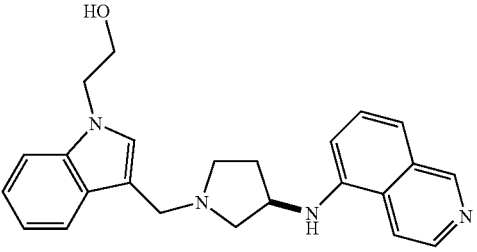<br>(R)-2-(3-((3-(isoquinolin-5-ylamino)pyrrolidin-1-yl)methyl)-1H-indol-1-yl)ethanol | 2c, 7, 8, 9, 10, 13, 16c |
| 2.073 | 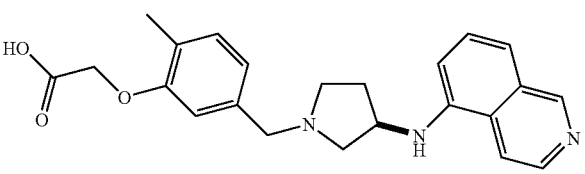<br>(R)-2-(5-((3-(isoquinolin-5-ylamino)pyrrolidin-1-yl)methyl)-2-methylphenoxy)acetic acid | 2c, 7, 8, 9, 10, 12a, 15c, 15d |
| 2.074 | 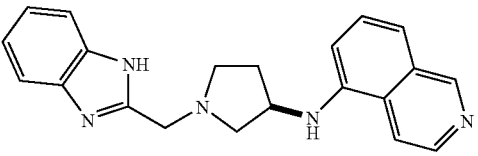<br>(R)-N-(1-((1H-benzo[d]imidazol-2-yl)methyl)pyrrolidin-3-yl)isoquinolin-5-amine | 2c, 7, 8, 9, 10 |
| 2.075 | 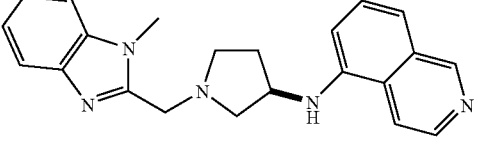<br>(R)-N-(1-((1-methyl-1H-benzo[d]imidazol-2-yl)methyl)pyrrolidin-3-yl)isoquinolin-5-amine | 2c, 7, 8, 9, 10 |
| 2.076 | 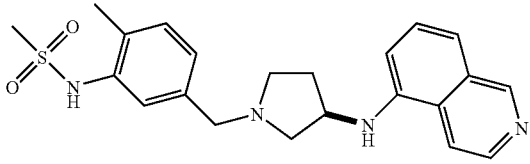<br>(R)-N-(5-((3-(isoquinolin-5-ylamino)pyrrolidin-1-yl)methyl)-2-methylphenyl)methanesulfonamide | 2c, 7, 8, 9, 10, 12a, 15c, 15d |
| 2.077 | 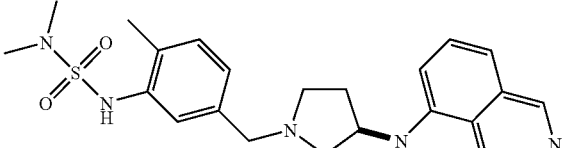<br>(R)-N-(5-((3-(isoquinolin-5-ylamino)pyrrolidin-1-yl)methyl)-2-methylphenyl)-N',N'-dimethylaminosulfonamide | 2c, 7, 8, 9, 10, 12a, 15c, 15d |

TABLE A-continued

Exemplified Compounds.

| Compound | Structure | Select Embodiments 1-16 |
|---|---|---|
| 2.078 | (R)-N-(3-((3-(isoquinolin-5-ylamino)pyrrolidin-1-yl)methyl)-2-methylphenyl)methanesulfonamide | 2c, 7, 8, 9, 10, 12a, 15c, 15d |
| 2.079 | (R)-N-(3-((3-(isoquinolin-5-ylamino)pyrrolidin-1-yl)methyl)-2-methylphenyl)-N',N'-dimethylaminosulfonamide | 2c, 7, 8, 9, 10, 12a, 15c, 15d |
| 2.080 | (R)-5-(1-(3-(2-hydroxyethoxy)-4-methylbenzyl)pyrrolidin-3-ylamino)isoquinoline 2-oxide | 2b, 6b, 8, 9, 10, 12a, 15b, 15d |
| 2.081 | (R)-5-(1-(3-(2-hydroxyethoxy)benzyl)pyrrolidin-3-ylamino)isoquinoline 2-oxide | 2b, 6b, 8, 9, 10, 12a, 15b, 15d |
| 2.082 | (R)-N-(1-((2-(methylthio)pyrimidin-4-yl)methyl)pyrrolidin-3-yl)isoquinolin-5-amine | 2c, 7, 8, 9, 10, 12b, 15c, 15e |
| 2.083 | (R)-N-(1-(pyrimidin-4-ylmethyl)pyrrolidin-3-yl)isoquinolin-5-amine | 2c, 7, 8, 9, 10 |

TABLE A-continued

Exemplified Compounds.

| Compound | Structure | Select Embodiments 1-16 |
|---|---|---|
| 2.084 | (R)-N-(1-(pyrimidin-5-ylmethyl)pyrrolidin-3-yl)isoquinolin-5-amine | 2c, 7, 8, 9, 10 |
| 2.085 | (R)-N-(1-(pyrimidin-2-ylmethyl)pyrrolidin-3-yl)isoquinolin-5-amine | 2c, 7, 8, 9, 10 |
| 2.086 | (R)-N-(1-(pyrazin-2-ylmethyl)pyrrolidin-3-yl)isoquinolin-5-amine | 2c, 7, 8, 9, 10 |
| 2.087 | (R)-2-((3-(isoquinolin-5-ylamino)pyrrolidin-1-yl)methyl)-1H-benzo[d]imidazole-6-sulfonamide | 2c, 7, 8, 9, 10, 12b, 15c, 15e |
| 2.088 | (R)-N-(1-thiophen-3-ylmethyl)pyrrolidin-3-yl)isoquinolin-5-amine | 2c, 7, 8, 9, 10 |
| 2.089 | (R)-N-(1-((5-nitrothiophen-3-yl)methyl)pyrrolidin-3-yl)isoquinolin-5-amine | 2c, 7, 8, 9, 10 |
| 2.090 | (R)-N-(1-thiophen-2-ylmethyl)pyrrolidin-3-yl)isoquinolin-5-amine | 2c, 7, 8, 9, 10 |

TABLE A-continued

Exemplified Compounds.

| Compound | Structure | Select Embodiments 1-16 |
|---|---|---|
| 2.091 | 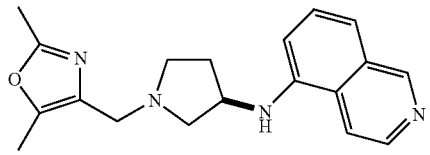<br>(R)-N-(1-((2,5-dimethyloxazol-4-yl)methyl)pyrrolidin-3-yl)isoquinolin-5-amine | 2c, 7, 8, 9, 10 |
| 2.092 | 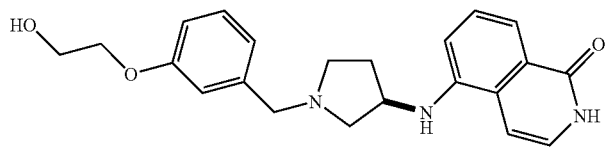<br>(R)-5-(1-(3-(2-hydroxyethoxy)benzyl)pyrrolidin-3-ylamino)isoquinoline-1(2H)-one | 2b, 6b, 8, 9, 10, 12a, 15b, 15d |
| 2.093 | 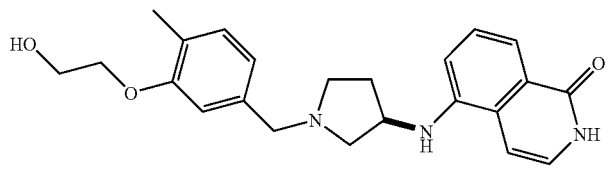<br>(R)-5-(1-(3-(2-hydroxyethoxy)-4-methylbenzyl)pyrrolidin-3-ylamino)isoquinolin-1(2H)-one | 2b, 6b, 8, 9, 10, 12a, 15b, 15d |
| 2.094 | 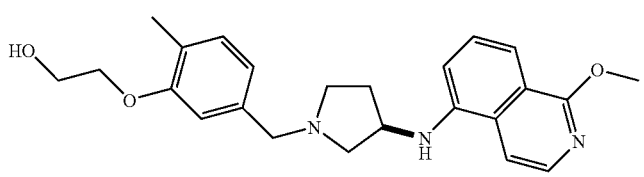<br>(R)-2-(5-((3-(1-methoxyisoquinolin-5-ylamino)pyrrolidin-1-yl)methyl)-2-methylphenoxy)ethanol | 2b, 6b, 8, 9, 10, 12a, 15b, 15d |
| 2.095 | 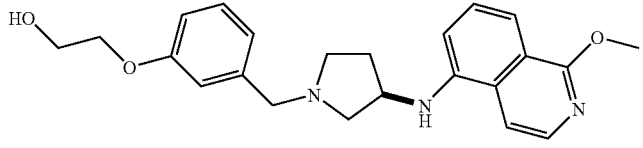<br>(R)-2-(3-((3-(1-methoxyisoquinolin-5-ylamino)pyrrolidin-1-yl)methyl)phenoxy)ethanol | 2b, 6b, 8, 9, 10, 12a, 15b, 15d |
| 2.096 | 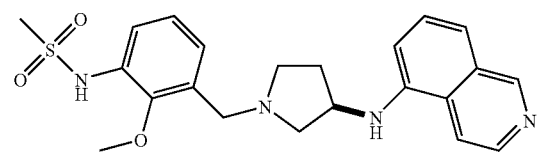<br>(R)-N-(3-((3-(isoquinolin-5-ylamino)pyrrolidin-1-yl)methyl)-2-methoxyphenyl)methanesulfonamide | 2c, 7, 8, 9, 10, 12a, 15c, 15d |

TABLE A-continued

Exemplified Compounds.

| Compound | Structure | Select Embodiments 1-16 |
|---|---|---|
| 2.097 | (R)-N-(3-((3-(isoquinolin-5-ylamino)pyrrolidin-1-yl)methyl)-2-methoxyphenyl)-N',N'-dimethylaminosulfonamide | 2c, 7, 8, 9, 10, 12a, 15c, 15d |
| 2.098 | (R)-N-(5-((3-(isoquinolin-5-ylamino)pyrrolidin-1-yl)methyl)-2-methoxyphenyl)methanesulfonamide | 2c, 7, 8, 9, 10, 12a, 15c, 15d |
| 2.099 | (R)-2-(5-((3-(isoquinolin-5-ylamino)pyrrolidin-1-yl)methyl)-2-methylphenoxy)acetamide | 2c, 7, 8, 9, 10, 12a, 15c, 15d |
| 2.100 | (R)-2-(2-((3-(isoquinolin-5-ylamino)pyrrolidin-1-yl)methyl)-1H-benzo[d]imidazol-6-yloxy)ethanol | 2c, 7, 8, 9, 10, 12a, 15c, 15d |
| 3.001 | N-(1-benzylpiperidin-3-yl)pyridin-4-amine | 3c, 7, 8, 9, 10 |
| 3.002 | N-(1-benzylpyrrolidin-3-yl)pyridin-4-amine | 3c, 7, 8, 9, 10 |
| 4.001 | N-(1-benzylpiperidin-3-yl)-1H-pyrrolo[2,3-b]pyridin-4-amine | 4c, 7, 8, 9, 10 |

TABLE A-continued

Exemplified Compounds.

| Compound | Structure | Select Embodiments 1-16 |
|---|---|---|
| 4.002 | N-(1-benzylpyrrolidin-3-yl)-1H-pyrrolo[2,3-b]pyridin-4-amine | 4c, 7, 8, 9, 10 |
| 5.001 | 4-(4-(1-benzylpiperidin-3-ylamino)phenyl)-1,2,5-oxadiazol-3-amine | 5a, 7, 8, 9, 10 |
| 5.002 | 4-(4-(1-benzylpyrrolidin-3-ylamino)phenyl)-1,2,5-oxadiazol-3-amine | 5a, 7, 8, 9, 10 |

Preferred ROCK inhibitor compounds of this invention include, but are not limited to the ROCK inhibitor compounds of embodiments 5, 14, 15, 16, 17, 18, 19, 20, and 21 as described above, and their associated salts, tautomers, solvates, or hydrates. In particular, preferred Compounds include 1.074, 1.075, 1.076, 1.077, 1.079, 1.091, 1.093, 1.108, 1.109, 1.123, 1.124, 1.126, 1.131, 1.132, 1.133, 1.134, 1.135, 1.136, 1.137, 1.138, 1.141, 1.148, 1.149, 1.150, 1.152, 1.153, 1.155, 1.156, 1.157, 1.158, 1.161, 1.162, 1.163, 1.164, 1.165, 1.166, 1.171, 1.173, 1.175, 1.176, 1.186, 1.193, 1.195, 1.197, 1.200, 1.206, 1.212, 1.213, 1.215, 1.217, 1.219, 1.223, 1.233, 1.236, 1.237, 1.238, 1.239, 1.249, 1.252, 1.253, 1.258, 1.259, 1.260, 1.261, 1.262, 1.270, 1.273, 1.275, 1.277, 1.281, 2.025, 2.026, 2.031, 2.038, 2.039, 2.041, 2.046, 2.047, 2.054, 2.055, 2.057, 2.058, 2.059, 2.060, 2.061, 2.064, 2.065, 2.066, 2.067, 2.068, 2.069, 2.072, 2.073, 2.076, 2.077, 2.078, 2.079, 2.082, 2.096, 2.097, and 2.099.

Pharmaceutical Formulations

The present invention provides a pharmaceutical formulation comprising compounds of Formula I or II and a pharmaceutically acceptable carrier. Pharmaceutically acceptable carriers can be selected by those skilled in the art using conventional criteria. Pharmaceutically acceptable carriers include, but are not limited to, saline solution, aqueous electrolyte solutions, isotonicity modifiers, water polyethers such as polyethylene glycol, polyvinyls such as polyvinyl alcohol and povidone, cellulose derivatives such as methylcellulose and hydroxypropyl methylcellulose, polymers of acrylic acid such as carboxypolymethylene gel, polysaccharides such as dextrans, and glycosaminoglycans such as sodium hyaluronate and salts such as sodium chloride and potassium chloride.

The pharmaceutical formulation useful for the present invention in general is an aqueous solution comprising water, suitable ionic or non-ionic tonicity modifiers, suitable buffering agents, and a compound of Formula I or II. In one embodiment, the compound is at 0.005 to 3% w/v, and the aqueous solution has a tonicity of 200-400 mOsm/kG and a pH of 4-9.

In one embodiment, the tonicity modifier is ionic such as NaCl, for example, in the amount of 0.5-0.9% w/v, preferably 0.6-0.9% w/v.

In another embodiment, the tonicity modifier is non-ionic, such as mannitol, dextrose, in the amount of at least 2%, or at least 2.5%, or at least 3%, and no more than 7.5%; for example, in the range of 3-5%, preferably 4-5% w/v.

The pharmaceutical formulation can be sterilized by filtering the formulation through a sterilizing grade filter, preferably of a 0.22-micron nominal pore size. The pharmaceutical formulation can also be sterilized by terminal sterilization using one or more sterilization techniques including but not limited to a thermal process, such as an autoclaving process, or a radiation sterilization process, or using pulsed light to produce a sterile formulation. In one embodiment, the pharmaceutical formulation is a concentrated solution of the active ingredient; the formulation can be serially diluted using appropriate acceptable sterile diluents prior to administration.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol.

Sweetening agents such as those set forth above, and flavoring agents can be added to provide palatable oral preparations. These compositions can be preserved by the addition of an anti-oxidant such as ascorbic acid.

Pharmaceutical compositions of the invention can be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions can also contain sweetening and flavoring agents.

Pharmaceutical compositions of the invention can be in the form of an aerosol suspension of respirable particles comprising the active compound, which the subject inhales. The respirable particles can be liquid or solid, with a particle size sufficiently small to pass through the mouth and larynx upon inhalation. In general, particles having a size of about 1 to 10 microns, preferably 1-5 microns, are considered respirable.

The pharmaceutical formulation for systemic administration such as injection and infusion is generally prepared in a sterile medium. The active ingredient, depending on the vehicle and concentration used, can either be suspended or dissolved in the vehicle. Adjuvants such as local anesthetics, preservatives and buffering agents can also be dissolved in the vehicle. The sterile injectable preparation can be a sterile injectable solution or suspension in a non-toxic acceptable diluent or solvent. Among the acceptable vehicles and solvents that can be employed are sterile water, saline solution, or Ringer's solution.

The pharmaceutical compositions for oral administration contain active compounds in the form of tablets, lozenges, aqueous or oily suspensions, viscous gels, chewable gums, dispersible powders or granules, emulsion, hard or soft capsules, or syrups or elixirs.

For oral use, an aqueous suspension is prepared by addition of water to dispersible powders and granules with a dispersing or wetting agent, suspending agent, one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anhydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use can also be presented as chewable gums by embedding the active ingredient in gums so that the active ingredient is slowly released upon chewing.

The pharmaceutical compositions can be in the form of suppositories, which are prepared by mixing the active ingredient with a suitable non-irritating excipient that is solid at ordinary temperatures but liquid at the rectal temperature and will thus melt in the rectum to release the compound. Such excipients include cocoa butter and polyethylene glycols.

Method of Treating Pulmonary Diseases Using Rho Kinase Inhibitor Compounds

The present invention is useful in treating diseases associated with excessive cell proliferation, tissue remodeling, inflammation, pulmonary edema, vasoconstriction, pulmonary artery constriction, bronchoconstriction and airway hyperreactivity. The present invention is effective in treating a pulmonary disease selected from the group consisting of asthma; chronic obstructive pulmonary disease; respiratory tract illness caused by respiratory syncytial virus; pulmonary arterial hypertension; acute respiratory distress syndrome and ventilator induced lung injury; cystic fibrosis; bronchiectasis; alpha-1-antitrypsin deficiency; rhinitis; rhinosinusitis; primary ciliary dyskinesia; pneumonia; bronchiolitis caused by agents other than respiratory syncytial virus; and interstitial lung diseases including lymphangioleiomyomatosis; idiopathic pulmonary fibrosis; obliterative bronchiolitis or bronchiolitis obliterans organizing pneumonia due to lung transplantation or HSCT; nonspecific interstitial pneumonia; cryptogenic organizing pneumonia; acute interstitial pneumonia; respiratory bronchiolitis-associated interstitial lung disease; desquamative interstitial pneumonia; and lymphocytic interstitial pneumonia; and pulmonary sarcoidosis.

Asthma

The inventors have discovered that Compounds of Formula I or II inhibit the ROCK-mediated regulation of chemotaxis, cytokinesis, cytokine and chemokine secretion, proliferation, cell motility, endothelial integrity and/or smooth muscle contraction. Furthermore, the inventors have discovered that Compounds of Formula I or II are useful in treating the defects in inflammation, pulmonary neutrophilia and eosinophilia, excessive cell proliferation, remodeling, airway and/or lung tissue edema, airway hyperreactivity or bronchoconstriction as well as preventing the development of airway hyperreactivity seen in asthma. The inventors have discovered that Compounds of Formula I or II maintain efficacy as bronchodilators under conditions of inflammation. The inventors have also discovered that local administration of Compounds of Formula I or II to the lung is sufficient to treat the pathophysiologies associated with asthma, especially the treatment of bronchoconstriction, inflammation and airway hyperreactivity as well as the prevention of the development of airway hyperreactivity.

The present invention is directed to a method of treating asthma. The method comprises the steps of first identifying a subject suffering from asthma, then administering to the subject an effective amount of a compound of Formula I or II to treat asthma.

A method for treating asthma is based on the properties of the Formula I or II compounds to reduce at least one of the following processes contributing to pathophysiologies that accompany this disorder: inflammation, excessive cell proliferation, remodeling, airway and/or lung tissue edema, airway hyperreactivity or bronchoconstriction.

Indicia of efficacy for treating asthma by the present method include demonstrable improvement in measurable signs, symptoms and other variables clinically relevant to asthma. Such improvements include increased blood oxygen saturation, decreased hypoxia and hypercapnia, decreased need for supplemental oxygen, decreased frequency of coughing and/or wheezing, improved forced expiratory volume ($FEV_1$), forced vital capacity (FVC) or other physiologically relevant parameter of respiratory function, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method such as amount of epithelial lining fluid, wet to dry lung weight, alveolar fluid clearance and/or radiographic visualization methods, increase in general quality of life, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing, or severity of coughing and/or wheezing.

COPD

The inventors have discovered that Compounds of Formula I or II are useful in treating the defects in inflammation, pulmonary neutrophilia and eosinophilia, excessive cell proliferation, remodeling, airway and/or lung tissue edema, airway hyperreactivity or bronchoconstriction as well as preventing the development of airway hyperreactivity seen in COPD. The inventors have also discovered that local administration of Compounds of Formula I or II to the lung is sufficient to treat the pathophysiologies associated with COPD, especially the treatment of bronchoconstriction, inflammation, neutrophilia and airway hyperreactivity as well as the prevention of the development of airway hyperreactivity. The inventors have discovered that Compounds of Formula I or II maintain efficacy as bronchodilators under conditions of inflammation seen in COPD.

The present invention is directed to a method of treating COPD. The method comprises the steps of first identifying a subject suffering from COPD, then administering to the subject an effective amount of a compound of Formula I or II to treat COPD.

A method for treating COPD is based on the properties of the Formula I or II compounds to reduce at least one of the following processes contributing to pathophysiologies that accompany this disorder: inflammation, pulmonary neutrophilia, excessive cell proliferation, remodeling, airway and/or lung tissue edema, airway hyperreactivity or bronchoconstriction.

Indicia of efficacy for treating COPD by the present method include demonstrable improvement in measurable signs, symptoms and other variables clinically relevant to COPD. Such improvements include decreased frequency of exacerbations, increased blood oxygen saturation, decreased hypoxia and hypercapnia, decreased need for supplemental oxygen, decreased frequency of coughing and/or wheezing, improved forced expiratory volume ($FEV_1$), forced vital capacity (FVC) or other physiologically relevant parameter of respiratory function, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method such as amount of epithelial lining fluid, wet to dry lung weight, alveolar fluid clearance or radiographic visualization methods, increase in general quality of life, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing, or severity of coughing and/or wheezing.

RSV Infection

The inventors have discovered that Compounds of Formula I or II inhibit the ROCK-mediated regulation of chemotaxis, cytokinesis, cytokine and chemokine secretion, endothelial cell integrity and smooth muscle contraction. Further, the inventors have discovered that Compounds of Formula I or II are useful in treating the inflammation, pulmonary neutrophilia, airway and/or lung tissue edema, remodeling, airway hyperreactivity or bronchoconstriction as well as preventing the development of airway hyperreactivity seen during RSV infection. The inventors have also discovered that local administration of Compounds of Formula I or II to the lung is sufficient to treat the pathophysiologies associated with RSV infection, especially the treatment of bronchoconstriction, inflammation and airway hyperreactivity as well the prevention of the development of airway hyperreactivity. The inventors have discovered that Compounds of Formula I or II maintain efficacy as bronchodilators under conditions of inflammation seen in RSV infection.

The present invention is directed to a method of treating respiratory illness caused by RSV infection. The method comprises the steps of first identifying a subject suffering from respiratory illness caused by RSV infection, then administering to the subject an effective amount of a compound of Formula I or II to treat said respiratory illness.

A method for treating respiratory problems stemming from RSV infection is based on the properties of the Formula I or II compounds to reduce at least one of the following processes contributing to pathophysiologies that accompany this disorder: inflammation, pulmonary neutrophilia, airway and/or lung tissue edema, remodeling, airway hyperreactivity or bronchoconstriction.

Indicia of efficacy for treating respiratory illness caused by RSV infection by the present method include demonstrable improvement in measurable signs, symptoms and other variables clinically relevant to RSV infection. Such improvements include decreased viral load in the lung tissue, sputum or bronchoalveolar lavage fluid, increased blood oxygen saturation, decreased hypoxia and hypercapnia, decreased need for supplemental oxygen, decreased frequency of coughing and/or wheezing, improved forced expiratory volume ($FEV_1$), forced vital capacity (FVC) or other physiologically relevant parameter of respiratory function, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method such as amount of epithelial lining fluid, wet to dry lung weight, alveolar fluid clearance or radiographic visualization methods, increase in general quality of life, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing, or severity of coughing and/or wheezing.

PAH

The inventors have discovered that Compounds of Formula I or II are useful in treating vascular growth, smooth muscle cell proliferation, remodeling, vasoreactivity, vasoconstriction or inflammation seen in PAH.

The present invention is directed to a method of treating PAH. The method comprises the steps of first identifying a subject suffering from PAH, and then administering to the subject an effective amount of a compound of Formula I or II to treat PAH.

A method of treating PAH is based on the properties of the Formula I or II compounds to reduce at least one of the following processes contributing to pathophysiologies that accompany this disorder: vascular growth, smooth muscle cell proliferation, remodeling, vasoreactivity, vasoconstriction or inflammation.

Indicia of efficacy for treating pulmonary arterial hypertension by the present method include demonstrable improvement in measurable signs, symptoms and other variables clinically relevant to PAH. Such improvements include reversing, stopping or slowing down of the pathological remodeling of the pulmonary vasculature, reversing, stopping or slowing down the hypertrophy of the right ventricle, decreasing the pulmonary arterial pressure, increasing cardiac output, improvement in cardiac patient class status, increased blood oxygen saturation, decreased hypoxia and hypercapnia, decreased need for supplemental oxygen, improved distance walked during the 6 minute walk test, decreased need for mechanical ventilation, lower amount of inflammatory cells infiltrating the lung, lower levels of proinflammatory cytokines and chemokines, decreased pulmonary edema as determined by any radiographic or other detection method such as amount of epithelial lining fluid, wet to dry lung weight, alveolar fluid clearance or radiographic visualization methods, increase in general quality of life, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, patient-reported or physician-observed signs such as ease of breathing, or severity of coughing and/or wheezing.

LAM

The inventors have discovered that Compounds of Formula I or II are useful in treating excessive smooth muscle cell proliferation, smooth muscle cell migration, remodeling, lung tissue edema or bronchoconstriction seen in LAM. The inventors have also discovered that Compounds of Formula I or II inhibit the proliferation of primary LAM derived cells from human patients. The inventors have also discovered that local administration of Compounds of Formula I or II to the lung is sufficient to treat the pathophysiologies associated with LAM, especially bronchoconstriction.

The present invention is directed to a method of treating LAM. The method comprises the steps of first identifying a subject suffering from LAM, and then administering to the subject an effective amount of a compound of Formula I or II to treat LAM.

A method for treating LAM is based on the properties of the Formula I or II compounds to reduce at least one of the following processes contributing to pathophysiologies that accompany this disorder: excessive smooth muscle cell proliferation, smooth muscle cell migration, remodeling, lung tissue edema or bronchoconstriction.

Indicia of efficacy for treating LAM by the present method include demonstrable improvement in measurable signs, symptoms and other variables clinically relevant to LAM. Such improvements include decreased frequency of pneumothorax, decrease frequency of pulmonary bleeding, increased blood oxygen saturation, decreased hypoxia and hypercapnia, decreased need for supplemental oxygen, decreased frequency of coughing and/or wheezing, improved forced expiratory volume ($FEV_1$), forced vital capacity (FVC) or other physiologically relevant parameter of respiratory function, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method such as amount of epithelial lining fluid, wet to dry lung weight, alveolar fluid clearance or radiographic visualization methods, increase in general quality of life, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing, angiomyolipoma volume reduction or severity of coughing and/or wheezing.

IPF

The inventors have discovered that Compounds of Formula I or II are useful in treating inflammation, pulmonary neutrophilia, fibrosis, excessive cell proliferation, remodeling, lung tissue edema, airway hyperreactivity, bronchoconstriction or decline in lung function as well as preventing the development of airway hyperreactivity seen in IPF The inventors have also discovered that local administration of Compounds of Formula I or II to the lung is sufficient to treat the pathophysiologies associated with IPF, especially the treatment of bronchoconstriction, inflammation and airway hyperreactivity as well as the prevention of the development of airway hyperreactivity. The inventors have discovered that Compounds of Formula I or II maintain efficacy as bronchodilators under conditions of inflammation seen in IPF.

The present invention is directed to a method of treating IPF. The method comprises the steps of first identifying a subject suffering from IPF, and then administering to the subject an effective amount of a compound of Formula I or II to treat IPF.

A method for treating IPF is based on the properties of the Formula I or II compounds to reduce at least one of the following processes contributing to pathophysiologies that accompany this disorder: inflammation, pulmonary neutrophilia, fibrosis, excessive cell proliferation, remodeling, lung tissue edema, airway hyperreactivity or bronchoconstriction.

Indicia of efficacy for treating IPF by the present method include demonstrable improvement in measurable signs, symptoms and other variables clinically relevant to IPF. Such improvements include increased blood oxygen saturation, decreased hypoxia and hypercapnia, decreased need for supplemental oxygen, decreased frequency of coughing and/or wheezing, improved forced expiratory volume ($FEV_1$), forced vital capacity (FVC) or other physiologically relevant parameter of respiratory function, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method, amount of epithelial lining fluid, wet to dry lung weight, alveolar fluid clearance, radiographic visualization methods, increase in general quality of life, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing, or severity of coughing and/or wheezing.

ARDS and VILI

The inventors have discovered that Compounds of Formula I or II inhibit the ROCK-mediated regulation of chemotaxis, cytokinesis, cytokine and chemokine secretion, endothelial integrity and/or smooth muscle contraction. Furthermore, the inventors have discovered that Compounds of Formula I or II are useful in treating the defects in inflammation, remodeling, airway and/or lung tissue edema, airway hyperreactivity or bronchoconstriction as well as preventing the development of airway hyperreactivity seen in ARDS and/or VILI. The inventors have also discovered that local administration of Compounds of Formula I or II to the lung is sufficient to treat the pathophysiologies associated with ARDS and VILI, especially the treatment of bronchoconstriction, inflammation and airway hyperreactivity and the prevention of the development of airway hyperreactivity. The inventors have discovered that Compounds of Formula I or II maintain efficacy as bronchodilators under conditions of inflammation seen in ARDS and VILI.

The present invention is directed to a method of treating ARDS and/or VILI. The method comprises the steps of first identifying a subject suffering from ARDS and/or VILI, then administering to the subject an effective amount of a compound of Formula I or II to treat ARDS and/or VILI.

A method for treating ARDS and/or VILI is based on the properties of the Formula I or II compounds to reduce at least one of the following processes contributing to pathophysiologies that accompany this disorder: inflammation, remodeling, airway and/or lung tissue edema, airway hyperreactivity or bronchoconstriction.

Indicia of efficacy for treating ARDS and/or VILI by the present method include demonstrable improvement in measurable signs, symptoms and other variables clinically relevant to ARDS and/or VILI. Such improvements include demonstrable improvement in measurable signs of edema and/or inflammation. Such signs of improvement include increased blood oxygen saturation or decreased frequency of coughing and/or wheezing, decreased hypoxia and hypercapnia, improved forced expiratory volume ($FEV_1$) forced vital capacity (FVC) or other physiologically relevant parameter of respiratory function, improved APACHE III score in the ICU, decreased need for mechanical ventilation, improved alveolar fluid clearance rate, decreased pulmonary edema as determined by any radiographic or other detection method such as the amount of epithelial lining fluid or radiographic visualization methods, bronchoscopy, brain natriuretic peptide levels, level of oxygenation/hypoxia, lower levels of inflammatory cells in the lung or outside of the lung in other anatomical compartments or spaces including systemic circulation, lower amounts of pro-inflammatory molecules including cytokines and chemokines in the lung or outside of the lung in other anatomical compartments or spaces including systemic circulation, pathological remodeling of the airway, patient-reported or physician-observed signs such as ease of breathing, or severity of coughing and/or wheezing, and feelings of well-being.

CF

The inventors have discovered that Rho kinase inhibitors such as Compounds of Formula I or II inhibit the ROCK-mediated regulation of chemotaxis, cytokinesis, cytokine and chemokine secretion, proliferation, cell motility, endothelial integrity and/or smooth muscle contraction. Furthermore, the inventors have discovered that Rho kinase inhibitors such as Compounds of Formula I or II are useful in treating the defects in inflammation, pulmonary neutrophilia, excessive cell proliferation, remodeling, airway and/or lung tissue edema, airway hyperreactivity or bronchoconstriction or vasoconstriction as well as preventing the development of airway hyperreactivity seen in CF. The inventors have also discovered that local administration of Compounds of Formula I or II to the lung is sufficient to treat the pathophysiologies associated with CF, especially the treatment of bronchoconstriction, inflammation and airway hyperreactivity as well as the prevention of the development of airway hyperreactivity. The inventors have discovered that Compounds of Formula I or II maintain efficacy as bronchodilators under conditions of inflammation seen in CF.

The present invention is directed to a method of treating CF. The method comprises the steps of first identifying a subject suffering from CF, then administering to the subject an effective amount of a Rho kinase inhibitor to treat CF.

The Rho kinase inhibitor useful to treat CF by the present invention is a compound which inhibits serine/threonine kinase activated with activation of Rho. Examples of Rho kinase inhibitors are compounds which inhibit ROCK2, or ROCK1, and other compounds which inhibit proteins having a serine/threonine kinase activity. In addition to Compounds of Formula I or II, specific Rho kinase inhibitors include (R)-trans-N-(pyridin-4-yl)-4-(1-aminoethyl)cyclohexanecarboxamide and (R)-(+)-N-(1H-pyrrolo[2,3-b]pyridin-4-yl)-4-(1-aminoethyl)-benzamide and other ROCK inhibitory compounds disclosed in WO 98/06433 and WO 00/09162, 1-(5-isoquinolinesulfonyl)homopiperazine and 1-(5-isoquinolinesulfonyl)-2-methylpiperazine and other ROCK inhibitory compounds disclosed in WO 97/23222 and Nature, 389, 990-994 (1997), (1-benzylpyrrolidin-3-yl)-(1H-indazol-5-yl)amine and other ROCK inhibitory compounds disclosed in WO 01/56988, (1-benzylpiperidin-4-yl)-(1H-indazol-5-yl)amine and other ROCK inhibitory compounds disclosed in WO 02/100833, N-[2-(4-fluorophenyl)-6,7-dimethoxy-4-quinazolinyl]-N-(1H-indazol-5-yl)amine and other ROCK inhibitory compounds disclosed in WO 02/076976, N-4-(1H-indazol-5-yl)-6,7-dimethoxy-N-2-pyridin-4-yl-quinazolin-2,4-diamine and other ROCK inhibitory compounds disclosed in WO 02/076977, and 4-methyl-5-(2-methyl-[1,4]diazepan-1-sulfonyl)isoquinoline and other ROCK inhibitory compounds disclosed in WO 99/64011, 2-(4-(1H-indazol-5-yl)phenyl)propan-2-amine and other ROCK inhibitory compounds disclosed in U.S. Ser. No. 07/129,404, N-(3-(4-(1H-indazol-5-ylamino)-6-(2-(dimethylamino)ethoxy)quinazolin-2-yl)phenyl)butyramide, 2-(3-(4-(1H-indazol-5-ylamino)quinazolin-2-yl)phenoxy)-N-(pyridin-3-yl)acetamide, and other ROCK inhibitory compounds disclosed in WO 06/105081, (R)-2- amino-3-phenyl-N-(4-(pyridin-4-yl)phenyl)propanamide and other ROCK inhibitory compounds disclosed in WO 07/26920, N-(6-fluoro-1H-indazol-5-yl)-2-methyl-6-oxo-4-(4-(trifluoromethyl)phenyl)-1,4,5,6-tetrahydropyridine-3-carboxamide and other ROCK inhibitory compounds disclosed in *J. Med. Chem.* 2007, 50, 6-9, N-(3-(2-(4-amino-1,2,5-oxadiazol-3-yl)-1-ethyl-1H-imidazo[4,5-c]pyridin-6-yloxy)phenyl)-4-(2-morpholinoethoxy)benzamide and other ROCK inhibitory compounds disclosed in WO 05/34866, WO 05/37197, and WO 05/37198, and 1-(1-(isoquinolin-5-ylsulfonyl)piperidin-4-yl)ethanamine and other ROCK inhibitory compounds disclosed in WO 05/80394.

A method for treating CF is based on the properties of Rho kinase inhibitors such as Formula I or II compounds to reduce at least one of the following processes contributing to pathophysiologies that accompany this disorder: inflammation, pulmonary neutrophilia, excessive cell proliferation, remodeling, pulmonary neutrophilia, excessive cell proliferation, remodeling, airway and/or lung tissue edema, airway hyperreactivity or bronchoconstriction or vasoconstriction.

Indicia of efficacy for treating CF by the present method include demonstrable improvement in measurable signs, symptoms and other variables clinically relevant to CF. Such improvements include decreases in the recurrence and progression of cough, chronic infection, pulmonary inflammation and airway damage, decreased chemotaxis and pulmonary infiltration of neutrophils and other inflammatory cells, decreased release of destructive enzymes and inflammatory cytokines from inflammatory cells, decreased rate of neutrophil apoptosis and increased removal of apoptotic cells, reduced amounts of DNA and cytosolic matrix proteins in the airway lumen, decreased viscosity of the airway mucus, decreased incidence and severity of bronchiectasis, irreversible lung damage, and respiratory failure, reduced incidence of spontaneous pneumothorax and hemoptysis, decreased parenchymal congestion, reduction in purulent secretions in dilated airways, reduction in cyst formation, decreased respiratory epithelial hyperplasia, erosion and squamous metaplasia, reduced mucoid plugging and inflammatory cells in the airway lumen, decreased submucosal gland hypertorphy and airway smooth muscle hyperplasia, decreased airway hyperreactivity, decreased lung hyperinflation, reduced need for surgical resection of damaged tissue, decreased ratio of residual volume to total lung capacity (RV/TLC) and increased $FEF_{25-75}$, increased forced expiratory volume in one second ($FEV_1$) and $FEV_1/FVC$, prevention of increases in TLC and RV, decreased incidence of acute pulmonary exacerbations, improved ventilation-perfusion, decreased hypoxemia, reduced requirement for oxygen supplementation, decreased hypercapnia, reduced vascular smooth muscle hypertrophy and pulmonary hypertension, decreased incidence of right ventricular hypertrophy, cor pulmonale and right heart failure, decreased need for lung transplant, and decreased mortality.

Bronchiectasis

The inventors have discovered that Compounds of Formula I or II inhibit the ROCK-mediated regulation of chemotaxis, cytokinesis, cytokine and chemokine secretion, proliferation, cell motility, endothelial integrity and/or smooth muscle contraction. Furthermore, the inventors have discovered that Compounds of Formula I or II are useful in treating the defects in inflammation, pulmonary neutrophilia, excessive cell proliferation, remodeling, airway and/or lung tissue edema, airway hyperreactivity or bronchoconstriction as well as preventing the development of airway hyperreactivity seen in bronchiectasis. The inventors have also discovered that local administration of Compounds of Formula I or II to the lung is sufficient to treat the pathophysiologies associated with bronchiectasis, especially the treatment of inflammation and airway hyperreactivity as well as the prevention of the development of airway hyperreactivity. The inventors have discovered that Compounds of Formula I or II maintain efficacy as bronchodilators under conditions of inflammation seen in RSV infection.

The present invention is directed to a method of treating bronchiectasis. The method comprises the steps of first identifying a subject suffering from bronchiectasis, then administering to the subject an effective amount of a compound of Formula I or II to treat bronchiectasis.

A method for treating bronchiectasis is based on the properties of the Formula I or II compounds to reduce at least one of the following processes contributing to pathophysiologies that accompany this disorder: inflammation, pulmonary neutrophilia, excessive cell proliferation, remodeling, airway and/or lung tissue edema, airway hyperreactivity or bronchoconstriction.

Indicia of efficacy for treating bronchiectasis by the present method include demonstrable improvement in measurable signs, symptoms and other variables clinically relevant to bronchiectasis. Such improvements include: increased blood oxygen saturation, decreased hypoxia and hypercapnia, decreased need for supplemental oxygen, decreased dyspnea, decreased frequency of coughing and/or wheezing, improved forced expiratory volume ($FEV_1$, forced vital capacity (FVC), reduced mean $H_2O_2$ concentration in exhaled breath condensate, improved chest radiograph or high-resolution CT scan or other physiologically relevant parameter of respiratory function, decreased ER and/or office visits, decreased hospitalizations, decrease in missed school or work days, decreased mortality or morbidity, decreased length of hospital stay, decreased need for mechanical ventilation, decreases bronchial wall thickening, decreased luminal dilation, lower amount of inflammatory cells infiltrating the lung, lower levels of pro-inflammatory cytokines and chemokines, improved alveolar fluid clearance rate, decreased pulmonary edema as determined by any radiographic or other detection method such as amount of epithelial lining fluid, wet to dry lung weight, alveolar fluid clearance or radiographic visualization methods, increase in general quality of life, the levels of inflammatory cells in the lung or outside of the lung in other anatomical compartments or spaces including systemic circulation, decreases in sputum expectoration, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing, or severity of coughing and/or wheezing, increased distance walked during a walk test and endurance capacity, feelings of well-being or other measurable variables related to quality of life,

AATD

The inventors have discovered that Compounds of Formula I or II inhibit the ROCK-mediated regulation of chemotaxis, cytokinesis, cytokine and chemokine secretion, proliferation, cell motility, endothelial integrity and/or smooth muscle contraction. Furthermore, the inventors have discovered that Compounds of Formula I or II are useful in treating the defects in inflammation, pulmonary neutrophilia, excessive cell proliferation, remodeling, airway and/or lung tissue edema, airway hyperreactivity or bronchoconstriction and preventing the development of airway hyperreactivity seen in AATD. The inventors have also discovered that local administration of Compounds of Formula I or II to the lung is sufficient to treat the pathophysiologies associated with AATD, especially the treatment of bronchoconstriction, inflammation and airway hyperreactivity as well as the prevention of the development of airway hyperreactivity. The inventors have discovered that Compounds of Formula I or II maintain efficacy as bronchodilators under conditions of inflammation seen in AATD.

The present invention is directed to a method of treating AATD. The method comprises the steps of first identifying a subject suffering from AATD, then administering to the subject an effective amount of a compound of Formula I or II to treat AATD.

A method for treating AATD is based on the properties of the Formula I or II compounds to reduce at least one of the following processes contributing to pathophysiologies that accompany this disorder: inflammation, pulmonary neutrophilia, excessive cell proliferation, remodeling, airway and/or lung tissue edema, airway hyperreactivity or bronchoconstriction.

Indicia of efficacy for treating AATD by the present method include demonstrable improvement in measurable signs, symptoms and other variables clinically relevant to AATD. Such improvements include: improvement in $FEV_1$, forced vital capacity (FVC) or other physiologically relevant parameter of respiratory function, reduction of cough, phlegm production, and wheezing, either chronically or with upper respiratory tract infections, reduction of dyspnea, increase in bronchodilator responsiveness, function, decreased ER and/or office visits, decreased hospitalizations, decrease in missed school or work days, decreased mortality or morbidity, decreased length of hospital stay, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method such as amount of epithelial lining fluid, wet to dry lung weight, alveolar fluid clearance or radiographic visualization methods, increase in general quality of life, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing.

Rhinitis

The inventors have discovered that Compounds of Formula I or II inhibit the ROCK-mediated regulation of chemotaxis, cytokinesis, cytokine and chemokine secretion, proliferation, cell motility, endothelial integrity and/or smooth muscle contraction. Furthermore, the inventors have discovered that Compounds of Formula I or II are useful in treating the defects in inflammation, excessive cell proliferation, remodeling, airway and/or lung tissue edema or airway hyperreactivity seen in rhinitis. The inventors have also discovered that local administration of Compounds of Formula I or II to the airway is sufficient to treat the pathophysiologies associated with rhinitis, especially inflammation and airway hyperreactivity.

The present invention is directed to a method of treating rhinitis. The method comprises the steps of first identifying a subject suffering from rhinitis, then administering to the subject an effective amount of a compound of Formula I or II to treat rhinitis.

A method for treating rhinitis is based on the properties of the Formula I or II compounds to reduce at least one of the following processes contributing to pathophysiologies that accompany this disorder: inflammation, excessive cell proliferation, remodeling, airway and/or lung tissue edema or airway hyperreactivity.

Indicia of efficacy for treating rhinitis by the present method include demonstrable improvement in measurable signs, symptoms and other variables clinically relevant to rhinitis. Such improvements include measurable reduction in the inflammation of the nasal passages including eliminating irritants and mucus secretions from the nasal passages, blockage of the constricting agents released from the inflammatory cells, and eliminating exposure to environmental allergens. Clinical indices of efficacy include improvements (relative to placebo) and the relief of signs and symptoms of rhinitis, including four nasal symptoms (nasal stuffiness/blockage, runny nose, itchy nose and sneezing) and three ocular symptoms (itching/burning, tearing/watering, and redness). Derived total nasal and ocular symptoms scores (such as daily and instantaneous) can also serve as indicia of efficacy. Nasal and ocular symptoms scores acceptable for demonstrating clinical efficacy are defined as follows:

Total Nasal Symptom Score Modified (TNSSm) defined as TNSS with the nasal stuffiness/blockage removed from the scoring; sum of 3 nasal symptoms only, including runny nose, itchy nose, and sneezing, 0-9 possible score Total Nasal Symptom Score (TNSS); sum of 4 nasal symptoms including runny nose, nasal itching, sneezing, and nasal stuffiness/blockage, 0-12 possible score Total Ocular Symptom Score (TOSS); sum of 3 ocular symptoms including itching/burning eyes, tearing/watering eyes, and ocular redness, 0-9 possible score Rhinosinusitis The inventors have discovered that Compounds of Formula I or II inhibit the ROCK-mediated regulation of chemotaxis, cytokinesis, cytokine and chemokine secretion, proliferation, cell motility, endothelial integrity and/or smooth muscle contraction. Furthermore, the inventors have discovered that Compounds of Formula I or II are useful in treating the defects in inflammation, excessive cell proliferation, remodeling, edema or airway hyperreactivity seen in rhinosinusitis. The inventors have also discovered that local administration of Compounds of Formula I or II to the airway is sufficient to treat the pathophysiologies associated with rhinosinusitis, especially inflammation and airway hyperreactivity.

The present invention is directed to a method of treating rhinosinusitis. The method comprises the steps of first identifying a subject suffering from rhinosinusitis, then administering to the subject an effective amount of a compound of Formula I or II to treat rhinosinusitis.

A method for treating rhinosinusitis is based on the properties of the Formula I or II compounds to reduce at least one of the following processes contributing to pathophysiologies that accompany this disorder: inflammation, excessive cell proliferation, remodeling, edema or airway constriction.

Indicia of efficacy for treating rhinosinusitis by the present method include demonstrable improvement in measurable signs, symptoms and other variables clinically relevant to rhinosinusitis. Such improvements include clearing of the sinus cavity, decreased congestion, alleviation of pain, restoration of normal mucus viscosity, decrease in inflammation, decrease in edema, relaxation of smooth muscle, attenuated pro-inflammatory cells and molecules including cytokines, increased ease of breathing, decreased incidence of facial pain, pressure and fullness, alleviation of nasal obstruction and congestion, attenuation of post nasal drip, increased sense of smell, decreased incidences of headache, lessening of fatigue, improved readings from sinus computed tomographic (CT) imaging, improvement as measured by physical or radiological examination, reduced duration of signs and symptoms, reduced incidence of infection, reduced need for antibiotics, steroids or other related treatments, and reduced flora in specimens from endoscopy.

PCD, Pneumonia, and Bronchiolitis Caused by Agents Other Than RSV

The inventors have discovered that Compounds of Formula I or II inhibit the ROCK-mediated regulation of chemotaxis, cytokinesis, cytokine and chemokine secretion, cell motility, endothelial integrity and/or smooth muscle contraction. Furthermore, the inventors have discovered that Compounds of Formula I or II are useful in treating the defects in inflammation, lung tissue edema, airway hyperreactivity or bronchoconstriction as well as preventing the development of airway hyperreactivity seen in PCD, pneumonia, and bronchiolitis caused by agents other than RSV. The inventors have also discovered that local administration of Compounds of Formula I or II to the lung is sufficient to treat the pathophysiologies associated with PCD, pneumonia and bronchiolitis caused by agents other than RSV, especially the treatment of bronchoconstriction, inflammation and airway hyperreactivity as well as the prevention of the development of airway hyperreactivity. The inventors have discovered that Compounds of Formula I or II maintain efficacy as bronchodilators under conditions of inflammation seen in PCD, pneumonia and bronchiolitis caused by agents other than RSV.

The present invention is directed to a method of treating PCD, pneumonia, and bronchiolitis caused by agents other than RSV. The method comprises the steps of first identifying a subject suffering from PCD, pneumonia or bronchiolitis caused by agents other than RSV, then administering to the subject an effective amount of a compound of Formula I or II to treat PCD, pneumonia or bronchiolitis caused by agents other than RSV.

A method for treating PCD, pneumonia or bronchiolitis caused by agents other than RSV is based on the properties of the Formula I or II compounds to reduce at least one of the following processes contributing to pathophysiologies that accompany this disorder: inflammation, lung tissue edema, airway hyperreactivity or bronchoconstriction.

Indicia of efficacy for treating PCD, pneumonia, and bronchiolitis caused by agents other than RSV by the present method include demonstrable improvement in measurable signs, symptoms and other variables clinically relevant to PCD, pneumonia, and bronchiolitis caused by agents other than RSV. Such improvements include increased blood oxygen saturation, decreased hypoxia and hypercapnia, decreased need for supplemental oxygen, decreased frequency of coughing and/or wheezing, improved forced expiratory volume ($FEV_1$), forced vital capacity (FVC) or other physiologically relevant parameter of respiratory function, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method such as amount of epithelial lining fluid, wet to dry lung weight, alveolar fluid clearance or radiographic visualization methods, the levels of inflammatory cells in the lung or outside of the lung in other anatomical compartments or spaces including systemic circulation, the amount of pro-inflammatory molecules including cytokines and chemokines in the lung or outside of the lung in other anatomical compartments or spaces including systemic circulation, pathological remodeling of the airway, patient-reported or physician-observed signs such as ease of breathing, or severity of coughing and/or wheezing.

OB/BOOP Due to Lung Transplantation or HSCT

The inventors have discovered that Compounds of Formula I or II are useful in treating inflammation, fibrosis, excessive cell proliferation, remodeling, airway hyperreactivity, bronchoconstriction or decline in lung function as well as preventing the development of airway hyperreactivity seen in OB/BOOP due to lung transplantation or HSCT. The inventors have also discovered that local administration of Compounds of Formula I or II to the lung is sufficient to treat the pathophysiologies associated with OB/BOOP due to lung transplantation or HSCT, especially the treatment of bronchoconstriction, inflammation and airway hyperreactivity as well as the prevention of the development of airway hyperreactivity. The inventors have discovered that Compounds of Formula I or II maintain efficacy as bronchodilators under conditions of inflammation seen in OB/BOOP due to lung transplantation or HSCT.

The present invention is directed to a method of treating OB/BOOP due to lung transplantation or HSCT. The method comprises the steps of first identifying a subject suffering from OB/BOOP due to lung transplantation or HSCT, and then administering to the subject an effective amount of a compound of Formula I or II to treat OB/BOOP due to lung transplantation or HSCT.

A method for treating OB/BOOP due to lung transplantation or HSCT is based on the properties of the Formula I or II compounds to reduce at least one of the following processes contributing to pathophysiologies that accompany this disorder: inflammation, fibrosis, excessive cell proliferation, remodeling, airway hyperreactivity or bronchoconstriction.

Indicia of efficacy for treating OB/BOOP due to lung transplantation or HSCT by the present method include demonstrable improvement in measurable signs, symptoms and other variables clinically relevant to OB/BOOP due to lung transplantation or HSCT. Such improvements include increased blood oxygen saturation, decreased hypoxia and hypercapnia, decreased need for supplemental oxygen, decreased frequency of coughing and/or wheezing, decreased fever, improved forced expiratory volume ($FEV_1$), forced vital capacity (FVC) or other physiologically relevant parameter of respiratory function, lower amount of inflammatory cells infiltrating the lung, lower levels of proinflammatory cytokines and chemokines, decreased bilateral diffuse interstitial infiltrates as determined by any radiographic or other detection method, improvement in histopathological changes of the pulmonary parenchyma, increase in general quality of life, improvement in gas exchange abnormalities including carbon monoxide diffusing capacity (DLCO).

Non-IPF IIP

The inventors have discovered that Compounds of Formula I or II are useful in treating inflammation, fibrosis, excessive cell proliferation, remodeling, airway hyperreactivity, bronchoconstriction or decline in lung function as well as preventing the development of airway hyperreactivity seen in non-IPF IIP. The inventors have also discovered that local administration of Compounds of Formula I or II to the lung is sufficient to treat the pathophysiologies associated with non-IPF IIP, especially the treatment of bronchoconstriction, inflammation and airway hyperreactivity as well as the prevention of the development of airway hyperreactivity. The inventors have discovered that Compounds of Formula I or II maintain efficacy as bronchodilators under conditions of inflammation seen in non-IPF IIP.

The present invention is directed to a method of treating non-IPF IIP. The method comprises the steps of first identifying a subject suffering from non-IPF IIP, and then administering to the subject an effective amount of a compound of Formula I or II to treat non-IPF IIP.

A method for treating non-IPF IIP is based on the properties of the Formula I or II compounds to reduce at least one of the following processes contributing to pathophysiologies that accompany this disorder: inflammation, fibrosis, excessive cell proliferation, remodeling, airway hyperreactivity or bronchoconstriction.

Indicia of efficacy for treating non-IPF IIP by the present method include demonstrable improvement in measurable signs, symptoms and other variables clinically relevant non-IPF IIP. Such improvements include increased blood oxygen saturation, decreased hypoxia and hypercapnia, decreased need for supplemental oxygen, decreased frequency of coughing and/or wheezing, decreased fever, improved forced expiratory volume ($FEV_1$), forced vital capacity (FVC) or other physiologically relevant parameter of respiratory function, lower amount of inflammatory cells infiltrating the lung, lower levels of proinflammatory cytokines and chemokines, decreased bilateral diffuse interstial infiltrates as determined by any radiographic or other detection method, improvement in histopathological changes of the pulmonary parenchyma, increase in general quality of life, improvement in gas exchange abnormalities including carbon monoxide diffusing capacity (DLCO).

ILD Other Than IPF, Non-IPF IIPs and OB/BOOP

The inventors have discovered that Compounds of Formula I or II are useful in treating inflammation, fibrosis, excessive cell proliferation, remodeling, airway hyperreactivity, bronchoconstriction or decline in lung function as well as preventing the development of airway hyperreactivity seen in ILD other than IPF, non-IPF IIPs and OB/BOOP. The inventors have also discovered that local administration of Compounds of Formula I or II to the lung is sufficient to treat the pathophysiologies associated with ILD other than IPF, non-IPF IIPs and OB/BOOP, especially the treatment of bronchoconstriction, inflammation and airway hyperreactivity as well as the prevention of the development of airway hyperreactivity. The inventors have discovered that Compounds of Formula I or II maintain efficacy as bronchodilators under conditions of inflammation seen in ILD other than IPF, non-IPF IIPs and OB/BOOP.

The present invention is directed to a method of treating ILD other than IPF, non-IPF IIPs and OB/BOOP. The method comprises the steps of first identifying a subject suffering from ILD other than IPF, non-IPF IIPs and OB/BOOP, and then administering to the subject an effective amount of a compound of Formula I or II to treat ILD other than IPF, non-IPF IIPs and OB/BOOP.

A method for treating ILD other than IPF, non-IPF IIPs and OB/BOOP is based on the properties of the Formula I or II compounds to reduce at least one of the following processes contributing to pathophysiologies that accompany this disorder: inflammation, fibrosis, excessive cell proliferation, remodeling, airway hyperreactivity or bronchoconstriction.

Indicia of efficacy for treating ILD other than IPF, non-IPF IIPs and OB/BOOP by the present method include demonstrable improvement in measurable signs, symptoms and other variables clinically relevant to ILD other than IPF, non-IPF IIPs and OB/BOOP. Such improvements include increased blood oxygen saturation, decreased hypoxia and hypercapnia, decreased need for supplemental oxygen, decreased frequency of coughing and/or wheezing, decreased fever, improved forced expiratory volume ($FEV_1$), forced vital capacity (FVC) or other physiologically relevant parameter of respiratory function, lower amount of inflammatory cells infiltrating the lung, lower levels of proinflammatory cytokines and chemokines, decreased bilateral diffuse interstial infiltrates as determined by any radiographic or other detection method, improvement in histopathological changes of the pulmonary parenchyma, increase in general quality of life, improvement in gas exchange abnormalities including carbon monoxide diffusing capacity (DLCO), improvements in arthralgia, myalgia, hemoptysis, rash or pneumothorax.

An effective amount of a Formula I or II compound is administered to a patient in need of such treatment. The patient either already has the symptoms of at least one above-mentioned disease, or is identified as being at risk of at least one above-mentioned disease. The compound is administered at a frequency that achieves desired efficacy. What constitutes desired efficacy is determined by a physician or other health-care professional. Whether or not sufficient efficacy has been reached is determined by indicia of efficacy for the specific disease. After an initial dose, additional doses are optionally administered if judged to be necessary by a health-care professional.

Methods of Administration

The present invention is particularly effective in treating pulmonary disease such as asthma, COPD, respiratory tract illness caused by respiratory syncytial virus infection, PAH, LAM, idiopathic pulmonary fibrosis, ARDS and VILI, CF, bronchiectasis, AATD, rhinitis, rhinosinusitis, PCD, pneumonia, and bronchiolitis caused by agents other than RSV, OB/BOOP due to lung transplantation or HSCT, non-IPF IIP and ILD other than IPF, non-IPF IIPs and OB/BOOP. Any method of delivering the compound to the relevant tissues of the lung, including local administration and systemic administration, is suitable for the present invention.

In a preferred embodiment, the active compound is delivered by local administration to the lung. Local administration includes inhalation, topical application or targeted drug delivery. Methods of inhalation include liquid instillation, instillation as a pressurized fluid preparation via metered dose inhaler or equivalent, or inhalation of an aerosolized solution via nebulizer (preferred), inhalation of dry powder (more preferred), and directing soluble or dried material into the air stream during mechanical ventilation (also more preferred).

One local administration method is administering to a subject an aerosol suspension of respirable particles comprising the active compound by inhalation. The respirable particles can be liquid or solid, with a particle size sufficiently small to pass through the mouth and larynx upon inhalation; in general, particles ranging from about 1 to 10 microns, but more preferably 1-5 microns, in size are considered respirable. The surface concentrations of active compounds delivered via inhalation can vary according to compounds; but are generally $1\times10^{-10}$-$1\times10^{-4}$ moles/liter, and preferably $1\times10^{-8}$-$1\times10^{-5}$ moles/liter.

In another embodiment, the active compound is delivered by systemic administration; the compound first reaches plasma and then distributes into the lung tissues. Examples of systemic administration include oral ingestion, intravenous, subcutaneous, intraperitoneal, intrathecal or intramuscular administration.

Additional method of systemic administration of the active compound to the lungs of a subject involves administering a suppository form of the active compound, such that a therapeutically effective amount of the compound reaches the target sites via systemic absorption and circulation.

Another method of systemically administering the active compounds to the lungs of the subject involves administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

The active compounds can also be systemically administered to the lungs of the subject through absorption by the skin using transdermal patches or pads. The active compounds are absorbed into the bloodstream through the skin. Plasma concentration of the active compounds can be controlled by using patches containing different concentrations of active compounds.

For systemic administration, plasma concentrations of active compounds delivered can vary according to compounds; but are generally $1\times10^{-10}$-$1\times10^{-4}$ moles/liter, and preferably $1\times10^{-8}$-$1\times10^{-5}$ moles/liter.

Dosage levels about 0.01-140 mg per kg of body weight per day are useful in the treatment or preventions of pulmonary diseases (about 0.5 mg to about 7 g per patient per day). Preferred dosage levels are about 0.05-100, 0.1-100, or 1-100 mg/kg body weight per day. The amount of active ingredient that can be combined with the carrier materials to produce a single dosage form will vary depending upon the host treated and the particular mode of administration. Dosage unit forms will generally contain between from about 1 mg to about 500 mg of an active ingredient.

Injection dose levels range from about 0.1 mg/kg/hour to at least 10 mg/kg/hour, all from about 1 to about 120 hours and especially 24 to 96 hours. A preloading bolus from about 0.1 mg/kg to about 10 mg/kg or more can be administered to achieve adequate steady state levels. The maximum total dose in general does not exceed about 2 g/day for a 40 to 80 kg human patient.

Frequency of dosage can also vary depending on the compound used and the particular disease treated. However, for treatment of most disorders, a dosage regimen of p.r.n, 4 times daily, three times daily, or less is preferred, with a dosage regimen of once daily or 2 times daily being particularly preferred.

It is understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

Preferred compounds of the invention will have favorable pharmacological properties. Such properties include, but are not limited to bioavailability, low toxicity, low serum protein binding and desirable in vitro and in vivo half-life.

Assays can be used to predict these desirable pharmacological properties. Assays used to predict bioavailability include transport across human intestinal cell monolayers, including Caco-2 cell monolayers. Toxicity to cultured hepatocycles can be used to predict compound toxicity.

An example of targeted drug delivery is enclosure of the compound within a liposome, where the liposome is coated with a specific antibody whose antigen is expressed in the targeted lung tissue. It can be advantageous to construe a controlled delivery system of the compounds since such an inhaled product targets the site of action, presents the compound of interest in small regimented quantities and reduces/minimizes any unwanted side effects.

Another example of a delivery system includes microparticulate compositions of the compound. In such a case, the compound is formulated as a microparticulate wherein the carrier is loaded with the compound; such a preparation is then filtered through a fine porous membrane or suitable filtering medium or is exposed to solvent interchanges to produce nanoparticles. Such preparations can be freeze dried or held in suspension in an aqueous or physiologically compatible medium. The preparation so obtained can be inhaled by suitable means.

Another example of a suitable preparation includes a reconstitutable preparation. In this case, the compound is formulated in a preparation to contain the necessary adjuvant to make it physiologically compatible. Such a preparation can be reconstituted by addition of water for injection or suitable physiological fluids, admixed by simple agitation and inhaled using appropriate techniques described above.

The compounds described above can also be prepared into dry powder or equivalent inhalation powders using the well known art of super critical fluid technology. In such a case, the compound is admixed with appropriate excipients and milled into a homogenous mass using suitable solvents or adjuvants. Following this, this mass is subjected to mixing using super critical fluid technology and suitable particle size distribution achieved. The particles in the formulation need to be of a desired particle size range such that the particles can be directly inhaled into the lungs using a suitable inhalation technique or introduced into the lungs via a mechanical ventilator. Alternatively, a formulation can be designed such that the particles are large enough in size thereby offering sufficient surface area to dissolve completely in a suitable fluid when admixed together or to dissolve sufficiently enough prior to nebulization into the lungs.

To prevent particle size growth and minimize crystal growth of the compound, one embodiment is to include the use of spray-dried particles that have better aerodynamic properties than micronized material. This can be further extended to coat the surface of the hydrophilic molecule with one or more layers of hydrophobic material.

The invention is illustrated further by the following examples that are not to be construed as limiting the invention in scope to the specific procedures described in them.

EXAMPLES

Example 1

Rho Kinase Inhibition Assay

Relevance:

This assay demonstrates a compound's ability to inhibit ROCK2 and ROCK1 in an in vitro setting using the isolated enzyme. Compounds having ROCK2 $IC_{50}$ values on the order of 2 µM or below have been shown to possess efficacy in many studies using in vivo models of the disease processes described in this application.

Protocol

Inhibition of ROCK2 and ROCK1 activity was determined using the IMAP™ Screening Express Kit (Molecular Devices product number #8073). ROCK2 enzyme (Upstate/Chemicon #14-451), ROCK1 (Upstate/Chemicon #14-601) and Flourescein tagged substrate peptide Fl-AKRRRLSSLRA (Molecular Devices product number R7184) was pre-incubated with a test compound (a Formula I or II compound or other rho kinase compound such as fasudil, H-1152, H7, Y-27632, Y-39983) for 5 minutes in buffer containing 10 mM Tris-HCl pH 7.2, 10 mM $MgCl_2$, and 0.1% BSA. Following the pre-incubation, 10 µM ATP was added to initiate the reaction. After 60 minutes at room temperature, Molecular Devices IMAP™ binding solution was added to bind phosphorylated substrate. After 30 minutes of incubation in the presence of the IMAP™ beads, the fluorescence polarization was read and the ratio was reported as mP. IC$_{50}$ values for compounds and EC$_{50}$ values for ATP were calculated using the Prism software from Graphpad.

Results:

TABLE 1

Rho Kinase I and II Potency Data

| Compound | ROCK1 Ki, Avg, nM | ROCK1 Ki, StdDev, nM | ROCK2 Ki, Avg, nM | ROCK2 Ki, StdDev, nM |
|---|---|---|---|---|
| 1.008 | 30.5 | 0.8 | 3.9 | 0.1 |
| 1.034 | 36.0 | 22.2 | 5.3 | 2.6 |
| 1.039 | 208.6 | 109.0 | 24.7 | 8.4 |
| 1.051 | 37.2 | 4.0 | 3.8 | 0.0 |
| 1.072 | 33.7 | 22.1 | 5.6 | 3.1 |
| 1.074 | 40.1 | 3.3 | 4.1 | 1.5 |
| 1.075 | 48.7 | 2.8 | 4.4 | 0.3 |
| 1.076 | 14.3 | 5.4 | 2.6 | 0.6 |
| 1.077 | 76.1 | 30.9 | 11.1 | 5.8 |
| 1.078 | 36.3 | 10.1 | 3.6 | 0.9 |
| 1.079 | 71.5 | 9.1 | 4.7 | 1.1 |
| 1.080 | 130.8 | 42.6 | 15.2 | 4.4 |
| 1.087 | 84.1 | 11.1 | 15.4 | 1.4 |
| 1.090 | 281.0 | 103.7 | 24.9 | 7.9 |
| 1.091 | 71.4 | 22.0 | 3.3 | 1.0 |
| 1.092 | 190.5 | 42.2 | 28.4 | 10.6 |
| 1.093 | 64.5 | 21.9 | 7.7 | 5.2 |
| 1.095 | 274.8 | 88.0 | 49.5 | 35.9 |
| 1.098 | 205.6 | 69.4 | 25.0 | 6.4 |
| 1.106 | 223.4 | 82.0 | 15.1 | 4.9 |
| 1.107 | 233.7 | 137.2 | 14.0 | 8.5 |
| 1.108 | 25.6 | 3.2 | 6.5 | 0.3 |
| 1.109 | 58.8 | 25.8 | 9.6 | 2.5 |
| 1.110 | 59.0 | 4.1 | 11.2 | 0.3 |
| 1.115 | 89.7 | 17.5 | 20.6 | 1.7 |
| 1.116 | 257.8 | 45.6 | 48.9 | 5.5 |
| 1.117 | 208.0 | 1.9 | 35.8 | 2.3 |
| 1.118 | 461.7 | 28.3 | 81.7 | 52.7 |
| 1.123 | 82.3 | 11.0 | 9.6 | 4.3 |
| 1.124 | 64.5 | 7.9 | 3.3 | 0.8 |
| 1.125 | 557.1 | 1.7 | 50.9 | 16.8 |
| 1.126 | 76.2 | 16.7 | 17.2 | 3.9 |
| 1.127 | 96.6 | 11.6 | 11.2 | 0.4 |
| 1.130 | 577.1 | 340.0 | 142.0 | 38.1 |
| 1.131 | 19.7 | 5.9 | 3.8 | 0.9 |
| 1.132 | 22.5 | 6.5 | 3.5 | 0.4 |
| 1.133 | 25.0 | 7.2 | 4.3 | 1.1 |
| 1.134 | 22.4 | 6.0 | 4.4 | 0.6 |
| 1.136 | 40.3 | 15.3 | 5.4 | 0.4 |
| 1.137 | 25.8 | 10.7 | 5.1 | 1.2 |
| 1.138 | 36.3 | 12.2 | 7.2 | 1.1 |
| 1.139 | 200.3 | 26.3 | 23.2 | 9.6 |
| 1.140 | 236.1 | 199.3 | 32.9 | 24.9 |
| 1.141 | 28.5 | 11.1 | 3.8 | 1.1 |
| 1.142 | 104.2 | 26.6 | 12.0 | 4.4 |
| 1.143 | 49.7 | 30.8 | 12.6 | 11.9 |
| 1.144 | 97.6 | 65.0 | 19.5 | 13.0 |
| 1.145 | 35.0 | 13.5 | 6.4 | 0.9 |
| 1.146 | 39.8 | 10.9 | 10.7 | 1.5 |
| 1.147 | 58.3 | 15.6 | 45.7 | 52.0 |
| 1.148 | 24.3 | 13.7 | 3.6 | 0.9 |
| 1.149 | 46.8 | 21.3 | 4.2 | 2.2 |
| 1.150 | 33.2 | 17.5 | 3.2 | 1.2 |
| 1.151 | 22.8 | 6.0 | 2.9 | 0.5 |
| 1.152 | 19.8 | 13.3 | 3.3 | 0.9 |
| 1.153 | 62.8 | 8.7 | 4.2 | 0.8 |
| 1.154 | 52.7 | 9.5 | 6.6 | 1.0 |
| 1.155 | 45.4 | 14.7 | 7.0 | 2.0 |
| 1.156 | 135.8 | 34.3 | 13.0 | 3.0 |
| 1.157 | 263.8 | 73.9 | 8.8 | 1.6 |
| 1.158 | 64.1 | 20.1 | 5.1 | 1.0 |
| 1.159 | 48.1 | 9.2 | 10.1 | 2.6 |
| 1.160 | 218.3 | 28.3 | 49.4 | 13.4 |
| 1.161 | 9.9 | 3.4 | 2.5 | 0.5 |
| 1.162 | 15.2 | 1.5 | 2.8 | 0.8 |
| 1.163 | 33.6 | 5.8 | 2.9 | 0.4 |
| 1.164 | 42.4 | 7.2 | 6.1 | 1.2 |
| 1.165 | 50.7 | 4.4 | 3.4 | 0.6 |
| 1.166 | 95.2 | 8.6 | 8.0 | 0.8 |
| 1.167 | 118.6 | 17.1 | 18.5 | 1.7 |
| 1.168 | 162.2 | 68.3 | 22.9 | 10.4 |
| 1.169 | 256.2 | 132.7 | 33.8 | 20.0 |
| 1.170 | 80.0 | 25.9 | 12.5 | 6.1 |
| 1.171 | 109.2 | 60.1 | 16.0 | 8.4 |
| 1.172 | 103.0 | 40.6 | 20.5 | 7.3 |
| 1.173 | 15.1 | 6.8 | 3.6 | 1.0 |
| 1.175 | 65.9 | 28.3 | 7.6 | 1.5 |
| 1.176 | 314.3 | 77.6 | 11.2 | 3.2 |
| 1.177 | 156.1 | 55.0 | 18.2 | 5.5 |
| 1.178 | 137.6 | 58.0 | 24.9 | 17.6 |
| 1.179 | 292.0 | 70.7 | 19.3 | 4.4 |
| 1.180 | 138.5 | 46.5 | 23.1 | 4.8 |
| 1.181 | 567.8 | 191.3 | 32.8 | 3.5 |
| 1.182 | 408.3 | 106.6 | 30.6 | 4.3 |
| 1.183 | 165.1 | 46.3 | 16.8 | 3.7 |
| 1.184 | 843.1 | 53.0 | 90.9 | 13.9 |
| 1.185 | 81.6 | 33.0 | 12.6 | 6.4 |
| 1.186 | 129.3 | 42.2 | 11.9 | 4.9 |
| 1.187 | 296.2 | 78.8 | 17.3 | 5.8 |
| 1.188 | 3468.8 |  | 652.7 |  |
| 1.189 | 187.9 | 62.0 | 34.3 | 5.1 |
| 1.190 | 325.6 | 38.9 | 71.8 | 9.0 |
| 1.191 | 147.3 | 24.7 | 33.4 | 2.0 |
| 1.192 | 158.4 | 33.5 | 37.7 | 4.7 |
| 1.193 | 64.9 | 4.2 | 14.8 | 1.2 |
| 1.194 | 175.7 | 6.3 | 20.2 | 2.4 |
| 1.195 | 196.2 | 58.0 | 10.3 | 3.6 |
| 1.196 | 710.7 | 191.7 | 39.8 | 15.0 |
| 1.197 | 120.2 | 36.0 | 5.0 | 1.4 |
| 1.198 | 584.5 | 139.5 | 24.7 | 9.9 |
| 1.199 | 1856.6 |  | 213.0 | 34.4 |
| 1.200 | 76.5 | 17.9 | 5.9 | 0.9 |
| 1.201 | 1585.4 |  | 229.5 |  |
| 1.202 | 203.5 | 40.9 | 33.0 | 2.1 |
| 1.203 | 329.4 | 67.4 | 41.6 | 6.4 |
| 1.204 | 196.1 | 42.0 | 31.9 | 2.2 |
| 1.205 | 498.1 | 95.2 | 46.4 | 3.7 |
| 1.206 | 64.4 | 15.1 | 9.1 | 3.8 |
| 1.207 | 516.3 | 27.5 | 43.7 | 1.1 |
| 1.208 | 54.2 | 25.0 | 12.9 | 2.8 |
| 1.209 | 4591.0 |  | 469.6 | 58.3 |
| 1.210 | 95.1 | 18.2 | 25.5 | 3.8 |
| 1.211 | 395.5 | 58.5 | 57.6 | 0.6 |
| 1.212 | 44.2 | 11.2 | 3.9 | 0.2 |
| 1.213 | 106.3 | 10.9 | 3.0 | 0.5 |
| 1.214 | 546.5 | 10.9 | 143.0 | 7.0 |
| 1.215 | 102.8 | 5.8 | 3.5 | 0.3 |
| 1.216 | 1885.4 |  | 402.9 | 79.5 |
| 1.217 | 70.1 | 9.5 | 12.1 | 1.1 |
| 1.218 | 401.8 | 34.4 | 30.7 | 3.0 |
| 1.219 | 343.6 | 37.6 | 15.4 | 2.3 |
| 1.221 | 264.4 | 41.6 | 30.0 | 2.6 |
| 1.222 | 228.8 | 41.9 | 75.5 | 1.2 |
| 1.223 | 239.5 | 21.5 | 15.7 | 1.9 |
| 1.224 | 487.0 | 151.5 | 77.5 | 23.0 |
| 1.225 | 605.0 | 133.2 | 189.4 | 48.9 |
| 1.226 | 91.7 | 31.5 | 8.8 | 2.6 |
| 1.227 | 47.5 | 2.8 | 5.3 | 0.4 |
| 1.228 | 1883.4 | 681.9 | 139.6 | 28.2 |
| 1.229 | 121.4 | 86.2 | 18.4 | 5.8 |
| 1.230 | 345.9 | 85.2 | 35.3 | 9.8 |
| 1.231 | 305.1 | 62.8 | 60.3 | 18.2 |
| 1.232 | 136.6 | 41.1 | 20.8 | 8.8 |
| 1.233 | 47.2 | 7.2 | 1.3 | 0.1 |
| 1.234 | 1735.2 | 179.0 | 166.4 | 11.6 |
| 1.235 | 1386.4 | 173.1 | 335.4 | 29.4 |
| 1.236 | 49.3 | 7.1 | 2.1 | 0.1 |
| 1.237 | 286.7 | 55.0 | 4.0 | 0.4 |
| 1.238 | 61.2 | 22.1 | 1.5 | 0.3 |
| 1.239 | 282.6 | 36.2 | 6.3 | 0.6 |

TABLE 1-continued

Rho Kinase I and II Potency Data

| Compound | ROCK1 Ki, Avg, nM | ROCK1 Ki, StdDev, nM | ROCK2 Ki, Avg, nM | ROCK2 Ki, StdDev, nM |
|---|---|---|---|---|
| 1.240 | 624.8 | 74.2 | 60.1 | 9.3 |
| 1.241 | 65.1 | 11.8 | 21.0 | 6.4 |
| 1.242 | 71.4 | 14.1 | 17.5 | 1.8 |
| 1.243 | 219.3 | 29.7 | 84.3 | 17.2 |
| 1.244 | 683.1 | 80.9 | 138.7 | 25.4 |
| 1.245 | 199.0 | 27.7 | 49.5 | 7.9 |
| 1.246 | 92.1 | 6.3 | 11.2 | 0.8 |
| 1.247 | 1312.4 | 268.7 | 242.6 | 53.1 |
| 1.248 | 2349.7 |  | 890.6 | 509.8 |
| 1.249 | 91.7 | 25.0 | 8.6 | 3.8 |
| 1.250 | 247.0 | 63.7 | 45.8 | 13.8 |
| 1.251 | 206.8 | 44.0 | 49.2 | 10.5 |
| 1.252 | 30.5 | 1.5 | 4.5 | 0.4 |
| 1.253 | 59.9 | 7.4 | 1.7 | 0.2 |
| 1.254 | 116.0 | 19.4 | 39.0 | 8.7 |
| 1.255 | 3559.3 | 1202.9 | 358.9 | 99.3 |
| 1.256 | 700.1 | 179.5 | 85.5 | 18.8 |
| 1.257 | 1273.7 | 237.3 | 168.0 | 35.4 |
| 1.258 | 9.5 | 3.5 | 1.3 | 0.4 |
| 1.259 | 19.5 | 11.6 | 2.1 | 0.3 |
| 1.260 | 70.9 | 48.0 | 7.1 | 1.9 |
| 1.261 | 307.4 | 139.0 | 14.8 | 6.5 |
| 1.262 | 54.9 | 13.3 | 4.0 | 0.7 |
| 1.263 | 2130.5 | 673.5 | 453.4 | 105.3 |
| 1.264 | 494.5 | 1.1 | 59.4 | 9.5 |
| 1.265 | 161.7 | 25.9 | 21.6 | 0.8 |
| 1.266 | 53.8 | 15.1 | 17.1 | 2.8 |
| 1.267 | 98.8 | 21.6 | 23.9 | 6.2 |
| 1.268 | 403.6 | 78.8 | 40.7 | 7.5 |
| 1.269 | 239.1 | 62.6 | 22.8 | 9.0 |
| 1.270 | 130.5 | 45.0 | 9.9 | 0.6 |
| 1.271 | 332.1 | 99.9 | 77.7 | 5.8 |
| 1.272 | 1823.7 | 1294.6 | 194.3 | 17.0 |
| 1.273 | 31.3 | 8.3 | 8.2 | 1.0 |
| 1.274 | 223.4 | 46.3 | 10.7 | 1.1 |
| 1.275 | 401.7 | 44.9 | 14.1 | 2.0 |
| 1.276 | 64.2 | 5.2 | 12.3 | 2.5 |
| 1.277 | 42.3 | 10.4 | 4.6 | 1.3 |
| 1.278 | 80.2 | 10.5 | 10.2 | 1.8 |
| 1.279 | 455.9 | 20.3 | 34.2 | 1.6 |
| 1.280 | 746.0 | 58.3 | 38.0 | 4.0 |
| 1.281 | 71.8 |  | 7.4 |  |
| 2.007 | 390.4 |  | 179.1 |  |
| 2.016 | 100.5 | 14.8 | 42.4 | 10.2 |
| 2.020 | 100.5 | 13.1 | 36.5 | 4.7 |
| 2.022 | 44.8 | 6.9 | 15.3 | 1.1 |
| 2.025 | 6.9 | 1.3 | 2.9 | 0.5 |
| 2.026 | 38.0 | 15.2 | 13.0 | 4.1 |
| 2.027 | 15.7 | 3.8 | 7.4 | 2.3 |
| 2.031 | 14.6 | 4.9 | 5.3 | 1.2 |
| 2.034 | 1002.6 | 392.4 | 221.1 | 312.7 |
| 2.035 | 601.0 |  | 201.9 |  |
| 2.036 | 579.5 | 139.9 | 232.8 |  |
| 2.037 | 920.8 |  | 182.2 |  |
| 2.038 | 28.9 | 4.5 | 6.3 | 1.0 |
| 2.039 | 18.8 | 9.6 | 6.7 | 1.9 |
| 2.040 | 59.6 | 10.7 | 25.4 | 5.0 |
| 2.041 | 30.8 | 2.6 | 9.6 | 2.6 |
| 2.043 | 49.4 | 9.5 | 21.5 | 2.4 |
| 2.044 | 81.4 | 20.2 | 24.1 | 3.7 |
| 2.045 | 90.6 | 64.6 | 88.0 | 57.3 |
| 2.046 | 16.7 | 1.1 | 5.6 | 0.8 |
| 2.047 | 26.4 | 3.6 | 7.0 | 2.3 |
| 2.048 | 71.5 | 22.8 | 34.6 | 9.7 |
| 2.049 | 113.0 | 42.1 | 48.0 | 17.1 |
| 2.050 | 367.7 | 115.4 | 250.7 |  |
| 2.051 | 1437.2 | 595.4 | 1179.8 |  |
| 2.052 | 508.5 | 169.1 | 142.6 |  |
| 2.053 | 951.6 | 157.1 | 182.4 |  |
| 2.054 | 17.1 | 2.3 | 3.7 | 0.1 |
| 2.055 | 16.0 | 5.3 | 6.4 | 1.2 |
| 2.056 | 106.6 | 12.7 | 48.7 | 26.5 |
| 2.057 | 6.2 | 1.3 | 3.7 | 0.7 |
| 2.058 | 15.3 | 2.8 | 3.3 | 0.6 |
| 2.059 | 3.9 | 0.3 | 2.7 | 0.2 |
| 2.060 | 4.9 | 0.3 | 3.2 | 0.1 |
| 2.061 | 10.5 | 3.2 | 1.8 | 0.4 |
| 2.062 | 63.4 | 25.1 | 30.5 | 2.2 |
| 2.063 | 206.2 | 88.8 | 73.9 | 3.5 |
| 2.064 | 4.1 | 1.8 | 2.2 | 0.4 |
| 2.065 | 4.1 | 1.4 | 1.8 | 0.2 |
| 2.066 | 10.2 | 3.4 | 2.3 | 0.4 |
| 2.067 | 19.6 | 5.8 | 4.2 | 0.5 |
| 2.068 | 8.0 | 2.0 | 5.8 | 0.4 |
| 2.069 | 16.7 | 4.9 | 2.4 | 0.3 |
| 2.070 | 285.9 | 122.0 | 48.4 | 6.1 |
| 2.071 | 21.2 | 2.7 | 11.9 | 0.5 |
| 2.072 | 7.5 | 1.4 | 4.4 | 0.5 |
| 2.073 | 12.7 | 2.6 | 4.2 | 0.4 |
| 2.074 | 133.3 | 31.1 | 36.4 | 7.7 |
| 2.075 | 123.0 | 25.7 | 21.7 | 1.5 |
| 2.076 | 8.0 | 1.8 | 2.4 | 0.3 |
| 2.077 | 33.7 | 12.5 | 5.0 | 0.8 |
| 2.078 | 18.3 | 4.4 | 2.6 | 0.0 |
| 2.079 | 18.5 | 5.5 | 2.3 | 0.2 |
| 2.080 | 213.7 | 18.5 | 125.9 | 17.7 |
| 2.081 | 1446.1 | 317.4 | 1111.2 | 989.8 |
| 2.082 | 131.7 | 30.1 | 9.0 | 2.9 |
| 2.083 | 1882.9 | 380.5 | 857.6 | 706.9 |
| 2.084 | 1174.6 | 172.9 | 349.6 | 116.2 |
| 2.085 | 2391.7 | 219.6 | 812.0 | 417.7 |
| 2.086 | 1246.0 | 57.7 | 358.0 | 28.5 |
| 2.087 | 896.4 | 67.0 | 59.3 | 6.2 |
| 2.088 | 38.7 | 6.1 | 13.6 | 1.6 |
| 2.089 | 102.1 | 3.7 | 32.9 | 3.1 |
| 2.090 | 53.3 | 10.2 | 19.5 | 2.4 |
| 2.091 | 776.1 | 94.2 | 236.7 | 16.1 |
| 2.092 | 1132.5 | 128.2 | 458.0 | 73.1 |
| 2.093 | 576.3 | 99.5 | 127.7 | 19.5 |
| 2.094 | 16570.6 | 1465.6 |  |  |
| 2.096 | 70.2 | 9.7 | 9.6 | 1.5 |
| 2.097 | 35.4 | 2.1 | 2.8 | 0.8 |
| 2.098 | 382.5 | 13.6 | 73.5 | 3.6 |
| 2.099 | 15.0 |  | 3.8 |  |
| fasudil | 346.3 | 17.6 | 96.4 | 6.4 |
| H-1152 | 18.5 | 5.3 | 2.0 | 0.3 |
| H7 |  |  | 124.7 | 5.6 |
| Y-27632 | 197.2 | 50.6 | 60.9 | 16.9 |
| Y-39983 | 34.7 | 11.1 | 3.6 | 0.9 |

Conclusion

Most of the compounds studied inhibited ROCK2 with a $K_i$ below 600 nM, many of these values below 60 nM. The most potent compounds in this assay showed $K_i$ values below 15 nM.

Example 2

NIH/3T3 Cell Morphology Assay

Relevance

The assay demonstrates that a compound's in vitro ROCK inhibition activity manifests itself in morphology changes, such as actin stress fiber disassembly and alteration in focal adhesions in intact cells leading to inhibition of acto-myosin driven cellular contraction. These morphology changes provide the basis for the beneficial pharmacological effects sought in the setting of the disease processes described in this application, specifically the disruption of the actin stress fibers and its impact on smooth muscle contractility; cell mobility (Howard et. al. *The J. of Cell Biology* 98:1265-1271, 1984); and endothelial and epithelial permeability (Stephens et al., *Am. Rev. Respir. Dis.* 137:4220-5, 1988 and Vandenbroucke et al., *Ann. N.Y. Acad. Sci.* 1123: 134-145, 2008.)

Protocol

NIH/3T3 cells were grown in DMEM-H containing glutamine and 10% Colorado Calf Serum. Cells were passaged regularly prior to reaching confluence. Eighteen to 24 hours prior to experimentation, the cells were plated onto Poly-L-Lysine-coated glass bottom 24-well plates. On the day of experimentation, the cell culture medium was removed and was replaced with the same medium containing from 10 nM to 25 µM of the test compound, and the cells were incubated for 60 minutes at 37° C. The culture medium was then removed and the cells were washed with warmed PBS and fixed for 10 minutes with warmed 4% paraformaldehyde. The cells were permeabilized with 0.5% Triton-X, stained with TRITC-conjugated phalloidin and imaged using a Nikon Eclipse E600 epifluorescent microscope to determine the degree of actin disruption. Results were expressed as a numerical score indicating the observed degree of disruption of the actin cytoskeleton at the test concentration, ranging from 0 (no effect) to 4 (complete disruption), and were the average of at least 2 determinations.

All compounds tested show measurable activity in the cell morphology assay, with most of the compounds providing substantial effects (score of $\geq 2$ at 1 µM) on the actin cytoskeleton at the tested concentration (see Table 2).

TABLE 2

Cell Morphology Assay Data

| Compound | Cell score at 1 µM |
| --- | --- |
| 1.002 | 1.4 |
| 1.004 | 1.8 |
| 1.005 | 1.3 |
| 1.006 | 2 |
| 1.008 | 2 |
| 1.024 | 2.4 |
| 1.025 | 2 |
| 1.034 | 2 |
| 1.039 | 2 |
| 1.041 | 2.5 |
| 1.046 | 2.5 |
| 1.048 | 1.5 |
| 1.051 | 2.5 |
| 1.052 | 2.8 |
| 1.062 | 2.3 |
| 1.066 | 2 |
| 2.002 | 1.8 |
| 2.006 | 2.8 |
| 2.008 | 1 |
| 2.016 | 1.8 |
| 2.017 | 2 |
| 2.018 | 1.8 |
| 2.026 | 2 |

Example 3

Tracheal Relaxation Assay

Relevance

The mechanism by which bronchoconstricting agents induce smooth muscle contraction is known to involve the activation of Rho kinase (Yoshii et al, Am J Respir Cell Mol Biol 20:1190-1200 (1999)). These data demonstrate that inhibition of Rho pathways with the described compounds induces relaxation of smooth muscle. Since diseases accompanied by airway hyperreactivity and/or bronchoconstriction, such as asthma, COPD, RSV infection, LAM and IPF, involve a contraction of airway smooth muscle, agents that induce a relaxant response in the tracheal smooth muscle can be candidates for treatment of such diseases. Standard clinical treatments for respiratory disorders involving airway hyperreactivity and/or bronchoconstriction, such as albuterol, formoterol and salmeterol, have been shown to demonstrate relaxant properties in tracheal smooth muscle (Battram et al, J Pharmacol Exp Therap 317:762-770 (2006)). Therefore, the activity of the present compounds in this ex vivo model supports the use of these agents in diseases of airway hyperreactivity, Protocol The effects of compounds to induce relaxation of precontracted rat trachealis were determined, Male Sprague-Dawley rats weighing 301-325 gm were sacrificed by asphyxiation in a $CO_2$ chamber. Trachea were excised, cleaned of connective tissue and cut into cylindrical segments of 2-3 mm length. Two stainless steel wires were guided through the lumen of the tracheal ring. One wire was fixed in the tissue bath and the other was connected to a force transducer via surgical silk. Preparations were mounted in 5 ml water-jacketed organ baths (Radnoti Glass Technology) filled with Krebs buffer (95 mM NaCl, 5 mM KCl, 2.6 mM $CaCl_2$, 1.2 mM $MgSO_4$, 24.9 mM $NaHCO_3$, 1.2 mM $KH_2PO_4$, 10 mM glucose) maintained at 37° C. and gassed with 95% $O_2$ and 5% $CO_2$. Indomethacin (1 µM), a cyclooxygenase inhibitor, was added to the Krebs buffer and was present throughout the experiments. Contractile tensions were measured using an isometric force transducer (Grass Instruments) and signals were analyzed using specialized software (Chart v5.5, ADInstruments). The preparations were allowed to equilibrate at a resting tension of 0.3 to 0.5 gm prior to two challenges with 60 mM KCl to assess tissue viability. After washing, tissues were treated with 1 µM carbachol for 10 to 15 minutes to induce a contractile response. Test Compounds were added cumulatively to the bath every 30 minutes and reductions in tension were recorded. Basal tension was subtracted from all values and data were reported as a percentage of the maximal carbachol-induced contraction. Data were fit to the Hill equation using GraphPad Prism v5 software.

FIG. 1A shows the dose response relationship for carbachol-induced contraction and the dose response relationship for representative compounds to induce a relaxant response in precontracted tracheal rings.

Table 3 shows (i) the $IC_{50}$ values of the listed compounds to induce a relaxant response in precontracted tracheal rings, and (ii) the efficacy at 10 µM of the listed compound reported as a percent of the maximal carbachol-induced contraction response.

TABLE 3

ROCK Inhibitor Potency and Efficacy in Tracheal Ring Relaxation $IC_{50}$ values and efficacy of 10 µM compounds are shown as a percent of the carbachol-induced contraction of rat trachea rings.

| Compound | $IC_{50}$ Avg, nM | Percentage of carbachol-induced contraction at 10 µM compound, Avg % | Percentage of carbachol-induced contraction at 10 µM compound, StdDev % |
| --- | --- | --- | --- |
| 1.074 | 729 | −15.1% | 3.4% |
| 1.091 | 103 | 14.3% | 20.0% |
| 1.092 | 453 | −2.9% | 22.5% |
| 1.107 | 1241 | 9.9% | 10.6% |
| 1.123 | 45 | 4.6% | 24.8% |
| 1.124 | 21 | 19.7% | 15.3% |
| 1.131 | 243 | 14.2% | 13.5% |
| 1.136 | 861 | 19.7% | 9.6% |
| 2.026 | 2859 | 17.1% | 18.7% |

TABLE 3-continued

ROCK Inhibitor Potency and Efficacy in Tracheal Ring Relaxation $IC_{50}$ values and efficacy of 10 µM compounds are shown as a percent of the carbachol-induced contraction of rat trachea rings.

| Compound | $IC_{50}$ Avg, nM | Percentage of carbachol-induced contraction at 10 µM compound, Avg % | Percentage of carbachol-induced contraction at 10 µM compound, StdDev % |
|---|---|---|---|
| 2.037 | 2115 | 21.3% | 4.8% |
| 2.038 | 272 | 10.2% | 4.9% |
| 2.039 | 343 | 6.2% | 18.2% |
| 2.041 | 162 | −5.4% | 12.2% |
| 2.045 | 2723 | 13.6% | 15.4% |
| fasudil |  | 43.0% | 40.1% |
| H-1152 | 164 | −6.5% | 12.0% |
| Y-27632 | 4783 | 23.4% | 17.8% |
| Y-39983 | 190 | −6.0% | 13.7% |

With the exception of fasudil, all compounds tested induced a relaxant response in carbachol precontracted tissue to values that are <25% of the maximal carbachol response and displayed $IC_{50}$ values of <5 µM. Fasudil was the least efficacious compound at the highest tested concentration of 10 µM. Due to the lack of potency and efficacy of fasudil, an $IC_{50}$ value could not be obtained with the tested concentrations.

Table 3a shows the efficacy at 1 µM of the listed compound reported as a percent of the maximal carbachol-induced contraction response. Y-27632 induced a relaxant response that was 83.7% of the carbachol-induced contraction. Most of the compound of Formula I or II displayed greater efficacy than Y-27632.

TABLE 3a

ROCK Inhibitor Efficacy in Tracheal Ring Relaxation Efficacy of 1 µM compounds are shown as a percent of the carbachol-induced contraction of rat trachea rings.

| Compound | Percentage of carbachol-induced contraction at 1 µM compound, Avg % | Percentage of carbachol-induced contraction at 1 µM compound, StdDev % |
|---|---|---|
| 1.072 | 33.1 | 10.1 |
| 1.074 | 39.6 | 11.8 |
| 1.075 | 39.1 | 10.5 |
| 1.078 | 39.6 | 17.5 |
| 1.091 | 35.4 | 21.2 |
| 1.092 | 67.7 | 7.6 |
| 1.123 | 46.7 | 13.1 |
| 1.124 | 37.8 | 12.1 |
| 1.131 | 37.4 | 8.7 |
| 1.132 | 42.4 | 13.0 |
| 1.136 | 45.0 | 18.1 |
| 1.141 | 35.3 | 17.0 |
| 1.148 | 51.2 | 8.0 |
| 1.149 | 34.4 | 14.5 |
| 1.150 | 39.7 | 12.8 |
| 1.151 | 33.1 | 16.2 |
| 1.152 | 34.4 | 13.4 |
| 1.153 | 40.9 | 16.4 |
| 1.161 | 40.3 | 20.9 |
| 1.162 | 34.4 | 21.5 |
| 1.163 | 35.4 | 6.4 |
| 1.165 | 29.8 | 15.7 |
| 1.173 | 32.8 | 14.1 |
| 1.184 | 88.6 | 6.6 |
| 1.196 | 96.2 | 8.0 |
| 1.197 | 41.7 | 17.7 |
| 1.200 | 91.5 | 6.1 |
| 1.212 | 40.1 | 20.8 |
| 1.213 | 29.3 | 11.0 |
| 1.215 | 40.6 | 15.5 |
| 2.025 | 33.3 | 14.8 |
| 2.038 | 57.2 | 14.7 |
| Y-27632 | 83.7 | 7.4 |
| Y-39983 | 26.5 | 11.7 |

Example 3a

Effect of Inflammatory Cytokines on Tracheal Relaxation

Relevance

Pulmonary disease such as asthma and COPD are accompanied by an inflammatory response in the lung that contributes to disease severity. These inflammatory cytokines can alter tissue function and may limit the efficacy of therapeutic interventions. Demonstration of compound efficacy in tissues that have been exposed to inflammatory cytokines in vitro supports the utility of these compounds as bronchorelaxants in disease states such as asthma that are accompanied by inflammation in vivo.

Protocol

Male Sprague-Dawley rats weighing 301-325 gm were sacrificed by asphyxiation in a $CO_2$ chamber. Trachea were excised, cleaned of connective tissue and cut into cylindrical segments of 2-3 mm length. Tissues were treated for 18 hours at 37° C. in F12 media with penicillin-streptomycin and 0.1% BSA alone or with 10 ng/ml IL-1β and 100 ng/ml TNF-α. Tissues were then washed free of cytokines with Krebs buffer. Contractile tensions were measured using an isometric force transducer (Grass Instruments) as described for Example 3 and signals were analyzed using specialized software (Chart v5.5, ADInstruments). Tissues were treated with 300 nM carbachol for 10 to 15 minutes to induce a contractile response. Test Compounds were added cumulatively to the bath every 30 minutes and reductions in tension were recorded. Basal tension was subtracted from all values and data were reported as a percentage of the maximal carbachol-induced contraction. Data were fit to the Hill equation using GraphPad Prism v5 software.

FIG. 1a shows the dose response relationship for representative compounds to induce a relaxant response in vehicle-pretreated and cytokine-pretreated tissues. Compound 1.091 is fully efficacious in relaxing tracheal rings from both vehicle-pretreated and cytokine-pretreated tissues and is slightly more potent in cytokine-pretreated tissues.

Example 4

Pulmonary Arterial and Aortal Relaxation Assay

The effects of compounds to induce relaxation of pre-contracted rat pulmonary artery and rat aorta were determined. Male Sprague-Dawley rats weighing 301-325 gm were sacrificed by asphyxiation in a $CO_2$ chamber. Pulmonary artery or aorta were excised, cleaned of connective tissue and cut into cylindrical segments of 2-3 mm length. The preparations were mounted in a tissue bath by tying two threads of surgical silk through the lumen of the vessel. One silk was used to anchor the tissue to a metal wire in the bath and the other silk was connected to a force transducer. Preparations were mounted in 5 ml water-jacketed organ baths (Radnoti Glass Technology) filled with Krebs buffer (95 mM NaCl, 5 mM KCl, 2.6 mM $CaCl_2$, 1.2 mM $MgSO_4$, 24.9 mM $NaHCO_3$, 1.2 mM $KH_2PO_4$, 10 mM glucose) maintained at 37° C. and gassed with 95% $O_2$ and 5% $CO_2$. Contractile tensions were measured using an isometric force transducer (Grass Instruments) and signals were analyzed using specialized software (Chart v5.5, ADInstruments). The preparations were allowed to equilibrate at a resting tension of 0.1 to 0.2 gm for pulmonary artery and 2.0 gm for aorta prior to two challenges with 80 mM KCl to assess tissue viability. After washing, tissues were treated with 100 nM norepinephrine for 5 to 10 minutes to induce a contractile response. For pulmonary artery, compounds were added cumulatively to the bath every 30 minutes and reductions in tension were recorded. Basal tension was subtracted from all values and data was reported as a percentage of the maximal norephinephrine-induced contracation. Data were fit to the Hill equation using GraphPad Prism v5 software. For aorta, a single dose of compound was added and reductions in tension were recorded.

Figure 2A:
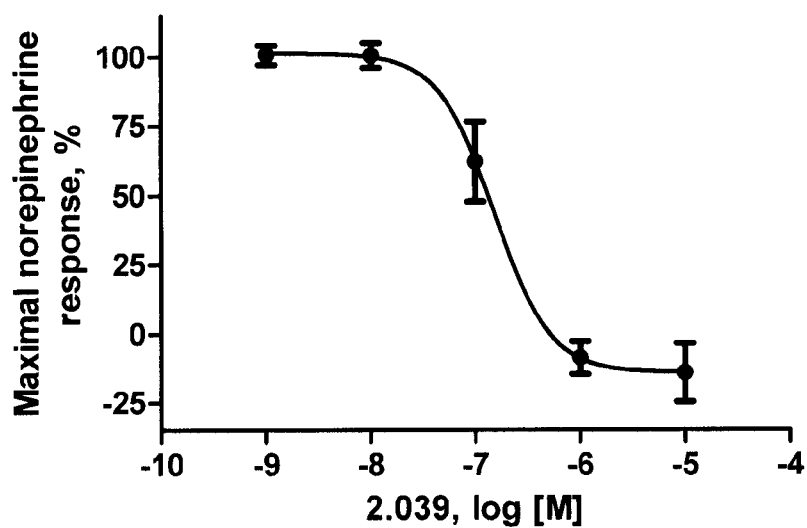
FIG. 2A shows the dose response curves for a representative compound, 2.039, to induce relaxation in 100 nM norepinephrine precontracted rings. Data are reported as a percent of the maximal norepinephrine response and are mean±SEM of 5 replicates.
Figure 2B:
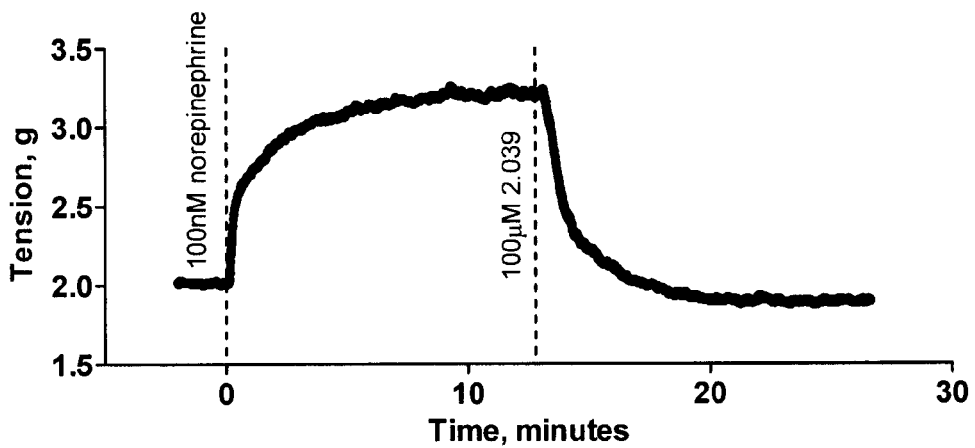
FIG. 2B shows the tension (in grams) recorded from an aortal ring. Addition of 100 nM norepinephrine induced a contractile response recorded as an increase in tension that was fully reversed upon addition of 100 μM compound 2.039.

FIG. 2a shows the dose response relationship for a representative compound to induce a relaxant response in precontracted pulmonary artery. The representative compound fully relaxed the pre-contracted pulmonary artery. The $IC_{50}$ for compound-induced relaxation was 151 nM, These data demonstrate that compounds of this class are able to induce a relaxant response in arterial smooth muscle. FIG. 2b shows the reduction in tension after addition of 100 μM compound in precontracted aorta. Tension returned to basal values upon addition of compound to the norepinephrine precontracted aortal rings. Smooth muscle contractile responses mediate hypertensive disorders and currently marketed therapeutics for hypertensive disorders, such as iloprost, demonstrate efficacy in norepinephrine pre-contracted pulmonary arteries (Walch et al, Brit J Pharmacol 126:859-866 (1999)). Therefore, the results indicate that the compounds are good candidates for treating diseases that involve constriction of arterial smooth muscle, such as pulmonary arterial hypertension or systemic hypertension.

Example 5

Bronchodilator Assay in Rodent Model of Asthma in Ovalbumin-Sensitized Mice

The main functional changes of the lungs associated with pulmonary diseases such as asthma and chronic obstructive pulmonary disease (COPD) include malfunctioning of the immune system, cellular infiltration composed primarily of eosinophils and neutrophils, acute and chronic inflammation, fluid accumulation (edema), excessive secretion of mucus, and changes in the airway walls that could lead to bronchial epithelial injury, fibrosis, and increased sensitivity to agents that cause bronchial constriction. These features need to be considered in order to understand the development and mechanics of the disease, and to develop treatments of the underlying disease process. Small animal models can be designed to mimic the airway inflammation, increased responsiveness to bronchial constrictors, changes in the airway wall, and the migration of the eosinophils and neutrophils to the lungs. Such animal models provide valuable tools to evaluate the effects of experimental compounds on these disease characteristics (Kips et al. *Eur Respir J* 2003; 22:374-382; Isenberg-Feig, et al. *Current Allergy and Asthma Reports.* 2003; 3: 70-79). A mouse model of asthma via ovalbumin sensitization was used to evaluate bronchodilator efficacy of compounds of Formula I and II.

Male BALB/c mice were ordered from Charles River Laboratories (Raleigh, N.C.). The animals were approximately 19 to 21 grams at time of receipt. Upon arrival, the animals were randomized into groups of five males per cage and assigned to a dosing group. Animals were quarantined for 7 days under test conditions. They were observed daily for general health status and ability to adapt to the water bottles.

Animals were sensitized on day 0 and 14 of study by an intraperitoneal injection with 20 μg of ovalbumin (ova) and 2.0 mg aluminum hydroxide (alum) which initiates the development of a specific T-helper (Th) cells type 2 resulting in asthmatic animals. One group of animals received an injection of saline to use as non-asthmatic control animals. All animals were challenged with aerosolized 1% ova once daily for 25 minutes on days 28, 29, and 30 (Zosky, et al. *Respiratory Research,* 2004; 5:15). Aerosol challenge consists of using an Aerogen Aeroneb nebulizer and controller with a particle size of 4-6 μm mass median aerodynamic diameter (MMAD) with a distribution of 400 μl per minute. This aerosol challenge is necessary to target the Th2-driven allergic inflammation in the lower airways.

Figure 3A:
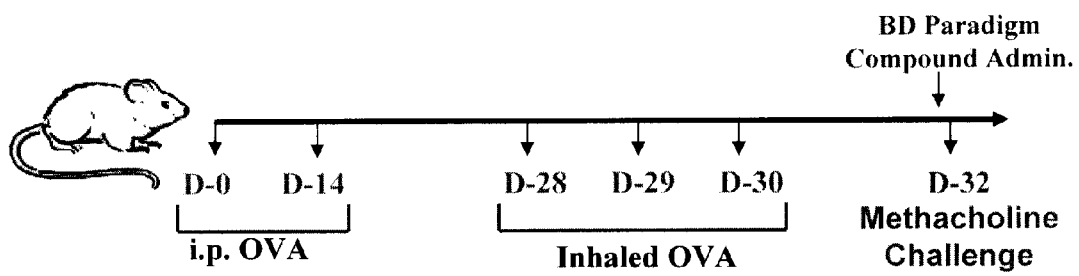
FIG. 3A shows the bronchodilator dosing paradigm.
Figure 3B:
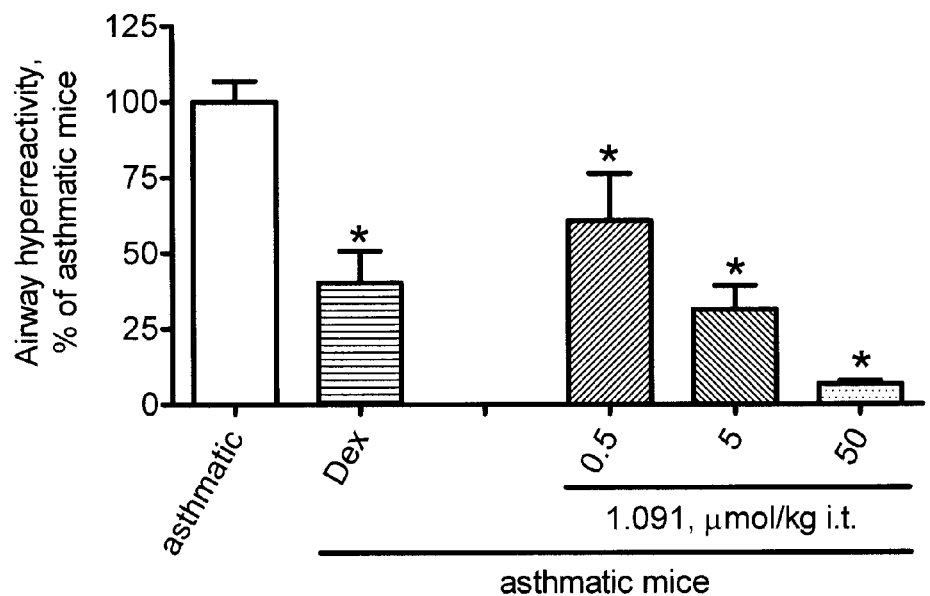
FIG. 3B shows the dose response effect of Compound 1.091 on airway hyperreactivity when dosed intratracheally using the bronchodilator dosing paradigm. Linear AUC values from compound treated mice were reported as a percent of linear AUC values from vehicle-treated ovalbumin-sensitized/ovalbumin-challenged (asthmatic) mice. *, $p<0.05$ using statistical analysis described in Example 5.

The test compounds and the control vehicle were administered to animals on the day of airway hyperreactivity evaluation 30 minutes to 1 hour before the evaluation to determine the bronchodilator effects of the compounds according to the bronchodilator dosing paradigm (FIG. 3A). Compounds were administered p.o. (orally), i.p. (intraperitoneally) at 15 μMol/kg unless otherwise noted (Table 4). Alternatively, compounds were administered i.t. (intratracheally) at varying doses as shown (FIG. 3B). On day 32 of the experiment, airway hyperreactivity was evaluated by placing conscious, unrestrained animals in a whole body plethysmometer (Buxco Wilmington, N.C.) and exposing them to escalating doses of nebulized methacholine, a known bronchial constrictor which acts through the muscarinic receptors of the lungs, (doses: 0.325-50 mg/ml). Exposure to the methacholine doses consisted of a 3 minute period during which a nebulizer was aerosolizing the methacholine and an additional 3 minute period following the cessation of nebulization. Over this 6 minute period, the plethysmometer monitors and generates numerical values for all parameters of the breath pattern. Enhanced pause (Penh), a unitless index of airway hyperreactivity, is derived from the expiratory side of the respiratory waveform measured via the plethysmograph and is used as an indirect measure of airway resistance and hyperreactivity. Penh is an indicator of changes in resistance within the airways and has been shown to be a valid marker for airway responsiveness to allergen challenge (Hamelmann, et al. *Am J Respir Crit. Care Med.* 1997; 156:768-775). Following the methacholine dose response, all animals were anesthetized, bled and euthanized.

Statistical Methods

Within each experiment, a mouse was given a single compound and exposed to increasing doses of methacholine [0 (baseline), 0.375, 0.75, 1.5, 3, 6, 12, 25, 50 mg/ml]. The Penh value at each of the dose levels of methacholine represents the 6-minute average response. Change from baseline (CFB) in Penh was calculated at each methacholine dose and the area under the curve (AUC) for these CFB values was calculated using the trapezoidal rule. This same approach was applied for each mouse across multiple experiments.

For statistical analyses, a linear mixed-effects model where the response was the log 10 transformed value of AUC described above was used. Data from equal experimental conditions across experiments performed on different days were pooled for statistical analysis and data reporting. The various compounds were compared adjusting for the log 10-transformed baseline value of Penh and the chamber (1 of 10) of the plethysmometer each mouse was contained in during an experiment. A random intercept for each experiment was assumed to account for possible similarities of the results obtained from a given experiment (i.e., as a "blocking effect"). Pairwise comparisons of the compounds were performed using approximate t-tests to test the null hypothesis of no compound difference of the least-squares means of log 10(AUC). p values of less than 0.05 were considered statistically significant Computations were performed using PROC MIXED (SAS Version 9.1).

For Table 4 and Table 5, Penh values are reported as log 10 transformed AUC values. For FIG. 3B and FIG. 5C, linear AUC values from compound treated mice were reported as a percent of linear AUC values from vehicle-treated ovalbumin-sensitized/ovalbumin-challenged (asthmatic) mice.

Results

Evaluation of the pulmonary mechanics data shows a methacholine dose response trend of increased Penh levels. The sensitized animals showed a heightened response to the methacholine, which indicated an asthma-like hyperresponsivness to the broncho-constricting agent when compared to the nonsensitized control animals exposed to inhaled ovalbumin or completely naïve animals.

Treating animals with oral doses of potent ROCK2 inhibitors of Formula I or II, which after oral dosing reached high plasma and lung tissue concentrations such as Compounds 1.131 or 2.038, yielded a statistically significant reduction in airway hyperresponsivness (Table 4). Compounds 1.131 and 2.038 all reached high Cmax values (nM) for peak plasma concentrations in rats (Table 7), high AUC values (nM*hr) for area-under-the-curve for plasma concentration vs. time curves in rats (Table 7), and high lung tissue concentrations in mice (Table 8) after oral dosing. These compounds also were readily detectable in mouse plasma 15 minutes after oral dosing (Table 8a).

Conversely, treating animals with oral doses of potent ROCK2 inhibitors of Formula I or II, which after oral dosing did not reach a detectable plasma concentration in the rat or low concentrations in the mouse, such as Compound 1.136 or 1.091, did not yield a significant reduction in airway hyperresponsivness (Table 4). Compounds 1.136 and 1.091 had Cmax values (nM) for peak plasma concentrations (Table 7), and AUC values (nM*hr) for area-under-the-curve for plasma concentration vs. time curves (Table 7) below the level of quantification in the rat. Dosing compounds such as Compound 1.136 or 1.091, which have poor oral bioavailability, via the i.p, route of administration yielded an enhanced reduction in airway hyperresponsiveness when compared to oral dosing (Table 4). These results are consistent with the current understanding that active compounds must reach the smooth muscle tissue in the airway in order to elicit bronchodilator efficacy. In support of these findings, direct application of compounds such as Compound 1.091 to the lung by intratracheal administration resulted in a robust bronchodilatory response (Table 4 and FIG. 3B).

TABLE 4

Bronchodilator Efficacy: Statistical Analysis of the AUC for Average Penh Values Determined During Experiment Normalized to Baseline for Each Animal

| Compound | Dosing concentration/route of administration | Number of animals per group | log10AUC (penh) | Standard Error | Student t-test p-value |
|---|---|---|---|---|---|
| asthmatic | Vehicle/all routes | 209 | 2.3205 | 0.02806 | |
| 1.136 | 15 µmol/kg/oral | 10 | 2.2490 | 0.1023 | 0.4853 |
| 1.091 | 15 µmol/kg/oral | 20 | 2.2309 | 0.07207 | 0.2123 |
| 1.136 | 15 µmol/kg/intraperitoneal | 10 | 2.1379 | 0.1017 | 0.0731 |
| 1.215 | 15 µmol/kg/intraperitoneal | 10 | 2.0081 | 0.1014 | 0.0022 |
| 2.025 | 15 µmol/kg/intraperitoneal | 10 | 1.9667 | 0.1014 | 0.0005 |
| 1.235 | 15 µmol/kg/intraperitoneal | 10 | 1.9362 | 0.1017 | 0.0002 |
| 1.162 | 15 µmol/kg/intraperitoneal | 10 | 1.7001 | 0.1017 | <.0001 |
| 2.038 | 15 µmol/kg/oral | 25 | 2.0813 | 0.06628 | 0.0003 |
| 1.091 | 15 µmol/kg/intraperitional | 59 | 2.0096 | 0.04474 | <.0001 |
| 1.131 | 15 µmol/kg/oral | 40 | 2.0283 | 0.05314 | <.0001 |
| Naïve | | 20 | 1.9978 | 0.07286 | <.0001 |
| 1.161 | 15 µmol/kg/intraperitional | 10 | 1.9042 | 0.1014 | <.0001 |
| 1.091 | 5 µmol/kg/intratracheal | 10 | 1.8127 | 0.09980 | <.0001 |
| non-asthmatic | Vehicle/oral | 100 | 1.9283 | 0.03624 | <.0001 |
| Y-27632 | 30 µmol/kg/oral | 59 | 2.0135 | 0.04523 | <.0001 |

The t-test was conducted for the comparison of compound-treated to vehicle-treated "asthmatic groups".

Example 6

Anti-Inflammatory Assay in Rodent Model of Asthma in Ovalbumin-Sensitized Mice

Figure 4:
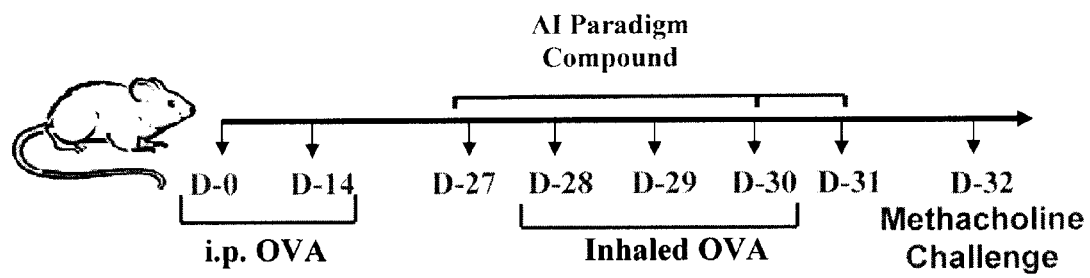
FIG. 4 shows the anti-inflammatory dosing paradigm.

Mouse model of asthma via ovalbumin sensitization was created as described in Example 5. The anti-inflammatory dosing paradigm (FIG. 4) was utilized to evaluate the anti-inflammatory effects of experimental compounds. The anti-inflammatory dosing paradigm consists of dosing the animals once a day starting on day 27 and finishing on either day 30 or 31 (1 hr prior to the aerosolized ovalbumin challenges on days 28 to 30) but not on day 32 when hyper-reactivity evaluation occurs.

Bronchoalveolar lavage fluid (BALF) was collected by infusing 3.0 ml of saline with 10% fetal calf serum into the lungs via the trachea and then withdrawing the fluid. The total amount of cells/ml of BALF fluid was determined via manual cell count on hemocytometer. The BALF was centrifuged, supernatant removed and analyzed for cytokine concentrations as described below, and cell pellet reconstituted in 500 µL of fluid. Cytospin slides were prepared from the cell pellet using 100 µL of fluid and spinning samples for 5 minutes at 5000 rpms in a cytospin centrifuge. Following Hema3 stain, relative percentages of individual leukocytes were determined on a 200 cell count for each sample. The final concentration of individual leukocyte cell types per ml of BALF was determined by multiplication of the relative percentage of individual leukocytes with the total amount of cells/ml of BALF fluid.

Figure 5A:
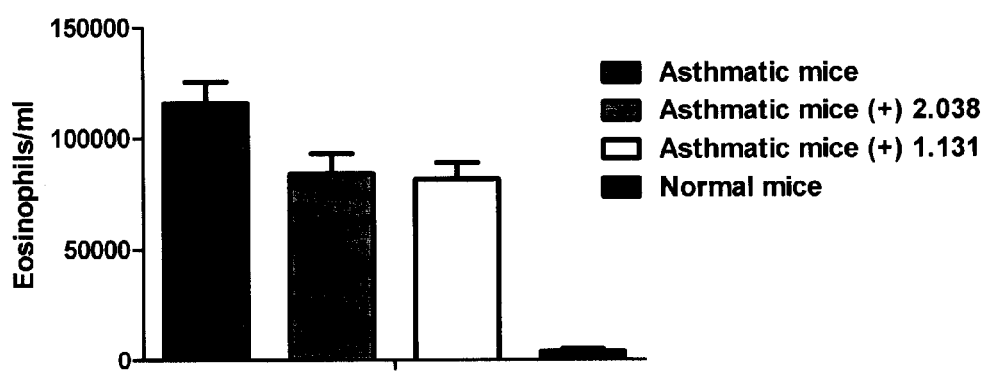
FIG. 5A shows the eosinophils per mL in asthmatic mice, mice treated with Compound 2.038, mice treated with Compound 1.131 and normal mice.

Evaluation of the differential counts performed on these samples showed an increased number of inflammatory cells in the asthmatic animals. FIG. 5A shows the eosinophils per ml of BALF in asthmatic mice, mice treated with Compound 2.038, mice treated with Compound 1.131 and normal mice. Compounds were dosed orally to day 31 according to the anti-inflammatory dosing paradigm shown in FIG. 4. Airway eosinophil infiltration was reduced in animals treated with the two tested compounds (FIG. 5A).

Figure 5B:
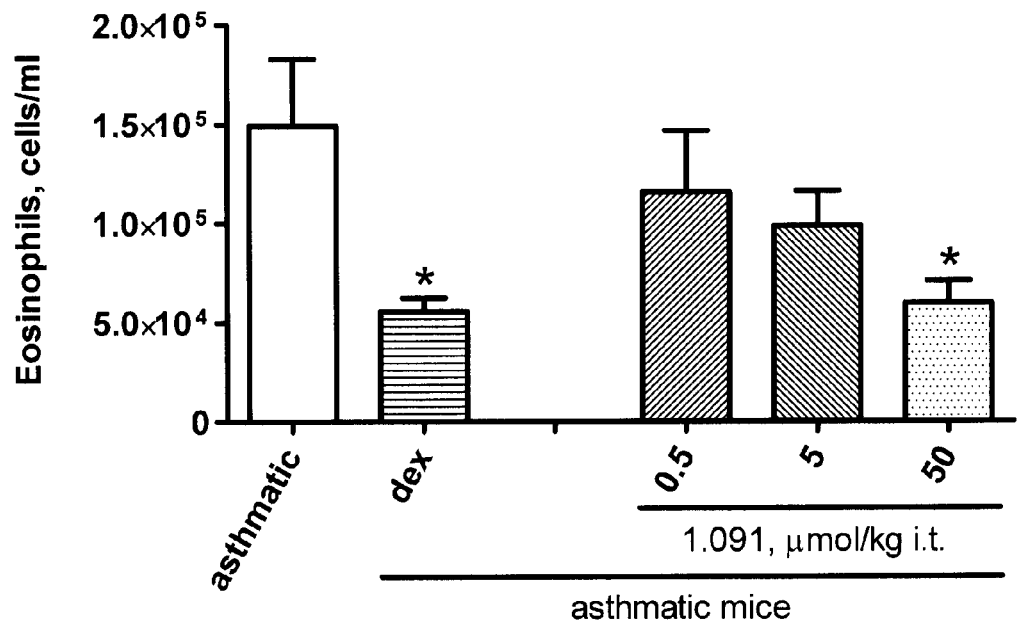
FIG. 5B shows the dose response effect of Compound 1.091 on eosinophil influx when dosed to asthmatic mice, *, $p<0.05$ when compared to asthmatic mice using Student's t-test.

Direct application of compound to the lung is sufficient to reduce airway eosinophil infiltration. As shown in FIG. 5B, Compound 1.091 generates a reduction of eosinophils when dosed i.t. to day 30 according to the anti-inflammatory dosing paradigm shown in FIG. 4. These results demonstrate these compounds display anti-inflammatory activity when systemic exposure is limited and that robust systemic exposure of these compounds is not necessary to achieve anti-inflammatory effects within the airways.

The concentrations of cytokines in the BALF samples were determined using commercially available Bio-plex kits (Bio-Rad) for the detection of mouse IL-5, IL-13, and Eotaxin. The analysis of cytokine levels was measured using the Bio-Plex 200 (Bio-Rad) system according to the manufacturer's instructions.

The main functional changes of the lungs associated with pulmonary diseases such as asthma and chronic obstructive pulmonary disease (COPD) include increased pulmonary inflammation including cellular infiltration into the interstitium and the lumen of the lung, increased pro-inflammatory cytokine concentrations, development of airway hyperreactivity, and remodeling of the airway. Substantial evidence suggests that cytokines play an important role in orchestrating and regulating this inflammatory process through the involvement of T-helper type 2 lymphocytes. Characteristics of T-cell mediated inflammatory immune response are dependent on the cytokines predominating during the course of the disease. The Th2 cytokines are associated with eosinophils, mast cell activation and preferential switching to IgE production, all being elements of the immune system associated with response to allergens. Therefore, a reduction in the levels of cytokines identified as key players in pulmonary inflammation is an indication of treating pulmonary inflammation.

Figure 6:
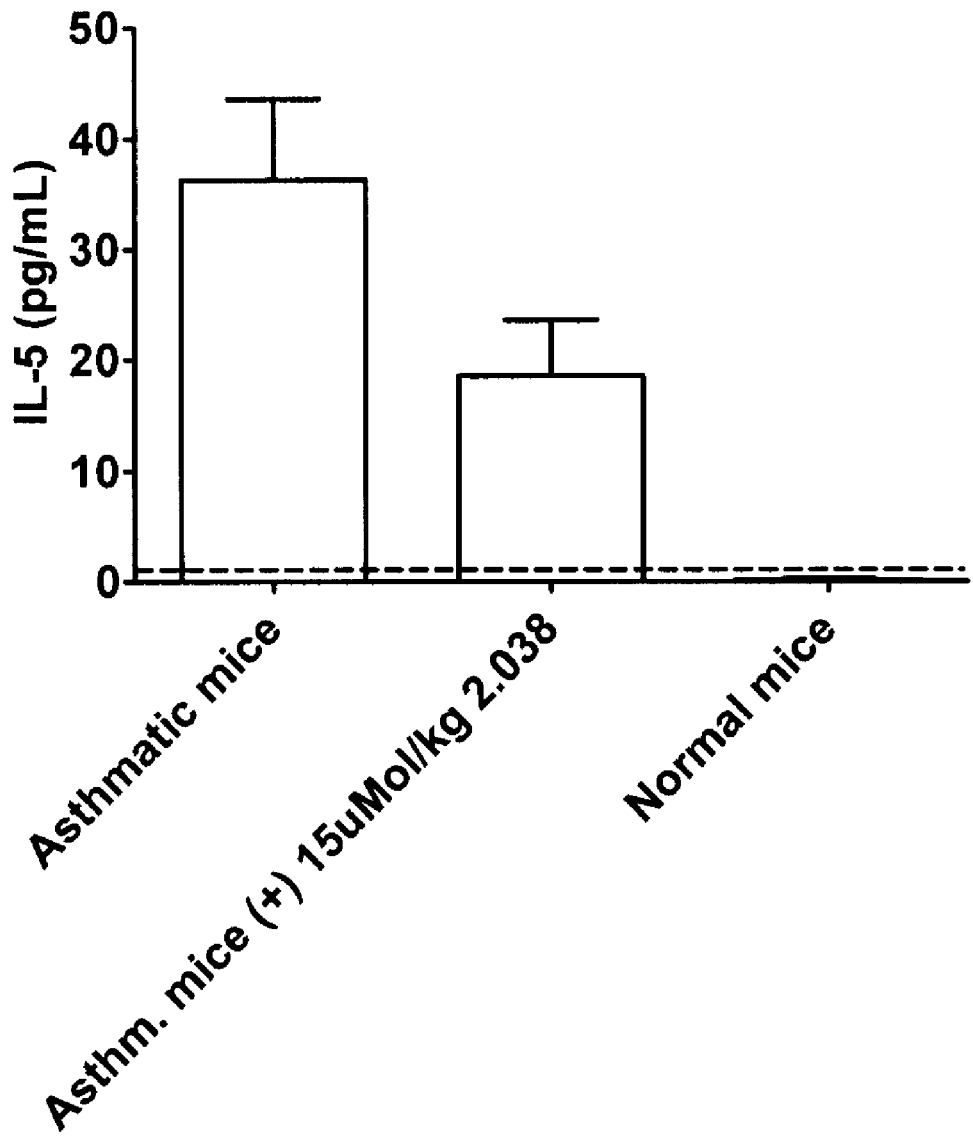
FIG. 6 shows the concentration of IL-5 (pg/mL) in bronchoaveolar lavage fluid (BALF) of (1) asthmatic mice, (2) asthmatic mice treated with Compound 2.038 (15 μmol/kg/oral), and (3) normal, saline-sensitized mice. Dashed line indicates the lower limit of detection for the cytokine of interest. Data represent mean±SEM, n=10 for asthmatic mice, treated or untreated; n=5 for normal mice.
Figure 7:
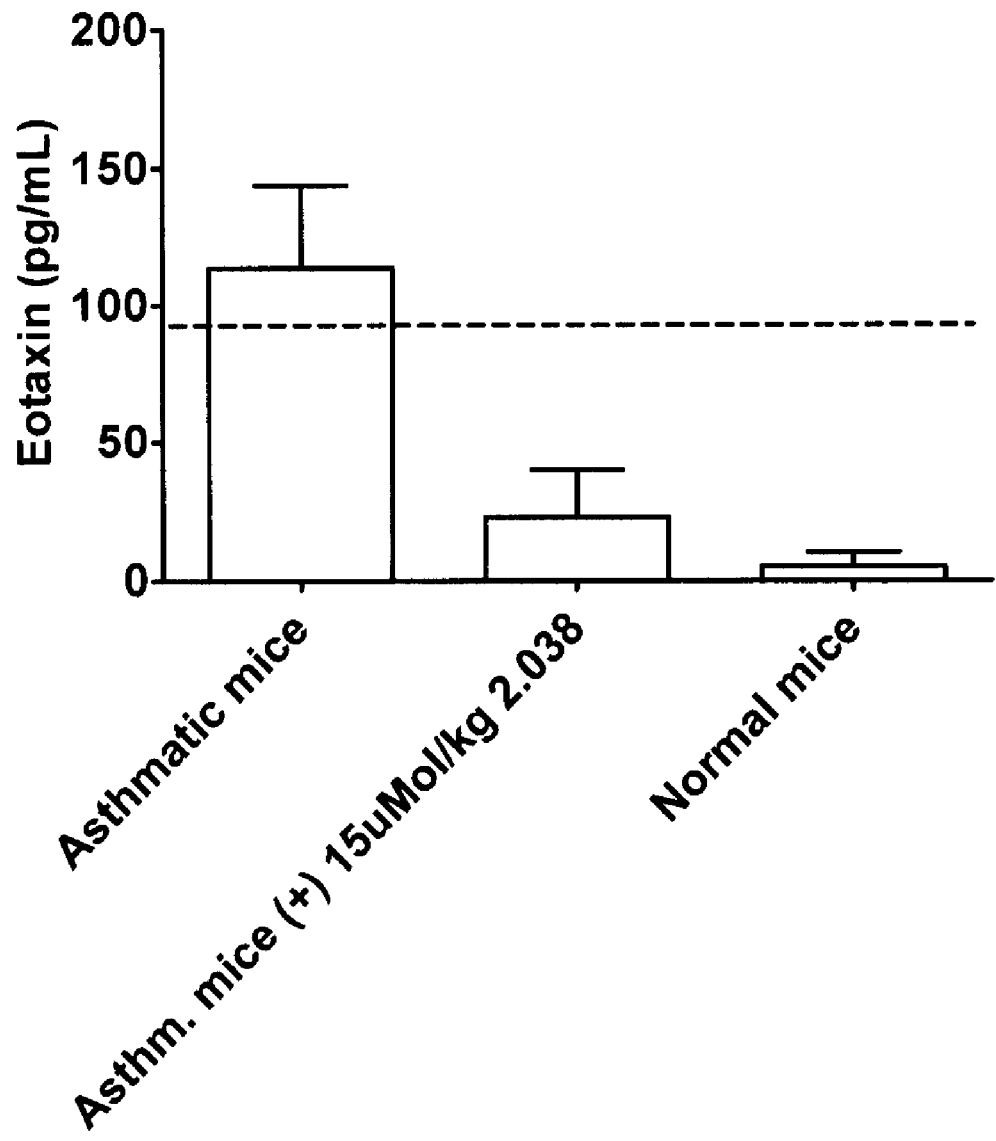
FIG. 7 shows the concentration of Eotaxin (pg/mL) in bronchoaveolar lavage fluid (BALF) of (1) asthmatic mice, (2) asthmatic mice treated with Compound 2.038 (15 μmol/kg/oral), and (3) normal, saline-sensitized mice. Dashed line indicates the lower limit of detection for the cytokine of interest. Data represent mean±SEM, n=10 for asthmatic mice, treated or untreated; n=5 for normal mice.
Figure 8:
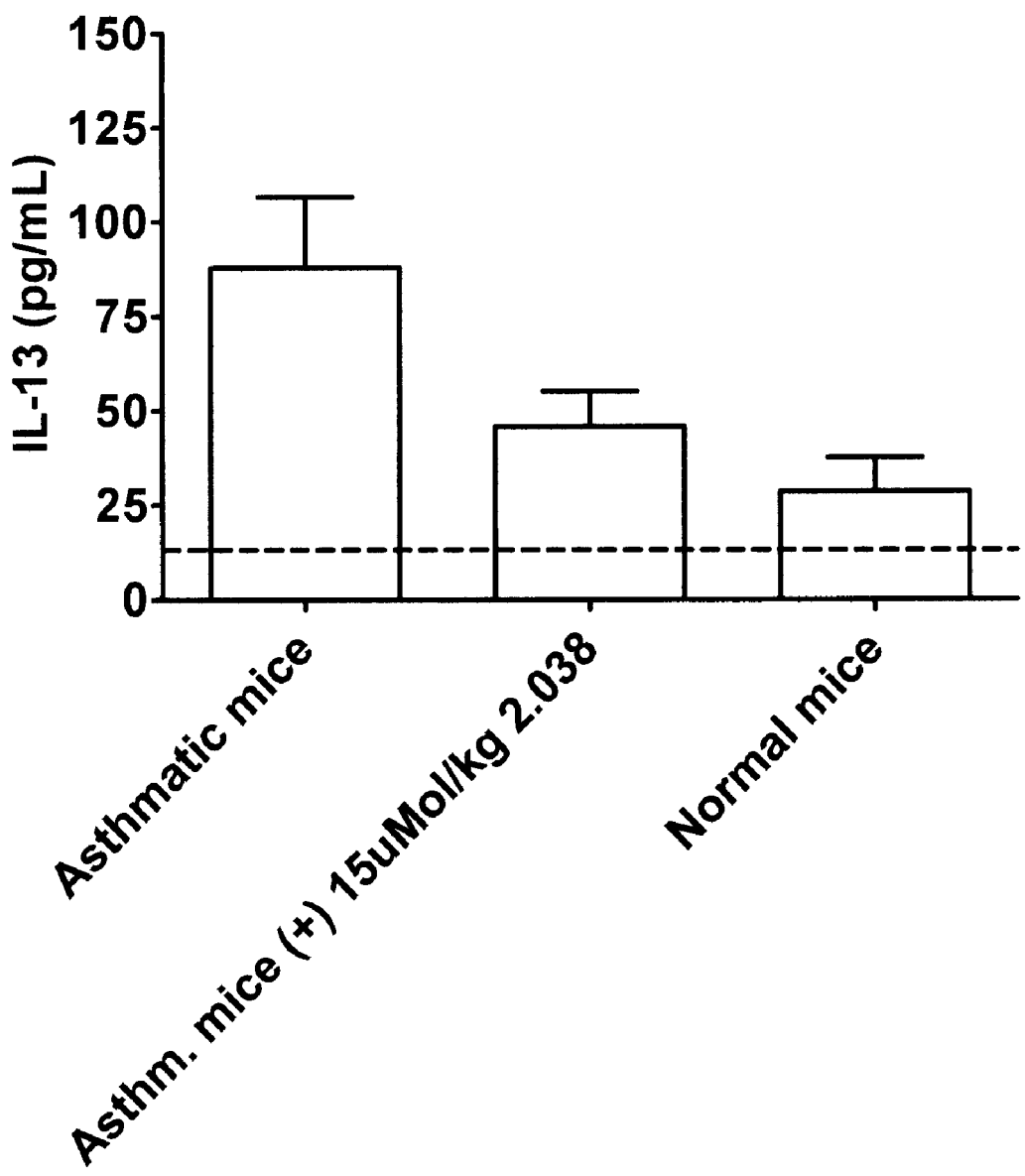
FIG. 8 shows the concentration of IL 13 (pg/mL) in bronchoaveolar lavage fluid (BALF) of (1) asthmatic mice, (2) asthmatic mice treated with Compound 2.038 (15 μmol/kg/oral), and (3) normal, saline-sensitized mice. Dashed line indicates the lower limit of detection for the cytokine of interest. Data represent mean±SEM, n—10 for asthmatic mice, treated or untreated; n=5 for normal mice.

FIGS. 6-8 show the concentration of IL-5, Eotaxin, and IL-13 in (1) asthmatic mice, (2) asthmatic mice treated with Compound 2.038 (15 µmol/kg/oral on days 27 to 31), and (3) normal, saline-sensitized mice. The results showed that asthmatic mice treated with Compound 2.038 had reduced levels of IL-5, Eotaxin, and IL-13.

Example 7

Prevention of Airway Hyperreactivity Development Via Decrease in Pulmonary Inflammation Mouse model of asthma via ovalbumin sensitization was created as described in Example 5. The anti-inflammatory dosing paradigm was utilized as described in Example 6. The objective of the experiment was to answer whether the decrease in pulmonary inflammation due to ROCK inhibitor anti-inflammatory dosing results in prevention of airway hyperreactivity/decrease in bronchial constriction as measured by Penh, as described in Example 5. Statistical analysis was performed as described in Example 5.

The oral administration of 15 µMol/kg of Compound 1.131 or 2.038 once a day during days 27 to 31 resulted in prevention of airway hyperreactivity to metacholine dosed on Day 32 (Table 5). These data support the use of these compounds to prevent inflammation and the development airway hyperreactivity. Statistical analysis was conducted as described in Example 5.

Figure 5C:
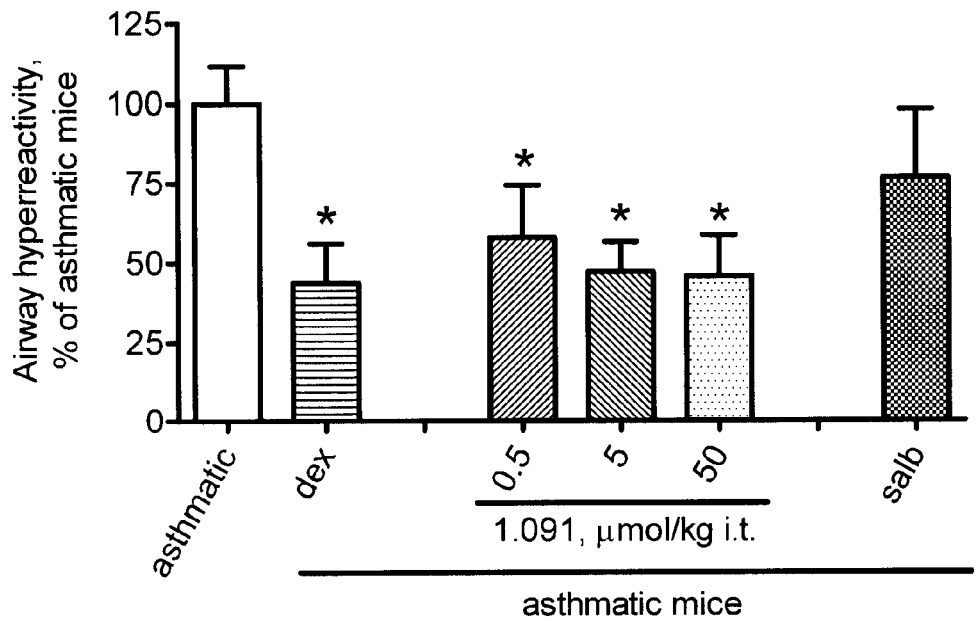
FIG. 5C shows the dose response effect of Compound 1.091 on airway hyperreactivity when dosed using the anti-inflammatory dosing paradigm on Days 27 to 30. *, $p<0.05$ using statistical analysis described in Example 7.

Direct application of compound to the lung is sufficient to prevent airway hyperreactivity. As shown in FIG. 5C and Table 5, intratracheal administration of Compound 1.091 once a day during days 27 to 30 (FIG. 5C) or Compounds 1.161, 2.066 or 2.059 once a day during days 27 to 31 (Table 5) according to the anti-inflammatory dosing paradigm shown in FIG. 4 resulted in prevention of airway hyperreactivity. Compound 1.091, 1.161, 2.066 or 2.059 had similar efficacy to dexamethasone, a corticosteroid anti-inflammatory control. Salbutamol, a direct bronchodilator, was ineffective using the anti-inflammatory dosing paradigm. These results demonstrate that these compounds display anti-inflammatory activity when systemic exposure is limited and that robust systemic exposure of these compounds is not necessary to achieve anti-inflammatory effects within the airways or to prevent airway hyperreactivity.

TABLE 5

Anti-inflammatory dosing: Statistical Analysis of the AUC for Average Penh Values Determined During Experiment Normalized to Baseline for Each Animal

|  | Dosing concentration/ route of administration | Number of animals per group | log10A UC (Penh) | Standard Error | Student t-test p-value |
| --- | --- | --- | --- | --- | --- |
| asthmatic | Vehicle/oral | 70 | 2.3354 | 0.04751 |  |
| 1.131 | 15 µmol/kg/oral | 10 | 2.0674 | 0.1061 | 0.0133 |
| 2.038 | 15 µmol/kg/oral | 20 | 1.8981 | 0.07966 | <0.0001 |

TABLE 5-continued

Anti-inflammatory dosing: Statistical Analysis of the AUC for Average Penh Values Determined During Experiment Normalized to Baseline for Each Animal

|  | Dosing concentration/ route of administration | Number of animals per group | log10A UC (Penh) | Standard Error | Student t-test p-value |
|---|---|---|---|---|---|
| 1.161 | 0.5 µmol/kg/ intratracheal | 10 | 2.0405 | 0.1083 | 0.0077 |
| 2.066 | 0.5 µmol/kg/ intratracheal | 10 | 2.0248 | 0.1091 | 0.0055 |
| 2.059 | 0.5 µmol/kg/ intratracheal | 10 | 1.9979 | 0.1084 | 0.0024 |
| Y-27632 | 30 µmol/kg/oral | 10 | 1.9942 | 0.1062 | 0.0017 |
| Dexamethasone | 1 mg/kg/oral | 30 | 2.0216 | 0.06546 | <0.0001 |
| non-asthmatic | Vehicle/oral | 20 | 1.7810 | 0.07973 | <0.0001 |

Compounds were administered on days 27 to 31 according to the anti-inflammatory dosing paradigm. The t-test was conducted for the comparison of compound-treated to vehicle-treated "asthmatic groups" based on the vehicle which was run in every study.

Example 8

IL-1β Monocyte Secretion Assay

IL-1β plays a major role in a number of inflammatory diseases including asthma and COPD. Increased level of IL-1β have been detected in the BALF of patients with COPD and asthma (Braddock M, et al., *Nature Reviews.* 3: 1-10, 2004). In the presence of increased IL-1β levels, certain tissues show an up-regulation of adhesion molecules, increased vascular permeability, and increased extravasation of leukocytes including neutrophils, macrophages, and lymphocytes. In this assay, lipopolysaccharide (LPS) was used as the inflammatory stimulus to induce cytokine production in human monocytes, and ATP was used to stimulate release of the pro-inflammatory cytokine IL-1β. Monocytes are known to orchestrate the innate immunity response to LPS by expressing a variety of inflammatory cytokines including IL-1β, TNF-α, IL-6, and many others (Gua M, et al., *Cellular Signalling.* 13: 85-94, 2001).

Peripheral blood from healthy human volunteers was collected and the monocytes isolated via Ficoll-paque density centrifugation. The resultant pellet was re-suspended in media containing 1 ng/mL lipopolysaccharide (LPS) and plated at a density of 500,000 cells/mL. After 3 hours of incubation (37° C., 5% $CO_2$, humidified air), monocytes were selected by adherence to the tissue culture plastic by washing wells with media. Following the media wash, cells were incubated for 2 minutes with the Rho kinase inhibitors (10 µM) prior to the addition of 1 mM ATP. Cells were allowed to incubate with compounds for 30 minutes at 37° C. after which the supernatant was removed for immediate determination of IL-1β concentration. The concentration of IL-1β in cell supernatants was measured using the Human IL-1β kit and Bio-Plex system (Bio-Rad) according to manufacture's instructions.

Figure 9:
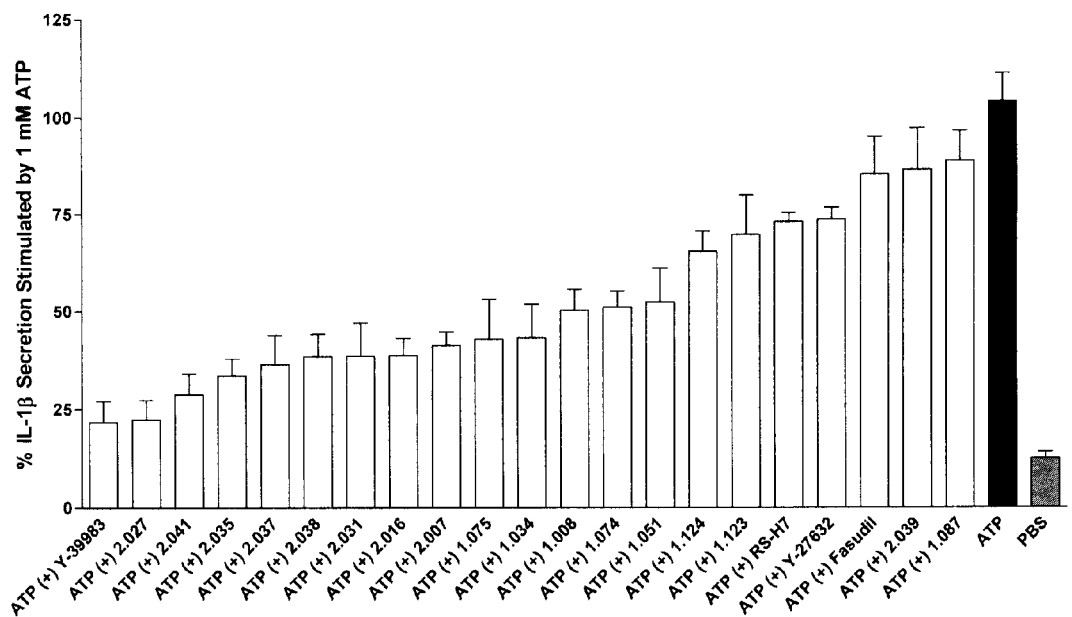
FIG. 9 shows the % inhibition of ATP-stimulated IL-1β Secretion in Human Monocytes by Rho Kinase Inhibitors. Data represent the mean±SD of at least n=2 experiments.

FIG. 9 shows percent inhibition of IL-1β secretion in human monocytes by rho kinase inhibitors. The tested Rho kinase inhibitors of Formula I or II at a 10 µM concentration demonstrated a varying efficacy range. Many compounds effectively reduced IL-1β secretion to low level.

Example 9

Human Neutrophil Chemotaxis

Neutrophils are thought to contribute actively to the pathogenesis of both asthma and COPD. The infiltration and presence of inflammatory cells such as macrophages and neutrophils in the airway is considered to be a hallmark of COPD. Neutrophils can contribute to the pathogenic features of COPD through generation of reactive oxygen intermediates, increased secretion of mucus, elastolytic enzymes, metalloproteases, and myeloperoxidase (Beeh, K M. *Clinical and Experimental Allergy.* 36:142-157, 2006). Although allergic asthma has been more strongly correlated with the presence of eosinophils, neutrophils are also present in the asthmatic airway and are activated and are able to release mediators that promote and prolong asthma symptoms. Increasing evidence suggests that neutrophils may be central players with an important role in the pulmonary inflammatory process present in asthma ((MacDowell, A L. *Current Allergy and Asthma Reports.* 7: 464-468, 2007). Inhibition of Rho Kinase in vitro has been shown in the literature to inhibit the chemotactic peptide induced migration of human neutrophils (Niggli, V. *FEBS Letters.* 445: 69-72. 1999). In addition, when a Rho Kinase inhibitor was administered to ovalbumin challenged mice, reductions in eosinophil recruitment in the airways was demonstrated (Taki, F. *Clinical and Experimental Allergy.* 37: 599-607, 2007).

Peripheral blood from healthy human volunteers was collected and the neutrophils were isolated by Ficoll-paque density centrifugation followed by dextran sedimentation and hypotonic lysis of the red blood cells. Neutrophil chemotaxis was assessed using a modified Boyden Chamber (Neuroprobe, 96-well) with a 3 µm pore polycarbonate membrane. The ability of the tested compounds to block chemotaxis induced by a 1 µM fMLP challenge during a one hour incubation at 37° C. with 5% $CO_2$ was assessed in a dose response manner. The results are shown in Table 6.

The results demonstrate that Rho Kinase inhibition by Formula I or II compounds inhibited human neutrophil migration toward a chemotactic stimulant in vitro with $IC_{50}$ potencies ranging from less than 1 µM to nearly 24 µM (Table 6).

TABLE 6

Inhibition of fMLP-induced neutrophil chemotaxis by Rho kinase inhibitors.

| Compound | Chemotaxis Avg $IC_{50}$, nM | Chemotaxis SEM, nM |
|---|---|---|
| 2.038 | 734 | 367 |
| Y-39983 | 1,390 | 803 |

TABLE 6-continued

Inhibition of fMLP-induced neutrophil chemotaxis by Rho kinase inhibitors.

| Compound | Chemotaxis Avg $IC_{50}$, nM | Chemotaxis SEM, nM |
|---|---|---|
| 1.131 | 1,587 | 916 |
| 2.039 | 1,643 | 949 |
| 2.025 | 1,650 | 636 |
| 1.138 | 1,850 | 212 |
| 1.091 | 2,332 | 2,077 |
| 1.136 | 2,600 | 424 |
| 1.092 | 2,747 | 1,586 |
| 2.036 | 2,767 | 1,597 |
| 1.123 | 3,050 | 778 |
| 1.124 | 3,402 | 1,964 |
| 2.026 | 3,800 | 2,970 |
| H-1152 | 4,350 | 1,202 |
| 1.087 | 4,500 | 2,598 |
| 2.034 | 4,733 | 2,733 |
| 1.034 | 5,601 | 3,234 |
| 2.035 | 6,600 | 3,811 |
| Y-27632 | 6,765 | 1,747 |
| Fasudil | 23,800 | 13,741 |

Example 10

Human and Murine Eosinophil Chemotaxis

Eosinophils are known to play a pivotal role in the pathogenesis of allergic asthma. Eosinophils are a major source of growth factors, lipids, basic granule proteins, cytokines and chemokines that contribute to the asthmatic disease state. Although infiltration and activation of other inflammatory cells actively contribute, it is the chemotaxis of eosinophils that is considered to be the single most important event in the pathogenesis of allergic inflammation (See Adachi, T et. al., *The Journal of Immunology.* 167: 4609-4615, 2001).

In a murine model of asthma, when a Rho kinase inhibitor was administered to ovalbumin challenged mice, reductions in eosinophil recruitment to the airways was demonstrated (Taki, F. et. al., *Clinical and Experimental Allergy.* 37: 599-607, 2007). Likewise, it has also been shown in vitro that Rho kinase is critical for eosinophil chemotaxis and inhibition of ROCK results in a dose-dependent inhibition of eotaxin-induced chemotaxis of human eosinophils (Alblas, J et. al., *Molecular Biology of the Cell.* 12: 2137-2145).

Human Eosinophil Isolation: Peripheral blood from healthy human volunteers was collected and the PMNs separated via Ficoll-paque density centrifugation followed by hypotonic lysis of the red blood cells. Subsequently, the human eosinophils were isolated from the cell suspension via StemCell Technologies Human Eosinophil Enrichment kit (Cat. No 19256) according to the manufacturer's recommendations. Briefly, unwanted cells were specifically labeled with dextran-coated magnetic nanoparticles using bispecific Tetrameric Antibody Complexes (TAC) directed against cell surface antigens on human blood cells: CD2, CD3, CD14, CD16, CD19, CD20, CD36, CD56, CD123, glycophorin A and dextran. The unwanted cells are then separated from the unlabelled eosinophils using the EasySep® magnetic isolation procedure.

Mouse Eosinophil Isolation: Bronchoalveolar lavage was collected from ovalbumin sensitized and challenged mice in a volume of 2.5 mL lavage buffer. The lavage buffer was 0.9% saline with 10% fetal bovine serum. The pooled lavages were maintained on ice until use. The murine eosinophils were isolated using MACS cell separation (Miltenyi Biotech) by depletion of B cells and T cells by positive selection following incubation with antibody conjugated magnetic beads specific for CD45-R (B220) and CD90 (Thy 1.2), which bind B cells and T cells, respectively.

Figure 10:
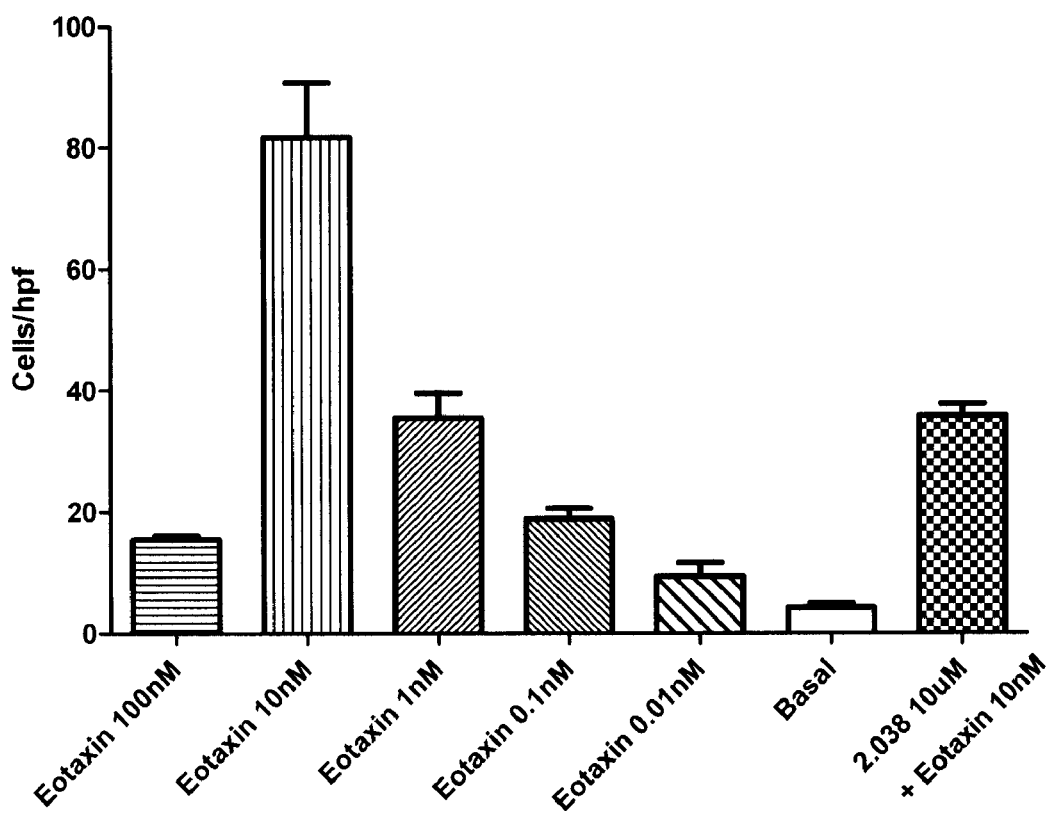
FIG. 10 shows the murine eosinophil chemotaxis. The data reported are mean number of migrated eosinophils per high power view field±SEM. Average of at least 2 view fields per well is presented, each treatment ran in triplicate.
Figure 11:
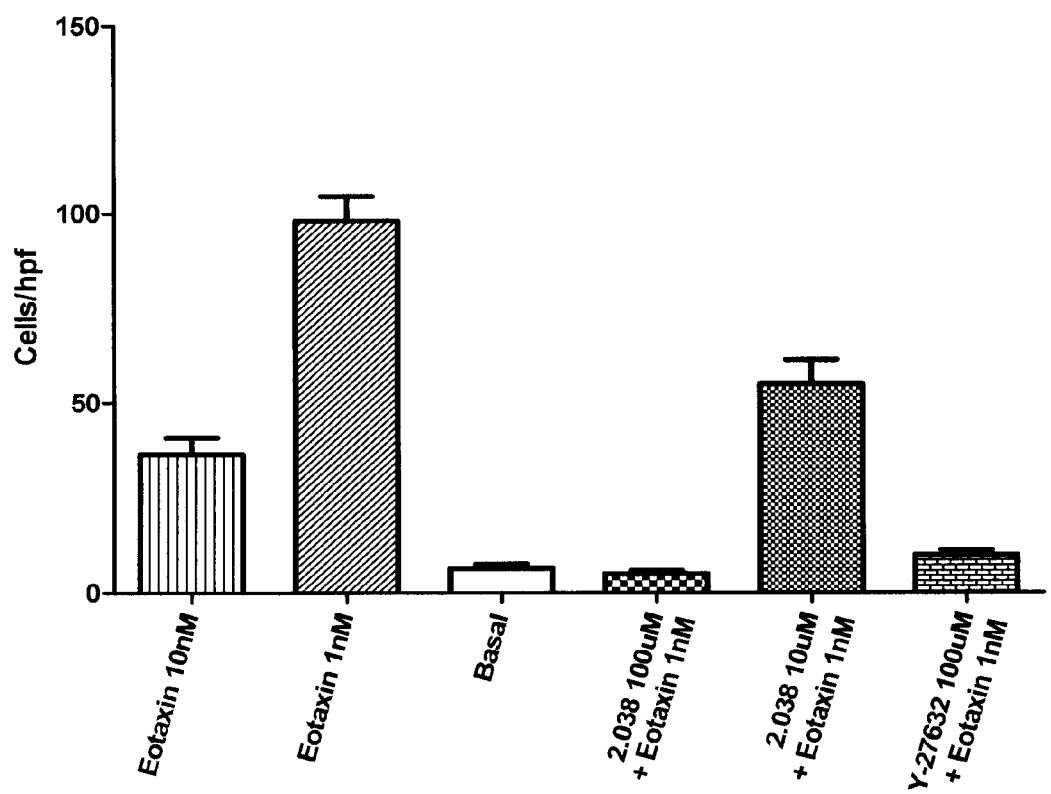
FIG. 11 shows the human eosinophil chemotaxis. The data reported are mean number of migrated eosinophils per high power view field±SEM. Average of at least 3 view fields per well is presented, each treatment ran in duplicate.

In Vitro Chemotaxis: Eosinophil chemotaxis was assessed using a modified Boyden Chamber (Neuroprobe, 96-well) with a 5 µm pore membrane. The ability of the tested compounds to block chemotaxis induced by a 10 nM eotaxin challenge (mouse) or 1 nM eotaxin challenge (human) during one hour incubation at 37° C. with 5% $CO_2$ was assessed. Chemotaxis was quantified via microscopy by counting the number of migrated cells in at least 3 view fields per treatment. The results are shown in FIGS. 10 and 11. FIG. 10 demonstrates that chemotaxis was induced by eotaxin in murine eosinophils; the chemotactic response was subsequently inhibited by Rho Kinase inhibitor Compound 2.038. FIG. 11 demonstrates that chemotaxis was induced by eotaxin in human eosinophils. The chemotactic response was subsequently inhibited by Rho Kinase inhibitor Compound 2.038.

Example 11

Smooth Muscle Proliferation Assay

Smooth muscle proliferation and remodeling play a role in the pathophysiology of several respiratory disease states including; PAH, COPD, Asthma, and LAM. Pulmonary arterial hypertension is characterized by structural changes in the pulmonary vasculature, as well as vasoconstriction. The arteriopathy exhibits recognizable morphologic features, including medial hypertrophy, cellular intimal proliferation, intimal fibrosis, and obstructive lesions (Davie et al., *Am J Respir. Crit. Care Med* 165: 398-405, 2002). Additionally, increase in airway smooth muscle mass, which is due to the enhanced proliferation (hyperplasia) and hypertrophy of airway smooth muscle cells, is one of the features that characterize airway remodeling in asthmatic patients and is a key determinant of the extent of their airflow obstruction (Fernandes et al. *Therapeutic Advances in Resp. Disease* 1(1): 25-33, 2007 and Hirst et. al., *J. Allergy Clin. Immunol.* 114:2 S2-17, 2004). Moreover, bronchial smooth muscle cells from asthmatic patients have shown abnormal cellular proliferation in vitro. Lymphangioleiomyomatosis (LAM) is a rare lung disease that is thought to be caused by a form of smooth muscle that is abnormally proliferative and underlies the formation of characteristic LAM nodules in the lung and angiolipomas in the kidney (Black et al., *Eur. Respir. J.* 26: 569-576, 2005).

Figure 12:
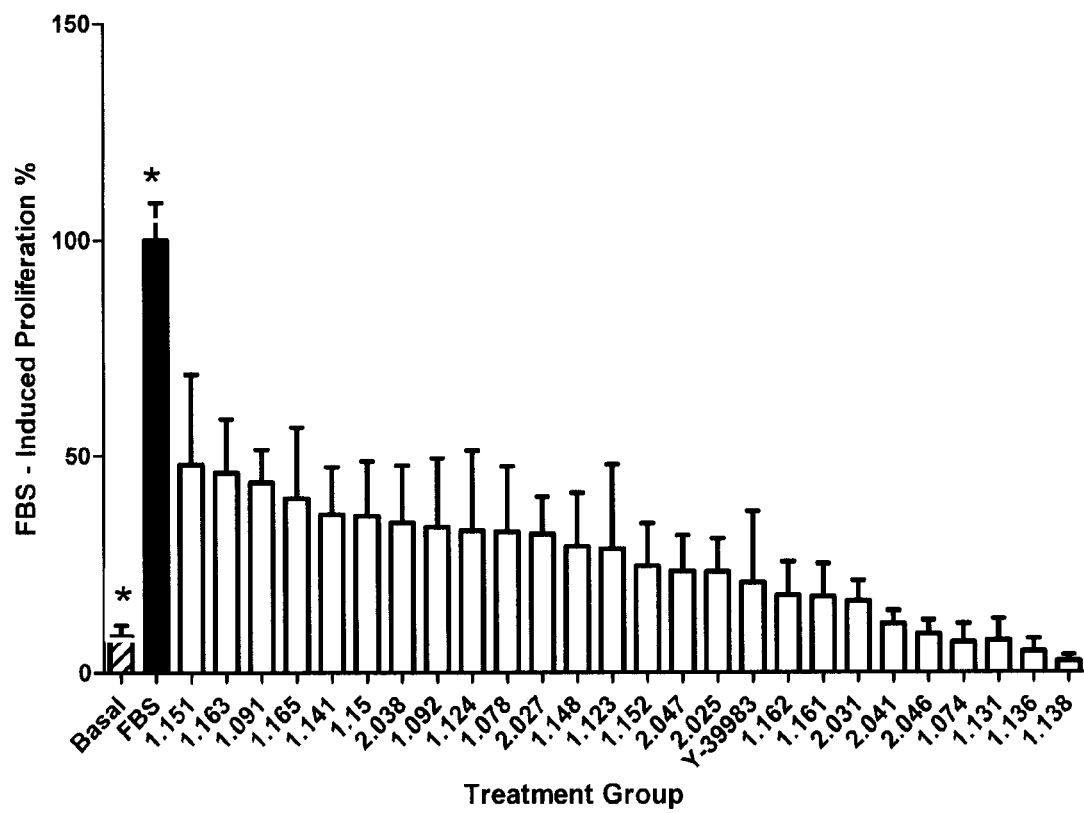
FIG. 12 shows percent of fetal bovine serum (FBS) induced proliferation. Each compound was tested at 30 μM and challenged with 10% FBS with an n=3. * indicates n=5.

Effects on cell proliferation were measured using a radiographic technique know as [$^3$H] thymidine incorporation. A-10 rat thoracic aorta cells (ATCC #CRL 1476) were grown on 24-well plates in Dulbecco's Modified Eagles Medium-High Glucose (Gibco cat. #11995-065) containing 10% Fetal Bovine Serum (Sigma EC#232-690-6) for 24 hrs in an incubator at 37° C. Growth media was then removed, the cells were washed with warmed PBS (Gibco cat#14190-144) and warmed serum free media containing 0.1% BSA in order to force the cells into a quiescent state. 24 hours later the media was removed and replaced with warmed serum free media containing from 10 nM to 30 µM of test compound. The cells were incubated for 60 min at 37° C. The cells were then stimulated with either 10% FBS or 10 ng/mL PDGF (BD Biosciences cat#354051) and placed in an incubator at 37° C. for 18 hrs. [$^3$H] thymadine (Perkin Elmer NET027A001MC) was then added to the cells at a final concentration of 3 uCi/mL and placed in an incubator at 37° C. for 24 hrs. The media was removed and the cells were washed with warmed PBS twice. 500 µL of warmed trypsin (Gibco cat#25300-054) was added to each well and they were place in an incubator at 37° C. for 15 min. To precipitate the DNA, 500 µL of ice cold 20% TCA (MP Biomedicals cat#152592) was added to each well. The resulting suspension was filtered using a vacuum manifold and glass fiber filters (Whatman cat#1827-025). The fiber filters were then counted using a liquid scintillation counter (Wallac 1409). Results were normalized to the total signal of the challenge, graphed using Graphpad Prism (Ver. 5.00) and reported as % of FBS stimulated proliferation. The results are shown in FIG. 12. The results demonstrate that the tested Rho kinase inhibitors of Formula I or II compounds reduced the smooth muscle cell proliferation in vitro. The majority of the tested compounds decreased the proliferation to less than 50% of the normal rate at a concentration of 30CM.

Example 12

Rodent Pharmacokinetic Analyses of ROCK Inhibitors

Plasma (EDTA K2 anticoagulant) was collected from male, cannulated, CD Sprague Dawley rats to determine the pharmacokinetics of formulations containing compound inhibitors of Rho kinase. Each animal was dosed orally with a 4 ml/kg solution or suspension of each test compound in 10 mM acetate buffered saline, pH 4.5 at a final concentration range of 20-30 µmol/kg. Blood was collected at 0.25, 0.5, 1, 2, 4, 6, 8, and 24 hours. Plasma samples were assayed for the concentration of the test compound using an on-line, solid phase extraction LC/MS/MS analysis system.

Samples were analyzed on a QSTAR Elite, hybrid quadrupole time-of-flight mass spectrometer (Applied Biosystems, Framingham, Mass.) coupled with a Symbiosis Pharma integrated, on-line SPE-HPLC system (Spark Holland Inc., Plainsboro, N.J.). Analyst QS 2.0 software was used for instrument control, data acquisition and processing. An aliquot of each sample was injected onto a Luna C18 column (50×2 mm, 4 um, 80A, Phenomenex, Torrance, Calif.), and elution was carried out using a gradient from 2-98% acetonitrile. Mobile Phase A consisted of 0.1% ammonium hydroxide in water and Mobile Phase B consisted of 0.1% formic acid in acetonitrile. Pharmacokinetic analyses were performed using WinNonlin software version 5.2 (Pharsight Corporation, Mountain View, Calif.).

The pharmacokinetic results based on the observed plasma concentrations of the test compounds in rats are shown in Table 7.

TABLE 7

Pharmacokinetic results from rat oral PK studies (mean plasma values for n = 3 rats)

| Compound | Tmax (hr) | Cmax (nM) | AUC (0-last) (nM * hr) | t½ (hr) | Vz_F (L/kg) |
| --- | --- | --- | --- | --- | --- |
| 1.131 | 0.83 | 5610 | 10825 | 1.55 | 6.8 |
| 1.092 | 0.25 | 2101 | 1849 | 1.74 | 19.0 |
| 1.123 | 0.33 | 2044 | 2064 | 0.9 | 14.8 |
| 2.038 | 0.5 | 1037 | 1283 | 0.71 | 22.5 |
| 2.039 | 0.33 | 783 | 905 | 1.13 | 59.4 |
| 1.074 | 0.42 | 735 | 1167 | 0.86 | 45.7 |
| 1.107 | 1.67 | 544 | 1586 | 1.28 | 36.3 |
| 1.124 | 0.5 | 415 | 535 | 1.39 | 93.4 |
| 2.045 | 0.67 | 223 | 456 | 1.59 | 226 |
| 1.108 | 0.83 | 209 | 415 | 1.36 | 116 |
| 1.091 | BLQ | BLQ | BLQ | BLQ | BLQ |
| 2.026 | BLQ | BLQ | BLQ | BLQ | BLQ |
| 1.136 | BLQ | BLQ | BLQ | BLQ | BLQ |

BLQ indicates that the compound was below the limit of quantitation in the assay As determined from the plasma concentration versus time curves, the time to peak and peak exposure are represented by the values Tmax and Cmax, respectively, The AUC values (nM*hr) shown were calculated as the areas under the plasma concentration versus time curves from time zero through the time of the last observable value and represent the total exposure of the compound over the course of the study. Half-life values or the amount of time required for the plasma levels of the compound to decline to half the initial value are represented as t1/2. The volume of distribution (Vz_F expressed in L/kg) relates the amount of theoretical volume needed to account for the observed concentration of a given dose of a compound. For rats, the total body water content is approximately 0.15 L/kg. Calculated volumes of distribution below 0.15 L/kg are considered low, whereas values between 5 and 100 L/kg are considered high. The volume of distribution varies depending on the degree of plasma protein binding as well as partitioning of the compound into fat and tissues. Table 7 provides evidence that our ROCK inhibiting compounds have a varying degree of pharmacokinetic properties that would allow them to be optimized for multiple routes of administration. These compounds are quickly absorbed, as indicated by a $T_{max}$ of generally less than 1 hour, with varying degrees of peak and total exposure as indicated by Cmax and AUC, with higher values indicating greater exposure. Regardless of exposure, these compounds demonstrate a similar clearance, t1/2.

Additionally, compound concentrations were determined in the plasma and lungs of male, ovalbumin-sensitized, Balb/c mice from a murine model of asthma. Test compounds were formulated in water or 1% polysorbate 80 and dosed at 15 µmol/kg for intraperitoneal (IP) or oral (PO) administration or formulated for intratracheal (IT) administration and dosed at 5 µmol/kg, which directly targets the lungs. Following completion of the in vivo study, mice were euthanized and blood and plasma collected approximately 2.5-3 hours post administration of test compound for bronchodialator (BD) studies and 24 hours post administration for anti-inflamatory (AI) studies. Lungs were homogenized in Matrix A lysing tubes using a FastPrep 24 tissue and cell homogenizer (MP Biomedicals, Solon, Ohio). Both plasma samples and lung extracts were assayed for compound concentrations using an on-line, solid phase extraction LC/MS/MS system. The actual lung tissue concentrations of each compound in mouse were extrapolated from the lung and plasma concentrations, data are shown in Table 8. The results of a set of experiments using unsensitized mice and collecting only plasma 15 minutes post administration of test compounds are shown in Table 8a.

TABLE 8

Compound concentrations in asthmatic mice lungs post IP, PO and IT administration (mean plasma corrected lung values for n = 9 or 10 mice)

| Compound | Efficacy Model | Route | Time Point, h | Lung, nM[1] |
| --- | --- | --- | --- | --- |
| 1.131 | BD | PO | 3 | 7353 |
| 2.038 | BD | PO | 3 | 440 |
| 1.092 | BD | PO | 3 | 152 |
| 1.091 | BD | IP | 3 | 117 |
| 1.091 | BD | IT | 2.5 | 123 |
| 1.131 | AI | PO | 24 | 33 |
| 2.038 | AI | PO | 24 | 11 |

[1] for calculation of lung concentrations, it was assumed that 22.6% of the lung mass was plasma (R. H. Storey, Cancer Research, 943-947, 1951)

TABLE 8a

Compound concentrations in mice at 15 min post administration (mean plasma values for n = 3 mice)

| Compound | Plasma Mean Concentration, nM | Plasma Concentration StdDev, nM |
|---|---|---|
| 1.072 | 1770.9 | 320.9 |
| 1.074 | 506.1 | 407.9 |
| 1.075 | 348.0 | 83.9 |
| 1.076 | 1715.0 | 474.9 |
| 1.077 | 25.9 | 0.2 |
| 1.078 | 1018.8 | 75.8 |
| 1.079 | 2442.5 | 302.9 |
| 1.090 | 5.9 | 5.2 |
| 1.091 | 333.8 | 82.7 |
| 1.092 | 314.3 | 60.4 |
| 1.093 | 362.6 | 148.7 |
| 1.106 | 441.4 | 146.7 |
| 1.107 | 211.1 | 129.5 |
| 1.108 | 394.5 | 9.0 |
| 1.109 | 187.2 | 36.0 |
| 1.110 | 792.0 | 311.9 |
| 1.123 | 71.4 | 11.8 |
| 1.124 | 118.0 | 2.4 |
| 1.126 | 0.0 | 0.0 |
| 1.127 | 980.2 | 757.5 |
| 1.131 | 444.5 | 130.0 |
| 1.132 | 982.4 | 207.7 |
| 1.133 | 1097.9 | 234.3 |
| 1.134 | 1550.8 | 623.9 |
| 1.135 | 656.8 | 115.4 |
| 1.136 | 25.9 | 6.3 |
| 1.137 | 556.9 | 279.8 |
| 1.138 | 1863.8 | 378.7 |
| 1.141 | 1643.1 | 368.6 |
| 1.142 | 329.7 | 171.6 |
| 1.143 | 274.5 | 68.8 |
| 1.145 | 109.0 | 117.9 |
| 1.146 | 1255.7 | 703.5 |
| 1.148 | 767.1 | 63.9 |
| 1.149 | 1559.4 | 789.6 |
| 1.150 | 1392.3 | 1278.3 |
| 1.151 | 478.6 | 173.6 |
| 1.152 | 435.4 | 44.5 |
| 1.153 | 521.5 | 61.3 |
| 1.154 | 1039.5 | 447.9 |
| 1.155 | 32.4 | 36.3 |
| 1.156 | 88.0 | 37.5 |
| 1.157 | 357.2 | 131.9 |
| 1.158 | 101.6 | 54.4 |
| 1.159 | 250.5 | 343.2 |
| 1.161 | 392.5 | 14.9 |
| 1.162 | 76.1 | 12.9 |
| 1.163 | 10.1 | 1.1 |
| 1.164 | 1504.3 | 580.6 |
| 1.165 | 93.5 | 49.6 |
| 1.166 | 342.4 | 118.1 |
| 1.168 | 587.5 | 258.9 |
| 1.170 | 638.6 | 154.7 |
| 1.171 | 368.8 | 208.9 |
| 1.172 | 111.1 | 32.0 |
| 1.173 | 144.4 | 72.6 |
| 1.175 | 1126.5 | 112.5 |
| 1.176 | 89.1 | 69.1 |
| 1.177 | 283.1 | 125.6 |
| 1.182 | 452.5 | 297.7 |
| 1.183 | 708.5 | 359.6 |
| 1.185 | 1023.6 | 492.8 |
| 1.186 | 2169.4 | 1599.1 |
| 1.191 | 260.0 | 58.8 |
| 1.193 | 55.4 | 26.0 |
| 1.194 | 355.0 | 133.5 |
| 1.195 | 107.9 | 23.1 |
| 1.197 | 453.1 | 354.0 |
| 1.198 | 643.2 | 112.1 |
| 1.200 | 0.0 | 0.0 |
| 1.202 | 129.7 | 71.9 |
| 1.203 | 1134.7 | 44.2 |
| 1.204 | 549.1 | 183.6 |
| 1.206 | 671.5 | 80.9 |
| 1.208 | 281.1 | 45.4 |
| 1.210 | 285.8 | 122.9 |
| 1.212 | 863.4 | 104.1 |
| 1.213 | 396.4 | 135.1 |
| 1.215 | 2651.2 | 529.0 |
| 1.217 | 292.5 | 176.0 |
| 1.219 | 1678.9 | 516.3 |
| 1.223 | 12.8 | 0.6 |
| 1.226 | 526.1 | 157.9 |
| 1.227 | 1859.4 | 603.7 |
| 1.229 | 1453.9 | 465.0 |
| 1.233 | 41.1 | 11.6 |
| 1.234 | 239.6 | 79.4 |
| 1.236 | 47.7 | 18.1 |
| 1.237 | 178.4 | 64.6 |
| 1.238 | 48.3 | 29.6 |
| 1.239 | 258.9 | 111.8 |
| 1.241 | 991.4 | 134.5 |
| 1.242 | 579.8 | 314.0 |
| 1.245 | 1524.0 | 127.5 |
| 1.246 | 587.4 | 299.7 |
| 1.249 | 2147.1 | 688.2 |
| 1.252 | 1259.2 | 1210.0 |
| 1.253 | 240.0 | 20.3 |
| 1.258 | 567.5 | 223.5 |
| 1.259 | 264.4 | 39.1 |
| 1.260 | 291.2 | 120.7 |
| 1.262 | 285.2 | 76.2 |
| 2.025 | 73.7 | 21.2 |
| 2.026 | 629.5 | 94.6 |
| 2.027 | 502.6 | 248.5 |
| 2.031 | 1430.4 | 139.2 |
| 2.034 | 664.7 | 649.4 |
| 2.036 | 1343.9 | 1603.3 |
| 2.038 | 728.9 | 222.8 |
| 2.039 | 92.0 | 47.6 |
| 2.041 | 986.5 | 287.0 |
| 2.043 | 60.8 | 24.7 |
| 2.046 | 488.1 | 96.1 |
| 2.047 | 3.0 | 1.7 |
| 2.054 | 765.5 | 214.3 |
| 2.055 | 656.1 | 172.6 |
| 2.056 | 1257.0 | 230.6 |
| 2.057 | 431.2 | 41.5 |
| 2.058 | 193.6 | 167.4 |
| 2.059 | 89.6 | 21.5 |
| 2.060 | 307.6 | 157.6 |
| 2.061 | 73.2 | 21.1 |
| 2.062 | 659.9 | 582.8 |
| 2.063 | 347.9 | 248.5 |
| 2.064 | 201.6 | 78.7 |
| 2.065 | 236.4 | 29.8 |
| 2.066 | 491.6 | |

The results of these quantitative analyses have enabled the selection of compounds for additional studies based on desirable pharmacokinetic profiles and preferential distribution in the target organ (lungs). Furthermore, there appears to be a correlation between compound levels observed in the lung and the bronchodialator (BD) and anti-inflammatory (AI) efficacy in the murine model of asthma as shown in Example 5. The compound concentrations must be present to have a bronchodilator effect and must be absent or below their Rho Kinase inhibitory effect in order to effectively evaluate their efficacy against airway hyperreactivity due to their anti-inflammatory effect. We have identified compounds which possess high bioavailability and efficacy against airway hyperreactivity when dosed orally, as well as compounds that are efficacious when administered intraperitoneally or intratracheally, but do not reach systemic levels when dosed orally and thus are not efficacious by the oral route. Additionally, we have identified that lower doses by the intratracheal route are needed to achieve the same level of BD effect and drug concentration level as by other routes. Characterization of the pharmacokinetic properties and distribution of these Rho Kinase inhibitors is an essential part of the selection of compounds for development as either oral or inhaled products.

Example 13

Efficacy of Compounds in Animal Model of Idiopathic Pulmonary Fibrosis

This example illustrates the efficacy of compounds of this invention in treatment of IPF in bleomyocin-induced pulmonary fibrosis in mice.
Protocol
The model is based on the description in Shimizu Y et al. *Am. J. Resp. Crit. Care Med.* 163: 210-217, 2001. Pathogen-free 6-wk-old female C57BL/6 mice are used for the experiments. The animals are maintained under standard conditions with free access to water and rodent laboratory food. The animals receive bleomyocin (BLM) i.p. injections on day 0, 2, 4, 6 and 8 at a dose of 40 mg/kg. BLM accumulates in the subpleural regions, resulting in the preferential development of lung fibrosis at subpleural lesions. This is very similar to the pathological features of human IPF (Ekimoto H et al. *Gan To Kagaku Ryoho* 10:2550-2557, 1983). Body weights are measured before every administration of the compounds. Compounds of Formula I or II are administered via i.p. administration every day at the dose of 1 mg/kg to 100 mg/kg of body weight starting on day 0 and continuing to day 40. A control group of animal receives i.p. saline.

At day 40, mice are sacrificed, and their thoraces are then exposed. The lungs are washed with cold phosphate-buffered saline (PBS) and surgically removed. The excised lungs are used for histopathological examination and assayed for OH-proline contents. The left lungs are used to evaluate the fibrotic score by histological examination, and the right lungs for measurement of OH-proline contents. Additional mice are used to determine cell differentiation in the lumen of the lung as determined by bronchoalveolar lavage (BAL). BAL is performed on Days 7, 14, 21, and 40 after initial injection of BLM. Mice are sacrificed, and BAL is performed.
Histologic Examination
Morphological evaluation of fibrotic changes in the lungs is performed on Day 40. The excised lungs are immediately fixed with 10% formaldehyde neutral buffer solution for 48 h, and then embedded in paraffin. Sagittal sections are cut at 2 mm thickness and stained with hematoxylin-eosin and Masson-trichrome. The total lung area of the sections is used for the fibrotic scale microscope evaluation (Olympus, BX50F4). Criteria for grading lung fibrosis are according to the method reported by Ashcroft and coworkers (Ashcroft T et al. *J Clin Pathol.* 41:467-470, 1988): Grade 0, normal lung; Grade 1, minimal fibrous thickening of alveolar or bronchiolar walls; Grade 3, moderate thickening of walls without obvious damage to the lung architecture; Grade 5, increased fibrous with definite damage to lung architecture and formation of fibrous bands or small fibrous masses; Grade 7, severe distortion of architecture and large fibrous area; Grade 8, total fibrous obliteration of the field. Severity of fibrotic changes in each lung section is assessed as the mean score for severity from the observed microscopic fields. The grade of lung fibrosis is scored on a scale from 0 to 8 by examining 20 randomly chosen regions per sample at a magnification of 3100. To minimize investigator variability, all histological specimens are randomly numbered and scored by another investigator in a single blinded fashion.
OH-Proline Assay
OH-proline contents of the lungs are measured objectively to estimate lung fibrosis (Green G D et al. *Anal Biochem.* 201:265-269, 1992). The right lungs of each mouse are dissected free from major bronchi, and the wet weights are measured. They are hydrolyzed in 500 ml of 12 N hydrochloric acid and in the same aliquot of distilled water at 11° C. 20 h, in dry block. After the resultant hydrolysate is neutralized with sodium hydroxide, a 100-ml supernatant is mixed in 1.5 ml of 0.3 N lithium hydroxide solution. The OH-proline content is determined by high-performance liquid chromatography (HPLC) and expressed as micrograms per right lung.
Bronchoalveolar Lavage and Cell Counting
Bronchoalveolar lavage fluid (BALF) is collected by infusing 3.0 ml of saline with 10% fetal calf serum into the lungs via the trachea and then withdrawing the fluid. The total amount of cells/ml of BALF fluid is determined via manual cell count on hemocytometer. The BALF is centrifuged, and cell pellet reconstituted in 500 µL of fluid. Cytospin slides are prepared from the cell pellet using 100 µL of fluid and spinning samples for 5 minutes at 5000 rpms in a cytospin centrifuge. Following Hema3 stain, relative percentages of individual leukocytes are determined on a 200 cell count for each sample. The final concentration of individual leukocyte cell types per ml of BALF is determined by multiplication of the relative percentage of individual leukocytes with the total amount of cells/ml of BALF fluid.
Results
At day 40 following the first BLM administration, the fibrotic changes in the lung, the hydroxyproline content in the lung, and the cell count of leukocytes (total cell count, macrophage cell count, lymphocyte cell count and/or nertrophil cell count) in BALF are measured and compared in the compound-treated mice vs. saline-treated mice. Improvement in at least one of the above-mentioned endpoints is observed.

Example 14

Increase of Endothelial Integrity and Decrease in Endothelial Permeability Following Treatment with Compounds of this Invention Endothelial integrity is crucial in the regulation of movement of fluid and extravasation of leukocytes into tissue. Increased endothelial integrity leads to decreased fluid movement and decreased extravasation of leukocytes into tissue thus resulting in decreased tissue edema (Dudek S M et al., *J Appl Physiol,* 91:1487-1500, 2001 and Vandenbroucke E et al., *Ann NY Acad Sci,* 1123:134-145, 2008).
Protocol
The assay is conducted essentially as in Tasaka S et al. *Am J Resp Cell Mol Biol,* 32:503-510, 2004. Pulmonary artery endothelial cells (PAECs) are collected and cultured in a humidified 5% $CO_2$ atmosphere in the medium provided by the manufacturer supplemented with 2% fetal calf serum. Endothelial cell monolayers are prepared on filters. In brief, tissue culture plate well inserts are incubated with bovine fibronectin at 37° C. for three hours to facilitate cell attachment. The fibronectin solution is aspirated, and the endothelial cells are suspended in the culture medium that is placed on a membrane filter at a density of $4 \times 10^5$ cells per filter insert. The inserts are placed into a 6-well culture plate, where each individual well is filled with 2 ml of culture medium and incubated at 37° C. in a humidified 5% $CO_2$ atmosphere until PAECs reach confluence on the filter.

In order to measure permeability, the albumin that is transferred across a cultured endothelial cell monolayer grown on a porous filter is measured. PAECs on the filter are pretreated with 0.1 µM to 100 µM of a compound of Formula I or II for thirty minutes and then incubated with $10^2$ U/ml of TNF-alpha for six or twenty-four hours. Following the incubation, the TNF-alpha containing supernatant is aspirated and 500 µl of phosphate buffered saline (PBS) containing 0.1% bovine albumin is added to the chamber located on the top of the filter insert. The insert is then placed into a culture plate well which is filled with 0.7 ml of PBS. This PBS solution is now surrounding the filter insert and occupies the lower chamber. After incubation for twenty minutes, the insert is removed from the well. The albumin concentration of the lower chamber is measured with a protein assay kit.

Results

The TNF-alpha induced permeability of the endothelial monolayer to albumin is decreased following the treatment of the EC monolayer with the Formula I or II compounds.

Example 15

Efficacy of Compounds of Formula I or II in Treating RSV-Infection Induced Airway Hyperresponsiveness Protocol The experiment is conducted essentially as in Hashimoto K et al. *Thorax,* 57:524-527, 2002. In summary, ovalbumin (OVA) sensitized mice, which are also RSV infected, demonstrate prolonged methacholine-induced airway hyperresponsiveness (AHR) when compared to OVA sensitized mice without RSV infection. According to past observations, ovalbumin (OVA)-induced AHR lasted only a few days past the discontinuance of OVA aerosol in mice that were ovalbumin sensitized and mock infected. In contrast, OVA-sensitized mice infected with RSV during the OVA aerosol treatments (OVA/RSV) had AHR for more than 2 weeks after infection (Peebles R S et al. *J. Med. Virol.* 57(2):186-92, 1999).

Pathogen free 8 week old female BALB/c mice are used. The A2 strain of RSV virus is prepared as previously described in Graham B S et al. *J Med Virol* 26:153-62, 1998, Mice are injected intraperitoneally with 0.1 ml (10 µg) ovalbumin complexed with 2 mg $Al(OH)_3$ as previously described (Peebles R S et al. *J Med. Virol.* 57(2):186-92, 1999). After 14 days, the mice are placed in an acrylic box and exposed to aerosols of 1% ovalbumin diluted in sterile phosphate buffered saline (PBS) using a nebulizer for 40 minutes each day for 8 days. Mice are infected with RSV (as previously described on day 3 of OVA inhalation (Peebles R S et al. *J. Med. Virol.* 57(2):186-92, 1999). Fourteen days after RSV inoculation (and 9 days after OVA inhalation), the mice undergo AHR testing via methacholine challenge. The mice are administered with Formula I or II compound i.p. at 1-100 mg/kg of body weight. AHR is measured one hour after the treatment (Peebles R S et al. *J. Med. Virol.* 57(2):186-92, 1999).

AHR Measurements

AHR is measured as previously described (Peebles R S et al. *J. Med. Virol.* 57(2): 186-92, 1999). Methacholine is dissolved in normal saline and administered intravenously at starting doses of 5 µg/kg and 6.25 µg/kg, respectively. The mean volume per methacholine dose is approximately 35 µl and 50 µl, respectively. The methacholine concentration is increased in multiples of three in the dose response challenge with methacholine.

Results

Airway hyperresponsiveness is measured as described above. Improvement in AHR is observed in OVA-sensitized, RSV-infected animals treated with compounds of this invention when compared to OVA-sensitized, RSV-infected animals treated with vehicle.

Example 16

Efficacy of Compounds in Treating PAH

Protocol

The experiment is conducted essentially as in Abe K et al. *Circ. Res.* 94: 385-393, 2004. Male Sprague Dawley rats are administered either monocrotaline or vehicle. Each MCT-treated rat receives a single subcutaneous injection (right or left flank) of MCT (60 mg/kg body weight) on day 0. Control animals receive a single subcutaneous injection of vehicle. A compound of this invention is administered daily starting on day 0 and continued until necropsy. Groups of animals are sacrificed on Days 21, 28, and 63, A compound of Formula I or II is administered i.p. or p.o. at 1-100 mg/kg of body weight.

Right Ventricle (RV) Hypertrophy

The RV is dissected from the left ventricle (LV) plus the septum (S) and weighed to determine the extent of RV hypertrophy (RVH) as follows: RV/(LV+S) (Cowan K N et al. *Nat. Med.* 6:698-702, 2000).

Survival Analysis

The effects of a compound of this invention on the survival of MCT-injected rats are examined. The day of MCT injection is defined as day 0. This survival analysis covers the entire experimental period to day 63.

Hemodynamic Measurements

After the animals are anesthetized with sodium pentobarbital (30 mg/kg, IP), polyethylene catheters are inserted into the RV through the jugular vein and into the carotid artery for hemodynamic measurements. RV systolic pressure (RVSP) is measured with a polygraph system (AP-601G, Nihon Kohden).

Morphometric Analysis of Pulmonary Arteries

After the hemodynamic measurements, lung tissue is prepared for morphometric analysis by using the barium injection method (Cowan K N et al. *Nat. Med.* 6:698-702, 2000). All barium-filled arteries of 15 to 50 µm in diameter, which are nonmuscular under normal conditions, are evaluated for muscularization of pulmonary microvessels (Cowan K N et al. *Nat. Med.* 6:698-702, 2000). For each artery, the median wall thickness (MWT) is expressed as follows: percent wall thickness=[(medial thickness×2)/external diameter]×100 (Cowan K N et al. *Nat. Med.* 6:698-702, 2000).

Results

The survival over the course of treatment from day 0 to day 63 after the MCT administration and the right ventricular hypertrophy, RVSP, MWT at day 21, 28 and 63 after the MCT administration are measured and compared in the compound-treated MCT-exposed rats vs. saline-treated MCT-exposed rats. Improvement in at least one of the above-mentioned endpoints is observed for at least one of the time points.

Example 17

Efficacy of Compounds in Treating LPS-Induced Lung Injury

Protocol

The LPS-induced lung injury model is often used to determine a potential efficacy of therapeutic approaches designed for treatment of COPD. A Formula I or II compound is administered i.p. at 1-100 mg/kg of body weight one hour prior to LPS exposure. A control group of animals receives i.p. vehicle. BALB/c mice are placed in a clear mass dosing Plexiglas chamber and exposed to aerosolized LPS ranging in dose from 1-100 ug for 25 minutes. Animals are free roaming and allowed to inhale the LPS aerosol. At 4-24 hours following the LPS challenge pulmonary mechanics is assessed or bronchoalveolar lavage is conducted. Pulmonary mechanics is assessed by exposing the animals to increasing doses of methacholine. For the lavage, animals are humanely euthanized followed by a bronchoalveolar lavage (BAL) to evaluate the cytokine concentrations in the bronchoalveolar lavage fluid (BALF).

In Vivo Assessment of Pulmonary Mechanics

The evaluation of airway sensitivity to bronchial constrictors is assessed using a whole body plethysmograph system. Conscious unrestrained mice are placed in the chamber and allowed to acclimate for 10 minutes followed by dose response ranging from 0.01 mg/ml to 50 mg/ml of methacholine dosed by nebulization into the chamber. The plethysmograph system generates a derived numerical value called Penh which is used to indicate bronchial constriction. Each dose of methacholine will last for a 3 minute nebulization period followed by a 3 minutes rest period for a total of 6 minutes of Penh measurement for each of the methacholine doses. Each animal will remain in the chamber for up to 2 hours for analysis.

In Vitro Assessment of Cytokine and Chemokine Levels

Supernatant retained from the bronchoalveolar lavage is analyzed for concentrations of proinflammatory cytokines and chemokines including but not limited to the following: Il-1beta, IL-1alpha, TNF-alpha, TNF-beta, RANTES, IL-6, IL-8, IL1-11, GM-CSF, MIP-1-alpha, MIP-1-beta, MCP1, MCP2, MCP3 and MCP4. The concentrations of these cytokines and chemokines in the BALF samples are determined using commercially available kits, Results Penh and cytokines in BALF are measured as described above four hours following the LPS exposure. Improvement in at least one of the above-mentioned endpoints is observed.

Example 18

Treatment of Human Patients Diagnosed with LAM

Patients suffering from LAM are administered a Formula I or II compound, which is delivered into the lumen of their lung in the amounts ranging from 0.001 to 100 mg; preferably 0.1 to 100 mg. Alternatively, patients suffering from LAM are administered a compound of this invention that is delivered systemically in the amounts ranging from 0.01 to 100 mg/kg of patient's body weight; preferably 0.1 to 100 mg/kg of patient's body weight. After initial dose, additional doses can be administered.

It is observed that the administration of a compound of this invention improves the health status of the patient as measured by improvement in at least one of the following measurable signs, symptoms and other variables clinically relevant to LAM. Such improvements include decreased frequency of pneumothorax, decrease frequency of pulmonary bleeding, increased blood oxygen saturation, decreased hypoxia and hypercapnia, decreased need for supplemental oxygen, decreased frequency of coughing and/or wheezing, improved forced expiratory volume ($FEV_1$), forced vital capacity (FVC) or other physiologically relevant parameter of respiratory function, decrease in angiomyolipoma volume, decreased mortality or morbidity, decreased length of hospital stay, decreased need for mechanical ventilation, lower amount of inflammatory cells infiltrating the lung, lower levels of proinflammatory cytokines and chemokines, improved alveolar fluid clearance rate, decreased pulmonary edema as determined by any radiographic or other detection method, amount of epithelial lining fluid, wet to dry lung weight, alveolar fluid clearance or radiographic visualization methods, decrease in the levels of inflammatory cells in the lung or outside of the lung in other anatomical compartments or spaces including systemic circulation, decrease in the amount of pro-inflammatory molecules including cytokines and chemokines in the lung or outside of the lung in other anatomical compartments or spaces including systemic circulation, decreased pathological remodeling of the airway, decrease in patient-reported or physician-observed signs such as difficulty of breathing, or severity of coughing and/or wheezing.

Example 19

Prevention of Acute Lung Injury by Compounds of Formula I or II in an Oleic-Acid Rat Model of ARDS The aspiration of stomach contents into the lungs during obstetric anesthesia (Am J Obstet Gynecol 1946; 52: 191) and aspiration of gastric contents is now recognized as an important risk factor for ARDS (Pepe P E et al. *Am J Surg*, 144: 124-30, 1982; Hudson L D et al. *Am J Respir Crit. Care Med*, 151:293-301, 1995; Doyle R L et al. *Am J Respir Crit. Care Med*, 152:1818-24, 1995). Oleic acid-induced lung injury is a well established model of ARDS (Dickey B F et al. *Am. J. Pathol.*, 103:376-383, 1981). It is characterized by diffuse interstitial and alveolar edema with focal hemorrhage and vascular congestion, and by interstitial and alveolar infiltration of leukocytes (Beilman G. *Lipids* 30:817-823, 1995).

Both sexes of Wistar rats are randomly separated into treatment groups: untreated control, oleic acid-treated control, oleic acid plus a Compound of Formula I or II, untreated plus a Compound of Formula I or II. All oleic acid treated animals receive a single intravenous (i.v.) administration while untreated animals receive a single i.v. administration of saline. Oleic acid and saline are injected into the tail vein under light anesthesia with ketamine. Acute lung injury is induced by intravenous administration of 100 mg/kg of oleic acid (cis-9-octadecanoic acid). Oleic acid is initially diluted in ethanol and saline is added to a final concentration of 25 mg/ml of oleic acid. A Compound of Formula I or II is administered at a dose from 1 to 100 mg/kg either orally, intravenously, intraperitoneally, intracheally or intranasally. Animals receive drugs or saline four hours prior to necropsy.

Four hours after the administration of the drugs, the rats are anaesthetized with a high dose of ketamine (80 mg/kg, i.m.), the thorax is opened and blood samples are taken by cardiac puncture for malondialdehyde, myeloperoxidase, 3-nitro-1-tyrosine and nitrite/nitrate analysis (as markers of lung injury). Thereafter, both lungs are harvested. Some pieces of lungs are preserved in formaldehyde solution (10%) for histopathologic evaluation. Haematoxylin-eosin-stained slides are prepared using standard methods. Other lung pieces are used for biochemical examination and Western blotting.

In oleic acid only treated animals, pronounced acute lung damage is observed. The lung tissue is much darker red in the oleic acid group than in the other groups. Furthermore, an increase in congestion, neutrophil infiltration and even derangement of pulmonary architecture is observed under light microscopy. Increases in serum and tissue nitrite/nitrate, 3-nitro tyrosine, myeloperoxidase and malondialdehyde levels are also observed. Western blot analysis indicates that oleic acid administration significantly upregulates the expression of Rho-kinase (ROCK-1 and ROCK-2).

Administration of a compound of Formula I or II causes a significant improvement in at least one of the following parameters: lung histology with score(s) assessing lung tissue damage, inflammation, and edema; gross appearance of the lung including the color of the lung similar to that in the sham group; normalization of serum nitrite/nitrate, myeloperoxidase and malondialdehyde or tissue 3-nitro tyrosine, myeloperoxidase or malondialdehyde levels; or western blot analysis confirming the restorative effect of Compounds of Formula I or II on expression of ROCK 1 and 2.

Example 20

Attenuation of Microvascular Leak in Rat Model of VILI

Microvascular leak is one of the defining features of the ARDS and VILI. Male Sprague-Dawley rats are anesthetized intraperitoneally with ketamine and diazepam. Rats are ventilated with room air at 85 breaths/minute for 2 hours either with a ventilation (VT) of 7 ml/kg (VT7) or 20 ml/kg (VT20) and zero end expiratory pressure. A group of animals with a VT of 20 ml/kg receives 10 ml/kg of normal saline (NS) to correct hypotension related to large VT (VT20NS). Airway pressure and systemic arterial pressure are monitored. A compound of Formula I or II (1-100 mg/kg) is given intraperitoneally 30 minutes before starting mechanical ventilation.

After 90 minutes of mechanical ventilation, an intravenous injection of 30 mg/kg Evans Blue Dye (EBD) (Sigma Chemical) is given through the internal jugular vein. EBD extravasation into the lung parenchyma as an estimate of protein permeability is quantitated as previously described (Green T P et al. *J Lab Clin Med*, 111: 173-183, 1988). EBD leak in the lung is significantly higher in VT20 and VT20NS groups compared with the VT7 group. There is no significant difference in EBD leak between VT20 and VT20NS. After administration of a compound of Formula I or II, an improvement in at least one of the following parameters is observed: EBD leak in the lung is decreased in VT20 (+) Compound of Formula I or II and/or VT20NS (+) Compound of Formula I or II groups compared with VT20 and VT20NS groups; and/or lung weight is significantly higher in VT20 and VT20NS groups compared with VT7 and compound of Formula I or II attenuates the increase in lung weight in the large VT groups.

Example 21

A Randomized Trial of a Compound of Formula I or II in Patients with ARDS

With the assent of the attending physician, informed consent is obtained from the patient or next of kin as soon as possible after case identification. Physiologic measurements and specimen collection begins at the time of entry into the study. Three days after the patient has met criteria for ARDS or at entry into the study (whichever is later), he/she is randomized to receive a Compound of Formula I or II (0.5-50 mg/kg) or placebo, administered by intravenous infusion or directly into the lumen of the lung once daily for 14 days.

The primary endpoint for this study is the duration of mechanical ventilation. Additional important endpoints include changes in the severity of physiologic derangements of respiratory gas exchange, non-respiratory organ failure, and incidence of ventilator-associated pneumonia. Additional assessments designed to determine the mechanism of benefit of Compound of Formula I or II include measures of lung epithelial cell integrity and measures of alveolar macrophage (lung inflammatory cell) function. It is observed that the administration of a Compound of Formula I or II improves ARDS by the improvement of any of the primary or secondary endpoints measured in this study.

Example 22

Efficacy of Compounds of Formula I or II in Attenuating Pathophysiologies Relevant to CF Treatment There are currently no animal models of CF lung disease. The examples listed below illustrate the ability of Compounds of Formula I or II to affect cellular and physiological processes known to be involved in the pathogenesis of CF lung disease in in vitro assays and in non-CF animal models with relevant pathological alterations of the respiratory system.

Efficacy of Compounds of Formula I or II in Airway Smooth Muscle Relaxation and Prevention of Airway Hyperreactivity Relevant to CF Relevance. The clinical manifestation of CF lung disease includes airway hyperreactivity involving the contraction of airway smooth muscle, and bronchodilators such as those used in the treatment of CF (albuterol, formoterol and salmeterol) have been shown to induce tracheal smooth muscle relaxation (Battram et al, *J Pharmacol Exp Therap* 317:762-770, 2006). Therefore, the properties of Compounds of Formula I or II as described in Examples 1, 2, 3, 5 and 7 demonstrate the therapeutic utility of these compounds in treatment of CF lung disease related to airway hyperreactivity and bronchoconstriction.

Efficacy of Compounds of Formula I or II in Attenuation of CF-Related Pulmonary Hypertension with Right Ventricular Hypertrophy Relevance. Advanced CF lung disease often involves pulmonary hypertension and associated right ventricular hypertrophy leading to heart failure (Eckles M and Anderson P. *Semin Respir Crit. Care Med* 24:323-30, 2003), and currently marketed therapeutics for hypertensive disorders demonstrate efficacy in norepinephrine pre-contracted pulmonary arteries (Walch et al, *Brit J Pharmacol* 126:859-866, 1999). CF lung disease is also characterized by excessive vascular smooth muscle cell proliferation (Hays S R et al. Thorax 60:226, 2005; Eckles M and Anderson P. *Semin Respir Crit. Care Med* 24:323-30, 2003). Therefore, the properties of Compounds of Formula I or II as described in Examples 1, 2, 4, 11, and 16 demonstrate the therapeutic efficacy of these compounds in treatment of CF lung disease related to pulmonary hypertension and associated right ventricular hypertrophy leading to heart failure.

Efficacy of Compounds of Formula I or II in Reduction of Pulmonary Inflammation Relevant to CF Relevance. CF lung disease is characterized by pulmonary inflammation, airway hyperreactivity, and pulmonary fibrosis, and anti-inflammatory drugs are important therapeutic agents in the treatment of CF (Schmitt-Grohe S and Zielen S. *Paediatr Drugs*. 7(6):353-63, 2005; Elizur A et al. *Chest* 133(2):489-95, 2008). Airway eosinophil infiltration plays a role in CF pathogenesis (Schmitt-Grohé S and Zielen S. *Paediatr Drugs*. 7(6):353-63, 2005). CF lung disease also involves infiltration of polymorphonuclear leukocytes (Elizur A et al. *Chest* 133(2):489-95, 2008). Therefore, the anti-inflammatory efficacy of Compounds of Formula I or II as described in Examples 6, 8, 9, and 10 demonstrate therapeutic utility of these compounds in treatment of CF.

Example 23

Efficacy of Compounds of Formula I or II in Reduction of Pulmonary Inflammation, Airway Hyperreactivity, Bronchoconstriction, Pulmonary Permeability and Edema Accompanying Bronchiectasis Pulmonary inflammation is a key pathophysiology accompanying bronchiectasis. Therefore, the anti-inflammatory efficacy of Compounds of Formula I or II as described in Examples 6, 7, 8, 9, and 10 demonstrate therapeutic utility of these compounds in treatment of bronchiectasis. Bronchoconstriction and airway hyperreactivity is a key pathophysiology accompanying bronchiectasis. Therefore, efficacy of Compounds of Formula I or II as described in Examples 3, 5 and 7 demonstrates therapeutic utility of these compounds in treatment of bronchiectasis. In addition, the following examples illustrate the efficacy of compounds of Formula I or II in reduction of LPS induced pulmonary permeability in rats and LPS-induced airway wall thickening in mice.

Protocol

Model is prepared essentially as in Eutamene et al Eur. Resp. J., 25(5):789-796, 2005. Male Wistar rats are anaesthetized using pentobarbital (60 mg/kg body weight-1 intraperitoneally) and anesthesia is maintained with half of this dose 2 h later. An endotracheal cannula equipped with a small catheter is inserted through a tracheotomy. For experiments using LPS from *P. aeruginosa* or vehicle (sterile 0.9% NaCl), an iso-osmolar solution is prepared, containing 5% bovine serum albumin in phosphate-buffered saline. The solution is filtered through a 0.2-mm filter and 0.5 mCi iodine-125-labelled human serum albumin ([125I] albumin) is added to the bovine serum albumin solution. Then LPS from *P. aeruginosa* (1 mg/rat-1) or vehicle is added to the instillate immediately prior to instillation into the trachea at a constant rate of 10 mL/min-1 for 15 min. Four hours after tracheal infusion of [$^{125}$I]-albumin labeled alveolar instillate plus LPS, radioactivity is measured in three compartments: plasma, lung airspace (via bronchoalveolar lavage (BAL)), and total lung tissue. For the evaluation of pulmonary permeability, rats are pretreated twice daily for 2 days with the compounds of Formula I or II (first bolus administered i.p. or p.o. at 1-100 mg/kg body weight and successive administrations at 1-100 mg/kg body weight) or vehicle (0.2 mL 10% ethanol). The last administration of kinase inhibitor or vehicle is performed 1 h before intratracheal infusion of LPS from *P. aeruginosa*. Four hours after LPS infusion, measurements of epithelial permeability are performed. Evaluations of airway epithelial barrier (AEB) permeability required measurement of residual [$^{125}$I]-albumin, the airspace protein tracer, in the lung, as well as accumulation of [$^{125}$I]-albumin in the plasma. Four hours after infusion of LPS from *P. aeruginosa*, residual [$^{125}$I]-albumin is measured in BAL fluid, lung tissue (after lavage) and plasma. Plasma [$^{125}$I]-albumin levels are measured in abdominal aorta blood samples. The plasma fraction is determined by multiplying the number of counts obtained by the plasma volume (0.07 body weight (1-haematocrit)). All of these residual counts (BAL fluid, lung tissue and plasma) are expressed as a percentage of the total number of counts of [125I]-albumin administered intratracheally (100%).

Results

Intratracheal infusion of LPS from *P. aeruginosa* enhances airway epithelial paracellular permeability to large molecules, and the percentage of [$^{125}$I] collected in lung tissue is significantly increased in LPS-treated rats compared to controls. In contrast, levels of [$^{125}$I] in BAL fluid are decreased in LPS animals compared to controls, confirming the increase in albumin passage from the airspace to lung tissue. Pretreatment with the compounds of Formula I or II reduces the increase in lung epithelial permeability induced by LPS and/or the compounds of Formula I or II restore [$^{125}$I] levels in BAL fluid from LPS-treated rats to values closer to controls.

Example 24

Efficacy of Compounds of Formula I or II in Reduction of Pulmonary Remodeling Accompanying Bronchiectasis The following example illustrates the efficacy of compounds of Formula I or II in treatment of bronchiectasis in mouse model of LPS induced airway wall thickening. Model is prepared essentially as in (Vernooy et al., Am. J. Respir. Cell Mol. Biol., 26:152-159, 2002.)

Protocol

Male Swiss mice 12 week old are used. Animals are housed individually in standard laboratory cages and allowed food and water ad libitum throughout the experiments. Mice are repeatedly challenged with LPS twice a week for a period of 12 weeks by intratracheal instillation in an attempt to induce a chronic pulmonary inflammation. The dose of LPS used is approximately 5 µg/instillation/mouse. Sham mice are instilled intratracheally with LPS-free sterile 0.9% NaCl, whereas control mice receive no treatment. Intratracheal instillation is performed by a nonsurgical technique. In brief, mice are anesthetized by intraperitoneal injection of xylazine/ketamine. A volume of 50 µL is instilled intratracheally via cannula, followed by 0.1 ml of air. After intratracheal treatment, the mice are kept in an upright position for 10 min to allow sufficient spreading of the fluid throughout the lungs. The compounds of Formula I or II are administered i.p. or p.o. at 1-100 mg/kg body weight daily starting with the first LPS administration into the animals over the course of the 12 weeks.

Airway wall thickening is determined using standard morphometric technique on alpha-SMA stained paraffin section cut from the upper part of the left lung. Conducting airways (width >190 µm) are captured at 20× with a digital camera and the smooth muscle cell area surrounding the airways is quantified by computerized morphometry using the an imaging analysis system. Increased width of the smooth muscle layer is taken as evidence of airway wall thickening. Standard morphometric technique is used to determine the presence of emphysematous changes in the lungs. In brief, H&E stained paraffin sections cut from the upper part of the left lung are used, and 10 randomly selected fields are sampled by projecting a microscopic image of the lung section on a screen with a square reference lattice containing one horizontally and one vertically placed test line. The number of intersections of alveolar walls on the test lines are quantified by computerized morphometry using an imaging analysis system and used to quantify alveolar mean linear intercept (LM, the average distance between alveolar walls). Increased LM was taken as evidence of alveolar enlargement.

Results

Treatment of LPS-exposed animals with Compounds of Formula I or II results in reduced airway wall thickening or decreases in LM during at least one of the time-points over the 12-week LPS exposure when compared to LPS-exposed untreated animals over the same time period.

Example 25

Efficacy of Compounds of Formula I or II in Attenuating Pathophysiologies Relevant to AATD Efficacy of Compounds of Formula I or II in Airway Smooth Muscle Relaxation and Prevention of Airway Hyperreactivity Relevant to AATD Relevance. The clinical manifestation of AATD lung disease includes airway hyperreactivity involving the contraction of airway smooth muscle, and bronchodilators such as those used in the treatment of AATD (formoterol and salmeterol) have been shown to induce tracheal smooth muscle relaxation (Battram et al, *J Pharmacol Exp Therap* 317:762-770, 2006). Therefore, the properties of Compounds of Formula I or II as described in Examples 1, 2, 3, 5 and 7 demonstrate the therapeutic utility of these compounds in treatment of AATD lung disease related to airway hyperreactivity and bronchoconstriction.

Efficacy of Compounds of Formula I or II in Reduction of Pulmonary Inflammation Relevant to AATD Relevance. AATD lung disease involves pulmonary inflammation, airway hyperreactivity, and pulmonary fibrosis, and anti-inflammatory drugs are important therapeutic agents in the treatment of AATD. Therefore, the anti-inflammatory efficacy of Compounds of Formula I or II as described in Examples 6, 7, 8, 9, and 10 demonstrate therapeutic utility of these compounds in treatment of AATD.

Example 26

Efficacy of Compounds of Formula I or II in an Animal Model of Rhinitis

Nasal congestion due to inflammation and tissue edema is one of the key pathophysiologies defining rhinitis. In the following dog model of ragweed-induced rhinitis, nasal congestion is measured via acoustic rhinometry and nasal resistance.

Protocol

Newborn dogs receive an intraperitoneal injection containing 200 μg of ragweed extract in 0.5 ml of 0.9% saline mixed with 30 mg of aluminum hydroxide within 24 hours of birth. (Becker et. al. *J Appl Physiol.* 1989. 66:2691-2697; Yeates et. al. *Proc Assoc Am Physicians.* 1997, 109: 440-52). Booster injections are repeated weekly for 6 weeks and biweekly until 16 weeks of age. Sensitization to the allergen is confirmed by analysis of ragweed-specific IgE levels in the serum of the animals. For the experiment, fasted dogs are anesthetized and intubated. A nasal catheter is placed in each nostril to facilitate measurements of airway resistance. Nasal congestion in ragweed-sensitized dogs is induced by local, acute administration of histamine as the challenging allergen. Acoustic rhinometry and nasal airway resistance are measured between 4 and 24 hr post histamine administration to evaluate benefit of formulated compounds (Tiniakov et al. *J Appl Physiol* 2003. 94: 1821-1828).

Compounds of Formula I or II are dosed via bilateral intranasal administration at 30-60 minutes before histamine challenge at a dose volume of 100 μL per nostril at a concentration range of 10 μM to 10 mM range. A control group receives bilateral nasal administration of vehicle (placebo) at the same administration volume as active.

Acoustic Rhinometry

Nasal resistance can be measured in both the right and left nasal passages by using an anterior constant flow nasal rhinomanometry device. Changes in the geometry of the nasal cavity can be estimated using Acoustic Rhinometry System. The acoustic wave tube is fitted with a handmade plastic tip designed to match to the shape of the dog's nostrils, Acoustic measurements of the geometric parameters of the right nasal passage are performed at various times after allergen or constricting agent is applied. Volume of the right nasal airway and cross-sectional areas of right nasal cavity at the levels of a nasal valve, anterior and posterior regions of maxilloturbinates, and the moturbinates can be calculated using acoustic rhinometry.

Measurement of Nasal Resistance

Airway resistance can be measured in combination with acoustic rhinometry. Nasal airways resistance is determined by measuring the air pressure required to achieve a constant predetermined flow through the nasal passage. This constant airflow is delivered to the nasal passage through a nasal catheter coupled to a pressure transducer. The nasal catheter is snugly placed into the nostril and the cuff inflated to form a seal. Nasal resistance is defined as the pressure differential between the input air pressure and atmospheric pressure divided by the airflow. In these studies, nasal resistance can be measured in the left nasal airway and geometric parameters of the right nasal airway are measured with the acoustic rhinometer, simultaneously. To do this, allergen or constricting agent is locally delivered to both nasal passages.

Results

Between 4 and 24 hours following nasal administration of histamine, animals are evaluated for acoustic rhinometry and nasal resistance, Improvement in either acoustic rhinometry or nasal resistance is observed between 4-hr to 24-hr in animals dosed with a Compound of Formula I or II when compared to animals that receive placebo.

Example 27

Efficacy of Compounds of Formula I or II in Attenuating Pathophysiologies Associated with Rhinosinusitis The following example illustrates the efficacy of compounds of this invention in treatment of inflammation in mouse model of sinusitis. Model is prepared essentially as in Blair, C., et al. J. Allergy Clin. Immunol, 108(3):424-9, 2001.

Protocol

Pathogen-free 6 to 8-week-old BALB/c mice of either sex are used. Each group of animals is kept isolated from the other groups in a biohazard containment facility. All mice use is in accordance with National Institutes of Health Laboratory Animal Care Guidelines.

A group of animals is pretreated with a compound of Formula I or II via intra-peritoneal administration b.i.d. at 1-100 mg/kg of body weight on Day 1-3 and one hour prior to inoculation on day 4 while the control group is dosed with vehicle. *S. pneumoniae* (ATCC49619) is used for induction of acute sinusitis. The strain is antigenically similar to type 19 *S. pneumoniae*, the most common strain cultured from human sinuses. The *S. pneumoniae* is grown on blood agar plates, and colonies are suspended in sterile saline solution immediately before inoculation of the mice. The mice are anesthetized with intraperitoneal injection of ketamine/xylazine, and sufficient amount of the *S. pneumoniae* suspension is placed in each naris to induce infection. The mice are killed on day 5 after infection; prior experiments have shown peak infection in the sinuses at that time point.

On the day of sacrifice, the mice are sedated with a respiratory-failure dose of pentobarbital sodium (Nembutal) at 120 mg/kg. The animal is transcardially (through the right atrium) perfused with lactated Ringer's solution; this is followed by perfusion with a solution of 4% formaldehyde and 0.5% glutaraldehyde in 0.1 mmol/L of phosphate buffer. Next, the animal is decapitated and sections of the nasal passages are cut at a thickness of 8 μm, mounted on glass slides, and stained with Luna stain or hematoxylin and eosin.

Light Microscopy and Enumeration of Inflammatory Cells

Three anatomically similar sections are chosen from each mouse for analysis: an anterior section at the level of the maxillary sinuses, a middle section (more posterior and sampling the end of the maxillary sinuses and the beginning of the ethmoidal turbinates), and a third posterior section. Individual sections are analyzed, after masking, by use of a computer-aided light microscope in conjunction with reconstruction software. To quantify the degree of inflammation, we use 400× magnification and trace the total sinus cavity area and the area of the sinus occupied by neutrophil clusters; this allows us to calculate the percent of the sinus cavity filled with neutrophil clusters. Mucosa adjacent to neutrophil clusters is also traced and examined for polymorphonuclear cells, allowing us to report the number of cells per square millimeter. A random sampling of 4 mucosal areas from each of the 3 sections from each mouse is evaluated for the parameters described above, and the average of these measurements is computed for each mouse and used for statistical analysis. Eosinophils and mononuclear cells, as well as eosinophils in the lung, are counted in similar manner.

Results

The resulting inflammatory cell counts demonstrate that treatment with a Compound of Formula I or II attenuates the inflammatory cell numbers identified in the nasal passage ways of mice with experimental sinusitis when compared to the non-treated animals with experimental sinusitis.

Efficacy of Compounds of Formula I or II in Sinus Cavity Smooth Muscle Relaxation Contraction of the smooth muscles surrounding sinus cavities is one of the key pathophysiologies present in rhinosinusitis. A relaxation of smooth muscle within the sinus cavities results in alleviation of pressure and mucosal blockage. Therefore, the properties of Compounds of Formula I or II as described in Examples 1, 2, 3, 5 and 7 demonstrate the therapeutic utility of these compounds in treatment of rhinosinusitis.

Efficacy of Compounds of Formula I or II in Decreasing Sinus Cavity Edema

Congestion, tissue edema and mucus secretion within the sinus cavities are key pathophysiologies present in rhinosinusitis. A decrease in endothelial and epithelial permeability following a treatment with Compounds of Formula I or II results in alleviation of these pathophysiologies. Therefore, the properties of Compounds of Formula I or II as described in Example 14 demonstrate the therapeutic utility of these compounds in treatment of rhinosinusitis.

Example 28

Human Monocyte Cytokine Secretion Assay

Relevance:

This assay demonstrates a compound's ability to inhibit the secretion of multiple pro-inflammatory cytokines from human monocytes. Reduction in the levels of pro-inflammatory cytokines is associated with improvement in disorders with an inflammatory component.

Protocol

Peripheral blood from healthy human volunteers was collected and the monocytes isolated via Ficoll-paque density centrifugation. Monocytes were purified via an Easy Sep© Monocyte Enrichment Kit (Product number 19059) according to the manufacturer's instructions. The purified monocytes were then plated in 96-well plates at a density of 300,000 cells/mL in RPMI 1640+10% heat inactivated FBS media. The cells were allowed to pre-incubate with test compound at the indicated concentration for 30 minutes (37° C., 5% $CO_2$, humidified air); after which the supernatant was removed and media containing compound and 1 ng/mL LPS was added. Cells were allowed to incubate with compounds and LPS for 4 hours at 37° C. after which the supernatant was removed and stored at −80° C. Cytokine concentrations in the supernatant were determined using commercially available Bio-Rad Bio-Plex™ kits according the manufacturer's instructions.

Results

Compounds of Formulae I and II inhibit the release of multiple cytokines from human monocytes when incubated at 10 μM concentration in vitro, as shown in Table 9. Shown further in Table 10, potency determinations on compounds 2.059 and 2.066, both potent inhibitors of ROCK1 and ROCK2 and both of the chemical class in which $R_2$ is $R_2$-2, dose-dependently reduced the secretion of IL-1β, TNF-α and IL-9 from LPS-stimulated human monocytes, with potencies ranging from approximately 170 nM to 1 μM.

TABLE 9

Percent inhibition values for inhibition of cytokine secretion at 10 μM of test compound

| Compound | IL-1β % | IL-6 % | TNF-α % |
|---|---|---|---|
| 1.072 | 98.2 | 96.1 | 83.8 |
| 1.074 | 43.9 | 96.0 | 87.7 |
| 1.075 | 49.7 | 73.9 | 51.6 |
| 1.076 | 51.0 | 81.2 | 78.9 |
| 1.077 | 30.3 | 43.3 | 52.3 |
| 1.078 | 60.4 | 111.0 | 88.1 |
| 1.079 | 59.3 | 31.1 | 56.5 |
| 1.091 | 165.5 | 108.2 | 104.6 |
| 1.093 | 109.0 | 49.7 | 76.1 |
| 1.106 | 121.5 | 95.0 | 80.6 |
| 1.107 | 111.3 | 122.1 | 83.1 |
| 1.108 | 131.3 | 89.8 | 116.7 |
| 1.109 | 190.5 | 312.9 | 118.3 |
| 1.110 | 133.6 | 111.7 | 118.6 |
| 1.123 | 82.6 | 64.7 | 62.7 |
| 1.124 | 99.5 | 101.4 | 61.5 |
| 1.127 | 198.0 | 67.3 | 97.3 |
| 1.131 | 48.3 | 68.6 | 85.2 |
| 1.132 | 58.6 | 72.5 | 80.3 |
| 1.133 | 54.5 | 70.7 | 66.2 |
| 1.134 | 43.2 | 74.6 | 69.1 |
| 1.135 | 57.0 | 123.2 | 108.0 |
| 1.136 | 66.3 | 95.0 | 71.5 |
| 1.137 | 40.3 | 46.2 | 58.0 |
| 1.138 | 257.4 | 76.6 | 130.9 |
| 1.141 | 50.4 | 71.7 | 75.7 |
| 1.142 | 82.8 | 40.7 | 68.6 |
| 1.143 | 76.8 | 130.5 | 66.4 |
| 1.145 | 129.2 | 95.1 | 88.9 |
| 1.146 | 85.2 | 128.0 | 97.7 |
| 1.148 | 63.9 | 78.6 | 56.1 |
| 1.149 | 69.8 | 121.5 | 119.9 |
| 1.150 | 78.2 | 89.2 | 94.4 |
| 1.151 | 84.5 | 114.1 | 88.9 |
| 1.152 | 74.7 | 94.7 | 120.1 |
| 1.153 | 64.1 | 106.2 | 74.3 |
| 1.154 | 52.3 | 104.4 | 86.4 |
| 1.155 | 76.7 | 121.8 | 79.7 |
| 1.156 | 60.7 | 92.5 | 70.5 |
| 1.157 | 121.4 | 92.6 | 65.1 |

TABLE 9-continued

Percent inhibition values for inhibition of cytokine secretion at 10 µM of test compound

| Compound | IL-1β % | IL-6 % | TNF-α % |
|---|---|---|---|
| 1.158 | 80.8 | 133.1 | 86.6 |
| 1.159 | 97.1 | 84.8 | 76.1 |
| 1.161 | 87.7 | 86.3 | 153.5 |
| 1.162 | 95.5 | 99.8 | 158.7 |
| 1.163 | 166.7 | 140.9 | 91.6 |
| 1.164 | 80.1 | 109.5 | 89.0 |
| 1.165 | 129.9 | 114.3 | 103.5 |
| 1.166 | 107.0 | 87.2 | 82.2 |
| 1.170 | 80.6 | 72.7 | 67.8 |
| 1.171 | 78.9 | 91.8 | 72.2 |
| 1.173 | 86.1 | 79.5 | 80.1 |
| 1.175 | 29.3 | 38.2 | 47.4 |
| 1.176 | 95.2 | 112.4 | 72.4 |
| 1.183 | 68.7 | 123.3 | 76.5 |
| 1.185 | 39.8 | 63.0 | 66.6 |
| 1.186 | 64.1 | 105.3 | 68.2 |
| 1.195 | 115.4 | 94.4 | 67.7 |
| 1.197 | 179.1 | 128.8 | 83.3 |
| 1.200 | 0.0 | 0.0 | 0.2 |
| 1.206 | 88.7 | 164.0 | 97.3 |
| 1.208 | 62.0 | 109.0 | 92.0 |
| 1.212 | 116.3 | 111.0 | 108.1 |
| 1.213 | 111.1 | 81.7 | 77.4 |
| 1.215 | 136.7 | 63.2 | 60.4 |
| 1.217 | 118.6 | 73.8 | 71.3 |
| 1.219 | 138.9 | 127.7 | 82.1 |
| 1.223 | 117.0 | 88.5 | 60.7 |
| 1.226 | 99.3 | 52.2 | 66.6 |
| 1.227 | 69.4 | 66.7 | 79.3 |
| 1.229 | 44.9 | 63.2 | 50.7 |
| 1.233 | 78.5 | 78.9 | 79.0 |
| 1.236 | 75.2 | 93.0 | 98.0 |
| 1.237 | 97.1 | 100.9 | 70.6 |
| 1.238 | 101.1 | 62.9 | 73.2 |
| 1.239 | 39.4 | 84.7 | 58.5 |
| 1.246 | 103.0 | 108.3 | 79.0 |
| 1.249 | 133.8 | 56.2 | 60.0 |
| 1.252 | 139.2 | 68.3 | 101.6 |
| 1.253 | 160.6 | 228.6 | 126.8 |
| 1.258 | 104.1 | 83.5 | 94.0 |
| 1.262 | 145.7 | 156.6 | 135.3 |
| 2.026 | 166.0 | 180.7 | 109.1 |
| 2.031 | 49.0 | 89.3 | 66.4 |
| 2.038 | 90.8 | 79.7 | 70.2 |
| 2.039 | 49.8 | 70.3 | 47.8 |
| 2.054 | 24.0 | 56.8 | 37.9 |
| 2.058 | 1.2 | 1.3 | 10.6 |
| 2.059 | 0.3 | 0.0 | 6.9 |
| 2.060 | 5.9 | 19.6 | 33.0 |
| 2.064 | 14.3 | 45.7 | 66.2 |
| 2.066 | 0.0 | 0.0 | 25.2 |

TABLE 10

IC$_{50}$ values for inhibition of cytokine secretion

| | IL-1β (nM) | TNF-α (nM) | IL-9 (nM) |
|---|---|---|---|
| Compound 2.059 | 169.4 ± 13.0 | 207.1 ± 17.0 | 268.6 ± 28.1 |
| Compound 2.066 | 346.2 ± 182.3 | 610.6 ± 154.1 | 934.9 ± 407.5 |

Example 29

LPS-Induced Neutrophilia and Cytokine Production Assay

Relevance

Marked neutrophilia in the lung upon tissue inflammation can be indicative of underlying diseases such as COPD. The LPS-induced neutrophilia model is often used to determine the potential efficacy of therapeutic approaches designed for treatment of COPD. This assay is an in vivo assay of neutrophil accumulation and cytokine production that can be used to evaluate the activity of Rho Kinase inhibitor compounds of Formula I or II in a whole animal model. Neutrophil accumulation and cytokine production is indicative of the inflammatory response and the activity of compounds to decrease neutrophil accumulation and cytokine production in this assay supports the use of these compounds to treat disorders with an inflammatory component, especially COPD.

Protocol

Male BALB/c mice, approximately 19 to 21 grams, were ordered from Charles River Laboratories (Raleigh, N.C.). All animals were challenged with aerosolized LPS (10 µg/ml) for 25 minutes on study day 0. LPS aerosol was generated using an Aerogen Aeroneb nebulizer and controller providing a flow of 400 µl/min and a particle size of 2-4 µm MMAD. Rolipram was administered i.p at 20 mg/kg. Compound 1.091 or Compound 2.059 was administered intratracheally (i.t.) at 0.5-50 µmol/kg body weight one hour prior to LPS challenge. Four hours following LPS challenge, BALF was collected using a total of 3 ml of 0.9% sodium chloride containing 10% fetal calf serum. Total cell counts were determined using the Coulter Counter. For differential evaluations, BALF was centrifuged and cytospin slides prepared and stained with Hema3 stain. Manual leukocyte counts were then completed on 200 cells. The final concentration of individual leukocyte cell types per ml of BALF was determined by multiplication of the relative percentage of individual leukocytes with the total amount of cells/ml of BALF fluid. The concentration of IL-1β in the BALF samples was determined using commercially available Bio-plex kits (Bio-Rad). The analysis of cytokine levels was measured using the Bio-Plex 200 (Bio-Rad) system according to the manufacturer's instructions.

Results

Figure 13:
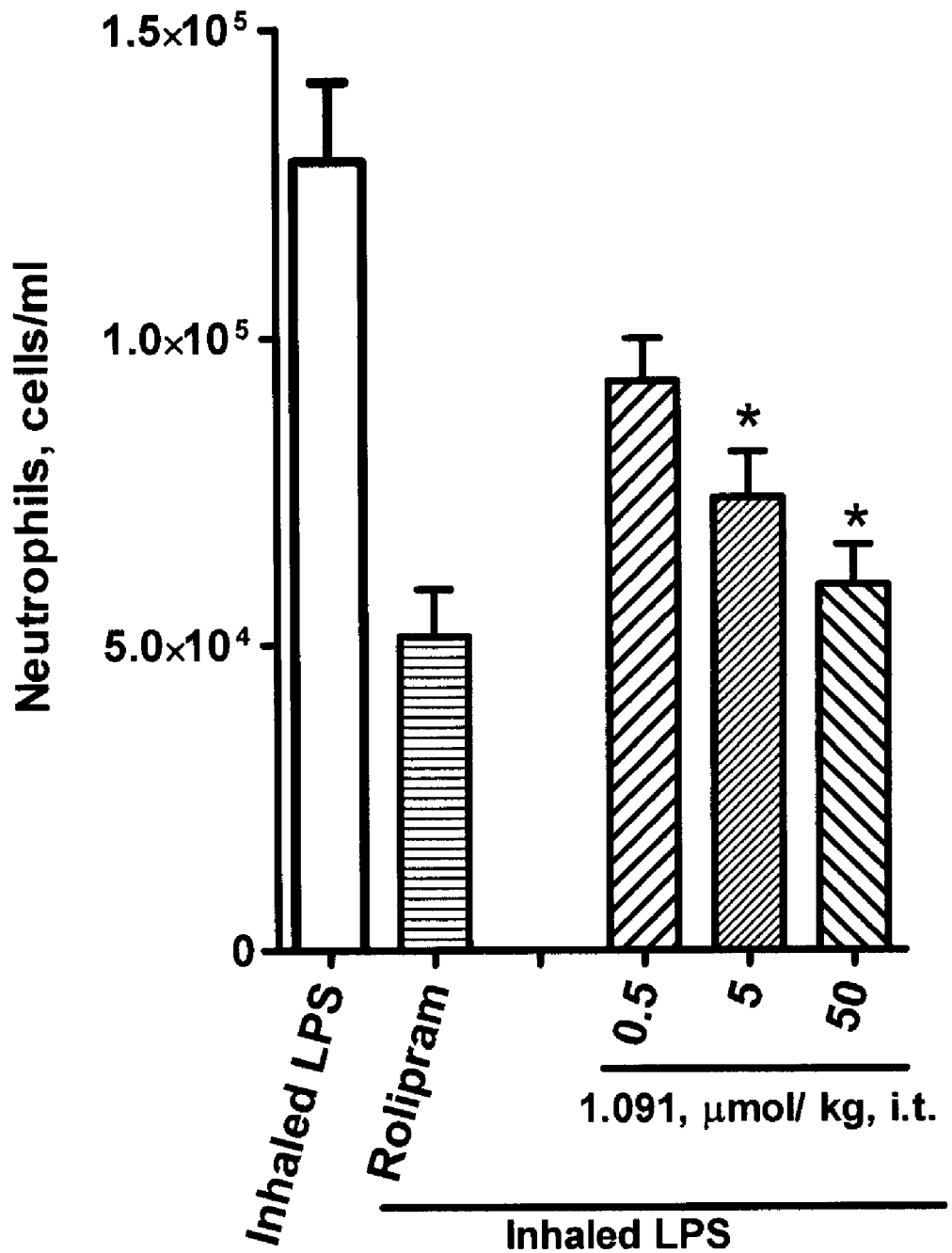
FIG. 13 shows the dose-dependent inhibition of LPS-induced neutrophilia by Compound 1.091 when dosed intratracheally to mice, Data are reported as cells/ml and are mean±SEM. *, $p<0.05$ when compared to asthmatic mice using Student's t-test.
Figure 14:
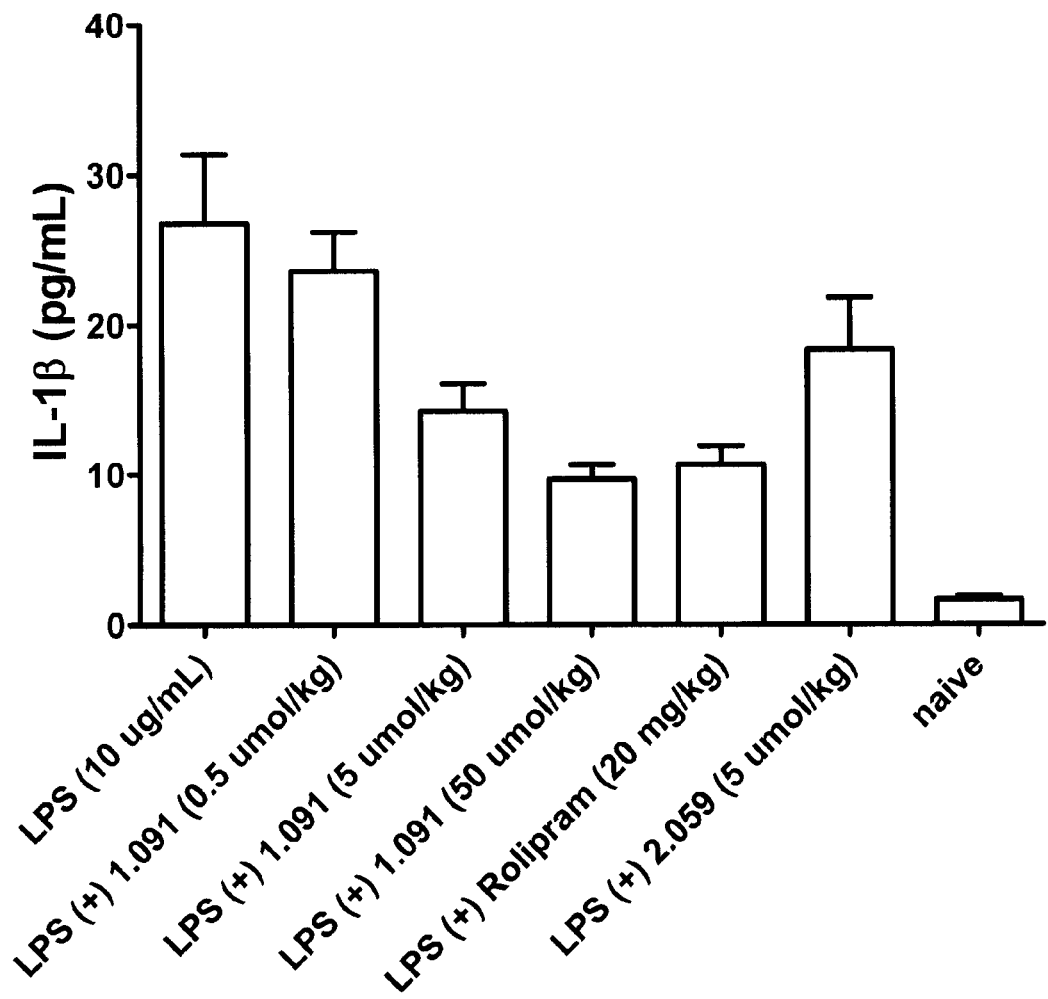
FIG. 14 shows the reduction of IL-1β levels in BALF from LPS-challenged mice upon intratracheal administration of Compound 1.091 or Compound 2.059. Data are reported as pg/mL of IL-1β and are mean±SEM.

FIG. 13 shows a significant reduction in pulmonary neutrophilia influx after intratracheal dosing of Compound 1.091. The efficacy of Compound 1.091 when dosed intratracheally is similar to the efficacy of the control compound rolipram dosed i.p. FIG. 14 shows the reduction in IL-1β after intratracheal administration of Compound 1.091 or Compound 2.059. These data demonstrate the efficacy of Rho kinase inhibitors of Formula I or II to inhibit inflammatory responses in vivo. These results also demonstrate that direct administration of the compounds of this invention to the lung is sufficient to reduce neutrophilia and that robust systemic exposure is not required.

Example 30

PDGF-Stimulated Smooth Muscle Cell Proliferation Assay

Relevance:

This assay demonstrates a compound's ability to inhibit the proliferation of smooth muscle cells in vitro, Smooth muscle proliferation and remodeling play a role in the pathophysiology of several disease states addressed in this invention, including PAH, COPD, Asthma, and LAM.

Protocol

Effects on cell proliferation were measured using a bromodeoxyuridine (BrdU) incorporation assay. A-10 rat thoracic aorta cells (ATCC #CRL 1476) were plated at 1000 cells per well in 96-well plates in Dulbecco's Modified Eagles Medium-High Glucose (Gibco cat. #11995-065) containing 10% Fetal Bovine Serum (Sigma EC#232-690-6) and allowed to grow for 24 hrs in an incubator at 37° C. Growth media was then removed and the cells were washed with warmed PBS (Gibco cat#14190-144). Serum free media containing 0.1% BSA was added to the cells. 24 hours later the media was removed and replaced with warmed serum free media. Cells were treated with either 1 µM or 10 µM of test compound and incubated for 60 min at 37° C. prior to the addition of 10 ng/mL PDGF (BD Biosciences cat. #354051) and placed in an incubator at 37° C. for 18 hrs with both compound and stimulant present. Proliferation was then monitored using the BrdU Cell Proliferation Assay, HTS (Calbiochem cat. #HTS01). BrdU was allowed to incorporate into cells for 24 hours prior to the addition of fixative/denaturing solution and the fluorometric detection of incorporated BrdU using a BrdU antibody as per manufacturer's directions. Data are reported as a percent of the PDGF-stimulated BrdU incorporation.

Results:

As shown in Table 11, compounds of Formulae I and II reduced PDGF-stimulated proliferation of A10 cells with efficacy ranging from 10-80% inhibition when dosed in vitro at 11M.

TABLE 11

Reduction of PDGF-stimulated proliferation of A-10 cells as a percent of the total challenge-stimulated proliferation.

| Compound | Percent of PDGF Induced Proliferation at 10 µM Avg | Percent of PDGF Induced Proliferation at 10 µM SEM | Percent of PDGF Induced Proliferation at 1 µM Avg | Percent of PDGF Induced Proliferation at 1 µM SEM |
| --- | --- | --- | --- | --- |
| 1.074 | 46.9 | 3.5 | 79.9 | 9.7 |
| 1.076 | 53.7 | 4.1 | 84.0 | 8.5 |
| 1.091 | 69.3 | 5.5 | 85.7 | 5.3 |
| 1.108 | 43.7 | 1.6 | 83.1 | 6.7 |
| 1.124 | 61.6 | 2.6 | 68.5 | 3.1 |
| 1.131 | 36.6 | 2.4 | 61.7 | 4.8 |
| 1.132 | 30.3 | 1.3 | 48.9 | 3.4 |
| 1.135 | 35.0 | 3.9 | 52.6 | 4.9 |
| 1.136 | 39.8 | 2.6 | 71.4 | 1.3 |
| 1.138 | 27.0 | 1.7 | 46.3 | 1.5 |
| 1.148 | 63.5 | 3.0 | 56.9 | 2.7 |
| 1.151 | 63.8 | 4.1 | 51.0 | 2.1 |
| 1.161 | 33.4 | 0.9 | 50.0 | 3.7 |
| 1.162 | 42.5 | 1.6 | 55.6 | 2.3 |
| 1.165 | 57.9 | 1.2 | 74.8 | 6.1 |
| 1.167 | 52.7 | 4.6 | 78.8 | 4.5 |
| 1.173 | 35.8 | 2.8 | 55.4 | 4.2 |
| 1.175 | 49.0 | 2.5 | 58.2 | 2.3 |
| 1.180 | 64.8 | 5.0 | 92.4 | 7.9 |
| 1.197 | 48.9 | 2.8 | 52.5 | 1.5 |
| 1.204 | 42.8 | 5.3 | 79.3 | 3.0 |
| 1.206 | 51.1 | 2.1 | 77.5 | 5.8 |
| 1.213 | 52.3 | 3.6 | 70.1 | 2.3 |
| 1.215 | 54.0 | 5.3 | 70.8 | 4.0 |
| 1.237 | 51.4 | 4.8 | 63.5 | 5.2 |
| 1.238 | 48.6 | 3.2 | 40.7 | 1.9 |
| 1.239 | 37.8 | 1.6 | 41.7 | 2.7 |
| 1.253 | 47.9 | 2.0 | 44.8 | 3.1 |
| 1.258 | 43.4 | 4.7 | 50.5 | 3.3 |
| 2.009 | 56.5 | 3.9 | 128.9 | 13.4 |
| 2.022 | 39.4 | 1.1 | 89.7 | 4.5 |
| 2.025 | 68.0 | 4.1 | 69.8 | 4.6 |
| 2.026 | 52.0 | 2.5 | 74.5 | 6.5 |
| 2.027 | 64.4 | 5.8 | 79.4 | 5.6 |
| 2.031 | 52.6 | 2.8 | 90.3 | 9.9 |
| 2.038 | 62.7 | 3.5 | 58.6 | 1.2 |
| 2.041 | 61.5 | 3.1 | 81.8 | 4.8 |
| 2.046 | 32.1 | 1.4 | 57.4 | 1.2 |
| 2.047 | 53.8 | 3.2 | 65.3 | 3.0 |
| 2.054 | 84.6 | 6.4 | 68.2 | 4.0 |
| 2.059 | 25.5 | 1.1 | 75.0 | 5.7 |
| 2.064 | 56.2 | 3.9 | 53.1 | 1.9 |
| 2.066 | 19.8 | 0.7 | 20.0 | 0.7 |

Example 31

Akt3 and p70S6K Inhibition Assay

Relevance:

This assay demonstrates a compound's ability to inhibit the kinases Akt3 and p70S6K in vitro. Both kinases are known to play a role in proliferation pathways in disease states addressed by this invention, such as LAM.

Protocol

Inhibition of Akt3 and p70S6K activity was determined using the IMAP™ FP Progressive Binding Kit (Molecular Devices product number R8127). Akt3 human enzyme (Upstate Chemicon #14-502), or p70S6K human enzyme (Upstate Chemicon #14-486), and Flourescein tagged substrate peptide (Molecular Devices product number R7110) or (Molecular Devices product number R7184), for Akt3 and p70S6K respectively, was pre-incubated with test compound for 5 minutes in buffer containing 10 mM Tris-HCL pH 7.2, 10 mM $MgCl_2$, 1 mM DTT and 0.1% BSA. Following the pre-incubation, 30 M ATP was added to initiate the reaction. After 60 minutes at RT, Molecular Devices IMAP™ binding solution was added to bind phosphorylated substrate. After 30 minutes of incubation in the presence of the IMAP™ beads the fluorescence polarization was read and the ratio was reported as mP. $IC_{50}$ results were calculated using the Prism software from Graphpad. The $K_i$ values were determined according to the following formula: $K_i = IC_{50}/(1+([ATP\ Challenge]/EC_{50}\ ATP))$.

Results:

As shown in Table 12, many compounds of Formulae I and II show sub-micromolar inhibitory potencies against both Akt3 and p70S6K.

TABLE 12

Akt3 and p70S6K potency data

| Compound | Akt3 Ki, Avg, nM | Akt3 Ki, StdDev, nM | p70S6K Ki, Avg, nM | p70S6K Ki, StdDev, nM |
| --- | --- | --- | --- | --- |
| 1.072 | 4752.1 | 617.1 | 1130.3 | 263.7 |
| 1.074 | 437.4 | 13.2 | 548.3 | 170.9 |
| 1.075 | 5321.5 | 61.8 | 974.6 | 166.8 |
| 1.076 | 240.9 | 6.2 | 414.3 | 162.7 |
| 1.077 | 5253.2 | 1422.9 | 715.5 | 291.5 |
| 1.078 | 3267.4 | 150.9 | 1678.1 | 640.4 |
| 1.079 | 7191.7 | 445.6 | 3012.8 | 963.8 |
| 1.091 | 5388.5 | 171.6 | 1420.4 | 78.5 |
| 1.093 | 1824.9 | 27.9 | 2025.6 | 356.8 |
| 1.106 | 3914.9 | 257.1 | 1329.1 | 268.0 |
| 1.107 | 16304.0 | 1575.9 | 3356.5 | 701.7 |
| 1.108 | 205.0 | 2.2 | 510.6 | 106.0 |
| 1.109 | 5190.9 | 318.3 | 2495.5 | 314.8 |
| 1.110 | 462.6 | 2.3 | 1298.2 | 175.9 |
| 1.123 | 2406.9 | 287.1 | 2810.7 | 597.6 |
| 1.124 | 7868.0 | 909.4 | 3325.3 | 542.0 |
| 1.127 | 975.4 | 126.4 | 2065.5 | 54.3 |
| 1.131 | 282.6 | 2.0 | 502.8 | 112.4 |
| 1.132 | 81.8 | 8.2 | 514.6 | 111.1 |
| 1.133 | 148.3 | 3.7 | 531.8 | 45.6 |
| 1.134 | 150.7 | 22.1 | 519.7 | 81.1 |
| 1.135 | 444.2 | 32.9 | 588.6 | 142.4 |
| 1.136 | 289.7 | 12.5 | 1236.7 | 413.1 |
| 1.137 | 197.9 | 10.3 | 353.6 | 132.2 |
| 1.138 | 91.3 | 48.3 | 443.5 | 36.3 |
| 1.141 | 1263.0 | 133.1 | 387.5 | 5.8 |
| 1.142 | 8268.5 | 702.6 | 2524.8 | 882.2 |
| 1.143 | 706.5 | 130.5 | 538.2 | 173.7 |
| 1.145 | 1190.5 | 63.5 | 2296.4 | 602.2 |
| 1.146 | 204.9 | 24.7 | 741.5 | 272.3 |
| 1.148 | 1131.4 | 161.7 | 435.5 | 138.0 |

TABLE 12-continued

Akt3 and p70S6K potency data

| Compound | Akt3 Ki, Avg, nM | Akt3 Ki, StdDev, nM | p70S6K Ki, Avg, nM | p70S6K Ki, StdDev, nM |
|---|---|---|---|---|
| 1.149 | 7395.9 | 410.0 | 1888.4 | 661.8 |
| 1.150 | 3183.1 | 98.7 | 1273.8 | 106.7 |
| 1.151 | 708.9 | 112.8 | 530.7 | 69.6 |
| 1.152 | 1976.2 | 155.8 | 523.5 | 295.5 |
| 1.153 | 9950.2 | 2150.4 | 2376.1 | 553.3 |
| 1.154 | 4947.5 | 541.2 | 1130.1 | 355.3 |
| 1.155 | 5680.5 | 644.8 | 1751.6 | 502.8 |
| 1.156 | 8772.6 | 427.6 | 3244.6 | 675.0 |
| 1.157 | 29192.3 | 10235.1 | 8693.4 | 2357.4 |
| 1.158 | 5905.2 | 343.4 | 1971.7 | 454.0 |
| 1.159 | 1232.9 | 459.5 | 2061.8 | 271.7 |
| 1.161 | 63.5 | 3.6 | 129.4 | 73.5 |
| 1.162 | 92.0 | 0.9 | 387.4 | 217.4 |
| 1.163 | 4423.8 | 182.3 | 1875.2 | 496.6 |
| 1.164 | 4306.8 | 26.6 | 1957.4 | 729.2 |
| 1.165 | 4140.0 | 293.7 | 1627.1 | 584.4 |
| 1.166 | 18132.9 | 4816.3 | 5163.5 | 1419.0 |
| 1.167 | 8247.3 | 802.7 | 1071.0 | 516.6 |
| 1.170 | 7814.3 | 82.1 | 2046.3 | 580.9 |
| 1.171 | 9326.9 | 448.0 | 3419.0 | 841.6 |
| 1.173 | 157.0 | 0.5 | 339.7 | 204.4 |
| 1.175 | 2820.2 | 294.6 | 853.0 | 92.0 |
| 1.176 | 20941.5 | 4664.9 | 8755.7 | 3209.3 |
| 1.178 | 711.4 | 5.8 | 1116.2 | 637.4 |
| 1.180 | 12022.9 | 416.9 | 1029.2 | 139.1 |
| 1.183 | 9007.8 | 1662.8 | 2477.1 | 1431.3 |
| 1.185 | 4216.6 | 403.6 | 1152.2 | 761.8 |
| 1.186 | 10237.7 | 1867.1 | 1612.5 | 982.8 |
| 1.195 | 21975.8 | 379.4 | 2731.0 | 1192.9 |
| 1.197 | 64051.2 | 47694.4 | 8688.8 | 366.2 |
| 1.200 | 10608.5 | 131.2 | 3903.1 | 3979.1 |
| 1.204 | 1908.2 | 34.3 | 926.8 | 122.9 |
| 1.206 | 529.1 | 22.0 | 314.4 | 209.6 |
| 1.208 | 345.7 | 19.4 | 720.6 | 705.8 |
| 1.212 | 390.2 | 3.8 | 894.0 | 580.3 |
| 1.213 | 3207.8 | 140.6 | 2097.2 | 112.7 |
| 1.215 | 14753.0 | 1613.1 | 1285.8 | 108.5 |
| 1.217 | 10301.1 | 93.6 | 3501.9 | 3691.2 |
| 1.219 | 38297.7 | 11679.7 | 4969.9 | 1893.5 |
| 1.223 | 11139.0 | 1467.2 | 3101.9 | 1629.9 |
| 1.226 | 531.0 | 1.1 | 1348.5 | 1389.6 |
| 1.227 | 3476.0 | 196.6 | 1580.9 | 623.5 |
| 1.229 | 24557.8 | 17008.1 | 3128.5 | 322.4 |
| 1.233 | 2628.6 | 182.4 | 2004.9 | 815.1 |
| 1.236 | 3716.5 | 474.9 | 2755.4 | 2914.8 |
| 1.237 | 7910.2 | 217.5 | 9873.2 | 7272.6 |
| 1.238 | 4171.1 | 173.1 | 2609.6 | 1573.2 |
| 1.239 | 17657.7 | 4393.7 | 10026.9 | 8534.5 |
| 1.246 | 1096.1 | 9.5 | 1879.2 | 1883.4 |
| 1.249 | 1599.7 | 63.8 | 937.5 | 226.8 |
| 1.252 | 205.0 | 11.9 | 170.7 | 84.1 |
| 1.253 | 2597.1 | 29.9 | 2515.0 | 1464.8 |
| 1.258 | 315.2 | 94.1 | 531.5 | 229.6 |
| 1.262 | 861.0 | 1.0 | 5436.6 | 49.5 |
| 2.009 | 3725.8 | 198.3 | 1280.8 | 361.0 |
| 2.022 | 4115.1 | 209.4 | 501.1 | 6.9 |
| 2.025 | 966.4 | 103.5 | 498.8 | 74.2 |
| 2.026 | 2076.0 | 196.5 | 536.0 | 4.6 |
| 2.027 | 657.7 | 58.8 | 509.0 | 70.6 |
| 2.031 | 1357.9 | 0.6 | 326.4 | 52.7 |
| 2.038 | 2553.9 | 184.2 | 1397.0 | 345.6 |
| 2.039 | 1988.0 | 66.7 | 1010.3 | 195.5 |
| 2.041 | 3443.4 | 187.8 | 2095.1 | 161.9 |
| 2.046 | 1975.4 | 142.9 | 758.9 | 401.2 |
| 2.047 | 1942.1 | 163.1 | 437.5 | 184.9 |
| 2.054 | 414.8 | 5.7 | 438.9 | 207.3 |
| 2.055 | 977.5 | 72.3 | 311.6 | 180.9 |
| 2.058 | 1936.0 | 136.7 | 212.6 | 44.7 |
| 2.059 | 119.8 | 24.5 | 207.9 | 173.8 |
| 2.060 | 328.8 | 10.3 | 181.3 | 102.7 |
| 2.064 | 382.0 | 6.7 | 178.2 | 103.4 |
| 2.066 | 2510.4 | 30.5 | 368.3 | 133.1 |

Example 32

Kinase Panel Screen

Relevance:

This assay demonstrates a compound's ability to inhibit members of a panel of kinases known to be involved in signaling pathways connected to inflammatory processes.

Protocol

Compounds of Formulae I and II were examined for activity against a selected panel of kinases using the KinaseProfiler™ enzyme profiling services (Upstate, Millipore Bioscience Division). Percent kinase activity at 10 μM and 1 μM test compound and 10 μM ATP was determined against 40 wild-type recombinant human kinases according to Upstate's standard protocol: ASK1, BTK, CSK, c-RAF, GCK, GSK3β, IKKα, IKKβ, IRAK1, IRAK4, JNK1α1, JNK2α2, JNK3, ERK1, ERK2, MAPKAP-K2, MAPKAP-K3, MEK1, MKK4, MKK6, MKK7β, Mnk2, MSK1, PAK3, PDK1, PRAK, ROCK1, Rsk2, SAPK2a, SAPK2b, SAPK3, SAPK4, SRPK1, SRPK2, Syk, TAK1, TBK1, PI3-Kβ, PI3-Kγ, PI3-Kδ.

Results:

Percent inhibition results are reported in Table 13 for four compounds against six kinases in the panel. Only compounds in which $R_2$ is $R_2$-2 were found to inhibit significantly GCK, ERK1/2, Mnk2 and IRAK1/2. Only ERK1/2 were inhibited by ~50% at 1 μM by both compounds 2.059 and 2.066.

TABLE 13

Percent inhibition data for six of the tested kinases

| | Compound 2.059 | | Compound 2.066 | | Compound 1.161 | | Compound 1.162 | |
|---|---|---|---|---|---|---|---|---|
| | 1 μM | 10 μM | 1 μM | μM | 1 μM | 10 μM | 1 μM | 10 μM |
| ERK1 | 37 | 4 | 52 | 15 | 97 | 75 | 84 | 50 |
| ERK2 | 56 | 12 | 50 | 12 | 104 | 92 | 89 | 60 |
| Mnk2 | 49 | 12 | 99 | 54 | 108 | 106 | 111 | 65 |
| IRAK4 | 63 | 22 | 77 | 25 | 96 | 109 | 105 | 88 |
| IRAK1 | 87 | 30 | 74 | 32 | 106 | 99 | 100 | 97 |
| GCK | 75 | 34 | 39 | 7 | 96 | 91 | 93 | 75 |

Example 33

Efficacy of Compounds of Formula I or II in Attenuating Pathophysiologies Associated with OB/BOOP Due to Lung Transplantation or HSCT Efficacy of Compounds of Formula I or II in Airway Smooth Muscle Relaxation and Prevention of Airway Hyperreactivity Relevant to OB/BOOP Due to Lung Transplantation or HSCT Relevance. The clinical manifestation of OB/BOOP in the lung includes airflow limitation in the airway involving inflammation and the contraction of airway smooth muscle, Therefore, the properties of Compounds of Formula I or II as described in Examples 1, 2, 3, 5 and 7 demonstrate the therapeutic utility of these compounds in treatment of OB/BOOP related to airway hyperreactivity and bronchoconstriction.

Efficacy of Compounds of Formula I or II in Reduction of Pulmonary Inflammation Relevant to OB/BOOP Due to Lung Transplantation or HSCT Relevance. OB/BOOP involves pulmonary inflammation, airway hyperreactivity, and pulmonary fibrosis, and anti-inflammatory drugs are important therapeutic agents in the treatment of OB/BOOP. Therefore, the anti-inflammatory efficacy of Compounds of Formula I or II as described in Examples 6, 7, 8, 9, 10, 28 and 29 demonstrate therapeutic utility of these compounds in treatment of OB/BOOP.

Efficacy of Compounds of Formula I or II in an Animal Model of BOOP

The following example illustrates the efficacy of compounds of Formula I or II in treatment of BOOP in an animal model of virally induced intraluminal fibrosis. The model is prepared essentially as in Majesky et al., *Am J Pathol*, 163: 1467-1479, 2003.

Protocol

Four- to 5-week-old female CBA/J mice are lightly anesthetized and infected by the intranasal (i.n.) application of $1 \times 10^6$ PFU of reovirus 1/L in 30 ml (15 ml in each nostril) in sterile saline on day 0. Control animals are inoculated with sterile saline alone. A compound of Formula I or II is administered to mice beginning on day 5 post-reovirus 1/L infection and given daily until the completion of the time-course. As a control standard compound, 10 mg/kg of methylprednisolone is administered i.p. to mice beginning on day 5 post-reovirus 1/L infection and given daily until the completion of the time-course. On days 7, 10, and 14 BAL fluid is taken for measurement of cytokines. On day 14 or day 21, animals are sacrificed for histological evaluation of the lung.

Cytokine Determination in BAL Fluid

BAL is performed in situ by injecting and withdrawing a 0.5 ml aliquot of Hank's balanced salt solution (HBSS) twice through an intubation needle (21 gauge). BAL fluid is analyzed for mouse IFN-γ and MCP-1 using commercially available ELISA kits.

Histology

On day 14 or 21, lungs are inflated in situ with 10% neutral buffered formalin (0.5 mls) by intratracheal (i.t.) intubation, removed, and suspended in an additional 10% neutral buffered formalin overnight before being embedded in paraffin. H&E stain and Mason's trichrome stain, which are used to visualize collagen deposition, are performed on 4-μm sections. Inflammatory infiltration with the development of follicular bronchiolitis (FB), which is defined as a mononuclear cell infiltrate that condenses into prominent peribronchiolar lymphoid accumulations, is blindly evaluated. FB is scored on a scale of 0 to 3:0, normal; 1, mild (less than 4 follicles per lobe); 2, moderate (between 5 and 8 follicles per lobe); 3, severe (greater than 8 follicles per lobe). Fibrosis is scored on a scale of 0 to 4:0, normal; 1, mild; 2, moderate; 3, severe; 4, very severe.

OH-Proline Assay

On day 14 or 21, OH-proline contents of the lungs are measured objectively to estimate lung fibrosis (Green G D et al. Anal Biochem. 201:265-269, 1992). The right lungs of each mouse are dissected free from major bronchi, and the wet weights are measured. They are hydrolyzed in 500 ml of 12 N hydrochloric acid and in the same aliquot of distilled water at 11° C. 20 h, in dry block. After the resultant hydrolysate is neutralized with sodium hydroxide, a 100-ml supernatant is mixed in 1.5 ml of 0.3 N lithium hydroxide solution, The OH-proline content is determined by high-performance liquid chromatography and expressed as micrograms per right lung.

Results

On the indicated day, the fibrotic changes in the lung, the hydroxyproline content in the lung, and the cytokine content in the BAL fluid are measured and compared in the compound-treated mice vs. saline-treated mice. Administration of Compounds of Formula I or II result in the improvement in at least one of the above-mentioned endpoints that is equal to or greater than the improvement seen with methylprednisolone.

Example 34

Efficacy of Compounds of Formula I or II in Attenuating Pathophysiologies Relevant to Non-IPF IIP Efficacy of Compounds of Formula I or II in Airway Smooth Muscle Relaxation and Prevention of Airway Hyperreactivity Relevant to Non-IPF IIP Relevance. The clinical manifestation of non-IPF IIP includes airflow limitation in the airway involving inflammation and the contraction of airway smooth muscle, Therefore, the properties of Compounds of Formula I or II as described in Examples 1, 2, 3, 5 and 7 demonstrate the therapeutic utility of these compounds in treatment of non-IPF IIP related to airway hyperreactivity and bronchoconstriction.

Efficacy of Compounds of Formula I or II in Reduction of Pulmonary Inflammation Relevant to Non-IPF IIP Relevance. Non-IPF IIP involves pulmonary inflammation, airway hyperreactivity, and pulmonary fibrosis, and anti-inflammatory drugs are important therapeutic agents in the treatment of non-IPF IIP, Therefore, the anti-inflammatory efficacy of Compounds of Formula I or II as described in Examples 6, 7, 8, 9, 10, 28 and 29 demonstrate therapeutic utility of these compounds in treatment of non-IPF IIP.

Example 35

Efficacy of Compounds of Formula I or II in Attenuating Pathophysiologies Relevant to the ILD Other Than IPF, Non-IPF IIPs and OB/BOOP Efficacy of Compounds of Formula I or II in Airway Smooth Muscle Relaxation and Prevention of Airway Hyperreactivity Relevant to ILD Other Than IPF, non-IPF IIPs and OB/BOOP Relevance. The clinical manifestation of ILD other than IPF, non-IPF IIPs and OB/BOOP in the lung includes airflow limitation in the airway involving inflammation and the contraction of airway smooth muscle, Therefore, the properties of Compounds of Formula I or II as described in Examples 1, 2, 3, 5 and 7 demonstrate the therapeutic utility of these compounds in treatment of ILD other than IPF, non-IPF IIPs and OB/BOOP related to airway hyperreactivity and bronchoconstriction.

Efficacy of Compounds of Formula I or II in Reduction of Pulmonary Inflammation Relevant to ILD Other Than IPF, Non-IPF IIPs and OB/BOOP Relevance. ILD other than IPF, non-IPF IIPs and OB/BOOP involves pulmonary inflammation, airway hyperreactivity, and pulmonary fibrosis, and anti-inflammatory drugs are important therapeutic agents in the treatment of ILD other than IPF, non-IPF IIPs and OB/BOOP. Therefore, the anti-inflammatory efficacy of Compounds of Formula I or II as described in Examples 6, 7, 8, 9, 10, 28 and 29 demonstrate therapeutic utility of these compounds in treatment of ILD other than IPF, non-IPF IIPs and OB/BOOP.

Example 36

Efficacy of Compounds of Formula I or II to Inhibit Proliferation of Primary Smooth-Muscle Like Cells Derived From Human LAM Patients Relevance This assay measures the ability of a compound to directly inhibit the proliferation of primary smooth-muscle like cells derived from human LAM patients. Since this assay is performed directly on human primary cells from the disease state of interest, activity of compounds in this assay supports the use of these compounds in the treatment of LAM.

Protocol

LAM cells were dissociated from LAM nodules from the lung of patients with LAM who have undergone lung transplant. In brief, cells were dissociated by enzymatic digestion in M199 medium containing 0.2 mM $CaCl_2$, 2 mg/ml collagenase D, 1 mg/ml trypsin inhibitor, and 3 mg/ml elastase. The cell suspension was filtered and then washed with equal volumes of cold DF8 medium, consisting of equal amounts of Ham's F-12 and Dulbecco's modified Eagle's medium supplemented with $1.6 \times 10^{-6}$ M ferrous sulfate, $1.2 \times 10^{-5}$ U/ml vasopressin, $1.0 \times 10^{-9}$ M triiodothyronine, 0.025 mg/ml insulin, $1.0 \times 10^{-8}$ M cholesterol, $2.0 \times 10^{-7}$ M hydrocortisone, 10 pg/ml transferrin, and 10% fetal bovine serum. The cells were cultured in DF8 medium and were passaged twice per week. All LAM cells had a high degree of proliferative activity in the absence of any stimuli. Two separate LAM cell lines were tested and denoted as LAM1 or LAM2 cells. LAM cells in subculture during the 3rd through 12th cell passages were used. DNA synthesis was measured using a [H]thymidine incorporation assay. In brief, near-confluent cells that were serum-deprived for 48 h were incubated with 10 μM of compound or with vehicle (control). After 18 h of incubation, cells were labeled with [methyl-3H]thymidine for 24 hours. The cells were then scraped and lysed, and DNA was precipitated with 10% trichloroacetic acid. The precipitants were aspirated on glass filters and extensively washed and dried, and [$^3$H]thymidine incorporation was counted (Goncharova et al., Mol Pharmacol 73:778-788, 2008)

Results

Figure 15A:
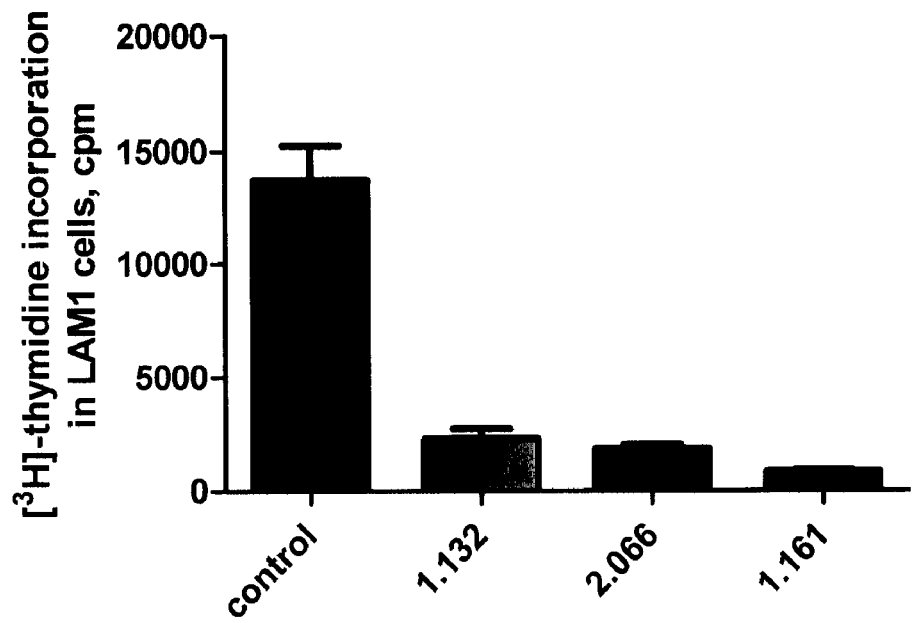
FIG. 15 shows [$^3$H]-thymidine incorporation in primary human LAM-derived cells. Cells were treated with vehicle alone (control) or with 10 μM of Compound 1.132, Compound 2.066 or Compound 1.161. Experiments were performed on two separate cell lines, LAM1 cells (shown in FIG. 15A) and LAM2 cells (shown in FIG. 15B). Data are reported as counts per minute (CPM) of incorporated [$^3$H]-thymidine and are mean±SEM.
Figure 15B:
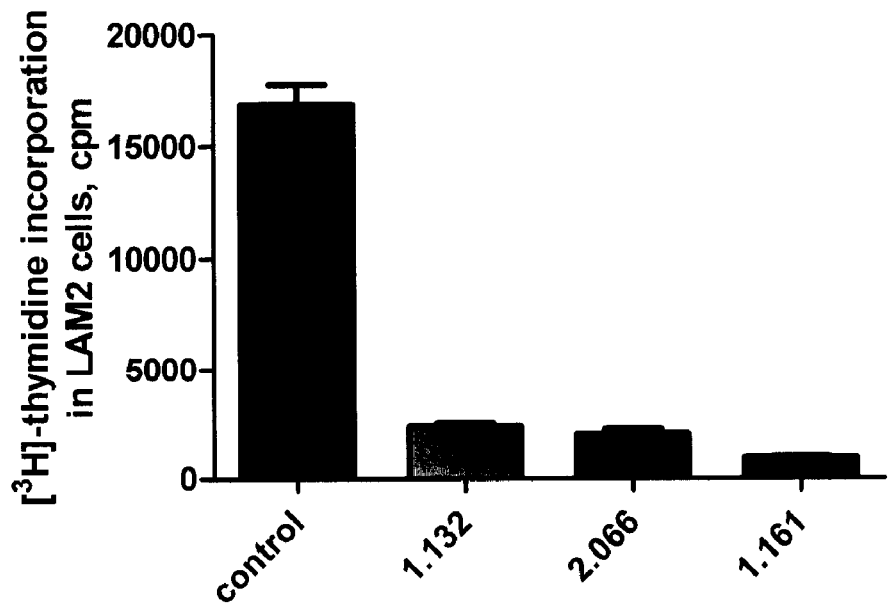

As shown in FIG. 15, compounds of Formula I and II reduced proliferation of LAM1 (FIG. 15A) and LAM2 (FIG. 15B) cells when dosed in vitro at 10 μM. These results demonstrate that Compounds of Formula I and II are efficacious in inhibiting the proliferation of primary cells derived from LAM patients and provide support for the use of these compounds to treat LAM.

Example 37

Summary of Data of Preferred Compounds

Principal biological data describing the preferred compounds of the invention have been collected into Table 14. Displayed in this table are ROCK1 and ROCK2 average Ki values in nM (as detailed in Example 1), Akt3 and p70S6K average $K_i$ values in nM (as detailed in Example 31), average percent of PDGF stimulated proliferation at 10 and 1 μM of test compound (as detailed in Example 30), average percent of stimulated IL-1β, IL-6, and TNF-α secretion from human monocytes at 10 μM of test compound (as detailed in Example 28), average $IC_{50}$ for inhibition of fMLP-induced neutrophil chemotaxis in μM (as detailed in Example 9), mean compound plasma concentrations in mice at 15 minutes post oral administration (as detailed in Example 12), and the average percentage of carbachol-induced rat trachael ring contraction at 1 μM of test compound (as detailed in Example 3).

TABLE 14

Summary of Data of Preferred Compounds

| Compound | ROCK1 Ki, nM | ROCK2 Ki, nM | Akt3 Ki, nM | p70S6K Ki, nM | Proliferation at 10 μM, % | Proliferation at 1 μM, % |
|---|---|---|---|---|---|---|
| 1.074 | 40.1 | 4.1 | 437.4 | 548.3 | 46.9 | 79.9 |
| 1.075 | 48.7 | 4.4 | 5321.5 | 974.6 | | |
| 1.076 | 14.3 | 2.6 | 240.9 | 414.3 | 53.7 | 84.0 |
| 1.077 | 76.1 | 11.1 | 5253.2 | 715.5 | | |
| 1.079 | 71.5 | 4.7 | 7191.7 | 3012.8 | | |
| 1.091 | 71.4 | 3.3 | 5388.5 | 1420.4 | 69.3 | 85.7 |
| 1.093 | 64.5 | 7.7 | 1824.9 | 2025.6 | | |
| 1.108 | 25.6 | 6.5 | 205.0 | 510.6 | 43.7 | 83.1 |
| 1.109 | 58.8 | 9.6 | 5190.9 | 2495.5 | | |
| 1.123 | 82.3 | 9.6 | 2406.9 | 2810.7 | | |
| 1.124 | 64.5 | 3.3 | 7868.0 | 3325.3 | 61.6 | 68.5 |
| 1.126 | 76.2 | 17.2 | | | | |
| 1.131 | 19.7 | 3.8 | 282.6 | 502.8 | 36.6 | 61.7 |
| 1.132 | 22.5 | 3.5 | 81.8 | 514.6 | 30.3 | 48.9 |
| 1.133 | 25.0 | 4.3 | 148.3 | 531.8 | | |
| 1.134 | 22.4 | 4.4 | 150.7 | 519.7 | | |
| 1.135 | 40.3 | 5.4 | 444.2 | 588.6 | 35.0 | 52.6 |
| 1.136 | 25.8 | 5.1 | 289.7 | 1236.7 | 39.8 | 71.4 |
| 1.137 | 36.3 | 7.2 | 197.9 | 353.6 | | |
| 1.138 | 41.1 | 6.3 | 91.3 | 443.5 | 27.0 | 46.3 |
| 1.141 | 28.5 | 3.8 | 1263.0 | 387.5 | | |
| 1.148 | 24.3 | 3.6 | 1131.4 | 435.5 | 63.5 | 56.9 |
| 1.149 | 46.8 | 4.2 | 7395.9 | 1888.4 | | |
| 1.150 | 33.2 | 3.2 | 3183.1 | 1273.8 | | |
| 1.152 | 19.8 | 3.3 | 1976.2 | 523.5 | | |
| 1.153 | 62.8 | 4.2 | 9950.2 | 2376.1 | | |
| 1.155 | 45.4 | 7.0 | 5680.5 | 1751.6 | | |
| 1.156 | 135.8 | 13.0 | 8772.6 | 3244.6 | | |
| 1.157 | 263.8 | 8.8 | 29192.3 | 8693.4 | | |
| 1.158 | 64.1 | 5.1 | 5905.2 | 1971.7 | | |
| 1.161 | 9.9 | 2.5 | 63.5 | 129.4 | 33.4 | 50.0 |
| 1.162 | 15.2 | 2.8 | 92.0 | 387.4 | 42.5 | 55.6 |
| 1.163 | 33.6 | 2.9 | 4423.8 | 1875.2 | | |
| 1.164 | 42.4 | 6.1 | 4306.8 | 1957.4 | | |
| 1.165 | 50.7 | 3.4 | 4140.0 | 1627.1 | 57.9 | 74.8 |
| 1.166 | 95.2 | 8.0 | 18132.9 | 5163.5 | | |

TABLE 14-continued

Summary of Data of Preferred Compounds

| | | | | | | |
|---|---|---|---|---|---|---|
| 1.171 | 109.2 | 16.0 | 9326.9 | 3419.0 | | |
| 1.173 | 15.1 | 3.6 | 157.0 | 339.7 | 35.8 | 55.4 |
| 1.175 | 65.9 | 7.6 | 2820.2 | 853.0 | 49.0 | 58.2 |
| 1.176 | 314.3 | 11.2 | 20941.5 | 8755.7 | | |
| 1.186 | 129.3 | 11.9 | 10237.7 | 1612.5 | | |
| 1.193 | 64.9 | 14.8 | | | | |
| 1.195 | 196.2 | 10.3 | 21975.8 | 2731.0 | | |
| 1.197 | 120.2 | 5.0 | 64051.2 | 8688.8 | 48.9 | 52.5 |
| 1.200 | 76.5 | 5.9 | 10608.5 | 3903.1 | | |
| 1.206 | 64.4 | 9.1 | 529.1 | 314.4 | 51.1 | 77.5 |
| 1.212 | 44.2 | 3.9 | 390.2 | 894.0 | | |
| 1.213 | 106.3 | 3.0 | 3207.8 | 2097.2 | 52.3 | 70.1 |
| 1.215 | 102.8 | 3.5 | 14753.0 | 1285.8 | 54.0 | 70.8 |
| 1.217 | 70.1 | 12.1 | 10301.1 | 3501.9 | | |
| 1.219 | 343.6 | 15.4 | 38297.7 | 4969.9 | | |
| 1.223 | 239.5 | 15.7 | 11139.0 | 3101.9 | | |
| 1.233 | 47.2 | 1.3 | 2628.6 | 2004.9 | | |
| 1.236 | 49.3 | 2.1 | 3716.5 | 2755.4 | | |
| 1.237 | 286.7 | 4.0 | 7910.2 | 9873.2 | 51.4 | 63.5 |
| 1.238 | 61.2 | 1.5 | 4171.1 | 2609.6 | 48.6 | 40.7 |
| 1.239 | 282.6 | 6.3 | 17657.7 | 10026.9 | 37.8 | 41.7 |
| 1.249 | 91.7 | 8.6 | 1599.7 | 937.5 | | |
| 1.252 | 30.5 | 4.5 | 205.0 | 170.7 | | |
| 1.253 | 59.9 | 1.7 | 2597.1 | 2515.0 | 47.9 | 44.8 |
| 1.258 | 9.5 | 1.3 | 315.2 | 531.5 | 43.4 | 50.5 |
| 1.259 | 19.5 | 2.1 | | | | |
| 1.260 | 70.9 | 7.1 | | | | |
| 1.261 | 307.4 | 14.8 | | | | |
| 1.262 | 54.9 | 4.0 | 861.0 | 5436.6 | | |
| 1.270 | 130.5 | 9.9 | | | | |
| 1.273 | 31.3 | 8.2 | | | | |
| 1.275 | 401.7 | 14.1 | | | | |
| 1.277 | 42.3 | 4.6 | | | | |
| 1.281 | 71.8 | 7.4 | | | | |
| 2.025 | 6.9 | 2.9 | 966.4 | 498.8 | 68.0 | 69.8 |
| 2.026 | 38.0 | 13.0 | 2076.0 | 536.0 | 52.0 | 74.5 |
| 2.031 | 14.6 | 5.3 | 1357.9 | 326.4 | 52.6 | 90.3 |
| 2.038 | 28.9 | 6.3 | 2553.9 | 1397.0 | 62.7 | 58.6 |
| 2.039 | 18.8 | 6.7 | 1988.0 | 1010.3 | | |
| 2.041 | 30.8 | 9.6 | 3443.4 | 2095.1 | 61.5 | 81.8 |
| 2.046 | 16.7 | 5.6 | 1975.4 | 758.9 | 32.1 | 57.4 |
| 2.047 | 26.4 | 7.0 | 1942.1 | 437.5 | 53.8 | 65.3 |
| 2.054 | 17.1 | 3.7 | 414.8 | 438.9 | 84.6 | 68.2 |
| 2.055 | 16.0 | 6.4 | 977.5 | 311.6 | | |
| 2.057 | 6.2 | 3.7 | | | | |
| 2.058 | 15.3 | 3.3 | 1936.0 | 212.6 | | |
| 2.059 | 3.9 | 2.7 | 119.8 | 207.9 | 25.5 | 75.0 |
| 2.060 | 4.9 | 3.2 | 328.8 | 181.3 | | |
| 2.061 | 10.5 | 1.8 | | | | |
| 2.064 | 4.1 | 2.2 | 382.0 | 178.2 | 56.2 | 53.1 |
| 2.065 | 4.1 | 1.8 | | | | |
| 2.066 | 10.2 | 2.3 | 2510.4 | 368.3 | 19.8 | 20.0 |
| 2.067 | 19.6 | 4.2 | | | | |
| 2.068 | 8.0 | 5.8 | | | | |
| 2.069 | 16.7 | 2.4 | | | | |
| 2.072 | 7.5 | 4.4 | | | | |
| 2.073 | 12.7 | 4.2 | | | | |
| 2.076 | 8.0 | 2.4 | | | | |
| 2.077 | 33.7 | 5.0 | | | | |
| 2.078 | 18.3 | 2.6 | | | | |
| 2.079 | 18.5 | 2.3 | | | | |
| 2.082 | 131.7 | 9.0 | | | | |
| 2.096 | 70.2 | 9.6 | | | | |
| 2.097 | 35.4 | 2.8 | | | | |
| 2.099 | 15.0 | 3.8 | | | | |

| Compound | IL-1β % | IL-6, % | TNF-α % | Chemotaxis IC50, μM | Mouse Oral PK, nM | Trachael Ring Contraction, % |
|---|---|---|---|---|---|---|
| 1.074 | 43.9 | 96.0 | 87.7 | | 506 | 40 |
| 1.075 | 49.7 | 73.9 | 51.6 | | 348 | 39 |
| 1.076 | 51.0 | 81.2 | 78.9 | | 1715 | |
| 1.077 | 30.3 | 43.3 | 52.3 | | 26 | |
| 1.079 | 59.3 | 31.1 | 56.5 | | 2443 | |
| 1.091 | 165.5 | 108.2 | 104.6 | 2.3 | 334 | 35 |
| 1.093 | 109.0 | 49.7 | 76.1 | | 363 | |
| 1.108 | 131.3 | 89.8 | 116.7 | | 395 | |
| 1.109 | 190.5 | 312.9 | 118.3 | | 187 | |

TABLE 14-continued

Summary of Data of Preferred Compounds

| | | | | | | |
|---|---|---|---|---|---|---|
| 1.123 | 82.6 | 64.7 | 62.7 | 3.1 | 71 | 47 |
| 1.124 | 99.5 | 101.4 | 61.5 | 3.4 | 118 | 38 |
| 1.126 | | | | | 0 | |
| 1.131 | 48.3 | 68.6 | 85.2 | 1.6 | 445 | 37 |
| 1.132 | 58.6 | 72.5 | 80.3 | | 982 | 42 |
| 1.133 | 54.5 | 70.7 | 66.2 | | 1098 | |
| 1.134 | 43.2 | 74.6 | 69.1 | | 1551 | |
| 1.135 | 57.0 | 123.2 | 108.0 | | 657 | |
| 1.136 | 66.3 | 95.0 | 71.5 | 2.6 | 26 | 45 |
| 1.137 | 40.3 | 46.2 | 58.0 | | 557 | |
| 1.138 | 257.4 | 76.6 | 130.9 | 1.9 | 1864 | |
| 1.141 | 50.4 | 71.7 | 75.7 | | 1643 | 35 |
| 1.148 | 63.9 | 78.6 | 56.1 | | 767 | 51 |
| 1.149 | 69.8 | 121.5 | 119.9 | | 1559 | 34 |
| 1.150 | 78.2 | 89.2 | 94.4 | | 1392 | 40 |
| 1.152 | 74.7 | 94.7 | 120.1 | | 435 | 34 |
| 1.153 | 64.1 | 106.2 | 74.3 | | 522 | 41 |
| 1.155 | 76.7 | 121.8 | 79.7 | | 32 | |
| 1.156 | 60.7 | 92.5 | 70.5 | | 88 | |
| 1.157 | 121.4 | 92.6 | 65.1 | | 357 | |
| 1.158 | 80.8 | 133.1 | 86.6 | | 102 | |
| 1.161 | 87.7 | 86.3 | 153.5 | | 392 | 40 |
| 1.162 | 95.5 | 99.8 | 158.7 | | 76 | 34 |
| 1.163 | 166.7 | 140.9 | 91.6 | | 10 | 35 |
| 1.164 | 80.1 | 109.5 | 89.0 | | 1504 | |
| 1.165 | 129.9 | 114.3 | 103.5 | | 94 | 30 |
| 1.166 | 107.0 | 87.2 | 82.2 | | 342 | |
| 1.171 | 78.9 | 91.8 | 72.2 | | 369 | |
| 1.173 | 86.1 | 79.5 | 80.1 | | 144 | 33 |
| 1.175 | 29.3 | 38.2 | 47.4 | | 1126 | |
| 1.176 | 95.2 | 112.4 | 72.4 | | 89 | |
| 1.186 | 64.1 | 105.3 | 68.2 | | 2169 | |
| 1.193 | | | | | 55 | |
| 1.195 | 115.4 | 94.4 | 67.7 | | 108 | |
| 1.197 | 179.1 | 128.8 | 83.3 | | 453 | 42 |
| 1.200 | 0.0 | 0.0 | 0.2 | | 0 | 92 |
| 1.206 | 88.7 | 164.0 | 97.3 | | 672 | |
| 1.212 | 116.3 | 111.0 | 108.1 | | 863 | 40 |
| 1.213 | 111.1 | 81.7 | 77.4 | | 396 | 29 |
| 1.215 | 136.7 | 63.2 | 60.4 | | 2651 | 41 |
| 1.217 | 118.6 | 73.8 | 71.3 | | 293 | |
| 1.219 | 138.9 | 127.7 | 82.1 | | 1679 | |
| 1.223 | 117.0 | 88.5 | 60.7 | | 13 | |
| 1.233 | 78.5 | 78.9 | 79.0 | | 41 | |
| 1.236 | 75.2 | 93.0 | 98.0 | | 48 | |
| 1.237 | 97.1 | 100.9 | 70.6 | | 178 | |
| 1.238 | 101.1 | 62.9 | 73.2 | | 48 | |
| 1.239 | 39.4 | 84.7 | 58.5 | | 259 | |
| 1.249 | 133.8 | 56.2 | 60.0 | | 2147 | |
| 1.252 | 139.2 | 68.3 | 101.6 | | 1259 | |
| 1.253 | 160.6 | 228.6 | 126.8 | | 240 | |
| 1.258 | 104.1 | 83.5 | 94.0 | | 567 | |
| 1.259 | | | | | 264 | |
| 1.260 | | | | | 291 | |
| 1.261 | | | | | | |
| 1.262 | 145.7 | 156.6 | 135.3 | | 285 | |
| 1.270 | | | | | | |
| 1.273 | | | | | | |
| 1.275 | | | | | | |
| 1.277 | | | | | | |
| 1.281 | | | | | | |
| 2.025 | | | | 1.7 | 74 | 33 |
| 2.026 | 166.0 | 180.7 | 109.1 | 3.8 | 629 | |
| 2.031 | 49.0 | 89.3 | 66.4 | | 1430 | |
| 2.038 | 90.8 | 79.7 | 70.2 | 0.7 | 729 | 57 |
| 2.039 | 49.8 | 70.3 | 47.8 | 1.6 | 92 | |
| 2.041 | | | | | 987 | |
| 2.046 | | | | | 488 | |
| 2.047 | | | | | 3 | |
| 2.054 | 24.0 | 56.8 | 37.9 | | 765 | |
| 2.055 | | | | | 656 | |
| 2.057 | | | | | 431 | |
| 2.058 | 1.2 | 1.3 | 10.6 | | 194 | |
| 2.059 | 0.3 | 0.0 | 6.9 | | 90 | |
| 2.060 | 5.9 | 19.6 | 33.0 | | 308 | |
| 2.061 | | | | | 73 | |
| 2.064 | 14.3 | 45.7 | 66.2 | | 202 | |
| 2.065 | | | | | 236 | |

TABLE 14-continued

Summary of Data of Preferred Compounds

| | | | | |
|---|---|---|---|---|
| 2.066 | 0.0 | 0.0 | 25.2 | 492 |
| 2.067 | | | | |
| 2.068 | | | | |
| 2.069 | | | | |
| 2.072 | | | | |
| 2.073 | | | | |
| 2.076 | | | | |
| 2.077 | | | | |
| 2.078 | | | | |
| 2.079 | | | | |
| 2.082 | | | | |
| 2.096 | | | | |
| 2.097 | | | | |
| 2.099 | | | | |

Although the invention has been described with reference to the presently preferred embodiments, it should be understood that various modifications could be made without departing from the scope of the invention.

What is claimed is:

1. A method of treating a pulmonary disease selected from the group consisting of asthma; chronic obstructive pulmonary disease; respiratory tract illness caused by respiratory syncytial virus; pulmonary arterial hypertension; acute respiratory distress syndrome and ventilator induced lung injury; cystic fibrosis; bronchiectasis; alpha-1-antitrypsin deficiency; rhinitis; rhinosinusitis; primary ciliary dyskinesia; pneumonia; bronchiolitis caused by agents other than respiratory syncytial virus; and interstitial lung disease;

the method comprises the steps of first identifying a subject suffering from the pulmonary disease, then administering to the subject an effective amount of a compound of Formula II to treat said disease;

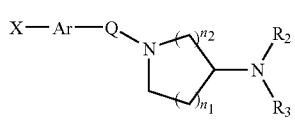

Formula II wherein:
Q is $(CR_4R_5)_{n3}$;
$n_1$ is 1, or 2;
$n_2$ is 1;
$n_3$ is 1, 2, or 3;
$R_2$ is $R_2$-1, optionally substituted:

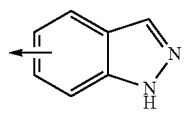

$R_2$-1

Ar is a monocyclic or bicyclic aryl or heteroaryl ring;
X is from 1 to 3 substituents on Ar, and each is independently selected from the group consisting of $OR_8$, $NR_8R_9$, $SR_8$, $SOR_8$, $SO_2R_8$, $SO_2NR_8R_9$, $NR_8SO_2R_9$, $CONR_8R_9$, $NR_8C(=O)R_9$, $NR_8C(=O)OR_9$, $OC(=O)NR_8R_9$, and $NR_8C(=O)NR_9R_{10}$;
$R_3$-$R_5$ are independently H, alkyl, alkenyl, alkynyl, cycloalkyl, cycloalkenyl, cycloalkylalkyl, cycloalkylalkenyl, or cycloalkylalkynyl, optionally substituted;

$R_8$-$R_{10}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; optionally substituted by one or more halogen or heteroatom-containing substituents selected from the group consisting of $OR_{11}$, $NR_{11}R_{12}$, $NO_2$, $SR_{11}$, $SOR_{11}$, $SO_2R_{11}$, $SO_2NR_{11}R_{12}$, $NR_{11}SO_2R_{12}$, $OCF_3$, $CONR_{11}R_{12}$, $NR_{11}C(=O)R_{12}$, $NR_{11}C(=O)OR_{12}$, $OC(=O)NR_{11}R_{12}$, and $NR_{11}C(=O)NR_{12}R_{13}$;
$R_{11}$-$R_{13}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle;

with the first proviso that if X is acyclic and is connected to Ar by a carbon atom, then X contains at least one nitrogen or sulfur atom, and with the second proviso that if X is acyclic and is connected to Ar by an oxygen or nitrogen atom, then X contains at least one additional oxygen, nitrogen or sulfur atom.

2. The method according to claim 1, wherein said compound of Formula II is a compound of Formula IIa, IIB, or IIc:

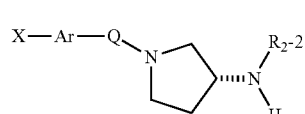

Formula IIa

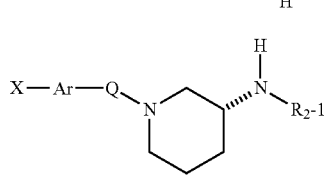

Formula IIb

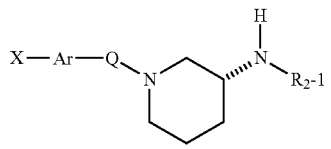

Formula IIc wherein Ar is phenyl, a 6,5-fused bicyclic heteroaryl ring, or a 6,6-fused bicyclic heteroaryl ring; Ar is substituted by 1 or 2 substituents X, and Q is $CH_2$.

3. The method according to claim 2, wherein Ar is 3-substituted phenyl; 4-substituted phenyl; 3,4-disubstituted phenyl; or 2,3-disubstituted phenyl.

4. The method according to claim 2, wherein Ar is benzofuran, benzothiophene, indole, and benzimidazole.

5. A method of treating a pulmonary disease selected from the group consisting of asthma; chronic obstructive pulmonary disease; respiratory tract illness caused by respiratory syncytial virus; pulmonary arterial hypertension; acute respiratory distress syndrome and ventilator induced lung injury; cystic fibrosis; bronchiectasis; alpha-1-antitrypsin deficiency; rhinitis; rhinosinusitis; primary ciliary dyskinesia; pneumonia; bronchiolitis caused by agents other than respiratory syncytial virus; and interstitial lung disease;

the method comprises the steps of first identifying a subject suffering from the pulmonary disease, then administering to the subject an effective amount of a compound, wherein said compound is Compound 1.074, which is (R)—N-(1-(4-(methylthio)benzyl)piperidin-3-yl)-1H-indazol-5-amine; Compound 1.075, which is (S)—N-(1-(4-(methylthio)benzyl)piperidin-3-yl)-1H-indazol-5-amine; Compound 1.091, which is (S)—N-(3-((3-(1H-indazol-5-ylamino)piperidin-1-yl)methyl)phenyl)methanesulfonamide; Compound 1.093, which is (R)—N-(3-((3-(1H-indazol-5-ylamino)piperidin-1-yl)methyl)phenyl)methanesulfonamide; Compound 1.123, which is (R)—N-(3-((3-(1H-indazol-5-ylamino)piperidin-1-yl)methyl)phenyl)ethanesulfonamide; Compound 1.124, which is (S)—N-(3-((3-(1H-indazol-5-ylamino)piperidin-1-yl)methyl)phenyl)ethanesulfonamide; Compound 1.126, which is (R)-2-(3-((3-(1H-indazol-5-ylamino)piperidin-1-yl)methyl)phenoxy)-N-(pyridin-3-yl)acetamide; Compound 1.152, which is (S)-2-(5-((3-(1H-indazol-5-ylamino)piperidin-1-yl)methyl)-2-methylphenoxy)ethanol; Compound 1.157, which is (S)—N-(1-(3-(methylsulfonylmethyl)benzyl)piperidin-3-yl)-1H-indazol-5-amine; Compound 1.158, which is (S)—N-(1-(3-(methylthio)benzyl)piperidin-3-yl)-1H-indazol-5-amine; Compound 1.161, which is (R)-2-(5-((3-(1H-indazol-5-ylamino)piperidin-1-yl)methyl)-2-methylphenoxy)ethanol; Compound 1.195, which is (S)-2-(3-((3-(1H-indazol-5-ylamino)piperidin-1-yl)methyl)phenoxy)acetamide; Compound 1.200, which is (S)-ethyl 2-(3-((3-(1H-indazol-5-ylamino)piperidin-1-yl)methyl)phenoxy)acetate; Compound 1.212, which is (R)—N-(5-((3-(1H-indazol-5-ylamino)piperidin-1-yl)methyl)-2-chlorophenyl)methanesulfonamide; Compound 1.213, which is (S)—N-(5-((3-(1H-indazol-5-ylamino)piperidin-1-yl)methyl)-2-chlorophenyl)methanesulfonamide; Compound 1.215, which is (S)-3-((3-(1H-indazol-5-ylamino)piperidin-1-yl)methyl)benzenesulfonamide; Compound 1.219, which is (S)-3-((3-(1H-indazol-5-ylamino)piperidin-1-yl)methyl)benzamide; Compound 1.233, which is (S)—N-(5-((3-(1H-indazol-5-ylamino)piperidin-1-yl)methyl)-2-methylphenyl)methanesulfonamide; Compound 1.236, which is (S)—N-(5-((3-(1H-indazol-5-ylamino)piperidin-1-yl)methyl)-2-methylphenyl)butane-1-sulfonamide; Compound 1.237, which is (S)—N-(2-((3-(1H-indazol-5-ylamino)piperidin-1-yl)methyl)-5-methylphenyl)-N',N' dimethylaminosulfamide; Compound 1.238, which is (S)—N-(5-((3-(1H-indazol-5-ylamino)piperidin-1-yl)methyl)-2-methylphenyl)propane-1-sulfonamide; Compound 1.239, which is (S)—N-(5-((3-(1H-indazol-5-ylamino)piperidin-1-yl)methyl)-2-methylphenyl)-4-methylbenzenesulfonamide; Compound 1.249, which is (R)-3-((3-(1H-indazol-5-ylamino)piperidin-1-yl)methyl)benzenesulfonamide; Compound 1.253, which is (S)—N-(5-((3-(1H-indazol-5-ylamino)piperidin-1-yl)methyl)-2-methylphenyl)ethanesulfonamide; Compound 1.258, which is (R)—N-(5-((3-(1H-indazol-5-ylamino)piperidin-1-yl)methyl)-2-methylphenyl)methanesulfonamide; Compound 1.259, which is (R)—N-(5-((3-(1H-indazol-5-ylamino)piperidin-1-yl)methyl)-2-methylphenyl)ethanesulfonamide; Compound 1.260, which is (R)—N-(5-((3-(1H-indazol-5-ylamino)piperidin-1-yl)methyl)-2-methylphenyl)-4-methylbenzenesulfonamide; Compound 1.261, which is (S)—N-(3-((3-(1H-indazol-5-ylamino)piperidin-1-yl)methyl)phenyl)-N',N' dimethylaminosulfamide; Compound 1.262, which is (R)—N-(2-((3-(1H-indazol-5-ylamino)piperidin-1-yl)methyl)-5-methylphenyl)-'N,N' dimethylaminosulfamide; Compound 1.270, which is (S)—N-(3-((3-(1H-indazol-5-ylamino)piperidin-1-yl)methyl)phenyl)piperidine-1-sulfonamide; Compound 1.275, which is (S)—N-(3-((3-(1H-indazol-5-ylamino)piperidin-1-yl)methyl)-2-methylphenyl)-N',N' dimethylaminosulfamide; and Compound 1.281, which is (R)-2-(5-((3-(1H-indazol-5-ylamino)piperidin-1-yl)methyl)-2-methylphenyl1H-indazol-5-ylamino)piperidin-1-yl)methyl)-2-methylphenoxy)acetamide.

6. The method according to claim 1, wherein said interstitial lung disease is lymphangioleiomyomatosis; idiopathic pulmonary fibrosis; obliterative bronchiolitis or bronchiolitis obliterans organizing pneumonia due to lung transplantation or HSCT; nonspecific interstitial pneumonia; cryptogenic organizing pneumonia; acute interstitial pneumonia; respiratory bronchiolitis-associated interstitial lung disease; desquamative interstitial pneumonia; and lymphocytic interstitial pneumonia; or pulmonary sarcoidosis.

7. The method according to claim 1, wherein Q is $CH_2$, and $R_3$ is H.

8. The method according to claim 1, wherein $R_4$ and $R_5$ are H.

9. The method of claim 1, wherein Ar is phenyl.

10. The method of claim 9, wherein the compound has a central piperidine ring.

11. The method of claim 10, wherein X is from 1 to 3 substituents on Ar, and X is $OR_8$ or $NR_8SO_2R_9$.

12. The method of claim 11, wherein $R_8$ is H, alkyl, arylalkyl, cycloalkylalkyl, optionally substituted with $OR_{11}$, $NR_{11}SO_2R_{12}$, or $CONR_{11}R_{12}$.

13. The method of claim 12, wherein the compound is Compound 1.091.

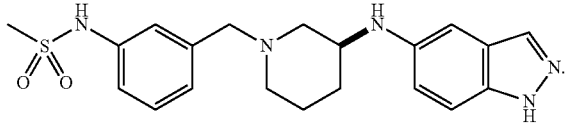

14. The method of claim 9, wherein the compound has a central pyrrolidine ring.

15. The method of claim 14, wherein X is from 1 to 3 substituents on Ar, and X is $OR_8$ or $NR_8SO_2R_9$.

16. The method of claim 15, wherein $R_8$ is H, alkyl, arylalkyl, cycloalkylalkyl, optionally substituted with $OR_{11}$, $NR_{11}SO_2R_{12}$, or $CONR_{11}R_{12}$.

17. The method of claim 1, wherein the pulmonary disease is asthma.

* * * * *